(12) United States Patent
Pearcy et al.

(10) Patent No.: US 8,940,539 B2
(45) Date of Patent: Jan. 27, 2015

(54) REAGENT PREPARATION AND DISPENSING DEVICE AND METHODS FOR THE SAME

(75) Inventors: Timothy Pearcy, Plymouth, MN (US); James G. Skakoon, St. Paul, MN (US)

(73) Assignee: Biolyph, L.L.C., Hopkins, MN (US)

( * ) Notice: Subject to any disclaimer, the term of this patent is extended or adjusted under 35 U.S.C. 154(b) by 51 days.

(21) Appl. No.: 12/992,552

(22) PCT Filed: May 14, 2009

(86) PCT No.: PCT/US2009/043966
§ 371 (c)(1),
(2), (4) Date: Feb. 9, 2011

(87) PCT Pub. No.: WO2009/140502
PCT Pub. Date: Nov. 19, 2009

(65) Prior Publication Data
US 2011/0127294 A1    Jun. 2, 2011

Related U.S. Application Data

(60) Provisional application No. 61/084,206, filed on Jul. 28, 2008, provisional application No. 61/127,581, filed on May 14, 2008.

(51) Int. Cl.
*G01N 33/00* (2006.01)
*G01N 35/10* (2006.01)
(Continued)

(52) U.S. Cl.
CPC ........... *G01N 35/1002* (2013.01); *A61J 1/2089* (2013.01); *B01L 3/0272* (2013.01); *A61J 1/06* (2013.01); *A61J 2001/2013* (2013.01);
(Continued)

(58) Field of Classification Search
USPC .......................... 422/514; 604/82; 436/4, 723
See application file for complete search history.

(56) References Cited

U.S. PATENT DOCUMENTS

| 2,176,041 A | 10/1939 | Pittenger |
| 2,591,706 A | 4/1952 | Lockhart |

(Continued)

FOREIGN PATENT DOCUMENTS

| DE | 19543240 A1 | 5/1997 |
| EP | 1103304 A2 | 5/2001 |

(Continued)

OTHER PUBLICATIONS

"International Application Serial No. PCT/US2009/043966, Search Report mailed Jul. 27, 2009", 7 pgs.

(Continued)

*Primary Examiner* — Sam P Siefke
(74) *Attorney, Agent, or Firm* — Schwegman Lundberg & Woessner, P.A.

(57) ABSTRACT

A reagent preparation and dispensing device includes a body. A reagent reservoir containing a reagent is disposed within the body. A solution reservoir containing a solution is disposed within the body. The device further includes an activator movably coupled with the body to open the reagent reservoir and the solution reservoir, The activator is operable to mix the solution with the reagent to form a specified amount of a reagent mixture. A dispensing reservoir tip is coupled with the body. The dispensing reservoir tip is sized and shaped to hold the specified amount of the reagent mixture and dispense the specified amount of the reagent mixture from the device.

33 Claims, 65 Drawing Sheets

(51) Int. Cl.
  *A61J 1/20* (2006.01)
  *B01L 3/02* (2006.01)
  *A61J 1/06* (2006.01)

(52) U.S. Cl.
  CPC .... *A61J2001/2079* (2013.01); *B01L 2200/028* (2013.01); *B01L 2200/016* (2013.01); *B01L 2300/0672* (2013.01); *B01L 2300/087* (2013.01); *B01L 2400/0478* (2013.01); *B01L 2400/049* (2013.01); *B01L 2400/0683* (2013.01)
  USPC .............................................. 436/43; 436/72

(56) References Cited

U.S. PATENT DOCUMENTS

| | | | |
|---|---|---|---|
| 3,834,387 | A | 9/1974 | Brown |
| 4,031,892 | A | 6/1977 | Hurschman |
| 4,226,236 | A | 10/1980 | Genese |
| 4,515,753 | A | 5/1985 | Smith et al. |
| 4,516,967 | A | 5/1985 | Kopfer |
| 4,693,706 | A * | 9/1987 | Ennis, III .................. 604/87 |
| 4,768,568 | A | 9/1988 | Fournier et al. |
| 4,834,149 | A | 5/1989 | Fournier et al. |
| 4,973,168 | A | 11/1990 | Chan |
| 5,000,922 | A | 3/1991 | Turpen |
| 5,071,769 | A | 12/1991 | Kundu et al. |
| 5,199,949 | A | 4/1993 | Haber et al. |
| 5,232,664 | A | 8/1993 | Krawzak et al. |
| 5,277,873 | A | 1/1994 | Hsei |
| 5,281,198 | A | 1/1994 | Haber et al. |
| 5,449,494 | A | 9/1995 | Seeney |
| 5,605,542 | A | 2/1997 | Tanaka et al. |
| 5,637,087 | A | 6/1997 | O'Neil et al. |
| 5,704,918 | A | 1/1998 | Higashikawa |
| 5,785,682 | A * | 7/1998 | Grabenkort .................. 604/82 |
| 5,827,262 | A | 10/1998 | Neftel et al. |
| 5,865,799 | A | 2/1999 | Tanaka et al. |
| 5,869,003 | A | 2/1999 | Nason |
| 5,879,635 | A | 3/1999 | Nason |
| 5,899,881 | A * | 5/1999 | Grimard et al. .............. 604/89 |
| 5,951,160 | A | 9/1999 | Ronk |
| 5,965,453 | A | 10/1999 | Skiffington et al. |
| 5,971,953 | A | 10/1999 | Bachynsky |
| 6,045,755 | A | 4/2000 | Lebl et al. |
| 6,048,735 | A | 4/2000 | Hessel et al. |
| 6,248,294 | B1 | 6/2001 | Nason |
| 6,284,549 | B1 | 9/2001 | Guthrie |
| 6,406,175 | B1 | 6/2002 | Marino |
| 6,419,656 | B1 | 7/2002 | Vetter et al. |
| 6,481,435 | B2 | 11/2002 | Hochrainer et al. |
| 6,488,894 | B1 | 12/2002 | Miethe et al. |
| 6,551,834 | B2 | 4/2003 | Carpenter et al. |
| 6,569,125 | B2 | 5/2003 | Jepson et al. |
| 6,632,681 | B1 | 10/2003 | Chu |
| 6,641,561 | B1 | 11/2003 | Hill et al. |
| 6,656,150 | B2 | 12/2003 | Hill et al. |
| 6,702,778 | B2 | 3/2004 | Hill et al. |
| 6,770,052 | B2 | 8/2004 | Hill et al. |
| 6,817,987 | B2 | 11/2004 | Vetter et al. |
| 6,863,866 | B2 | 3/2005 | Kelly et al. |
| 6,878,338 | B2 | 4/2005 | Taylor et al. |
| 6,924,498 | B2 | 8/2005 | Feldsine et al. |
| 6,953,445 | B2 | 10/2005 | Wilmot et al. |
| 6,986,346 | B2 | 1/2006 | Hochrainer et al. |
| 7,030,403 | B2 | 4/2006 | Feldsine et al. |
| 7,040,311 | B2 | 5/2006 | Hochrainer et al. |
| 7,090,803 | B1 | 8/2006 | Gould et al. |
| 7,329,235 | B2 | 2/2008 | Bertron et al. |
| 7,967,779 | B2 | 6/2011 | Bertron et al. |
| 8,329,119 | B2 | 12/2012 | Pearcy et al. |
| 2001/0016703 | A1 | 8/2001 | Wironen et al. |
| 2003/0039588 | A1 | 2/2003 | Miethe et al. |
| 2003/0157564 | A1 | 8/2003 | Smith et al. |
| 2003/0209653 | A1 | 11/2003 | Feldsine et al. |
| 2003/0235512 | A1 | 12/2003 | Carpenter et al. |
| 2004/0097874 | A1 | 5/2004 | Griffiths et al. |
| 2004/0138611 | A1 | 7/2004 | Griffiths et al. |
| 2004/0170533 | A1 | 9/2004 | Chu |
| 2005/0075602 | A1 * | 4/2005 | Cherif-Cheikh et al. ....... 604/87 |
| 2005/0075604 | A1 | 4/2005 | Lee |
| 2006/0052747 | A1 | 3/2006 | Nishimura et al. |
| 2006/0116644 | A1 | 6/2006 | Norton |
| 2006/0139631 | A1 | 6/2006 | Feldsine et al. |
| 2006/0169348 | A1 | 8/2006 | Yigal |
| 2006/0184103 | A1 | 8/2006 | Paproski et al. |
| 2006/0216196 | A1 | 9/2006 | Satoh et al. |
| 2007/0014690 | A1 | 1/2007 | Lawrence et al. |
| 2008/0188828 | A1 * | 8/2008 | Reynolds et al. ............. 604/520 |
| 2008/0300551 | A1 * | 12/2008 | Schiller et al. ................ 604/220 |
| 2009/0117646 | A1 | 5/2009 | Stordeur et al. |
| 2010/0249753 | A1 | 9/2010 | Gaisser et al. |
| 2011/0224610 | A1 | 9/2011 | Lum et al. |
| 2011/0224611 | A1 | 9/2011 | Lum et al. |
| 2011/0224612 | A1 | 9/2011 | Lum et al. |
| 2012/0179137 | A1 | 7/2012 | Bartlett et al. |
| 2012/0201726 | A1 | 8/2012 | Pearcy et al. |
| 2013/0030412 | A1 | 1/2013 | Bartlett et al. |
| 2013/0208558 | A1 | 8/2013 | Pearcy et al. |
| 2014/0048556 | A1 | 2/2014 | Pearcy et al. |
| 2014/0322102 | A1 | 10/2014 | Pearcy et al. |

FOREIGN PATENT DOCUMENTS

| | | |
|---|---|---|
| EP | 2405961 A2 | 1/2012 |
| WO | WO-8603589 A1 | 6/1986 |
| WO | WO-9103224 A1 | 3/1991 |
| WO | WO-9210225 A1 | 6/1992 |
| WO | WO-9703209 A1 | 1/1997 |
| WO | WO-2010104858 A2 | 9/2010 |
| WO | WO-2011123762 A1 | 10/2011 |
| WO | WO-2012006185 A1 | 1/2012 |
| WO | WO-2012/067619 A1 | 5/2012 |
| WO | WO-2013043861 A2 | 3/2013 |
| WO | WO-2013163598 A2 | 10/2013 |
| WO | WO-2014004695 A1 | 1/2014 |

OTHER PUBLICATIONS

"International Application Serial No. PCT/US2009/043966, Written Opinion mailed Jul. 27, 2009", 6 pgs.

"International Application Serial No. PCT/US10/57238, International Search Report mailed Jan. 26, 2011", 2 pgs.

"International Application Serial No. PCT/US10/57238, Written Opinion mailed Jan. 26, 2011", 9 pgs.

"International Application Serial No. PCT/US2009/043966, International Preliminary Report on Patentability mailed Jul. 27, 2011", 36 pgs.

"U.S. Appl. No. 13/450,365, Notice of Allowance mailed Aug. 16, 2012", 13 pgs.

"U.S. Appl. No. 13/450,365, Preliminary Amendment filed Jul. 27, 2012", 12 pgs.

"International Application Serial No. PCT/US2010/057238, International Preliminary Report on Patentability mailed Dec. 14, 2012", 41 pgs.

"U.S. Appl. No. 13/805,166, Preliminary Amendment filed Dec. 18, 2012", 8 pgs.

"U.S. Appl. No. 13/988,279, Preliminary Amendment filed May 17, 2013", 9 pgs.

"Australian Application Serial No. 2009246306, Voluntary Amendment filed Jan. 25, 2011", 42 pgs.

"Australian Application Serial No. 2010363976, Office Action mailed May 13, 2013", 2 pgs.

"Australian Application Serial No. 2011276396, Voluntary Amendment filed Dec. 17, 2012", 14 pgs.

"International Application Serial No. PCT/US2010/057238, Response to Written Opinion filed Sep. 18, 2012", 14 pgs.

"International Application Serial No. PCT/US2011/042443, International Preliminary Report on Patentability mailed Jul. 31, 2012", 29 pgs.

"International Application Serial No. PCT/US2011/042443, International Search Report mailed Nov. 25, 2011", 2 pgs.

(56) References Cited

OTHER PUBLICATIONS

"International Application Serial No. PCT/US2011/042443, Response to Written Opinion filed Apr. 27, 2012", 11 pgs.

"International Application Serial No. PCT/US2011/042443, Written Opinion mailed Nov. 25, 2011", 4 pgs.

"International Application Serial No. PCT/US2009/043966, Demand and Response filed Mar. 12, 2010 to Written Opinion mailed Jul. 31, 2009", 36 pgs.

"U.S. Appl. No. 13/988,279, Notice of Allowance mailed Feb. 4, 2014", 9 pgs.

"Australian Application Serial No. 2011276396, First Examination Report mailed Dec. 11, 2013", 3 pgs.

"European Application Serial No. 10859869.9, Office Action mailed Jul. 5, 2013", 2 pgs.

"European Application Serial No. 10859869.9, Response filed Jul. 19, 2013 to Office Action mailed Jul. 5, 2013", 54 pgs.

"European Application Serial No. 11804202.7, Office Action mailed Apr. 10, 2013", 2 pgs.

U.S. Appl. No. 13/805,166, Restriction Requirement mailed Jul. 22, 2014, 8 pgs.

U.S. Appl. No. 13/988,279, Notice of Allowance mailed Apr. 1, 2014, 8 pgs.

U.S. Appl. No. 13/988,279, PTO Response to Rule 312 Communication mailed Jun. 30, 2014, 2 pgs.

Australian Application Serial No. 2009246306, Office Action mailed Mar. 13, 2014, 4 pgs.

Australian Application Serial No. 2010363976, Amendment filed Apr. 29, 2014, 17 pgs.

Australian Application Serial No. 2010363976, Response filed May 22, 2013 to Office Action mailed May 13, 2013, 58 pgs.

Australian Application Serial No. 2011276396, Notice of Acceptance mailed Apr. 24, 2014, 2 pgs.

Australian Application Serial No. 2011276396, Response filed Apr. 10, 2014 to Office Action mailed Dec. 11, 2013, 19 pgs.

Canadian Application Serial No. 2,803,375, Office Action mailed Jun. 5, 2014, 2 pgs.

European Application Serial No. 10859869.9, Extended European Search Report mailed May 2, 2014, 7 pgs.

European Application Serial No. 11804202.7, Extended European Search Report mailed Jul. 7, 2014, 6 pgs.

International Application Serial No. PCT/US2009/043966, Demand and Response filed Mar. 12, 2010 to Written Opinion mailed Jul. 31, 2009, 36 pgs.

U.S. Appl. No. 13/805,166, Notice of Allowance mailed Oct. 15, 2014, 8 pgs.

U.S. Appl. No. 13/805,166, Response filed Sep. 25, 2014 to Restriction Requirement Jul. 22, 2014, 14 pgs.

U.S. Appl. No. 13/988,279, Notice of Allowability mailed Nov. 21, 2014, 2 pgs.

U.S. Appl. No. 14/331,431, Preliminary Amendment filed Sep. 18, 2014, 9 pgs.

\* cited by examiner

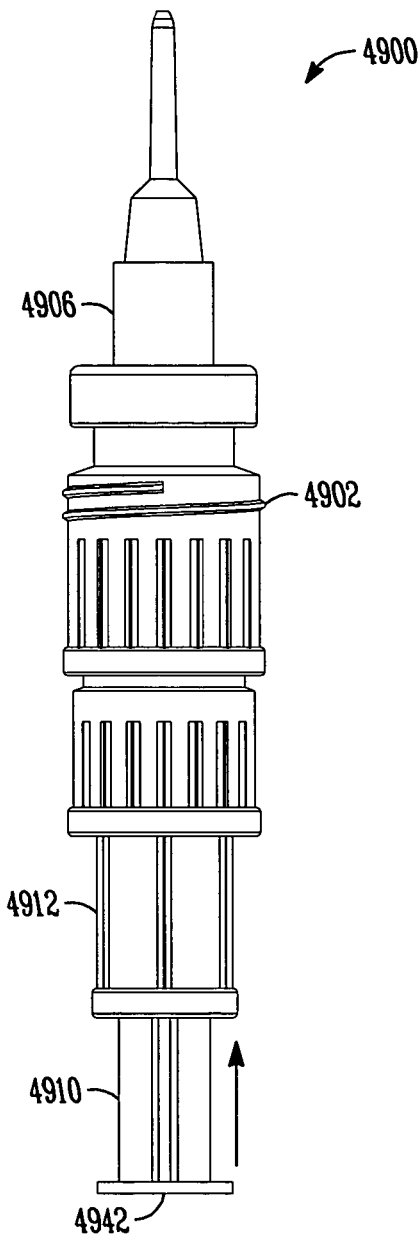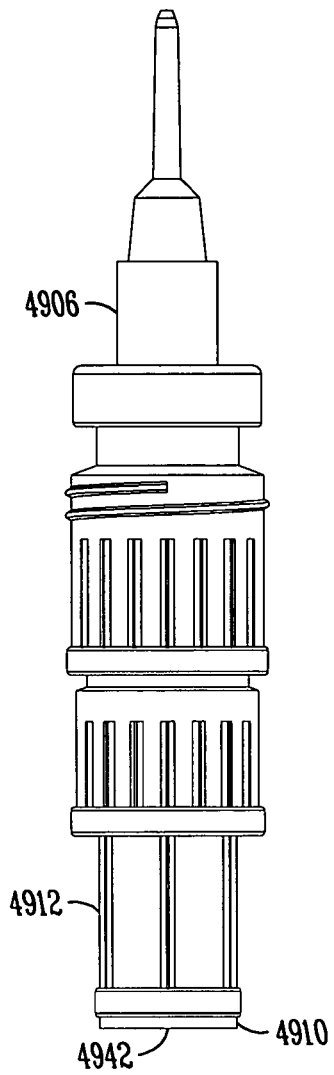
FIG. 51E
FIG. 51F

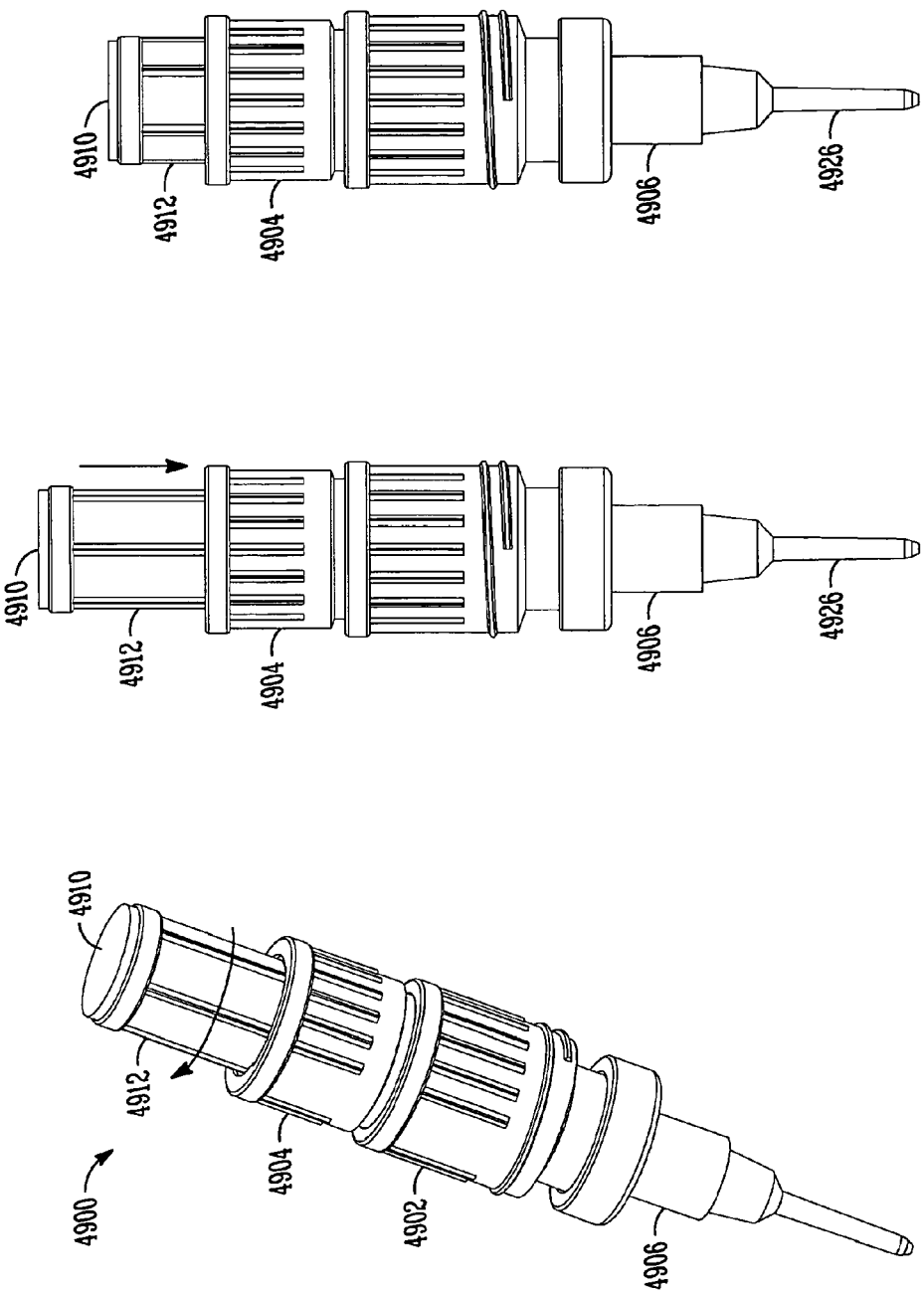

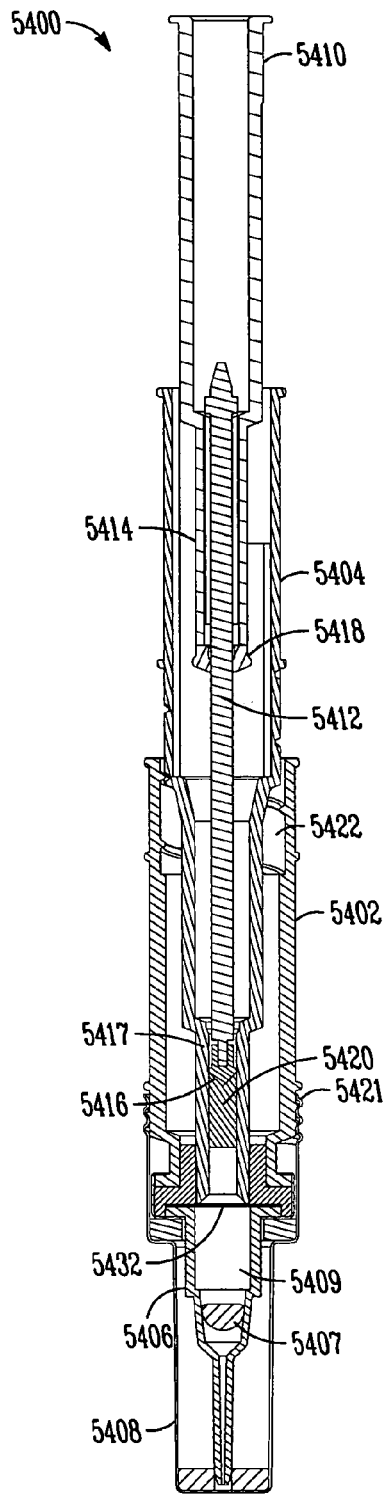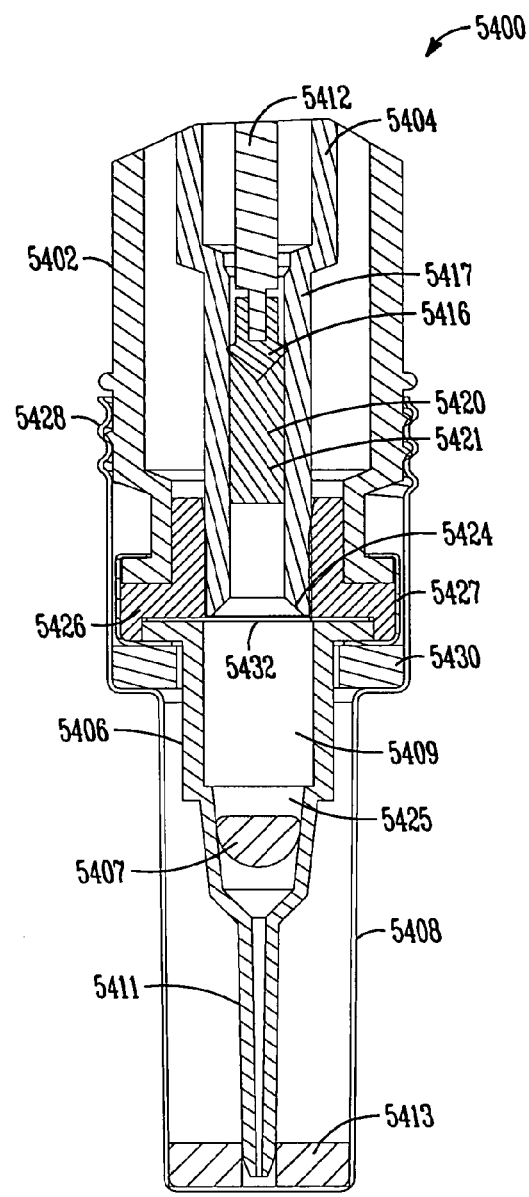
FIG. 54A
FIG. 54B

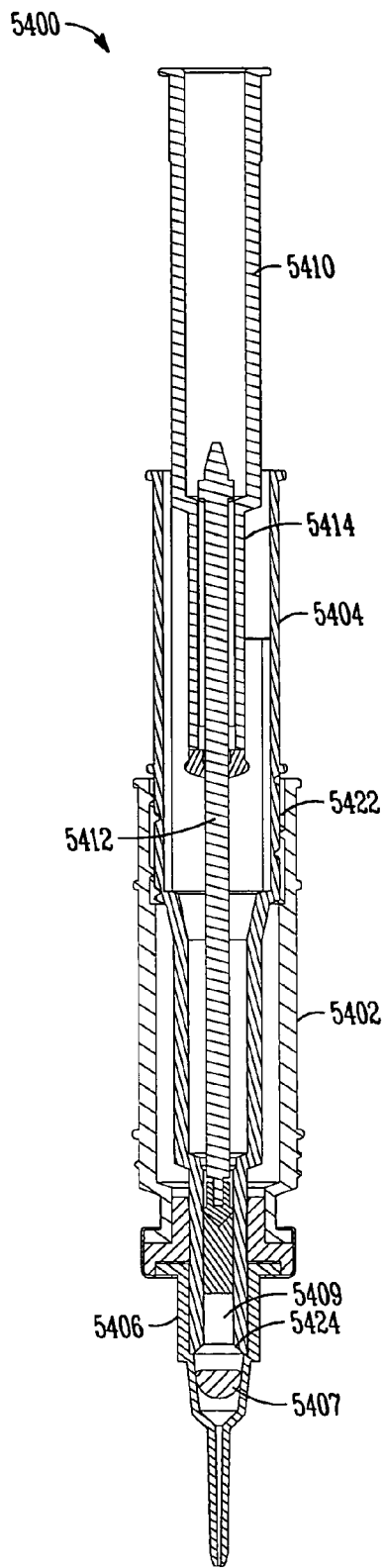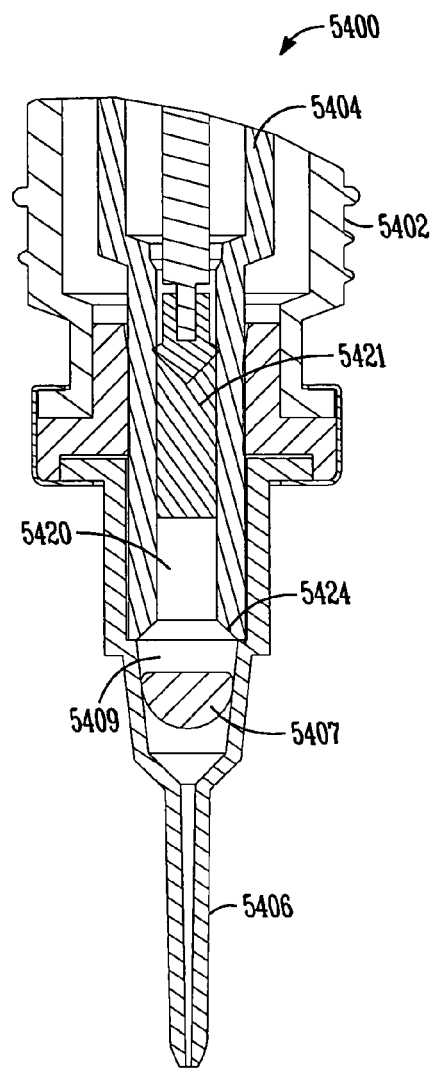
FIG. 55A
FIG. 55B

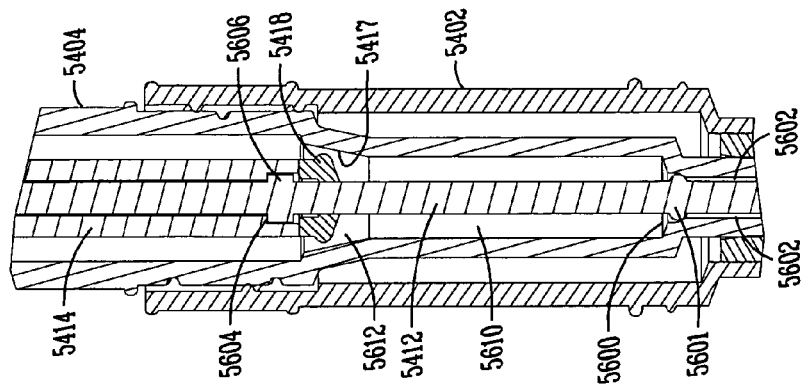
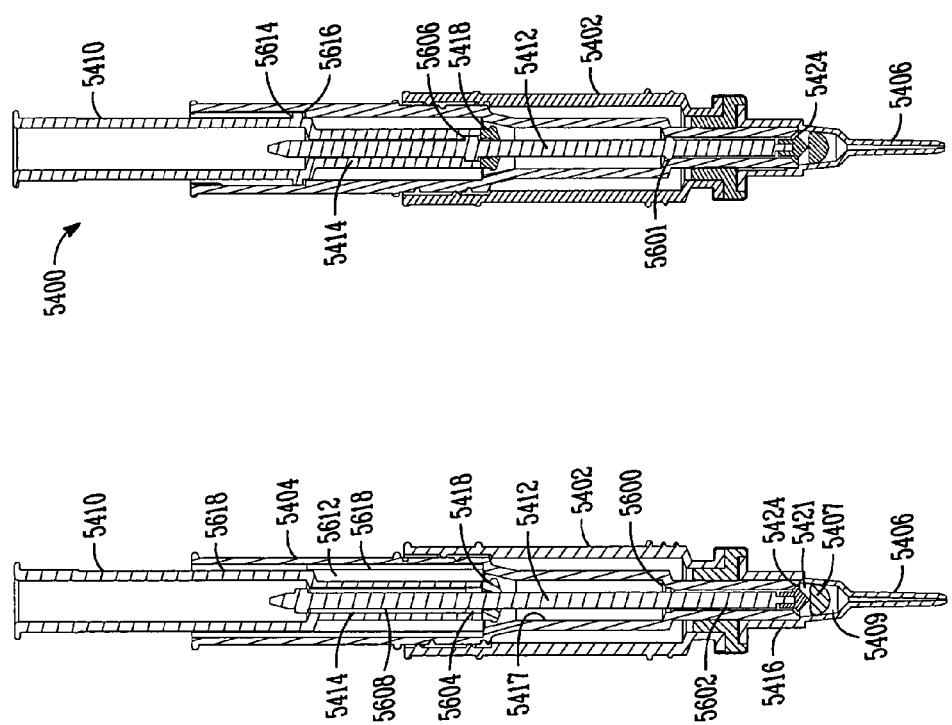
FIG. 56A
FIG. 56B
FIG. 56C

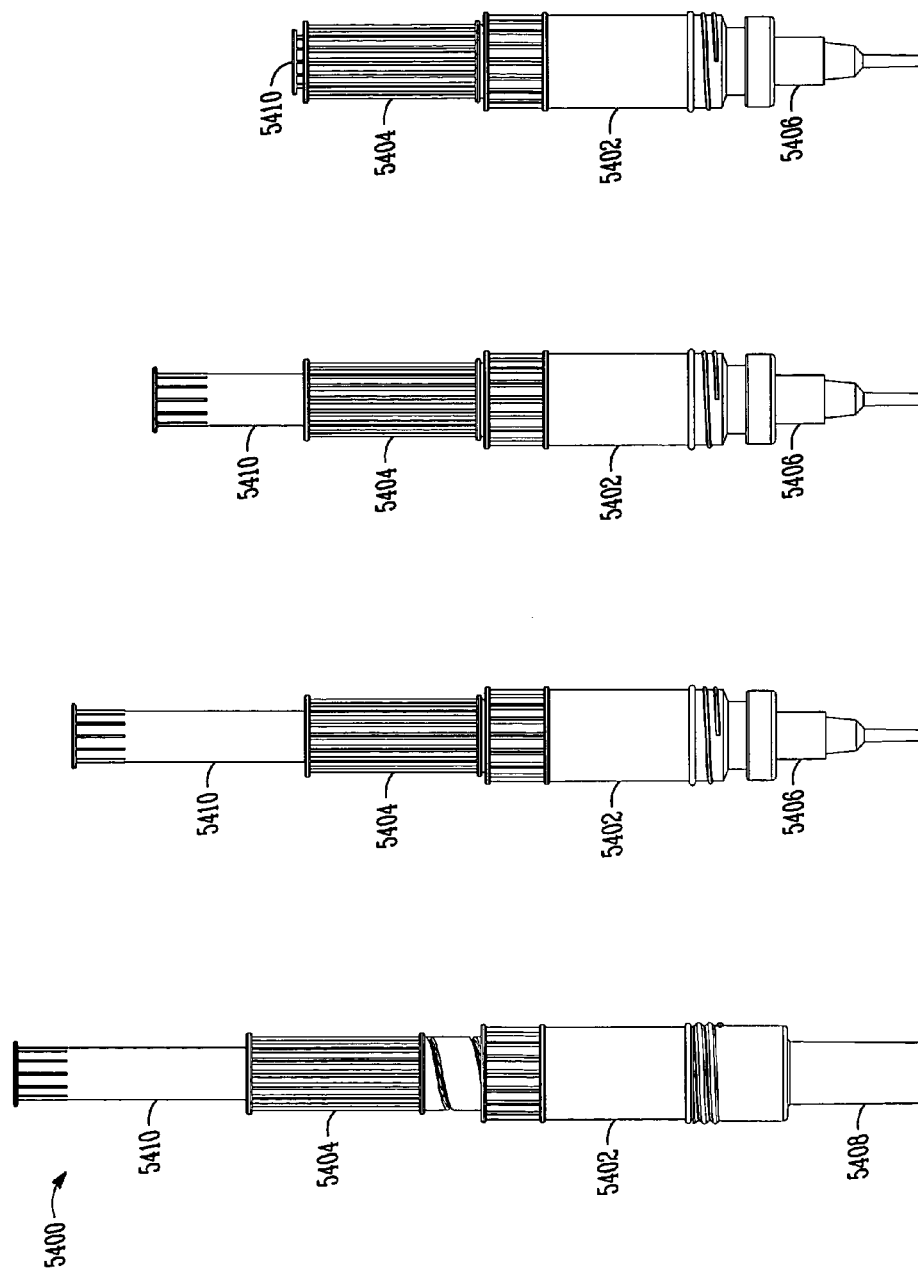

REAGENT PREPARATION AND DISPENSING DEVICE AND METHODS FOR THE SAME

RELATED APPLICATIONS

This patent application is a continuation under 35 U.S.C. 111(a) of International Patent Application serial no. PCT/US2009/043966, filed May 14, 2009, and published on Nov. 19, 2009 as WO 2009/140502A1, which claims priority benefit of U.S. Provisional Patent Application Ser. No. 61/127,581 filed May 14, 2008 and U.S. Provisional Patent Application Ser. No. 61/084,206 filed Jul. 28, 2008, which applications and publication are incorporated herein by reference in their entirety.

TECHNICAL FIELD

Storage, preparation and dispensing of solutions.

BACKGROUND

Some examples of diagnostic, life science research and drug discovery reagents require preparation prior to use. For instance, reagents may require measuring a diluent (or solution) and using the diluent to rehydrate a dry reagent. In other examples, preparation of the reagent requires measuring and mixing of a sample solution (e.g., a patient biological sample; an environmental sample such as, water or soil; an agricultural sample such as food and the like) with a reagent in a dried or liquid form. In still other examples, preparation of the reagent requires mixing of two or more liquid components, such as a reagent and another solution.

Manufacturers of diagnostic, life science research and drug discovery reagents use precision and standardized procedures in order to produce high quality reagents. These reagents are often prepared at their point of use. The quality of the reagents (e.g., the precise amount of reagent solution, the purity of the reagent solution and the like) is easily compromised at the point of use because of errors in preparation procedures that are used by personnel responsible for preparing the reagent. For instance, the reagent is handled in an unclean environment having contaminants (e.g., a humid atmosphere; a biologically active environment contaminated with microorganisms, DNA, RNA, ATP and the like; a chemically active environment, and the like), the wrong amount of solution is used, the wrong solution is used, and the like. In other examples, the reagent and solution or diluent are not allowed to mix thoroughly. In still other examples, the reagent solution is dispensed from a device but fails to deliver the full specified amount of reagent solution as a result of operator error or device performance (e.g., a portion of the solution is left within the device).

Where lyophilized reagents (e.g., dried or freeze-dried reagents) are used, unwanted exposure to contaminants including, but not limited to, moisture or moisture vapor during storage and prior to reconstitution may contaminate or compromise the stability of the lyophilized reagent. Compromising the reagent decreases its ability to rapidly rehydrate thereby creating difficulties in preparing a reagent at the proper concentration. Additionally, compromising the reagent from a dry state (where biological and chemical activities of the reagent are arrested) may reactivate the reagent and allow it to prematurely break down thereby decreasing the effectiveness of the reagent.

Even small errors in preparation leading to an improperly prepared reagent (e.g., mis-measuring of a solution, failure to fully reconstitute the reagent or diluting the reagent and the like) may have undesirable consequences, including, but not limited to, false positives, inaccurate diagnoses leading to inaccurate or inappropriate treatments, and false negatives (undetected diagnoses resulting in no treatment where treatment is needed).

SUMMARY

In Example 1 a device may comprise a reagent preparation and dispensing device including a body; a reagent reservoir containing a reagent, the reagent reservoir disposed within the body; a solution reservoir containing a solution, the solution reservoir disposed within the body; a means for reconstituting the reagent into a specified amount of a reagent mixture; a dispensing reservoir tip coupled with the body, the dispensing reservoir tip sized and shaped to hold the specified amount of the reagent mixture; and a means for dispensing the reagent mixture from the dispensing reservoir tip.

In Example 2, the device of Example 1 may include the means for reconstituting the reagent including the means for dispensing the reagent mixture.

In Example 3, the device of any one or any combination of Examples 1-2 may include the reagent including a dried reagent.

In Example 4, the device of any one or any combination of Examples 1-3 may include the dispensing reservoir tip sized and shaped to hold the specified amount of the reagent mixture includes the reagent reservoir.

In Example 5, the device of any one or any combination of Examples 1-4 may include one or more of the reagent reservoir and the solution reservoir are reservoirs separate from the body and configured for loading within the body.

In Example 6, the device of any one or any combination of Examples 1-5 may include one or more of the reagent reservoir and the solution reservoir are slidably received within the body.

In Example 7, the device of any one or any combination of Examples 1-6 may include the means for reconstituting the reagent includes an activator slidably received in the body, the activator is movable from a first activator position to at least a second activator position, the activator is sized and shaped to fracture at least one of the reagent reservoir and the solution reservoir when moved from the first position to the second position, and the activator is movable to mix the solution with the reagent to form the specified amount of the reagent mixture.

In Example 8, the device of any one or any combination of Examples 1-7 may include a first safety interposed between the body and the activator in a first safety position, while in the first safety position the first safety prevents movement of the activator relative to the body, and in a second safety position the activator is movable relative to the body.

In Example 9, the device of any one or any combination of Examples 1-8 may include the means for reconstituting the reagent includes a capillary tube containing the solution reservoir, and the capillary tube contains the solution by a vacuum.

In Example 10, the device of any one or any combination of Examples 1-9 may include the means for reconstituting the reagent includes an activator having a bulb, and in a deflected orientation the bulb engages with the capillary tube and fractures the capillary tube along a weakened portion.

In Example 11, the device of any one or any combination of Examples 1-10 may include a support skeleton coupled between the body and the capillary tube, the support skeleton holds the capillary tube without movement relative to the body.

In Example 12, the device of any one or any combination of Examples 1-11 may include the means for reconstituting the reagent includes a piercing tip coupled with the capillary tube, and the piercing tip is configured to pierce a seal interposed between the capillary tube and the reagent reservoir.

In Example 13, the device of any one or any combination of Examples 1-2 may include one or more of the means for reconstituting the reagent and the means for dispensing the reagent mixture include a multi-stage activator movably coupled with the body, the multi-stage activator is movable between first, second, third and fourth discrete positions, where the multi-stage activator is moved from the first to the second discrete position a reservoir seal is pierced, where the multi-stage activator is moved from the second to the third discrete position the solution is forced over the reagent, where the multi-stage activator is moved from the third to the fourth discrete position a dispensing reservoir tip seal is pierced and the specified amount of the reagent mixture is dispensed out of the dispensing reservoir tip.

In Example 14, the device of any one or any combination of Examples 1-13 may include an activator key coupled between the body and the multi-stage activator, the activator key is movable relative to the multi-stage activator to limit movement of the activator, the activator key includes first, second, third and fourth key positions, where the multi-stage activator is not movable from the first discrete position when the activator key is in the first key position, the multi-stage activator is only movable from the first discrete position to the second discrete position when the activator key is in the second key position, the multi-stage activator is only movable from the second discrete position to the third discrete position when the activator key is in the third key position, and the multi-stage activator is only movable from the third discrete position to the fourth discrete position when the activator key is in the fourth key position.

In Example 15, the device of any one or any combination of Examples 1-14 may include one or more of the means for reconstituting the reagent and means for dispensing the reagent mixture includes an activator with a piercing tip sized and shaped to pierce at least one of a reagent reservoir seal and a solution reservoir seal with movement of the activator; movement of the activator from the first position forces the solution over the reagent and mixes the solution and the reagent to form the specified amount of the reagent mixture and forces the specified amount of the reagent mixture into the dispensing reservoir tip, and movement of the activator into the second position forces the specified amount of the reagent mixture out of the dispensing reservoir tip.

In Example 16, the device of any one or any combination of Examples 1-15 may include means for reconstituting the reagent includes a second piercing tip projecting from the solution reservoir, and the second piercing tip is sized and shaped to pierce the reagent reservoir seal, and movement of the activator engages the activator with the solution reservoir and moves the second piercing tip toward the reagent reservoir seal.

In Example 17, the device of any one or any combination of Examples 1-16 may include the second piercing tip includes a nozzle sized and shaped to dispense solution into the reagent reservoir.

In Example 18, the device of any one or any combination of Examples 1-7 may include the means for reconstituting the reagent includes a piercing element interposed between the dispensing reservoir tip and the reagent reservoir, the piercing element is sized and shaped to pierce one or more of a reagent reservoir seal and a solution reservoir seal.

In Example 19, the device of any one or any combination of Examples 1-18 may include the means for reconstituting the reagent includes an activator movable from a first position to a second position, movement of the activator moves the reagent reservoir and the solution reservoir into engagement with the piercing element and pierces the reagent reservoir seal and the solution reservoir seal.

In Example 20, the device of any one or any combination of Examples 1-19 may include the means for reconstituting the reagent includes the solution reservoir includes a piercing tip at a first end of the solution reservoir adjacent to the reagent reservoir, the means for reconstituting the reagent includes a snap tube at a second end of the solution reservoir, the solution is held within the solution reservoir by vacuum while the snap tube is in an unbroken condition.

In Example 21, the device of any one or any combination of Examples 1-20 may include a reservoir seal interposed between the reagent reservoir and the solution reservoir; and one or more of the means for reconstituting the reagent and the means for dispensing the reagent mixture include: a first activator movably coupled with the body, movement of the first activator moves the reservoir seal toward the piercing tip and pierces the reservoir seal, and a second activator movably coupled with the body, movement of the second activator breaks the snap tube and releases the vacuum in the solution reservoir; repeated movement of the second activator moves the solution into the reagent reservoir and mixes the solution with the reagent to form a specified amount of reagent mixture within the dispensing reservoir tip, additional movement of the second activator dispenses the reagent mixture out of the dispensing reservoir tip.

In Example 22 the device of any one or any combination of Examples 1-21 may include a reagent reservoir seal extending over the reagent reservoir; one or more of the means for reconstituting the reagent and the means for dispensing the reagent mixture include: a barrel movably coupled within the body, the barrel comprising: a barrel nozzle including the solution reservoir, and a piercing edge sized and shaped for piercing of the reagent reservoir seal, the piercing edge at a first barrel end, and an activator slidably coupled with an inner surface of the barrel nozzle, the activator is movable to force the solution from the barrel nozzle into the reagent reservoir to form the specified amount of the reagent mixture.

In Example 23, the device of any one or any combination of Examples 1-22 may include the barrel is movable between a first position and a second advanced position, in the second advanced position the barrel nozzle is disposed within the reagent reservoir and decreases a reagent reservoir volume.

In Example 24, the device of any one or any combination of Examples 1-3 may include one or more of the means for reconstituting the reagent and the means for dispensing the reagent mixture include: a barrel movably coupled within the body, the barrel comprising: a barrel shaft including the solution reservoir, and a piercing edge sized and shaped for piercing of the reagent reservoir seal, the piercing edge at a first barrel end; a primary activator, the primary activator is configured to move the solution into the reagent reservoir to form the specified amount of the reagent mixture, the primary activator includes: a primary activator shaft, and a primary stopper gasket coupled at a first end of the primary activator shaft, the primary stopper gasket coupled with the barrel shaft seals the solution reservoir in a first primary activator orientation; and a secondary activator, the secondary activator is configured to move the reagent mixture out of the dispensing reservoir tip, the secondary activator includes: a secondary activator shaft, the primary activator shaft extends through the secondary activator shaft, and a secondary stopper gasket coupled with the secondary activator shaft, the primary activator shaft is slidably coupled with the secondary stopper gasket, and the secondary stopper gasket seals around the primary activator shaft and is sealed against a barrel inner wall.

In Example 25, the device of any one or any combination of Examples 1-24 may include one or more of the means for reconstituting the reagent and the means for dispensing the reagent mixture include a flushing chamber filled with a flushing fluid, the flushing chamber is formed by the barrel inner wall and the secondary stopper gasket.

In Example 26, the device of any one or any combination of Examples 1-25 may include wherein when the primary activator is in a second primary activator orientation the primary stopper gasket is disengaged from the barrel shaft and the flushing chamber is in communication with the reagent reservoir.

In Example 27, the device of any one or any combination of Examples 1-26 may include one or more of the means for reconstituting the reagent and the means for dispensing the reagent mixture include fluid flushing passages extending longitudinally from the flushing chamber toward the reagent reservoir, and the fluid flushing passages extend along the primary activator shaft.

In Example 28, the device of any one or any combination of Examples 1-27 may include one or more of the means for reconstituting the reagent and the means for dispensing the reagent mixture include: a barrel movably coupled within the body, the barrel includes a piercing edge sized and shaped for piercing of a reagent reservoir seal interposed between the reagent reservoir and the solution reservoir, the piercing edge is movable to pierce the reagent reservoir seal according to movement of the barrel relative to the body, and the piercing edge is near a first barrel end; a first plunger movably coupled with the barrel and the activator, the first plunger is configured to move the solution into the reagent reservoir; and a second plunger movably coupled with the barrel and coupled with the activator, the barrel and the second plunger form a flushing chamber, the second plunger is configured to force flushing fluid into the reagent reservoir and correspondingly force the specified amount of reagent mixture through the dispensing reservoir tip.

In Example 29, the device of any one or any combination of Examples 1-28 may include the first plunger includes a first plunger gasket slidably coupled with the barrel, and the second plunger includes a second plunger gasket configured for selective sealing with the barrel, and the barrel and the second plunger gasket form the flushing chamber.

In Example 30, the device of any one or any combination of Examples 1-29 may include one or more of the means for reconstituting the reagent and the means for dispensing the reagent mixture include an activator, and the first plunger is engaged with the activator in a first configuration, and the first plunger is slidably coupled with the activator and the second plunger in a second configuration, and the activator and the second plunger move longitudinally relative to the first plunger in the second configuration.

In Example 31, the device of any one or any combination of Examples 1-30 may include the first plunger includes drive lugs, and: in the first configuration the drive lugs are positioned within a drive lug recess on the activator, and in the second configuration the drive lugs are positioned within a drive lug slot of the activator, and the activator and the second plunger are moved over the drive lugs when the drive lugs are positioned within the drive lug slot.

In Example 32, the device of any one or any combination of Examples 1-31 may include the first plunger, the second plunger and the activator move together in the first configuration.

In Example 33, the device of any one or any combination of Examples 1-32 may include the second plunger is recessed from the barrel in an unsealed condition and engaged with the barrel in a sealed condition, and: in the unsealed condition a flushing fluid vent extends between the second plunger and a barrel wall allowing the flushing fluid in the flushing chamber to vent to atmosphere, and in the sealed condition the flushing fluid vent is sealed and movement of the activator and the second plunger forces the flushing fluid into the reagent reservoir.

In Example 34, the device of any one or any combination of Examples 1-33 may include one or more of the means for reconstituting the reagent and the means for dispensing the reagent mixture include flushing passages extending between the first plunger and the barrel wall from the flushing chamber to the reagent reservoir.

In Example 35, the device of any one or any combination of Examples 1-34 may include the barrel is movably coupled with the body by a mechanical interfitting, and rotation of the barrel relative to the body advances the barrel and the piercing edge through the reagent reservoir seal.

In Example 36 a method of using a reagent preparation and dispensing device may comprise providing a body, the body including: a reagent reservoir containing a reagent, and a solution reservoir containing a solution; a step for reconstituting the reagent into a specified amount of a reagent mixture; retaining the reagent mixture in a dispensing reservoir tip sized and shaped to receive the specified amount of the reagent mixture; and a step for dispensing the specified amount of the reagent mixture through a dispensing reservoir tip and out of the device.

In Example 37 the method of Example 36 may include the step for reconstituting the reagent includes the step for dispensing the specified amount of the reagent mixture.

In Example 38 the method of any one or any combination of Examples 36-37 may include retaining the reagent mixture in the dispensing reservoir tip includes retaining the reagent mixture in the reagent reservoir where the dispensing reservoir tip includes the reagent reservoir.

In Example 39 the method of any one or any combination of Examples 36-38 may include providing the body includes providing the body with one or more of the reagent reservoir and the solution reservoir loaded within the body and separate from the body.

In Example 40 the method of any one or any combination of Examples 36-39 may include the step for reconstituting the reagent includes one or more of: fracturing the reagent reservoir with an activator movable relative to the body, the activator fractures the reagent reservoir when moved from a first position to a second position, and fracturing the solution reservoir with the activator, the activator fractures the solution reservoir when moved from the first position to the second position.

In Example 41 the method of any one or any combination of Examples 36-40 may include the step for reconstituting the reagent includes moving an activator from a first position to a second position to force the solution over the reagent.

In Example 42 the method of any one or any combination of Examples 36-41 may include retaining the reagent mixture in the dispensing reservoir tip includes moving the specified amount of the reagent mixture into the dispensing reservoir tip coupled with the body.

In Example 43 the method of any one or any combination of Examples 36-42 may include the step for reconstituting the reagent includes fracturing a capillary tube containing the solution reservoir, fracturing the capillary tube releases a vacuum holding the solution in the capillary tube.

In Example 44 the method of any one or any combination of Examples 36-43 may include the step for reconstituting the reagent includes engaging an activator against the capillary tube to fracture the capillary tube along a weakened capillary tube portion.

In Example 45 the method of any one or any combination of Examples 36-44 may include one or more of the step for reconstituting the reagent and the step for dispensing the specified amount of the reagent mixture includes moving an activator relative to the body, movement of the activator piercing the capillary tube containing the solution through a seal interposed between the capillary tube and the reagent reservoir.

In Example 46 the method of any one or any combination of Examples 36-45 may include the step for reconstituting the reagent includes: moving an activator key from a first key position to a second key position, and in the first key position, a multi-stage activator is prevented from moving, and moving a multi-stage activator from a first to a second discrete position to pierce a reagent reservoir seal, and the multi-stage activator is prevented from moving beyond the second discrete position by the activator key in the second key position; and mixing the solution with the reagent includes: moving the activator key from the second key position to a third key position, and moving the multi-stage activator from the second to a third discrete position to force the solution over the reagent, and the multi-stage activator is prevented from moving beyond the third discrete position by the activator key in the third key position; and the step for dispensing the specified amount of the reagent mixture includes: moving the activator key from the third key position to the fourth key position, and moving the multi-stage activator from the third to a fourth discrete position to pierce a reservoir tip seal and dispense the specified amount of the reagent mixture out of the dispensing reservoir tip.

In Example 47 the method of any one or any combination of Examples 36-46 may include moving an activator key between first, second, third and fourth key positions, where the multi-stage activator is not movable from the first discrete position when the activator key is in the first key position, the multi-stage activator is only movable from the first discrete position to the second discrete position when the activator key is in the second key position, the multi-stage activator is only movable from the second discrete position to the third discrete position when the activator key is in the third key position, and the multi-stage activator is only movable from the third discrete position to the fourth discrete position when the activator key is in the fourth key position.

In Example 48 the method of any one or any combination of Examples 36-47 may include the step for reconstituting the reagent includes: moving an activator with a piercing tip from a first position to pierce a reagent reservoir seal, moving the activator with the piercing tip from the first position to pierce a solution reservoir seal, and forcing the solution over the reagent by moving the activator from the first position; and the step for dispensing the specified amount of the reagent mixture includes forcing the specified amount of the reagent mixture from the dispensing reservoir tip by moving the activator into a second position.

In Example 49 the method of any one or any combination of Examples 36-48 may include the step for reconstituting the reagent includes piercing a second piercing tip of the solution reservoir through the reagent reservoir seal, and the second piercing tip includes a nozzle configured to dispense the solution into the reagent reservoir.

In Example 50 the method of any one or any combination of Examples 36-49 may include the step for reconstituting the reagent includes piercing a reagent reservoir seal and a solution reservoir seal with a piercing element interposed between the dispensing reservoir tip and the reagent reservoir.

In Example 51 the method of any one or any combination of Examples 36-50 may include the step for reconstituting the reagent includes moving the reagent reservoir and the solution reservoir over the piercing element with an activator.

In Example 52 the method of any one or any combination of Examples 36-51 may include the step for reconstituting the reagent includes: piercing a reservoir seal interposed between the reagent reservoir and the solution reservoir with a piercing tip at a first end of the solution reservoir, movement of a first activator causing translation of the reservoir seal toward the piercing tip, fracturing a snap tube positioned at a second end of the solution reservoir, fracture of the snap tube releases a vacuum within the solution reservoir, movement of a second activator relative to the body fracturing the snap tube, deforming the second activator to force the solution from the solution reservoir into the reagent reservoir; and the step for dispensing the specified amount of the reagent mixture includes deforming the second activator to force the reagent mixture out of the dispensing reservoir tip.

In Example 53 the method of any one or any combination of Examples 36-52 may include the step for reconstituting the reagent includes: rotating a barrel relative to the body, the barrel is movably coupled with the body, and rotation of the barrel moves the barrel toward a reagent reservoir seal, piercing the reagent reservoir seal with a piercing edge disposed around a barrel nozzle of the barrel, and mixing the solution with the reagent by moving an activator relative to the body and pushing a solution through the barrel nozzle into the reagent reservoir; and the step for dispensing the specified amount of the reagent mixture includes further moving the activator relative to the body and pushing the reagent mixture out of the dispensing reservoir tip.

In Example 54 the method of any one or any combination of Examples 36-53 may include the step for reconstituting the reagent includes moving the barrel nozzle into the reagent reservoir and shrinking the volume of the reagent reservoir.

In Example 55 the method of any one or any combination of Examples 36-54 may include the step for reconstituting the reagent includes: moving a barrel relative to the body where the barrel and the body are movably coupled, and movement of the barrel pierces the reagent reservoir seal with a piercing edge disposed around a barrel shaft of the barrel, and mixing the solution with the reagent by moving a primary activator relative to the body to push a solution through a solution reservoir nozzle in the barrel shaft into the reagent reservoir; and the step for dispensing the specified amount of the reagent mixture includes: moving a secondary activator with the primary activator including, moving a primary stopper gasket out of engagement with the barrel shaft, and moving a secondary stopper gasket toward a barrel seat, movement of the secondary stopper gasket forcing flushing fluid around the primary stopper gasket into the reagent reservoir, the flushing fluid dispensing the specified amount of the reagent mixture.

In Example 56 the method of any one or any combination of Examples 36-55 may include moving the barrel relative to the body includes rotating the barrel relative to the body where the barrel and body are rotatably coupled with threading.

In Example 57 the method of any one or any combination of Examples 36-56 may include moving the barrel relative to the body includes positioning the barrel shaft within the reagent reservoir and the volume of the reagent reservoir decreases.

In Example 58 the method of any one or any combination of Examples 36-57 may include moving the barrel relative to the body includes positioning the solution reservoir nozzle near the reagent.

In Example 59 the method of any one or any combination of Examples 36-58 may include moving the secondary activator with the primary activator includes rotating the secondary activator relative to the barrel, and correspondingly positioning a safety tab within a substantially vertical portion of a safety groove.

In Example 60 the method of any one or any combination of Examples 36-59 may include the step for reconstituting the reagent includes: moving a barrel relative to the body, movement of the barrel rupturing a reagent reservoir seal and allowing the solution reservoir to communicate with the reagent reservoir; mixing the solution with the reagent in a first stage including moving an activator relative to at least one of the barrel and the body, the activator moving a first plunger and forcing the solution out of the solution reservoir and into the reagent reservoir; and the step for dispensing the specified amount of the reagent mixture includes in a second stage moving the activator and a second plunger relative to the first plunger and at least one of the barrel and the body, moving the activator relative to the first plunger including: sealing a flushing chamber with the second plunger coupled with the activator, forcing flushing fluid out of the flushing chamber and into the reagent reservoir with the second plunger, and forcing the specified amount of the reagent mixture out of a dispensing reservoir tip with the flushing fluid.

In Example 61 the method of any one or any combination of Examples 36-60 may include the step for dispensing the specified amount of the reagent mixture includes rotating the activator relative to the first plunger and disengaging the first plunger from the activator.

In Example 62 the method of any one or any combination of Examples 36-61 may include rotating the activator relative to the first plunger includes aligning drive lugs on the first plunger with drive lug slots in one or more of the activator and the second plunger.

In Example 63 the method of any one or any combination of Examples 36-62 may include the step for dispensing the specified amount of the reagent mixture comprises moving the activator and the second plunger relative to the first plunger including moving the activator and the second plunger over the first plunger and the drive lugs slide within the drive lug slots.

In Example 64 the method of any one or any combination of Examples 36-63 may include venting flushing fluid within the flushing chamber to atmosphere through a flushing fluid vent extending between the second plunger and the activator and the barrel.

In Example 65 the method of any one or any combination of Examples 36-64 may include sealing the flushing chamber includes moving the second plunger into sliding engagement with the barrel and sealing the flushing fluid vent.

In Example 66 the method of any one or any combination of Examples 36-65 may include forcing flushing fluid out of the flushing chamber and into the reagent reservoir with the second plunger includes forcing flushing fluid through a flushing passage extending from the flushing chamber to the reagent reservoir between the first plunger and a barrel wall.

In Example 67 the method of any one or any combination of Examples 36-66 may include forcing flushing fluid out of the flushing chamber and into the reagent reservoir with the second plunger includes disengaging a first plunger gasket from the barrel when the first plunger gasket is moved out of the barrel, and the flushing passage extends around the first plunger gasket and into the reagent reservoir.

In Example 68 the method of any one or any combination of Examples 36-67 may include moving the barrel relative to the body includes rotating the barrel relative to the body and advancing a piercing edge of the barrel through the reagent reservoir seal.

BRIEF DESCRIPTION OF THE DRAWINGS

FIG. 1b is a cross sectional view of the reagent preparation and dispensing device shown in FIG. 1a.

FIG. 2 is an exploded view of the reagent preparation and dispensing device shown in FIG. 1a.

FIG. 3 is an illustrated flow chart showing one example of a multi-step method of use for the reagent preparation and dispensing device shown in FIG. 1a.

FIG. 4b is a cross sectional view of the reagent preparation and dispensing device shown in FIG. 4a.

FIG. 5 is an exploded view of the reagent preparation and dispensing device shown in FIG. 4a.

FIG. 6 is an illustrated flow chart showing one example of a multi-step method of use for the reagent preparation and dispensing device shown in FIG. 4a.

FIG. 9b is a cross sectional view of the reagent preparation and dispensing device shown in FIG. 9a.

FIG. 10 is an exploded view of the reagent preparation and dispensing device shown in FIG. 9a.

FIG. 11 is an illustrated flow chart showing one example of a multi-step method of use for the reagent preparation and dispensing device shown in FIG. 9a.

FIG. 12b is a cross sectional view of the reagent preparation and dispensing device shown in FIG. 12a.

FIG. 13 is an exploded view of the reagent preparation and dispensing device shown in FIG. 2a.

FIG. 14 is an illustrated flow chart showing one example of a multi-step method of use for the reagent preparation and dispensing device shown in FIG. 9a.

FIG. 17b is a cross sectional view of the reagent preparation and dispensing device shown in FIG. 17a.

FIG. 18 is an exploded view of the reagent preparation and dispensing device shown in FIG. 17a.

FIG. 19 is an illustrated flow chart showing one example of a multi-step method of use for the reagent preparation and dispensing device shown in FIG. 17a.

FIG. 20b is a cross sectional view of the reagent preparation and dispensing device shown in FIG. 20a.

FIG. 21 is an exploded view of the reagent preparation and dispensing device shown in FIG. 20a.

FIG. 22 is an illustrated flow chart showing one example of a multi-step method of use for the reagent preparation and dispensing device shown in FIG. 20a.

FIG. 23b is a cross sectional view of the reagent preparation and dispensing device shown in FIG. 23a.

FIG. 24 is an exploded view of the reagent preparation and dispensing device shown in FIG. 23a.

FIG. 25 is an illustrated flow chart showing one example of a multi-step method of use for the reagent preparation and dispensing device shown in FIG. 23a.

FIG. 26b is a cross sectional view of the reagent preparation and dispensing device shown in FIG. 23a.

FIG. 27 is an exploded view of the reagent preparation and dispensing device shown in FIG. 23a.

FIG. 28 is an illustrated flow chart showing one example of a multi-step method of use for the reagent preparation and dispensing device shown in FIG. 23a.

FIG. 29a is a side view of one example of a reagent preparation and dispensing device including a multi-stage key and lock system.

FIG. 29b is a cross sectional view of the reagent preparation and dispensing device shown in FIG. 29a.

FIG. 30 is an exploded view of the reagent preparation and dispensing device shown in FIG. 29a.

FIG. 31 is an illustrated flow chart showing one example of a multi-step method of use for the reagent preparation and dispensing device shown in FIG. 29a.

FIG. 32b is a cross sectional view of the reagent preparation and dispensing device shown in FIG. 32a.

FIG. 33 is an exploded view of the reagent preparation and dispensing device shown in FIG. 29a.

FIG. 34 is an illustrated flow chart showing one example of a multi-step method of use for the reagent preparation and dispensing device shown in FIG. 29a.

FIG. 45b is a detailed cross-sectional view of the reagent and solution reservoirs of the device shown in FIG. 45a.

FIG. 49b is a cross-sectional view of the device shown in FIG. 49a.

FIG. 51e is a side view of the device shown in FIGS. 49a, b with the device in an inverted orientation and the primary activator is moved toward the body to move the solution into the reagent reservoir for mixing with the reagent to form a specified amount of the reagent mixture.

FIG. 51f is a side view of the device shown in FIGS. 49a, b with the primary activator seated within the activator recess of the secondary activator.

FIG. 51g is a perspective view of the device shown in FIGS. 49a, b with the secondary activator rotated relative to the barrel to position the safety tab within a vertical portion of the safety groove.

FIG. 51h is a side view of the device shown in FIGS. 49a, b with the primary and secondary activators moved toward the barrel and body.

FIG. 51*i* is a side view of the device shown in FIGS. 49*a, b* with the reagent mixture dispensed from the dispensing reservoir tip.

FIG. 54*a* is a cross-sectional view of one example of a reagent preparation and dispensing device including a multiple function activator.

FIG. 54*b* is a detailed cross-sectional view of the reagent preparation and dispensing device of FIG. 54*a* showing the reagent and solution reservoirs.

FIG. 55*a* is a cross-sectional view of the reagent preparation and dispensing device of FIG. 54*a* showing the reagent reservoir opened and in communication with the solution reservoir.

FIG. 55*b* is a detailed cross-sectional view of the reagent preparation and dispensing device in the orientation shown in FIG. 55*a*.

FIG. 56*a* is a cross-sectional view of the reagent preparation and dispensing device of FIG. 54*a* showing the solution moved into the reagent reservoir to reconstitute the reagent.

FIG. 56*b* is a cross-sectional view of the reagent preparation and dispensing device in the orientation shown in FIG. 56*a* with the device rotated 90 degrees around the device longitudinal axis.

FIG. 56*c* is a detailed cross-sectional view of the reagent preparation and dispensing device in the orientation shown in FIG. 56*b* showing the drive lugs of the first plunger engaged within the drive recesses of the second plunger.

FIG. 58*a* is a side view of the reagent preparation and dispensing device of FIG. 54*a* in a ready position with the cap coupled over the dispensing reservoir tip.

FIG. 58*b* is a side view of the reagent preparation and dispensing device of FIG. 58*a* with the barrel rotated relative to the body and the reagent reservoir seal pierced.

FIG. 58*c* is a side view of the reagent preparation and dispensing device of FIG. 58*b* with the activator moved to force the solution into the reagent reservoir from the solution reservoir.

FIG. 58*d* is a side view of the reagent preparation and dispensing device of FIG. 58*c* with the activator moved to force the reagent mixture out of the device.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents. While the devices and methods presented in the detailed description describe devices for uses, non-pharmaceutical uses and the like, the devices and methods are applicable to at least some pharmaceutical applications that do not require administration to a subject by injection of with a syringe needle. Additionally, the reagents described below include, but are not limited to, lyophilized reagents, liquid reagents, powder reagents and the like. Further, the solutions described below include, but are not limited to, liquid solutions such as, saline, distilled water, tap water, pH buffered water, chemical solutions capable of breaking down the reagents and the like. In another example, the solutions include, but are not limited to, biological or environmental samples in a liquid form or suspended within a liquid, such as blood, urine, fecal matter, saliva, perspiration, soil, ground water, fresh water, salt water, explosives, explosive residues, toxins and the like.

Figure 1A:
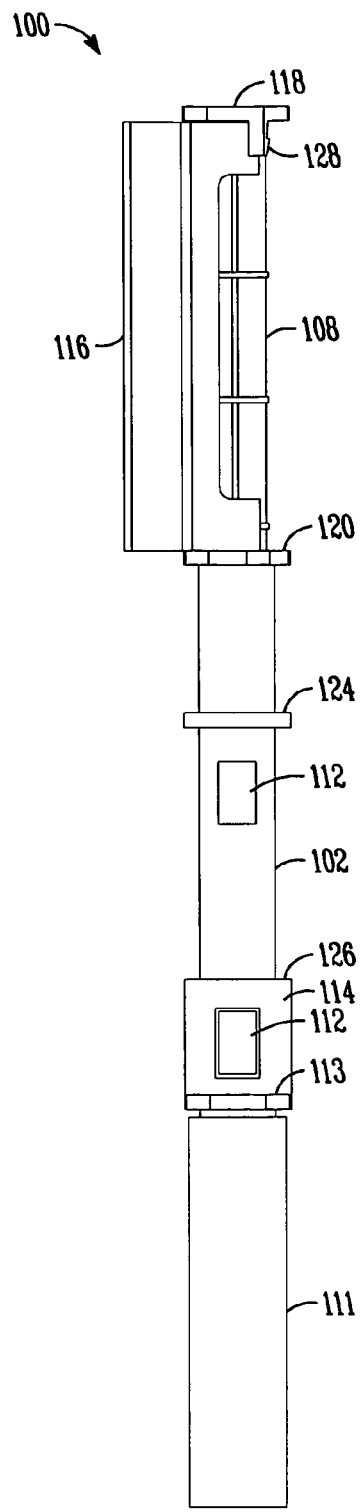
FIG. 1a is a side view of one example of a reagent preparation and dispensing device including breakable ampoules.
Figure 1B:
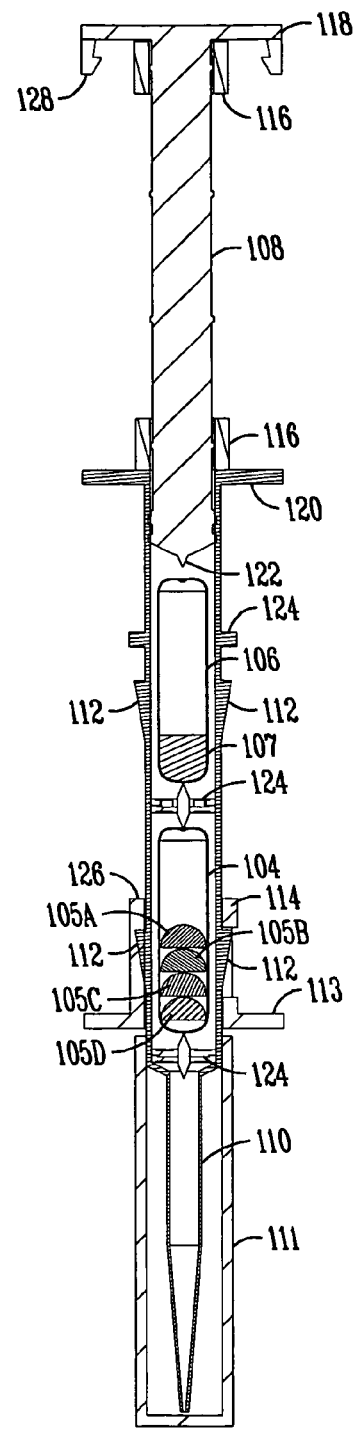
Figure 2:
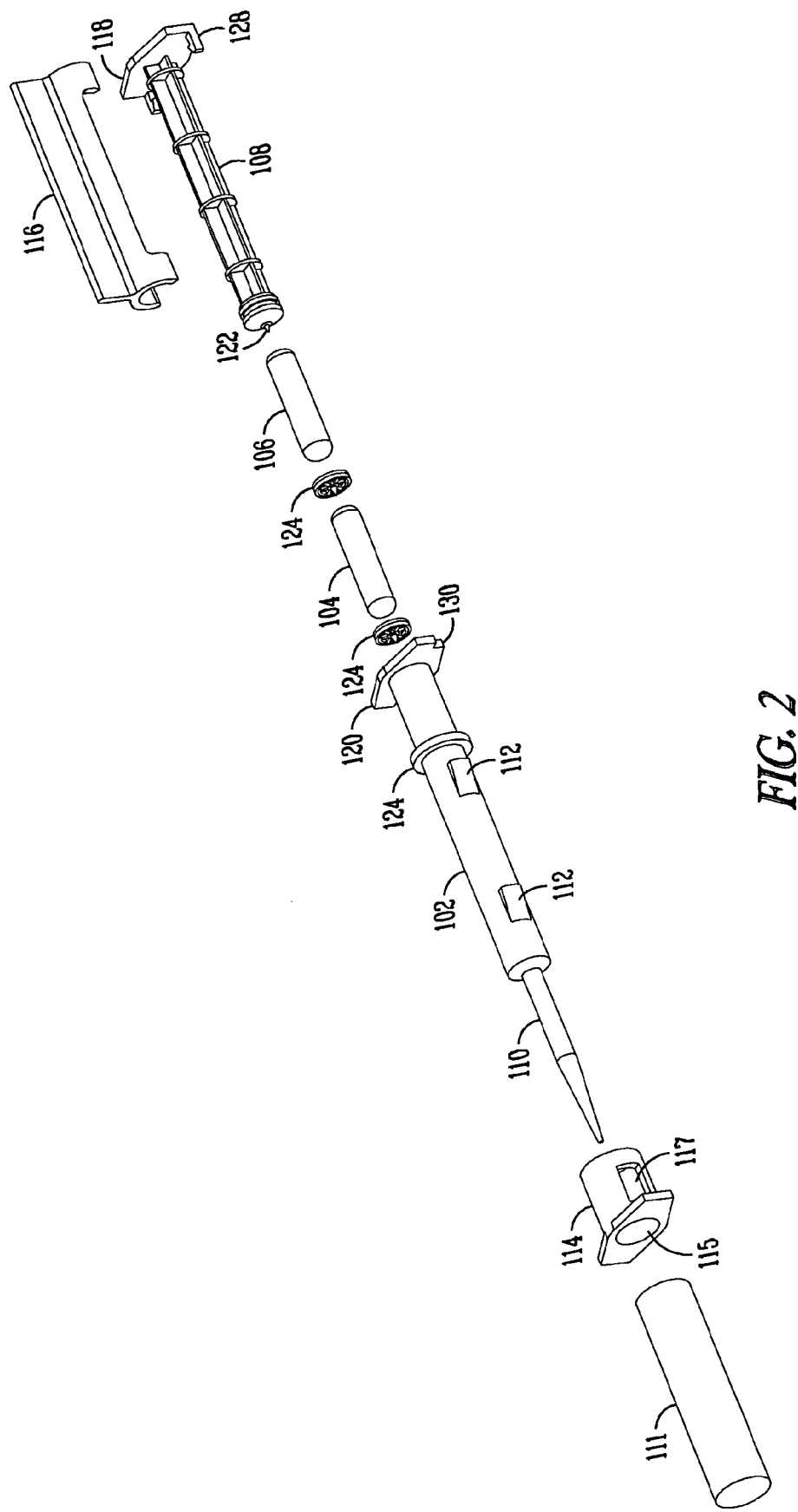

As shown in FIGS. 1A, 1B and 2 the reagent preparation and dispensing device (hereinafter the device) 100 includes the body 102. Within the body a reagent reservoir 104 and a solution reservoir 106 (e.g. ampules) are included. The reagent reservoir 104 includes at least one reagent, but may include multiple reagents, such as reagents 105A, 105B, 105C and 105D reagents 105A through D include reagents. For instance, reagents used for diagnostic and testing purposes. In another example, the reagent reservoir 104 includes at least one reagent, including but not limited to, therapeutic and pharmaceutical reagents. Solution reservoir 106 includes a solution 107, for example, saline, pH buffered water, distilled water and the like. An activator 108 is movably coupled with the body 102 (e.g., a plunger). The activator 108 is sized and shaped to slide with respect to the body 102 and thereby engage the ampules 106 and 104 and crush the reservoirs 104, 160.

As shown in FIGS. 1A and 1B the body further includes a dispensing reservoir tip 110. The dispensing reservoir tip, in one example, is integrally formed with the body 102. In another example, the dispensing reservoir tip 110 is coupled with the body separately, for instance, by welding, adhesives and the like. Dispensing reservoir tip 110 is sized and shaped to receive and hold a specified amount of reagent solution formed by the mixing of the solution 107 in the solution reservoir 106 and the reagents 105*a-d* in the reagent reservoir 104.

As shown in FIGS. 1A, B and 2 the device 100 further includes a cap 111 coupled over the dispensing reservoir tip 110. The cap 111 covers the tip 110 to contain the sterility of the tip and protect the tip from any damage during transport and prior to use. Referring again to the body 102, the body includes interference tabs 112 as shown in FIGS. 1A and 1B the interference tabs are formed adjacent to the positions of the solution reservoir 106 and the reagent reservoir 104. The device 100 further includes an ampule breaker 114 the ampule breaker is sized and shaped to slide along the body 102 and as shown in FIG. 2 the ampule breaker includes orifices 117 sized and shaped to receive the interference tabs 112. As described below, the interference tabs 112 engage with the ampule breaker to deflect the body 102 and thereby crush the ampules 104 and 106 to allow intermixture between the solution reservoir 106 and reagent reservoir 104.

Referring again to FIGS. 1A, B and 2 the activator 108 is shown in FIGS. 1A and B in a fully extended state with a locking bar 116 (e.g., safety) interposed between activator thumb rest 118 and the body end 120. The locking bar 116 is sized and shaped to engage therebetween and prevent movement of the activator 108 until removed. As further described below, while the locking bar 116 is interposed between thumb rest 118 and the end of the body 120 movement of the activator is transmitted along the body 102 and the body 102 is slid through the ampule breaker 114 to open the reservoirs 104, 106.

Referring now to FIGS. 1B and 2 the body 102 further includes piercing filters 124. The first piercing filter 124 is interposed between the reagent reservoir 104 and the solution reservoir 106. In one example, a second piercing filter 124 is interposed between the dispensing reservoir tip 110 and the reagent reservoir 104. The piercing filters 124 allow fluid to flow through the filters while still engaging with the reservoirs and providing a surface upon which the reservoirs may rupture. The activator 108 further includes a piercing tip 122. The piercing filters 124 and piercing tip 122 are sized and shaped to engage against the ampules 104, 106 to fracture and crush the ampules thereby releasing their contents for intermixture to form a reagent solution. Optionally, a single piercing surface, such as the piercing filter 124 between the reagent and solution reservoirs 104, 106 opens the reservoirs. Device 100 further includes locking tabs 128. Locking tabs 128 in one example are shown attached to the thumb rest 118. During movement of the thumb rest 118 relative to the body (e.g., when the locking bar 116 is removed) the thumb rest is depressed until it engages with the end of the body 120. As shown in FIG. 2, the body 102 includes notches 130 on the end of the body 120. The locking features 128 engage with the notches 130 to thereby prevent backwards movement of the activator 108 relative to the body 102.

Figure 3:
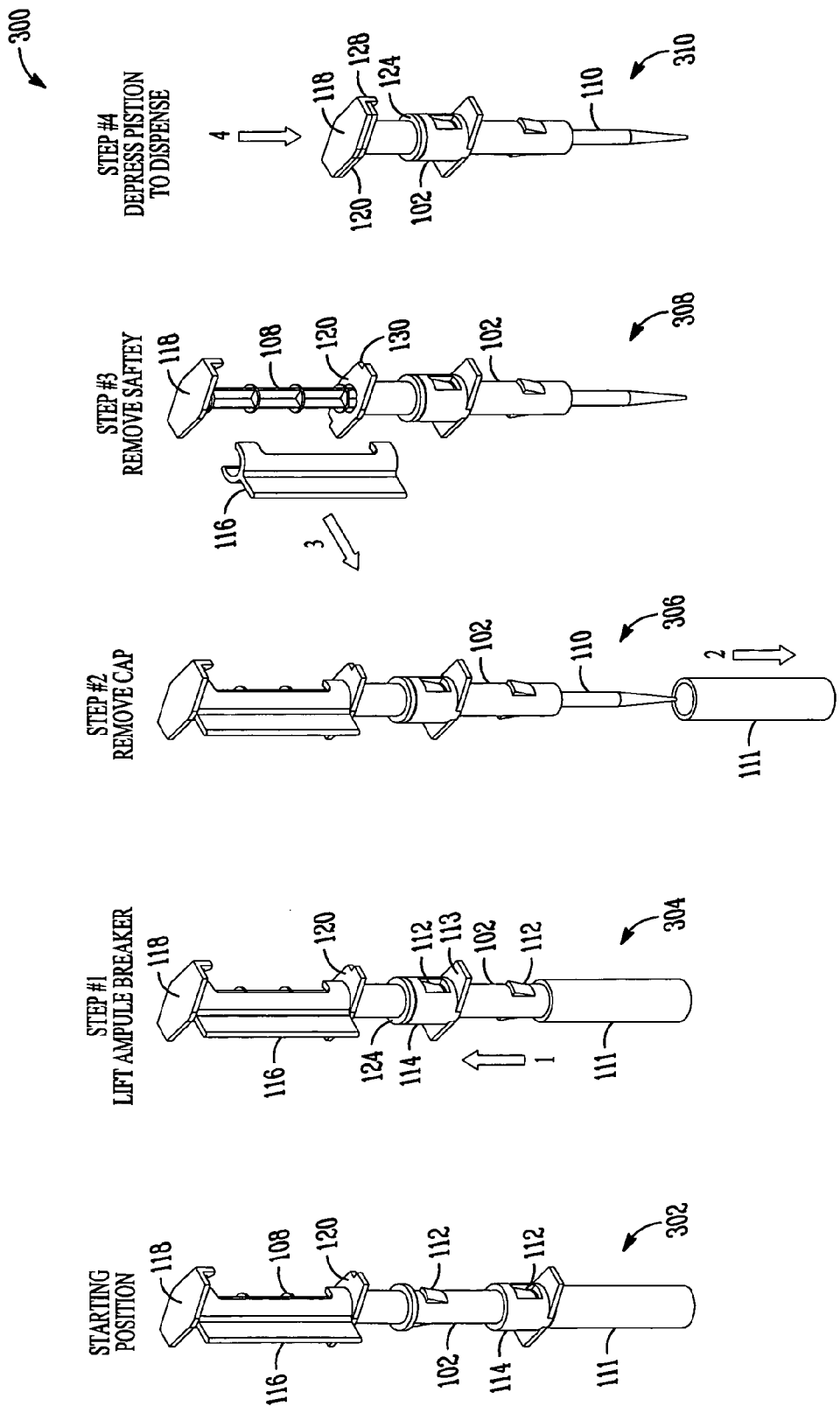

Turning now to FIG. 3, one example of a method 300 for using the reagent preparation and dispensing device 100 is shown. At 302 a starting position of the device 100 is shown. The activator 108 is shown in its fully extended position away from the body 102, the locking bar 116 (e.g., safety) is interposed between the thumb rest 118 and the end 120 of the body 102. Interference tabs 112 are shown in an undeflected state and the tabs adjacent to the reagent reservoir are positioned within the orifices 117 of the ampule breaker 114. At 304 the ampule breaker 114 is slid up along the body 102. As the ampule breaker 114 is slid up the body 102 a collar 113 on the ampule breaker is slid over and deflects the interference tabs 112 adjacent to the reagent reservoir 104 and solution reservoir 106. As the cover 112 deflects the interference tabs 112 the interior of the body 102 is engaged against the reservoirs 104, 106 and crushes the reservoirs thereby releasing the reagents 105a-d and solution within the respective reservoirs 104, 106. The ampule breaker 114 is moved into a second position adjacent to a flange 124 on the body 102. In this position the ampule breaker comes to rest and because of the wedge shape of the interference tabs 112 is prevented from moving back down the body 102 towards the dispensing reservoir tip 110. The ampule breaker 114 is thereby held in place on the body 102 and prevented from further movement. At 306 the cover 111 is removed thereby exposing the dispensing reservoir tip 110. At 308 the locking bar 116 is removed from between the thumb rest 118 and the end of the body 120. The removal of the locking bar 116 allows movement of the activator 108 relative to the body 102. At 310 once the locking bar 116 has been removed as described in step 308 the activator 108 is moved downwardly relative to the body 102. The operator is able to grasp the end of the body 102 and the thumb rest 118 with a single hand and press the activator downward into the body. The thumb rest 118 is fully depressed down onto the end of the body 120 and the locking features 128 engage against the notches 130 as shown on FIG. 2. Once the locking features 128 are engaged against the notches 130 on the end of the body 120 the activator 108 is thereafter prevented from moving in reverse. This substantially prevents any drawing of fluids, for example, biological fluids to be tested, previously dispensed solutions and the like.

Referring now to FIG. 1B, as shown, when the activator 108 is moved downward the piercing tip 122 cooperates with the piercing filters 124 to further crush the reagent reservoir 104 and solution reservoir 106 beyond the rupturing provided by deflection of the body 102 with the interference tabs 112. The activator 108 acts as a plunger and moves the solution of the solution reservoir 106 over the reagents 105A through D and thereby mixes the reagent and solution together. Further movement of the activator 108 pushes the reagent solution formed by the mixture of the solution with the reagents into dispensing reservoir tip 110. Further movement of the activator 108 forces the reagent solution out of the dispensing reservoir tip 110 for diagnostic or testing purposes.

The reagent preparation dispensing device 100 is constructed of but not limited to, plastics, deflectable metals and the like. Body 102 including the areas of the body 102 substantially adjacent to the reagent reservoir 104 and the solution reservoir 106 (see FIGS. 1B and 2) is formed of a deflectable material, for example, a softer plastic. As previously described the ampule breaker 114 is slid over the interference tabs 112 at these portions of the body 102 and thereby deflects the body. As the body is deflected these portions of the body engage on the interior with the reagent reservoir 104 and 106 to crush and rupture those reservoirs and thereby release there contents. Reagent reservoirs 104 and 106 in one example include glass ampules. Another example of the reagent and solution reservoirs 104, 106 includes any sort of reservoir slidably receivable within the body to position the reservoirs adjacent to the interference tabs 112. For instance, the reservoirs 104 and 106 include a brittle plastic, a brittle metal and the like. In another example the ampule breaker 114 is constructed of a more rigid plastic. The more rigid ampule breaker 114 engages against the interference tabs 112 and deflects the interference tabs as previously described. The ampule breaker 114 should have sufficient strength to be able to engage against these tabs 112 and force the tabs to deflect while the ampule breaker remains substantially undeformed.

Another example of a reagent preparation and dispensing device 400 is shown in FIGS. 4A, 4B, 5 and 6. The device 400 includes body 102. The body contains reagent reservoir 104 and a solution reservoir 106. The reagent reservoir 104, as in the previous examples, includes at least one reagent such as reagents 105A-D. In another example, the reagent reservoir 104 includes a single reagent such as reagent 105A. The reagents 105A-D include, but are not limited to, lyophilized (i.e., freeze-dried) reagents, liquid reagents, powdered reagents, and the like. As previously described for device 100, the device 400 similarly includes a dispensing reservoir tip 110 and a cap 111 coupled around the dispensing reservoir tip to protect the tip during transport and prior to use. The dispensing reservoir tip is sized and shaped to hold a specified amount of reagent solution. The dispensing reservoir tip includes a blunt nozzle for dispensing the solution outside of the device 400.

Figure 4A:
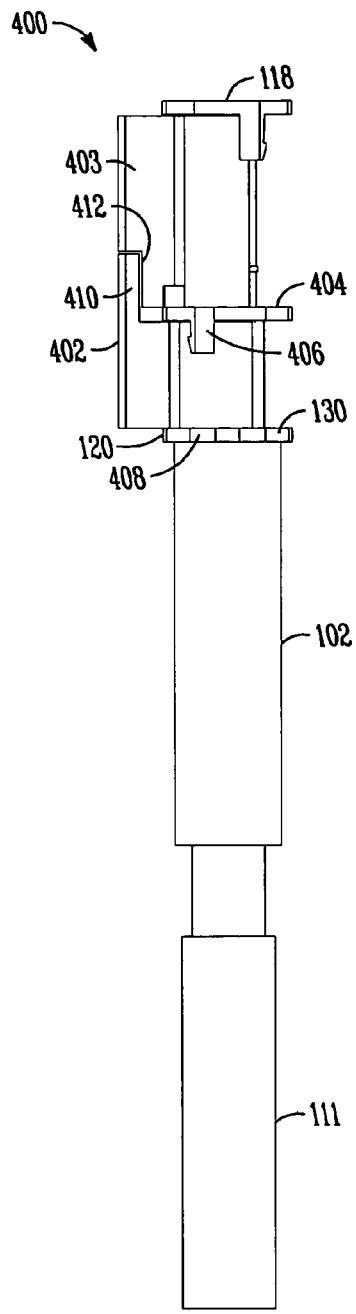
FIG. 4a is a side view of one example of a reagent preparation and dispensing device including breakable ampoules and dual safety devices.
Figure 4B:
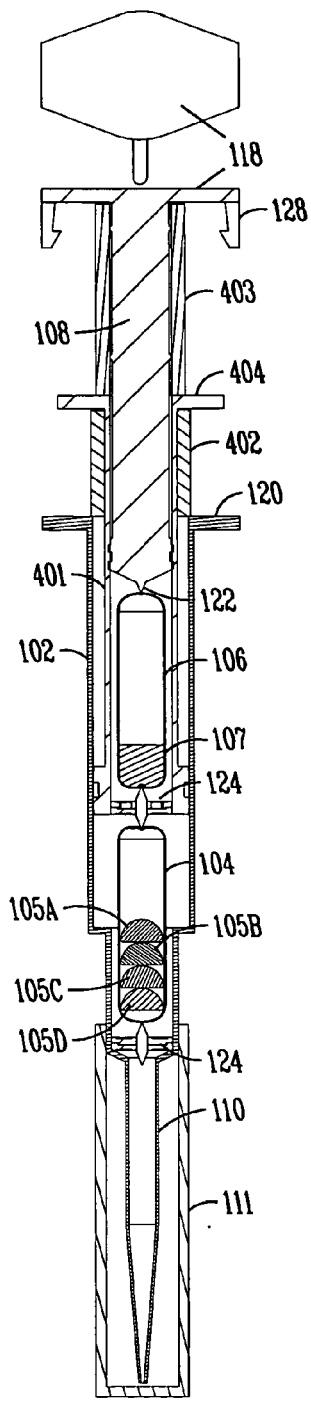
Figure 5:
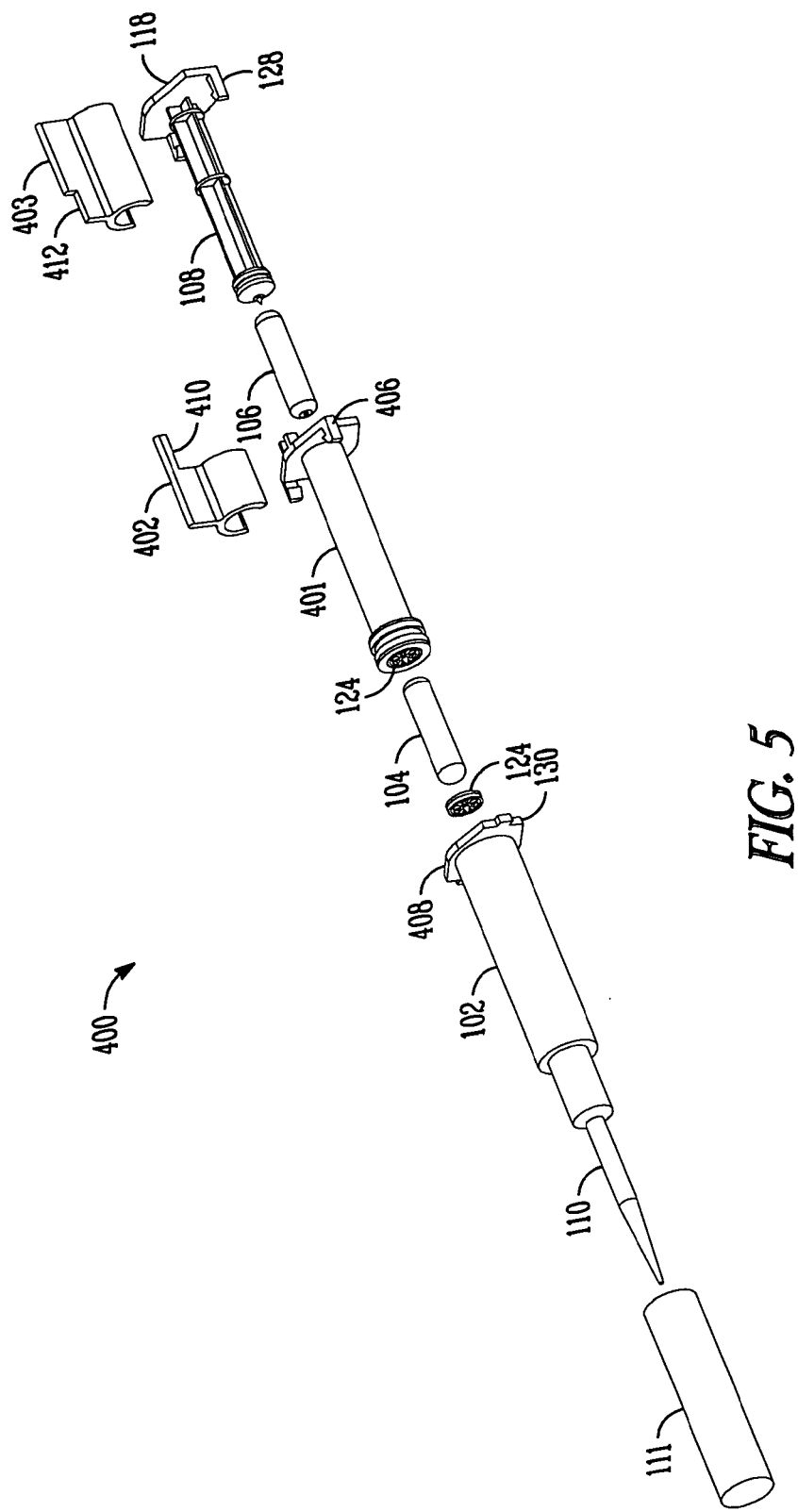

The device 400 further includes two activators the first activator 108 (such as a plunger) and a second activator 401 slidably coupled around the first activator 108, see FIGS. 4B and 5. The second activator 401 includes the solution reservoir 106 as shown in FIGS. 4B and 5. The solution reservoir 106 is slidably received within the second activator 401, in one example. The first activator 108 is then slidably received within the second activator 401 and positioned adjacent to the solution reservoir 106. As shown in FIG. 4B, the first activator 108 includes a piercing tip 122. The second activator 401 includes a piercing filter 124 similar to the piercing filter 124 used in the device 100. The solution reservoir 106 is retained between the piercing tip 122 of the first activator 108 and the piercing filter 124 of the second activator 401. In another example, device 400 includes a single piercing surface, for example, only the piercing surface on the piercing tip 122 on the first activator 108 or the piercing filter 124 associated with the second activator 401. In yet another example, the body 102 includes a piercing filter 124 interposed between the reagent reservoir 104 and the dispensing reservoir tip 110. The piercing filter 124 interposed therebetween includes a piercing surface sized and shaped to engage with the reagent reservoir 104 to pierce and rupture the reservoir.

Referring now to FIGS. 4A, 4B and 5, the device 400 further includes a first safety 402 and a second safety 403. The first safety 402 is interposed between a second activator flange 404 and an end flange 120 of the body 102. The second safety 403 is interposed between the thumb rest 118 and the flange 404 of the second activator 401. When interposed between the various surfaces of the device 400 the safeties 402, 403 prevent movement of the first activator 108 and the second activator 401. Once the safeties 402 and 403 are removed the first activator 108 and the second activator 401 are free to move relative to the body 102. In one example, the first safety 402 is removed to allow movement of the first activator 108 and the second activator 401 relative to the body 102. In another example, the second safety 403 is then removed allowing movement of the first activator 108 relative to the second activator 401 and the body 102.

As shown in FIGS. 4A, 4B and 5 the device further includes locking features 128, 406. Locking features 128 and 406 are sized and shaped to engage with the end flange 120 of the body 102. When engaged with the end flange 120 the locking features 128 and 406 substantially prevent reverse movement of the first and second activators 401, 108. As previously described, one or both of the safeties 402, 403 are removed to allow movement of the first activator 108 and the second activator 401. Once the safeties 402, 403 are removed the activators are moved relative to the housing, for example, the second activator flange 404 is moved toward the end flange 120 where the locking feature 406 is engaged against the notch 408. The locking feature 406 substantially prevents the activator 401 from moving in a backwards direction away from the body 102 when engaged with the notch 408. Similarly, when the first activator 108 is moved relative to the body towards the end flange 120 the locking feature 128 is moved to engage with a notch 130 (also see similar features in device 100). Thumb rest 118 is moved into engagement with the activator flange 404 and is adjacent to the end flange 120 of the body 102. The locking feature 128 is received in the notch 130 thereby preventing reverse movement of the first activator 108 relative to the body 102.

Referring now to FIGS. 4A and 5 the safeties 402 and 403 further include, in one example, interlocking features 410, 412. The interlocking features 410, 412 are sized and shaped to allow removal of the first safety 402 prior to the second safety 403. The geometry of the interlocking features 410 and 412 allows the user to intuitively remove the first safety 402 before removal of the second safety 403 is permitted. As described below, this allows the user to open (e.g., fracture, rupture, unseal and the like) the reagent reservoir 104 and the solution 106 reservoir in a desired order to ensure proper mixing of the solution with the reagent.

Figure 6:
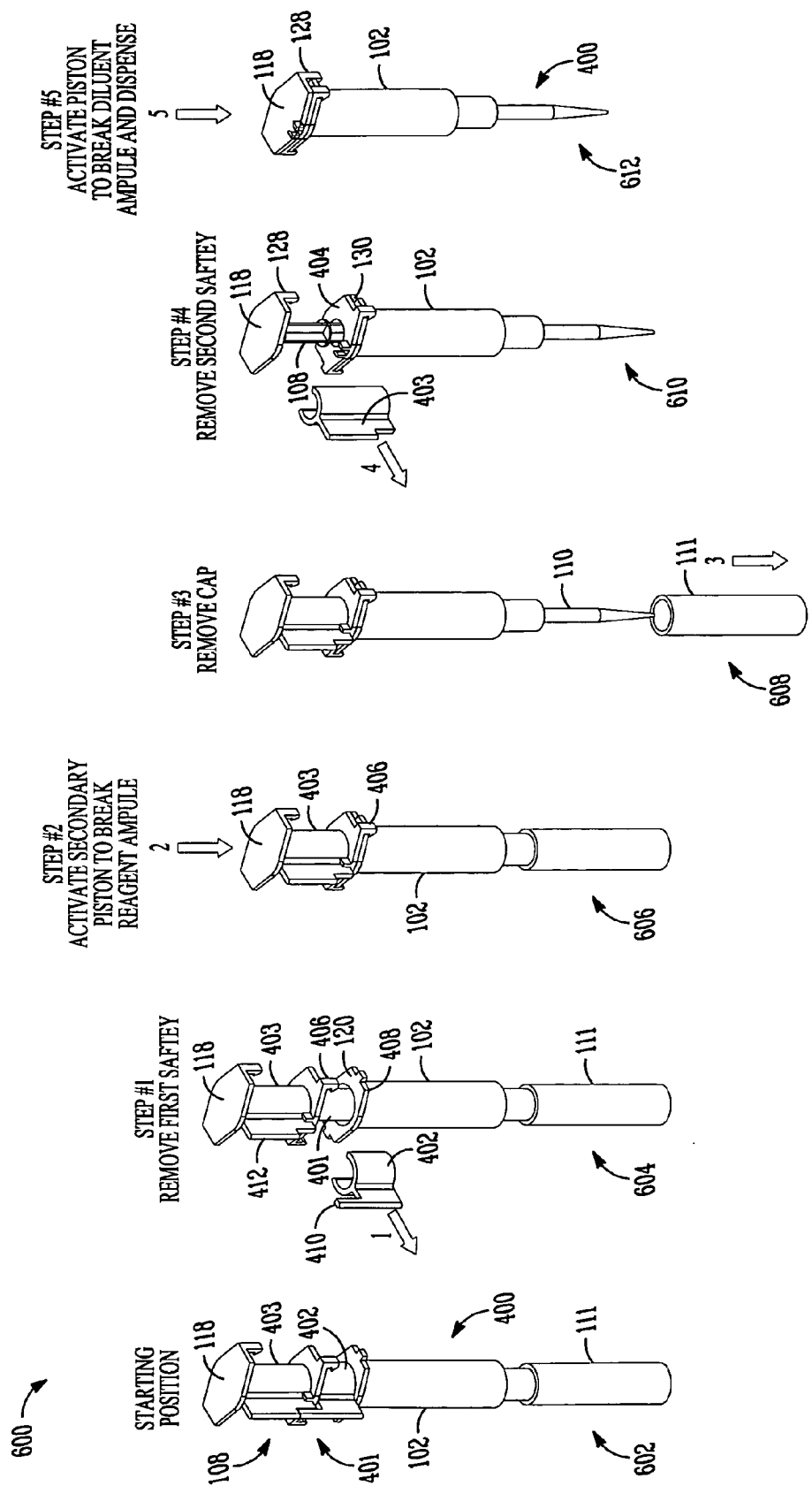

Referring now to FIG. 6, one example of a method 600 for using the reagent preparation and dispensing device 400 is shown. At 602, the device 400 is shown in a starting position the first and second safeties 402, 403 are shown in their positions adjacent the device body 402 thereby preventing movement of the first activator 108 and the second activator 401. The cap 111 is disposed over the dispensing reservoir tip 110. At 604, the first safety 402 is removed. As shown, the first safety 402 has the interlocking feature 410 engaged over the complementary interlocking feature 412 of the second safety 403. The user is thereby able to intuitively remove the first safety 402 prior to the second safety 403. The second activator 401 and the first activator 108 (concealed by the second safety 403) are thereby free to move relative to the body 102. At 606, the first and second activators 108, 401 are moved relative to the body 102. Referring briefly to FIG. 1B as shown when the first activator 108 and second activator 401 are moved toward the dispensing reservoir tip 110 the piercing filter 124 interposed between the solution reservoir 106 and the reagent reservoir 104 as well as the piercing filter interposed between the reagent reservoir and the dispensing reservoir tip 110 engages against the reagent reservoir and crushes the reservoir releasing its contents (at least one reagent 105A, B, C, D) relative to the housing 102.

Referring again to 606, once the first and second activators 108 and 401 are moved toward the body 102 the locking features 406 engage with the notches 408 to substantially prevent backward movement of the second activator 401 relative to the body 102. At 608, the cap 111 is removed thereby exposing the dispensing reservoir tip 110 prior to mixing of the solution and dispensing of the solution through the reservoir tip. At 610, the second safety 403 is removed from the device 400. As the second safety 403 is removed the first activator 108 is exposed thereby allowing movement of the first activator relative to the body 102. At 612, the first activator 108 is moved relative to the body 102. As the thumb rest 118 approaches the second activator flange 404 the locking features 128 are engaged with the notches 130 on the end flange 120 of the body 102. Engagement of the locking features 128 as well as the locking features 406 substantially prevents movement of the first and second activators 108, 401 relative to the body 102. As the first activator 108 is moved into the position where it is locked against the end flange 120 the solution reservoir 106 as shown in FIG. 1B is crushed between the piercing filter 124 and the piercing tip 122 of the first activator 108. This releases the solution 107, and further movement of the first activator 108 into the engaged position with the body 102 moves the solution over the reagents 105A, B, C, D thereby mixing the solution with the reagents and forming a specified amount of the reagent solution. The reagent solution is forced down into the dispensing reservoir tip 111 where it is held and the final movements of the first activator 108 into the end flange 120 of the body 102 dispenses the specified amount of the reagent solution out of the device 400. With the locking features 128 and 406 in their engaged positions with the notches 130 and 408 the activators 108 and 401 are substantially prevented from being drawn up relative to the body 102. This prevents drawing of test solution, for example, a reagent solution as well as biological materials and the like.

Figure 7:
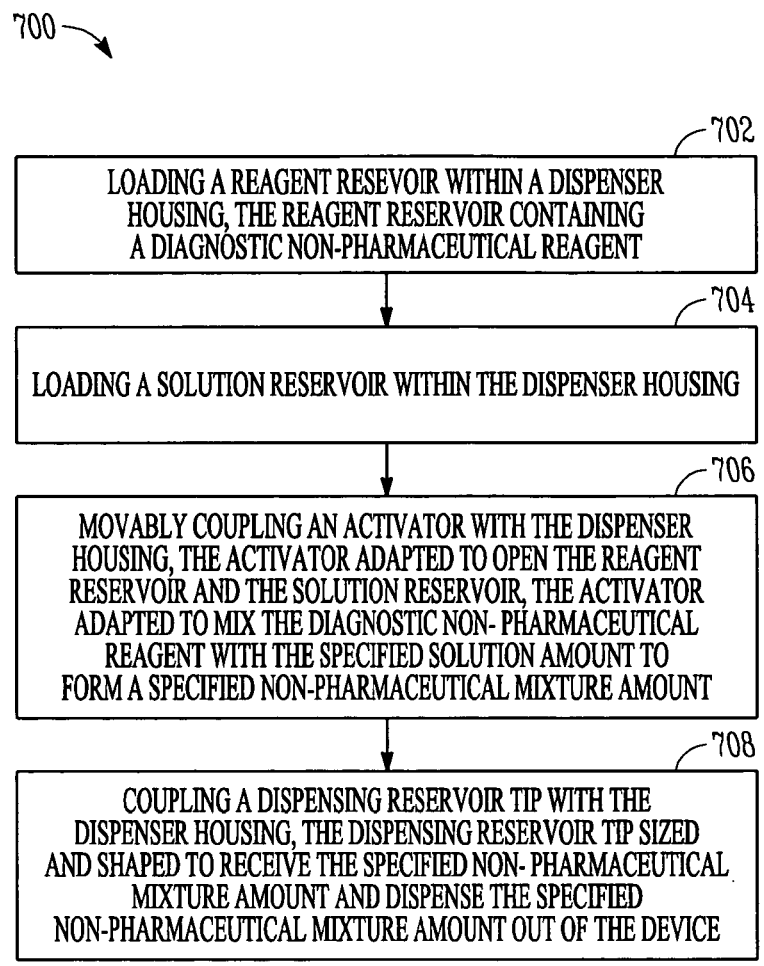
FIG. 7 is a block diagram showing one example of a method of making the devices shown in FIGS. 1a-6.

A method 700 for making a reagent preparation and dispensing device is shown in FIG. 7 (e.g., see devices shown in FIGS. 1A-6). Reference is made to example elements previously shown in FIGS. 1A-6 and described above. For convenience only elements from FIGS. 1A-3 will be discussed with specific element numbers.

At 702 a reagent reservoir 104 is loaded within a dispenser body, for example, the body 102 shown in FIGS. 1A, 1B and 2. Reagent reservoir 104 contains a diagnostic reagent such as reagent 105 (e.g., reagents 105A through D including multiple reagents). In one example, where the reagent is a lyophilized reagent, the reagent is prepared (e.g., by freeze-drying) in a step isolated from the dispenser body 102. Separate preparation of the reagent from the device prevents exposure of the device to the harsh environment needed to prepare the reagent. The device is thereby able to maintain structural integrity, precise fitting of parts and the like while storing a reagent that is otherwise formed under conditions adverse to the device. In another example, the prepared reagent is positioned within the reservoir after preparation, and the reservoir is then sealed and ready for loading in the dispenser body. The devices, reagents and methods described below are constructed or performed in a similar manner, in still another example.

At 704 a solution reservoir 106 is loaded within the dispenser body 102. As previously described, a solution reservoir 106 is shown in FIG. 1B and is sized and shaped to hold the solution 107 such as saline, pH buffered water, distilled water and the like used to mix with the reagents 105A through D to form a reagent solution as described below. In another example, the solution 107 includes a sample (biological, environmental, diagnostic and the like) for mixing with the reagent to form a reagent solution that reacts with the sample to provide a diagnostic or test result. The solution reservoir 106 and reagent reservoir 104, in one example, are loaded within the body 102, for instance, the reagent reservoir 104 and solution reservoir 106 are slidable within the body and positioned in order with the reagent reservoir closest to the dispensing reservoir tip 110 and the solution reservoir 106 closest to the end flange 120 of the body 102. At 706, an activator 108 is movably coupled with the dispensing body 102. The activator 108 is adapted to open the reagent reservoir 104 and the solution reservoir 106. In one example, one or more activators 108, 401 are movably coupled with the dispensing body 102 (see FIGS. 4A-6) The activator 108 is further adapted to mix the diagnostic reagent with the specified solution 107 to form a specified mixture amount. In one example, the solution reservoir contains a specified amount of solution and mixes entirely with reagents (i.e., without unused reagent or solution) to produce a specified amount of reagent solution having a specified concentration.

At 708 a dispensing reservoir tip 110 is coupled with the dispenser body 102. The dispensing reservoir tip 110 is sized and shaped to retain and dispense the specified amount of a reagent solution. Another example of a dispensing reservoir tip includes a blunt nozzle that is integrally molded with the body 102. In another example, the dispensing reservoir tip 110 includes a blunt nozzle that is separately coupled with the body 102 (e.g., adhered, welded and the like).

Figure 8:
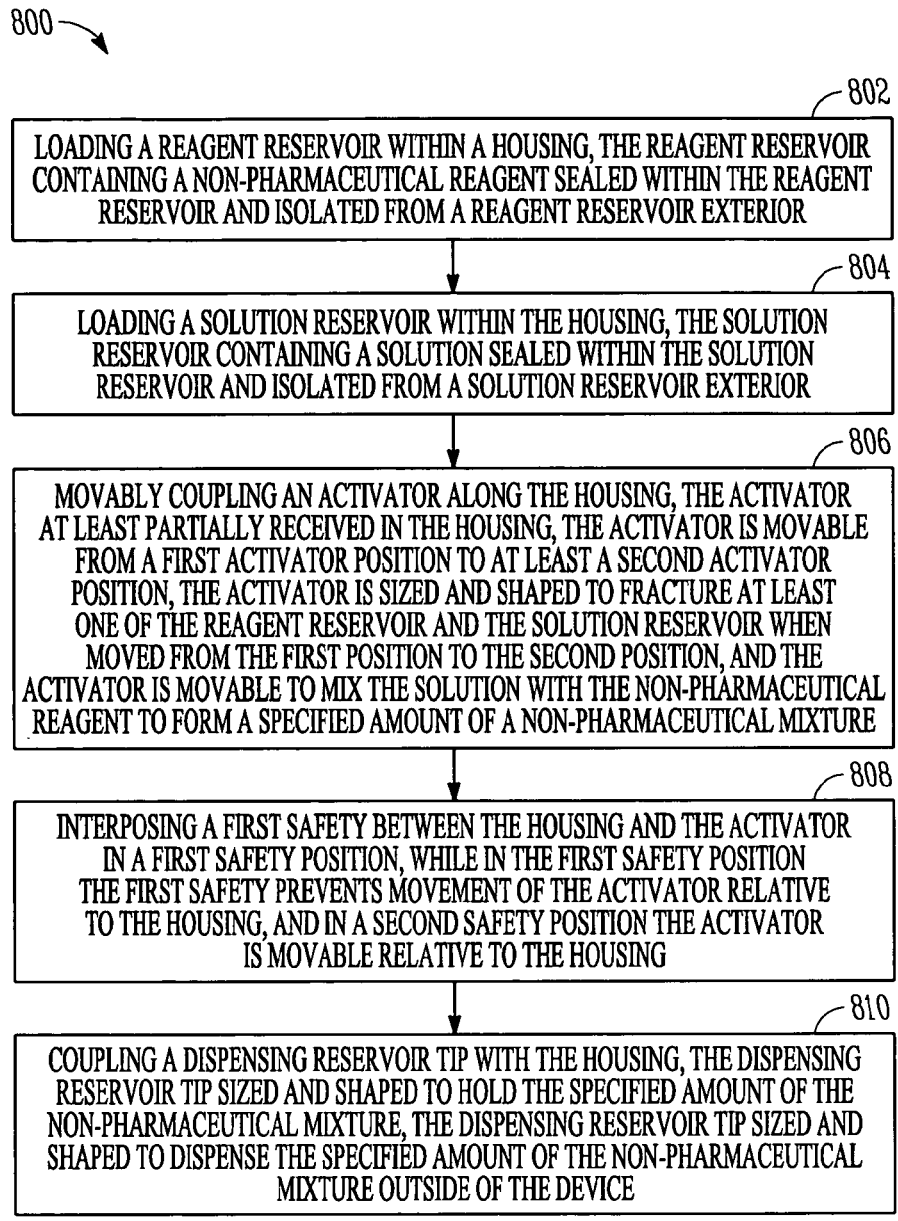
FIG. 8 is a block diagram showing another example of a method of making the devices shown in FIGS. 1a-6.

A method 800 for making a reagent preparation dispensing device (e.g., devices shown in FIGS. 1A-6) is shown in FIG. 8. Reference is made to example elements previously shown in FIGS. 1A-6 and described above. For convenience only elements from FIGS. 1A-3 will be discussed with specific element numbers unless otherwise noted.

At 802 a reagent reservoir 104 shown in FIGS. 1A and 2 is loaded within a body 102. The reagent reservoir 104 contains a reagent, for example, reagents 105A through D (one or more reagents). The reagents 105A through D are sealed within the reagent reservoir 104 and thereby isolated from a reservoir exterior, for instance, the interior of the body 102 or the exterior of the body 102.

At 804, a solution reservoir 106 is loaded within the body 102. The solution reservoir 106 contains a solution 107 sealed within the solution reservoir that is isolated from a solution reservoir exterior (for example, the interior of the body 102 or the exterior of the body). As previously described, the solution 107 in the solution reservoir 106 includes but is not limited to saline, distilled water and the like.

At 806 an activator 108 is movably coupled along the body 102 (as previously described the activator 108 may include a plunger or the like). The activator 108 is at least partially received in the body 102, and the activator is movable from a first activator position to at least a second activator position. The activator 108 is sized and shaped to fracture at least one of the reagent reservoir 104 and the solution reservoir 106 when moved from the first position to the second position. The activator 108 is movable to mix the solution 107 with the reagent (e.g., one or more of 105A-D) to form a specified amount of a reagent solution. In one example, the solution reservoir 106 contains a specified amount of solution used to mix with the reagents to form a predetermined amount of reagent solution having a specified and predetermined concentration. In another example, the activator includes one or more activators, such as activators 108, 401 as shown in FIGS. 4A-6 and described above.

At 808 a first safety is interposed between the body 102 and the activator 108 (for example, the first safety may include the locking bar 116 as shown in FIGS. 1A through 3). The first safety 116 is positioned at a first safety position between the body 102 and the activator 108. In the first safety position the first safety 116 is positioned to prevent movement of the activator 108 relative to the body 102 and when removed the activator 108 is moveable relative to the body. In one example, where the first safety 116 is positioned between the thumb rest 118 and the body 102, the activator is substantially prevented from moving and thereby rupturing one or both of the solution reservoir 106 and the reagent reservoir 104. In another example, first and second safeties 402, 403 (FIGS. 4A-6) are interposed between the body 102 and the activator, such as activators 108 and 401. As previously described, the safeties 402, 403 substantially prevent movement of the activator and rupturing of the reservoirs 104, 106. Removing the first safety 402 allows movement of the activators 108, 401 into a first position where the activator ruptures the reagent reservoir 104. With the second safety 403 still in position, movement of the activator 108 beyond this first position is substantially prevented and the solution reservoir 106 is not ruptured. Removing the second safety 403 allows movement of the activator 108 into a second position where the activator 108 ruptures the solution reservoir 106 and forces the solution 107 over the reagent to form the specified amount of the reagent solution. Additionally, movement of the activator 108 into the second position forces the reagent solution out of the device 100, as described above.

At 810 a dispensing reservoir tip 110 as shown in FIGS. 1A, B and 2 is coupled with the body 102. The dispensing reservoir tip 102 is sized and shaped to hold the specified amount of the reagent solution. The dispensing reservoir tip 110 is further sized and shaped to dispense the specified amount of the reagent solution outside of the device. In another example, coupling the dispensing reservoir tip 110 with the body 102 includes integrally forming the dispensing reservoir tip with the body 102. In another example, coupling the dispensing reservoir tip 110 with the body 102 includes coupling the dispensing reservoir tip with the body, for instance, by adhesives, welds and the like.

Figure 9A:
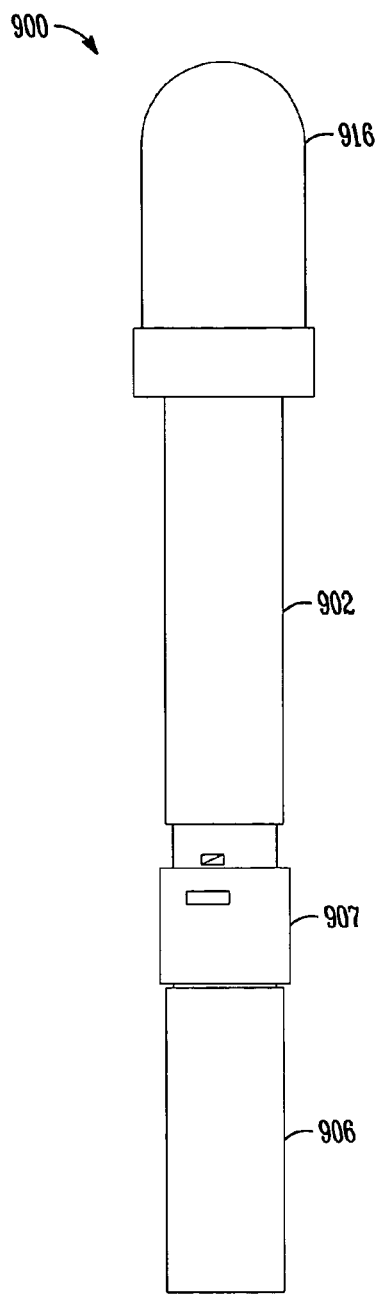
FIG. 9a is a side view of one example of a reagent preparation and dispensing device including a capillary tube solution reservoir.
Figure 9B:
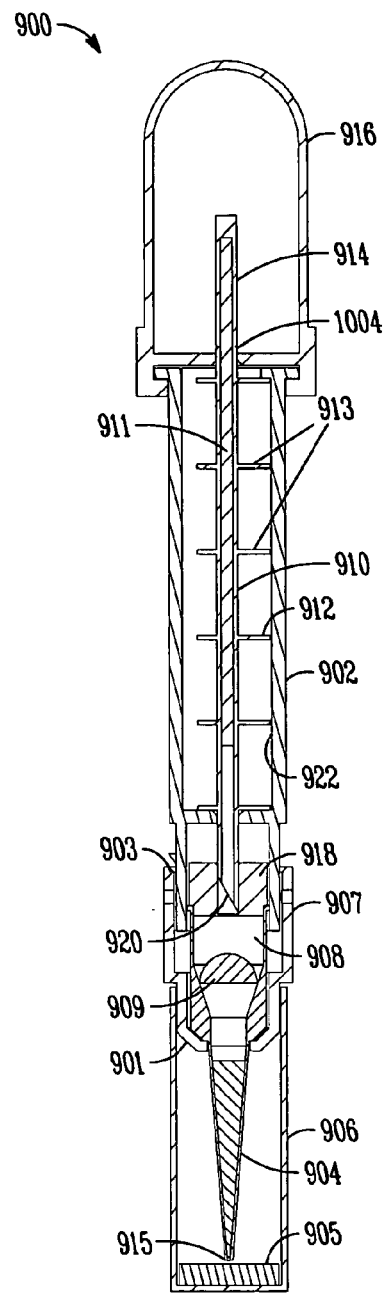
Figure 10:
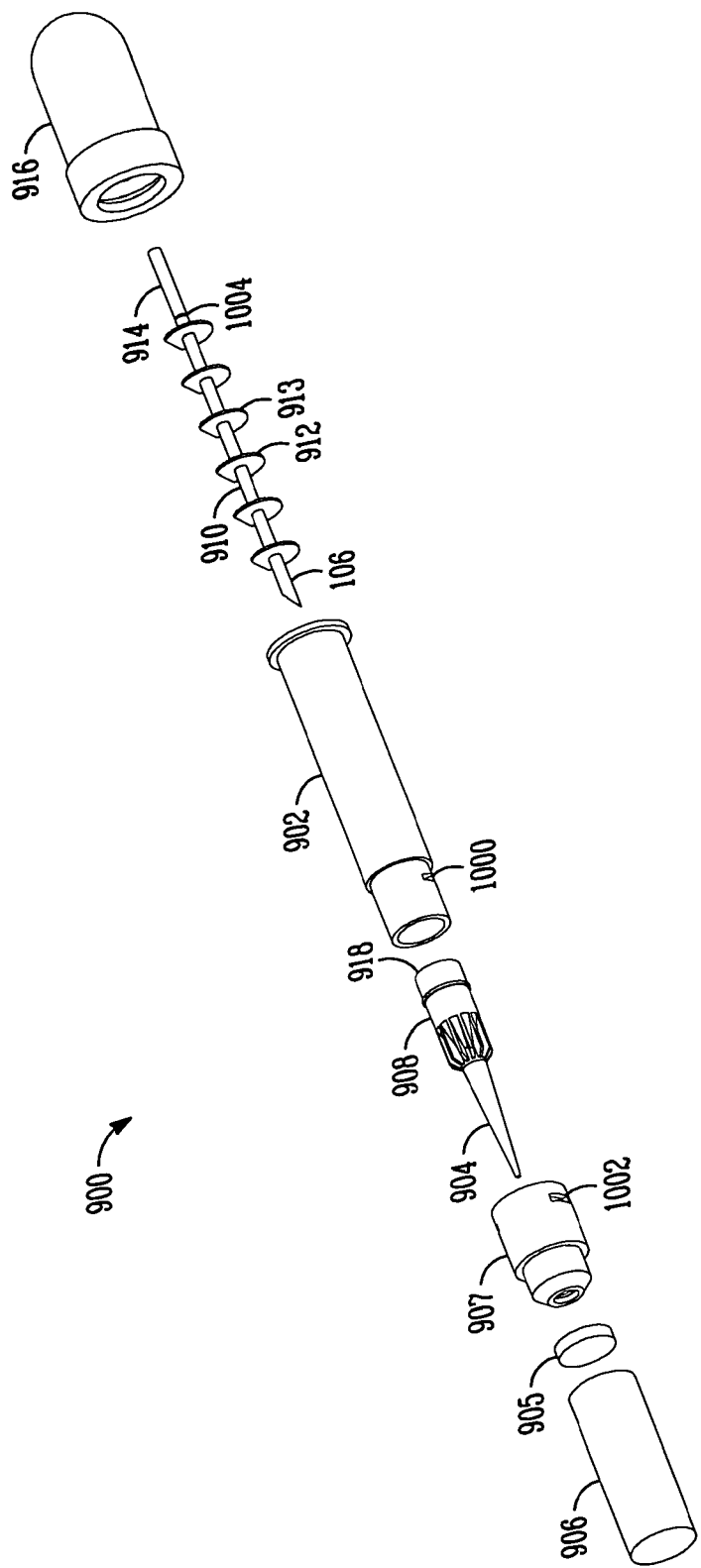

Another example of a reagent preparation and dispensing device 900 is shown in FIGS. 9A, 9B and 10. The device 900 includes a body 902. A dispensing reservoir tip 904 is coupled to the body 102, and at least one activator 916 coupled to an end of the body 902 opposed to the dispensing reservoir tip 904. In one example, the activator 916 includes a deflectable bulb sized and shaped to apply pressure to a solution within the body 902 to move the solution in the body toward the dispensing reservoir tip 904. A cap 906 is coupled around the dispensing reservoir tip 904 to cover the dispensing reservoir tip during transport and prior to operation of the device 900. As shown in FIGS. 9b and 10, a desiccant 905 is positioned in the cap 906. When the cap 906 is coupled with the body 902, the desiccant 905 is positioned near the discharge outlet 915 of the dispensing reservoir tip 904. The desiccant 905 is thereby able to easily draw moisture out of the dispensing reservoir tip 904, reagent reservoir 908 and the space between the cap 906 and tip 904.

As shown in FIGS. 9B and 10, the body 102 includes a solution reservoir 910. The solution reservoir, in one example, includes a capillary tube, the capillary tube includes a solution 911 held within the capillary tube via a vacuum. Device 900 further includes a reagent reservoir 908. As previously described in other examples, the reagent reservoir 908 includes a reagent. The reagent mixes with the solution 911 to produce a specified amount of a reagent solution. The reagent solution is used for diagnostic testing, biological testing and the like. Device 900 further includes a seal 918 interposed between the solution reservoir 910 and the reagent reservoir 908. One example of the seal 918 includes a rubber seal. Another example of the seal 918 includes a fracturable seal such as a foil, brittle material or the like. As seen in FIGS. 10 and 9B, the device 900 further includes a first activator 907 (e.g., the first activator 907 include a collar fit with the body 900 slidably, rotatably and the like). As described below, activator 916 is described as the second activator 916, but is not intended to be limited to an activator necessarily included with the first activator 907. That is to say, the first and second activators 907, 916 are usable alone or together in example devices.

Referring again to FIGS. 9B and 10, the seal 918 is shown at one end of the dispensing reservoir tip 904. The seal 918 is sized and shaped to move relative to the body 902. As shown in FIG. 9B, the first activator 907 is coupled between the dispensing reservoir tip 904 and the body 902. Engagement of the first activator 907 with the dispensing reservoir tip 90 moves the dispensing reservoir tip including the seal 918 toward the second activator 916 as further described below. In another example, the solution reservoir 910 includes a piercing tip 920 sized and shaped to pierce the seal 918. Upon movement of the first activator 907 the piercing tip 920 of the capillary tube 910 engages against the seal 918, penetrates the seal, and thereby allows communication between the solution reservoir 910 and the reagent reservoir 908.

In another example, the first activator 907 includes features 903 sized and shaped to move the dispensing reservoir tip 904 relative to the body 902. For instance, the features 903 include threading on an interior surface of the first activator sized and shaped to engage threading on the body 902. Optionally, the features 903 include a sliding surface that allows slidable movement along the body 902 by the first activator 907. Movement of the first activator 907 relative to the body 902 engages a cup 901 of the first activator with the dispensing reservoir tip 904 and moves the dispensing reservoir tip toward the piercing tip 920. Where the features 903 include threading, rotation of the first activator 907 relative to the body 102 moves the rubber seal 918 toward the piercing tip 920 of the solution reservoir 910 thereby piercing the seal 918 between the reagent reservoir 908 and solution reservoir 910.

Referring now to FIG. 10, the first activator 907 further includes orifices 1002. Body 902 includes corresponding tabs 1000 sized and shaped for reception in the orifices 1002 upon movement of the first activator 907 toward the body 902. The orifices 1002 of the first activator 907 are slid over the tabs and the tabs 1000 are received within the orifices thereby locking the first activator 907 relative to the body 902 and preventing removal or movement of the first activator 907 away from the body 902.

Referring again to FIGS. 9B and 10, the solution reservoir 910 is shown as a capillary tube, in one example. The solution reservoir 910 including the capillary tube includes a support skeleton 912 disposed around at least a portion of the capillary tube. The support skeleton 912 includes, in another example, multiple ribs 913 extending away from the capillary tube toward the interior 922 of the body 902. In another example, there are a plurality ribs 913 extending along the capillary tube from near the second activator 916 toward the seal 918. The plurality of ribs 913 of the support skeleton 912 are sized and shaped to engage against the interior 922 of the body 902 to substantially prevent lateral movement of the solution reservoir 910 relative to the body 902 and thereby prevent unwanted fracture of the solution reservoir 910. The solution reservoir 910 is constructed with, but not limited to, a material including glass, metal or plastic. Optionally, the solution reservoir 910 is constructed with brittle materials that benefit from the protection provided by the support skeleton 912.

As shown in FIG. 10, the solution reservoir 910 further includes a weakened portion 1004. In one example, the weakened portion 1004 is disposed adjacent to an end 914 of the solution reservoir 910. As previously described, the solution 911 is retained within the solution reservoir 910 by a vacuum. Referring to FIG. 10, the solution reservoir 910 includes at an end 914 a seal, for example, a wax or a heat seal that retains the solution 911 contained therein under the vacuum. Weakened portion 1004 is opened (e.g., fractured, ruptured or the like) during movement of the second activator 916 and relieves the solution reservoir 910 of this vacuum thereby allowing the solution 911 to flow through the capillary tube solution reservoir 910 due to gravity towards the dispensing reservoir tip 904. Optionally, fracturing of the weakened portion 1004 allows the second activator 916, for example a deflectable bulb, to communicate with the reagent reservoir 908 and the solution reservoir 910. Deflection of the second activator 916, such as by squeezing, is thereby able to push the solution 911 into the reagent reservoir 908 where it may mix with the reagent 909. Further deflection of the second activator 916 is thereby able to move the reagent solution formed by the mixing of the reagent and the solution into the dispensing reservoir tip 904 where it is held prior to being dispensed. Second activator 916, when deflected again, dispenses the reagent solution out of the device 900, in still another example.

Figure 11:
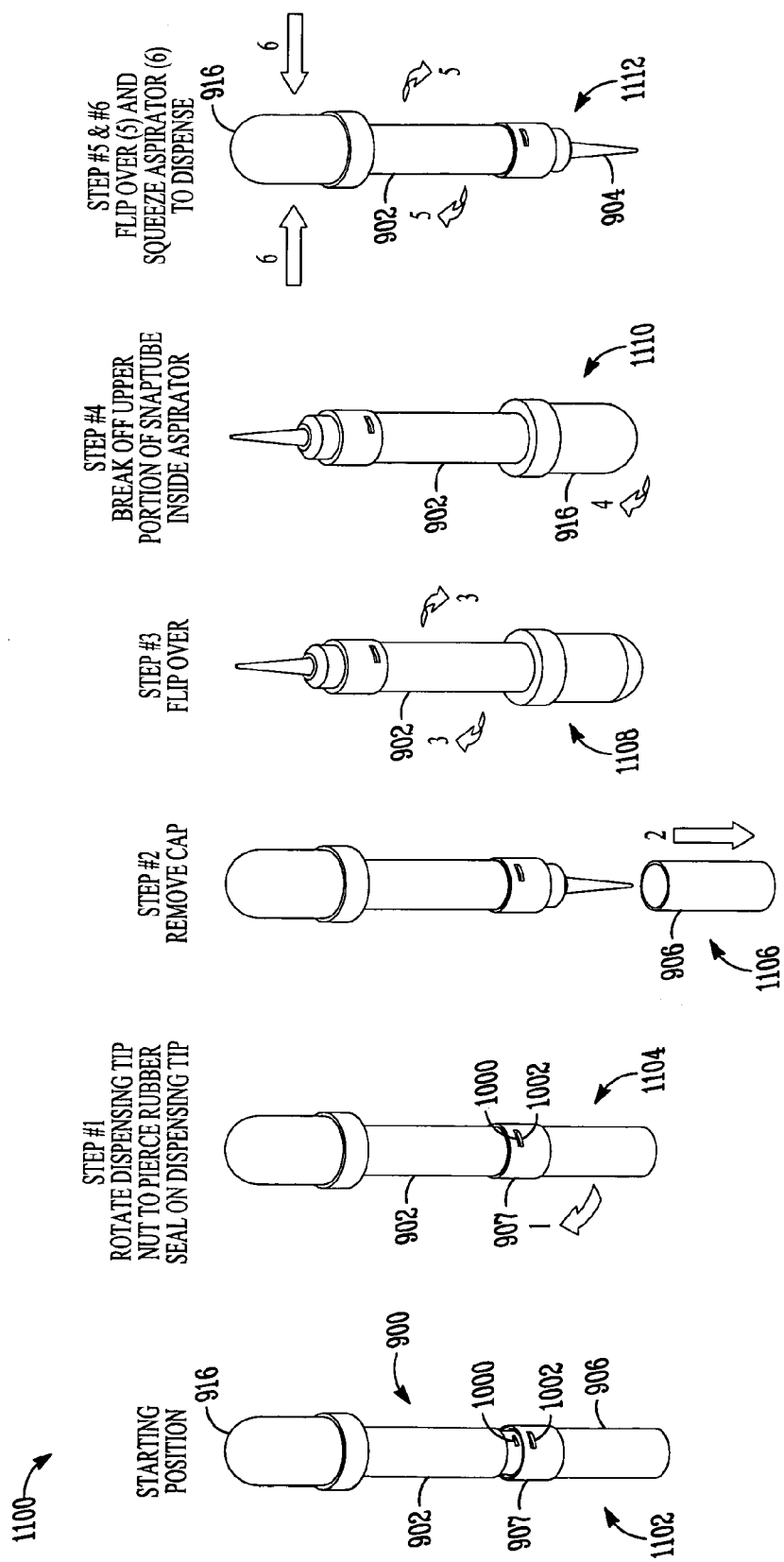

A method 1100 is for using the reagent preparation dispensing device 900 (FIGS. 9A, 9B and 10) is shown in FIG. 11. At 1102 the device 900 is shown in the starting position where the cap 906 is engaged with the body 902. The first activator 907 is spaced from a portion of the body 902 (e.g., away from the body 902 prior to movement that brings the seal 918 into piercing engagement with the solution reservoir 910). At 1104, the first activator 907 is moved toward the body 902, in one example, the first activator 907 is rotated and through engagement between threading of the body and the first activator 907 or threading of the first activator 907 and the dispensing reservoir tip 904 the first activator is moved toward the body 902. As previously described, and shown in FIG. 9B, the piercing tip 920 of the solution reservoir 910 is moved into engagement with the seal 918 by movement of the first activator 907 and the piercing tip 920 pierces the seal 918 and allows communication between the solution reservoir 910 and reagent reservoir 908. Once the first activator 907 has moved, in one example, the orifices 1002 on the first activator are slid over the tabs 1000 on the body 902. The tabs 1000 are then positioned within the orifices 1002 and the first activator 907 is substantially prevented from moving away from the body 902 and is thereafter locked into position. At 1106, the cap 906 over the dispensing reservoir 904 is removed prior to dispensing the reagent solution out of the device 900.

At 1108 the device 900 is flipped over and the dispensing tip 904 is in an upwardly pointing orientation. Device 900 is flipped into this orientation to substantially prevent unwanted movement of the solution 911 out of the solution reservoir 910 in later steps.

At 1110, the second activator 916 is grasped and moved relative to the body 902. In one example, as previously discussed, the second activator includes a deflectable bulb. The interior of the deflectable bulb is used to grasp or engage with the end 914 of solution reservoir 910. Engagement of the end 914 with the solution reservoir 910 moves the end 914 relative to the reservoir and allows the solution reservoir to open (break, rupture, fracture and the like) at the weakened portion 1000 thereby releasing the vacuum in the solution reservoir 910. Release of the vacuum allows the solution 911 to flow out of the solution reservoir 910 when the device 900 is in an upright position.

At 1112, the device 900 is reoriented in the upright position and the second activator 916 is further moved to move the solution 911 out of the solution reservoir and into the reagent reservoir 908. In another example, the solution 911 leaves the solution reservoir due to gravity without needing movement of the second activator 916. In the reagent reservoir the solution 911 mixes with the reagent 909 to form a specified amount of a reagent solution. The reagent solution then flows by gravity into dispensing reservoir tip 904. Further movement of the second activator 916 (e.g., deflection of the bulb) forces the reagent solution out of the dispensing reservoir tip 904 and out of the device 900.

Figure 12A:
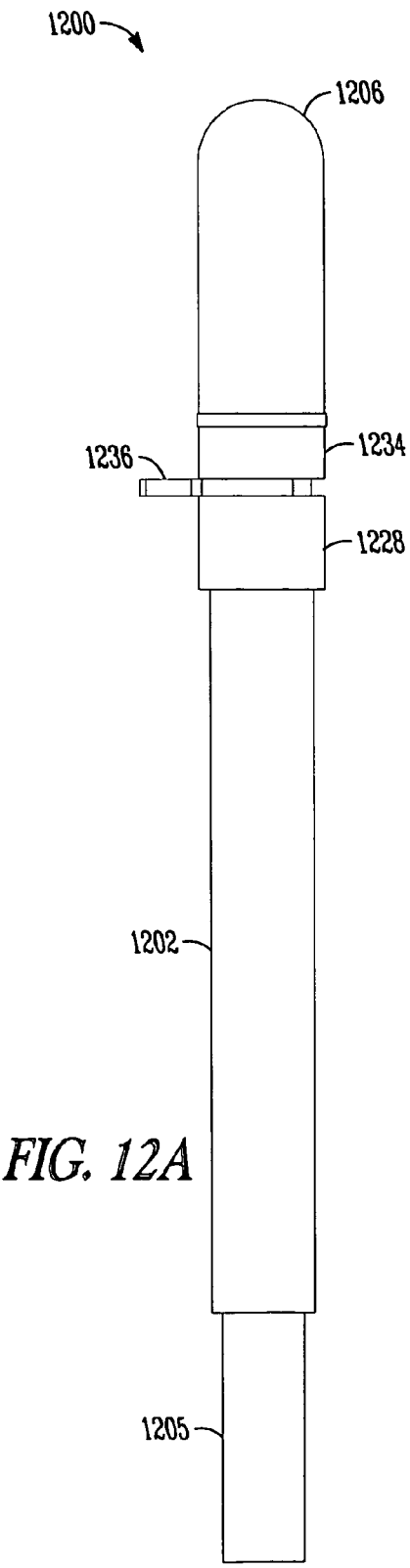
FIG. 12a is a side view of one example of a reagent preparation and dispensing device including a capillary tube solution reservoir having a piercable seal.
Figure 12B:
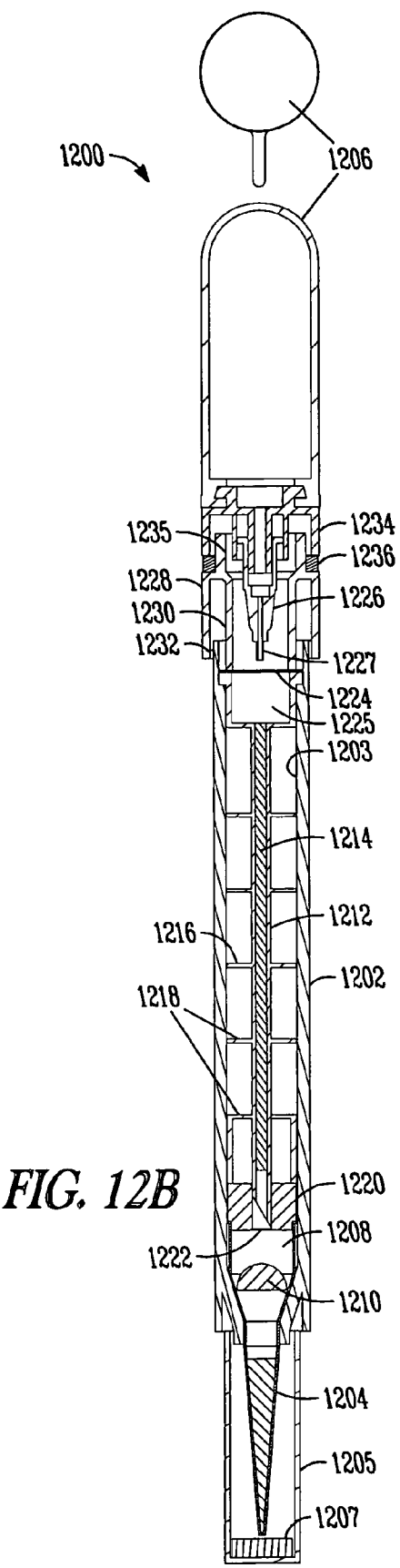
Figure 13:
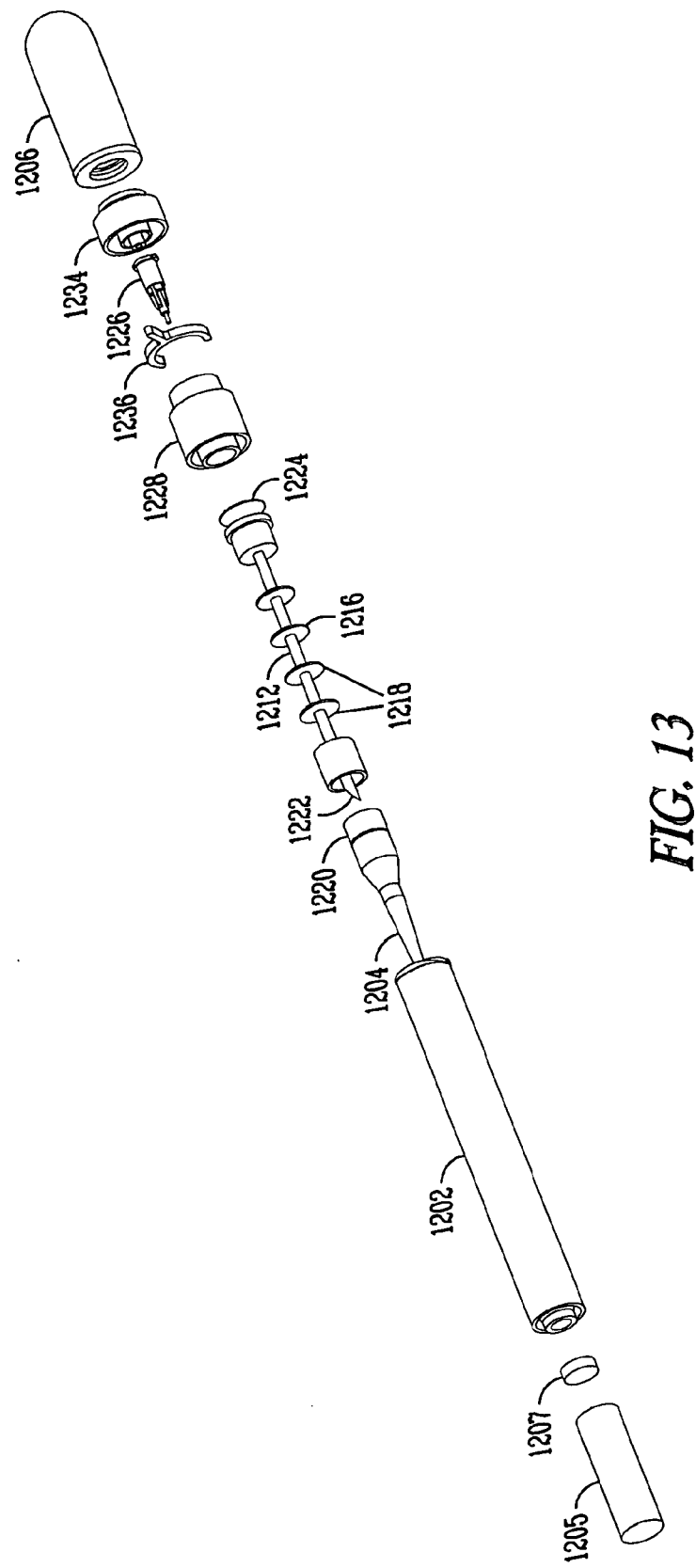

Another example of a reagent preparation and dispensing device 1200 is shown in FIGS. 12A, 12B and 13. The device 1200 includes a body 1202, a dispensing reservoir tip 1204 coupled with the body 1202. As shown in FIGS. 12A and 12B the dispensing reservoir tip is covered with a cap 1205. Referring to FIGS. 12B and 13, in one example, the cap 1205 includes a desiccant 1207 disposed at one end of the cap 1205. The desiccant 1207 is adapted to absorb moisture present within the cap and within the reagent reservoir 1208 prior to use of device 1200. Reagent reservoir 1208 is disposed at one end of the body 1202. The reagent reservoir 1208 contains at least one reagent 1210. As previously described the reagent 1210 includes a reagent for testing and diagnostic purposes. In one example, the reagent 1210 includes a lyophilized reagent (e.g., freeze-dried reagent). Another example of the reagent reservoir 1208 includes multiple reagents. As shown in FIGS. 12B and 13, the body 1202 further contains a solution reservoir 1212 containing a solution 1214 therein. In one example, the solution reservoir 1212 includes a capillary tube to hold the solution 1214 under a vacuum. At another end of the body 1202 is a first activator 1228 and a second activator 1206. The first activator 1228, in one example, includes a rotatable collar coupled between the body 1202 and a second activator mount 1234 coupled with the second activator 1206. The second activator 1206, in another example, includes a deflectable bulb.

As previously described in other examples, the reagent reservoir 1208 and the solution reservoir 1212 are separated from each other. In one example, and as shown in FIGS. 12B and 13, the reagent reservoir 1208 and the solution reservoir 1212 are separated by a seal 1220 interposed therebetween. The solution reservoir 1212 includes a piercing tip 1222 sized and shaped to engage with the seal 1220 and penetrate through the seal to put the solution reservoir 1212 and the reagent reservoir 1208 in communication with each other.

The solution reservoir 1212 further includes a support skeleton 1216 extending along the solution reservoir 1212. Optionally, the support skeleton 1216 extends from one end of the body 1202 to another end of the body 1202. In another example, the support skeleton 1216 extends over only a portion of the solution reservoir 1212 and extends along a corresponding portion of the body 1202. As shown in FIGS. 12b and 13, the support skeleton 1216, includes a series of ribs 1218 extending away from the solution reservoir 1212 into engagement with an interior surface 1203 of the body 1202. The ribs 1218, in one example, extend fully around the solution reservoir 1212 and thereby engage a full revolution of the interior of the body 1202. In another example, the ribs 1218 extend around only a portion of the solution reservoir 1212 and thereby only engage a corresponding section of the interior 1203 of the body 1202. The support skeleton 1216, in still another example, is a solid or hollow structure extending between the solution reservoir 1212 and the interior surface 1203.

Referring again to FIGS. 12B and 13, the solution reservoir 1212, as shown, includes a seal 1224 extending across an end 1225 of the solution reservoir. In one example, the seal 1224 is a piercable seal sized and shaped to extend across the reservoir 1212. The second activator 1206 and the second activator mount 1234 are sized and shaped to move a piercing element 1226 into engagement with the seal 1224. Piercing of the seal 1224 releases the vacuum within the capillary tube of the solution reservoir 1212. As previously described in another example, the release of the vacuum in the capillary tube allows the solution 1214 to flow by gravity into the reagent reservoir 1208 when the seal 1220 has been pierced.

As shown in FIG. 12B, threading 1232 extends between the first activator 1228 and the body 1202. Rotation of the first activator 1228 relative to the body 1202 correspondingly moves a flange 1230 of the second activator 1228 into engagement with the solution reservoir 1212. Engagement of the flange 1230 with the solution reservoir 1212 by rotation of the first activator 1228 moves the first activator toward the reagent reservoir 1208. As previously described, the solution reservoir 1212 includes a piercing tip 1222. As the solution reservoir 1212 is moved toward the reagent reservoir 1208 the piercing tip 1222 is engaged against the seal 1220 and thereby pierces the seal allowing the solution reservoir 1212 and the reagent reservoir 1208 to communicate.

Once the safety 1236 is removed as shown in FIGS. 12A and 12B the second activator 1206 and second activator mount 1234 are free to rotate relative to the first activator 1228. As shown in FIG. 12B, threading 1235 extends between the first activator 1228 and the second activator mount 1234. Rotation of the second activator and second activator mount 1234 moves the second activator 1234 along this threading and correspondingly moves the piercing element 1226 coupled thereto into engagement with the seal 1224. Engagement of the piercing element 1226 with the seal 1224 punctures the seal 1224 and thereby releases the vacuum in the capillary tube of the reservoir 1212. The solution 1214 is thereby able to move by gravity into the reagent reservoir 1208 where it mixes with the reagent 1210. Optionally, the second activator 1206 is moved (e.g., deflected) to force the solution 1214 out of the solution reservoir 1212 by pressure generated in the second activator.

In another example, the features at 1232 and 1235 include a slidable coupling. The slidable coupling between the first activator 1228 and the body 1202 permits axial movement of the first activator 1228 relative to the body 1202 to open the seal 1220. Where the feature 1235 is replaced with a sliding coupling between the second activator mount 1234 and the first activator 1228, axial movement of the second activator mount 1234 relative to the first activator 1228 is permitted to open the seal 1224.

Once the seals 1224 and 1220 have been opened the solution 1214 of the solution reservoir 1212 is moved into the reagent reservoir 1208 where it is mixed with the reagent 1210. The reagent solution then falls by gravity into the dispensing reservoir tip 1204. Movement of the second activator 1206, for example, a deflectable bulb provides a pressure near one end of the body 1202 which is transmitted, in one example, to a nozzle 1227 of the piercing element 1226. The pressure generated by the deflectable bulb and the second activator 1206 is then transmitted along the capillary tube of the solution reservoir 1212 into the dispensing reservoir 1208. This pressure then moves the reagent solution out of the dispensing reservoir tip 1204 and out of the device 1200.

Figure 14:
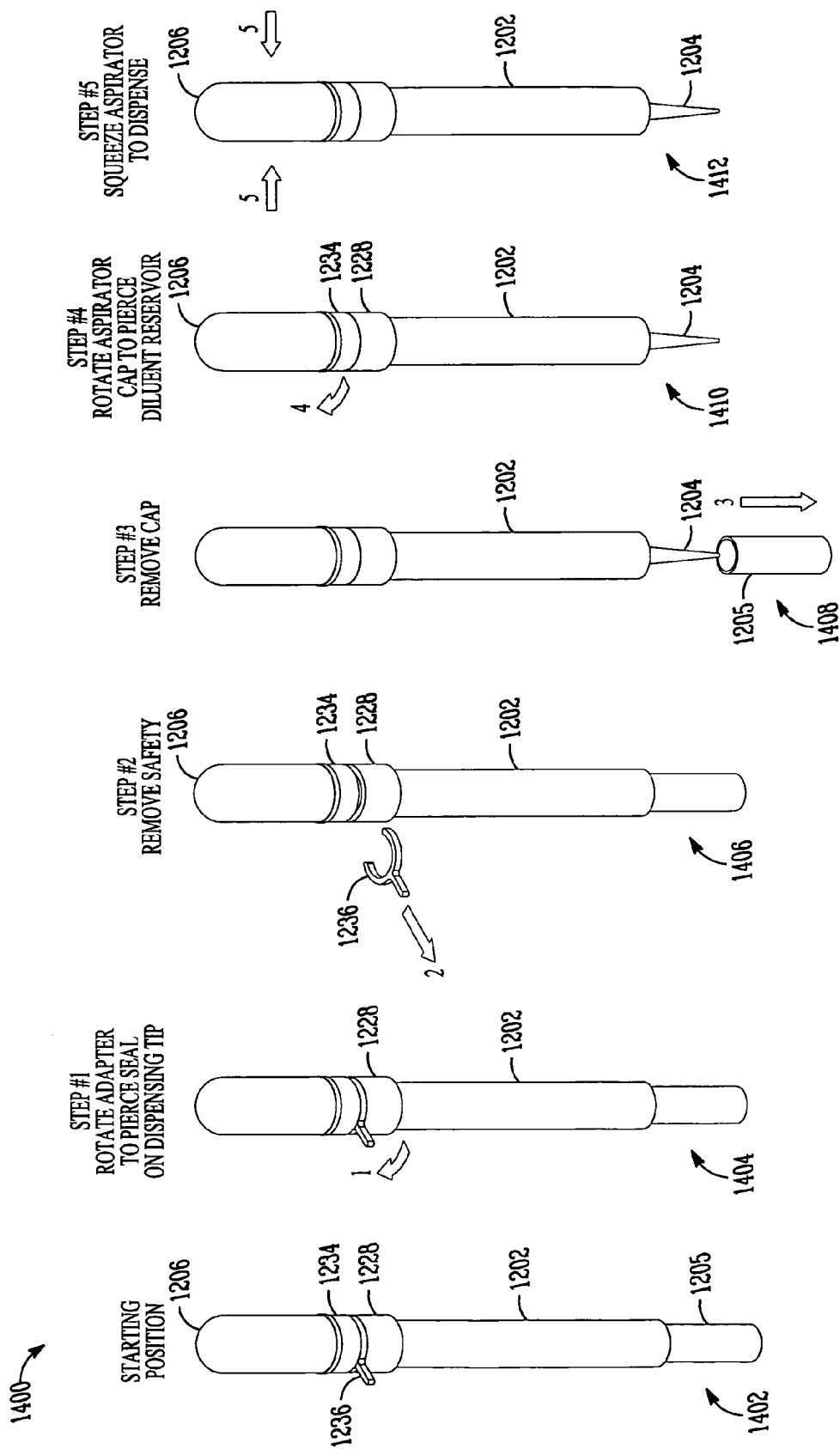

Turning now to FIG. 14, one example of a method 1400 for using the reagent preparation dispensing device 1200 shown in FIGS. 12A, 12B and 13 is shown. At 1402, the device 1200 is shown in a starting position where the safety 1236 is interposed between the second activator mount 1234 and the first activator 1228. As previously described, the safety 1236 prevents rotational movement of the second activator mount 1234 and second activator 1206 relative to the first activator 1228 thereby preventing piercing of the reservoir seal 1224. The cap 1205 is coupled with the body 1202 and protects the dispensing reservoir tip 1204 during transport and prior to use. At 1404, the first activator 1228 is rotated relative to the body 1202. As described above, rotation of the first activator 1228 moves the piercing tip 1222 of the solution reservoir 1212 into engagement with the seal 1220 (see FIGS. 12B and 13). Penetration of the piercing tip 1222 through the seal 1220 pierces the seal 1220 and allows communication between the solution reservoir 1212 and the reagent reservoir 1208. At 1406, the safety 1236 is removed thereby allowing rotation of the second activator mount 1234 and the second activator 1206 relative to the first activator 1228. At 1408, the cap 1205 is removed from the body 1202 thereby exposing the dispensing reservoir tip 1204. At 1410, the second activator mount 1234 coupled with the second activator 1206 is rotated relative to the first activator 1228. As previously described, rotation of the second activator mount 1234 moves the piercing element 1226 into engagement with the solution reservoir seal 1224. Piercing element 1226 pierces the solution reservoir seal 1224 and thereby releases a vacuum in the solution reservoir 1212. The solution 1214 is then able to flow by gravity through the solution reservoir into the reagent reservoir 1208 where it then mixes with the reagent to form a specified amount of the reagent solution. As shown in FIG. 12B the dispensing reservoir tip is coupled adjacent to the reagent reservoir 1208 and thereby receives the reagent solution. At 1412, the second activator 1206 is moved. As previously described in one example, the second activator 1206 includes a deflectable bulb. When the activator 1206 is deflected, as shown in FIG. 14, the reagent solution held within the reagent reservoir 1208 and the dispensing reservoir tip 1204 is dispensed outside of the device 1200.

Figure 15:
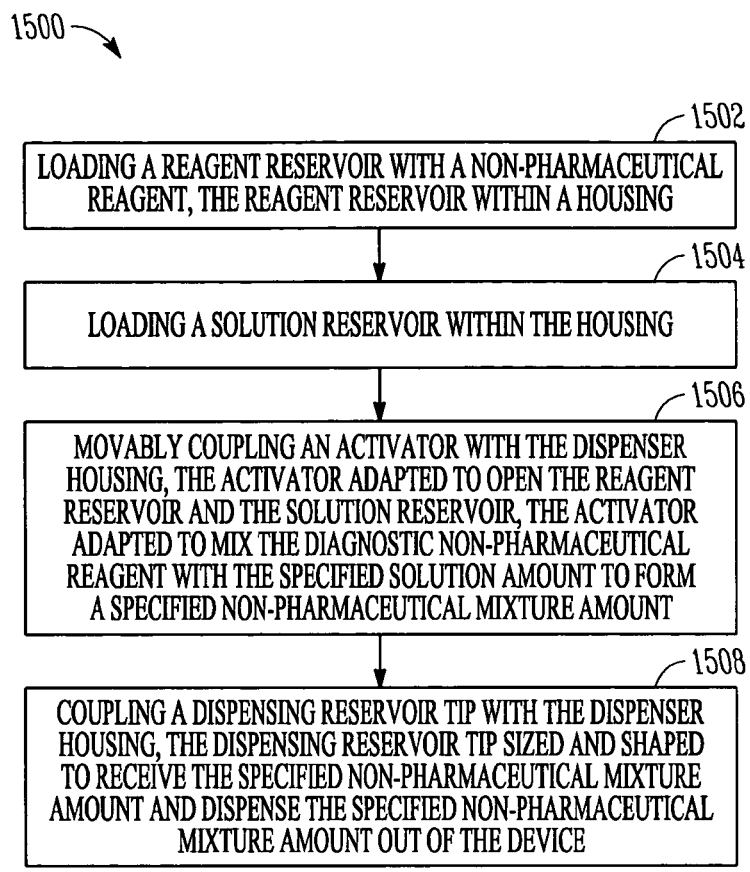
FIG. 15 is a block diagram showing one example of a method of making the devices shown in FIGS. 9a-14.

A method 1500 for making a reagent preparation dispensing device (such as the devices 900 and 1200 shown in FIGS. 9A through 14) is shown in FIG. 15. Reference is made to example elements provided previously in FIGS. 9A through 14 and described above. For convenience, elements from both devices 900 and 1200 will be discussed with specific element numbers here.

At 1502, a reagent reservoir 908, 1208 is loaded with a reagent 909, 1210. The reagent reservoir is contained within a housing such as housing 902, 1202. The reagent reservoir 908, 1208 contains a diagnostic reagent such as reagent 909, 1210. In another example, the reagent reservoir includes multiple diagnostic reagents. In yet another example, multiple reagent reservoirs, each with a separate reagent are loaded within the housing 902, 1202. The reagents in still another example, include but are not limited to, lyophilized reagents (e.g., freeze-dried reagents), liquid reagents, powdered reagents and the like.

At 1504, a solution reservoir (reservoir 910, 1212) is loaded within the housing 902, 1202. The solution 911, 1214 include, for example, a saline solution, a pH buffered water, a distilled water and the like. The solution is configured to mix with the reagent and produce a specified amount of a reagent solution, as described above and as described below.

At 1506, an activator (such as activators 916, 907, 1228, 1206, 1234 and the like) is coupled with the dispensing housing 902, 1202. The activator is adapted to open the reagent reservoir 908, 1208 and the solution reservoir 910, 1212. In one example, the activator is adapted to mix the diagnostic reagent with the specified solution amount to form a specified mixture amount. Optionally, the solution contained within the solution reservoir is a specified amount of solution intended to mix with the reagent to fully consume the reagent and produce a specified amount of the reagent solution having a predetermined concentration. As described above, the activators include, but are not limited to, deflectable bulbs, slidable elements, rotatable elements, rotatable elements engaged to the body by threading therebetween, slidable elements engaged with the body by slidable features therebetween and the like.

At 1508, a dispensing reservoir tip 904, 1204 is coupled with the dispensing housing 902, 1202. In one example, the dispensing reservoir tip 904, 1204 is sized and shaped to receive the specified amount of reagent solution and dispense that same specified amount of solution out of the device 900, 1200. In another example, the dispensing reservoir tip 904, 1204 includes a transparent or semi-transparent material that allows viewing of the reagent solution prior to dispensing from the device 900, 1200.

Figure 16:
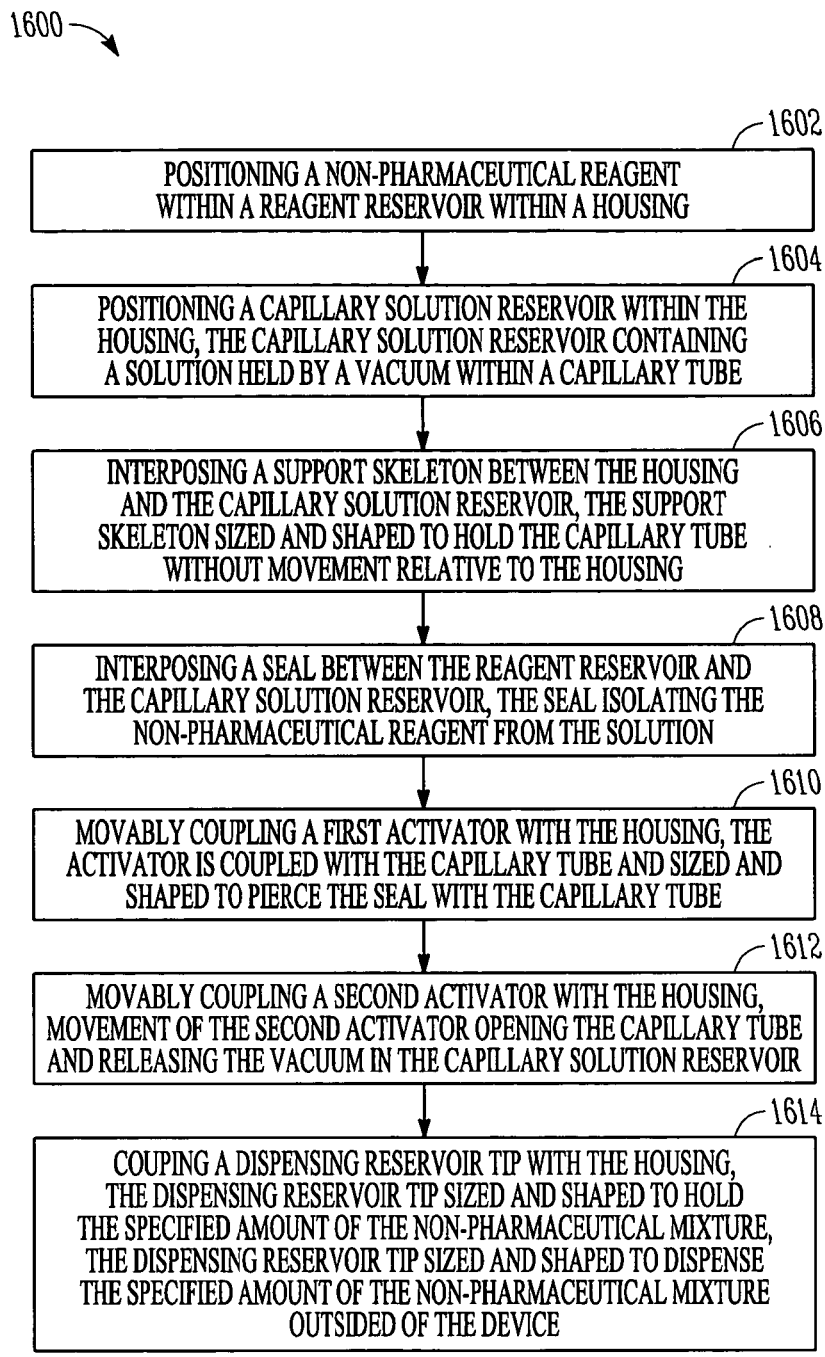
FIG. 16 is a block diagram showing another example of a method of making the devices shown in FIGS. 9a-14.

A method 1600 for making a reagent preparation dispensing device (such as the devices 900, 1200) is shown in FIG. 16. Reference is made to example elements previously shown in FIGS. 9A through 14 and described above. For convenience, elements from both devices 900 and 1200 will be discussed with specific element numbers unless otherwise noted.

At 1602, a reagent is positioned within a reagent reservoir such as reservoir 908, 1208. The reagent reservoir is contained within housing 902, 1202. As shown in FIGS. 10 and 13, the reagent reservoir 908, 1208 are separate portions of the device 900 and 1200 that are loaded within the housing 902, 1202. In another example, the reagent reservoir 908, 1208 are integral portions of the bodies 902, 1202. For instance, the reagent reservoirs 908, 1208 are integrally molded with the body 902, 1202. As previously described above, the reagent reservoirs 908, 1208 include reagents 909, 1210, for instance, reagents such as lyophilized reagents, liquid reagents, powdered reagents, and the like. Still in another example, the reagent reservoir 908, 1208 include multiple reagents.

At 1604, a capillary solution reservoir (such as reservoir 910, 1212) is positioned within the housing 902, 1202. The capillary solution reservoir contains a solution held by a vacuum within a capillary tube. In one example, the solution reservoir 910, 1212 is an upright cylinder contained within the housing 902, 1202. One end of the solution reservoir is positioned adjacent to the reagent reservoir 908, 1208, in yet another example.

At 1606, a support skeleton 912, 1216 is interposed between the housing 902, 1202 and the capillary solution reservoir 910, 1212. The support skeleton 912, 1216 is sized and shaped to hold the capillary tube without movement relative to the housing 902, 1202. As previously described, the support skeleton 912, 1216 includes ribs 913, 1218 that extend away from the solution reservoir 910, 1212 toward an interior wall of the housing 902, 1202 (such as surfaces 922, 1203). Additionally, the support skeleton 912, 1216 aligns the solution reservoir 910, 1212 with the body 902, 1202 to insure the solution reservoir is in a substantially parallel orientation relative to the housing, and movement of the reservoir is thereby guided towards the seals (described below).

At 1608, seal 918, 1220 is interposed between the reagent reservoir 908, 1208 and the capillary solution reservoir 910, 1212. Seal 918, 1220 isolates the reagent in the reagent reservoir 908, 1208 from the solution 911, 1214 in the solution reservoir. In one example, the seal 918, 1220 is an integral portion of the reagent reservoir 908, 1208. In another example, the seal 918, 1218 is a portion of the solution reservoir 910, 1212. Optionally, the seal 918, 1220 is constructed with, but not limited to, a soft pliable material that is pierceable, such as pliable plastics, rubber, latex and the like.

At 1610, a first activator 907, 1228 is movably coupled with the housing 902, 1202. Movement of the first activator 907, 1228 is adapted to move a piercing tip of the capillary tube 920, 1222 into engagement with the seal 918, 1220 thereby piercing the seal and allowing communication between the solution reservoir 910, 1212 and the reagent reservoir 908, 1208, respectively. In one example, the activator 907 is rotatably coupled with the housing 902 and the dispensing reservoir tip 904 (described below). The first activator 907 is indirectly coupled with the seal 918 and moves the seal when rotated relative to the piercing tip 920 of the solution reservoir 910. In another example, the first activator 1228 as shown in FIG. 12B is engaged against the solution reservoir 1212. Movement of the first activator 1228 advances the solution reservoir 1212 toward the seal 1220 thereby engaging a piercing element 1222 of the solution reservoir against the seal 1220 and penetrating the seal thereby allowing the reagent reservoir 1208 to communicate with the solution reservoir 1212.

At 1612, a second activator 916, 1206, 1234 is movably coupled with the housing 902, 1202. An element of the second activator opens the solution reservoir 902, 1212 and releases the vacuum in the capillary solution reservoir allowing the solution 911 and 1214 to flow out of the solution reservoir. In one example, the second activator 916 is coupled directly with the device body 902. Movement of the second activator 916 including deflection of a pliable bulb operates to move a portion of capillary tube 914 having a weakened portion 1004 thereby fracturing the capillary tube at the weakened portion 1004 to release the vacuum in the solution reservoir 910. In another example, as shown in FIG. 12B, the second activator includes a deflectable bulb 1206 and a second activator mount 1234 indirectly coupled with the body 1202 through the first activator 1228. Rotation of the second activator 1206 and the second activator mount 1234 relative to the first activator 1228 and the body 1202 drives a piercing element 1226 into a seal 1224 at one end of the solution reservoir 1212. Piercing of the seal 1224 releases the vacuum in the solution reservoir and allows flow of the solution 1214 out of the solution reservoir and into the reagent reservoir 1208 where the seal 1220 has already been pierced.

At 1614, a dispensing reservoir tip 904, 1204 is coupled with a housing 902, 1202. The dispensing reservoir tip 904, 1204 is sized and shaped to hold specified amounts of a reagent solution. The dispensing reservoir tip is sized and shaped to dispense the specified amount of the reagent solution outside of the device 900, 1200. In another example, the dispensing reservoir tip 904, 1204 is constructed with but not limited to a transparent or semi-transparent material to allow inspection of the reagent solution prior to dispensing. In yet another example, the dispensing reservoir tip 904, 1204 has a graduated geometry to a blunt nozzle that provides a steady stream of solution out of the device 900, 1200. Optionally, coupling the dispensing reservoir tip 904, 1204 with the dispenser housing 902, 1202, includes integrally forming the reservoir tip with the dispenser housing, for example, molding the dispensing reservoir tip with the housing.

Figure 17A:
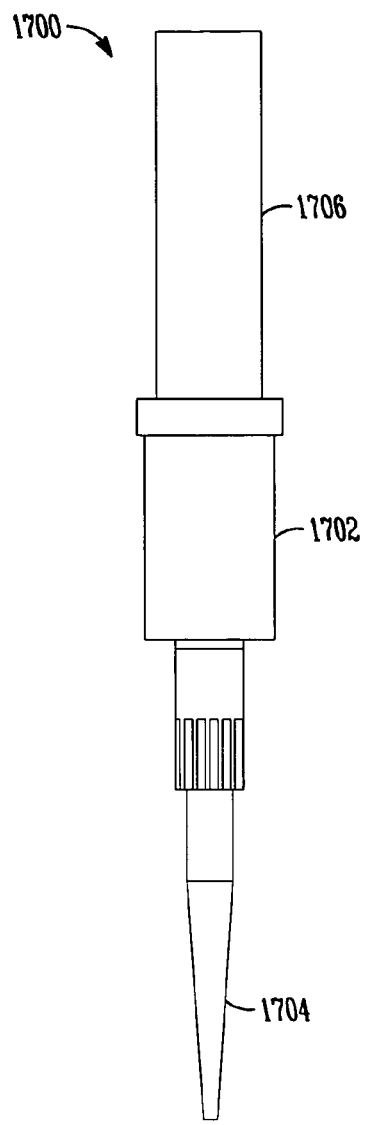
FIG. 17a is a side view of one example of a reagent preparation and dispensing device including a plunger activator having a solution reservoir disposed within the activator.
Figure 17B:
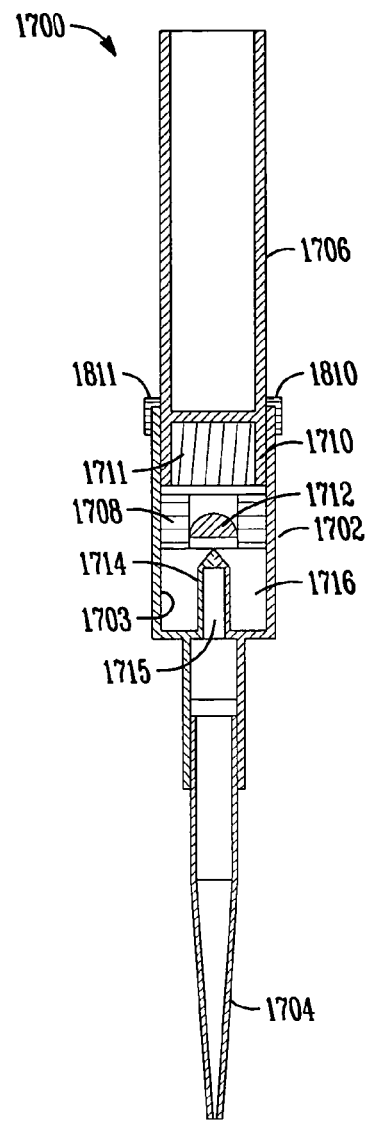
Figure 18:
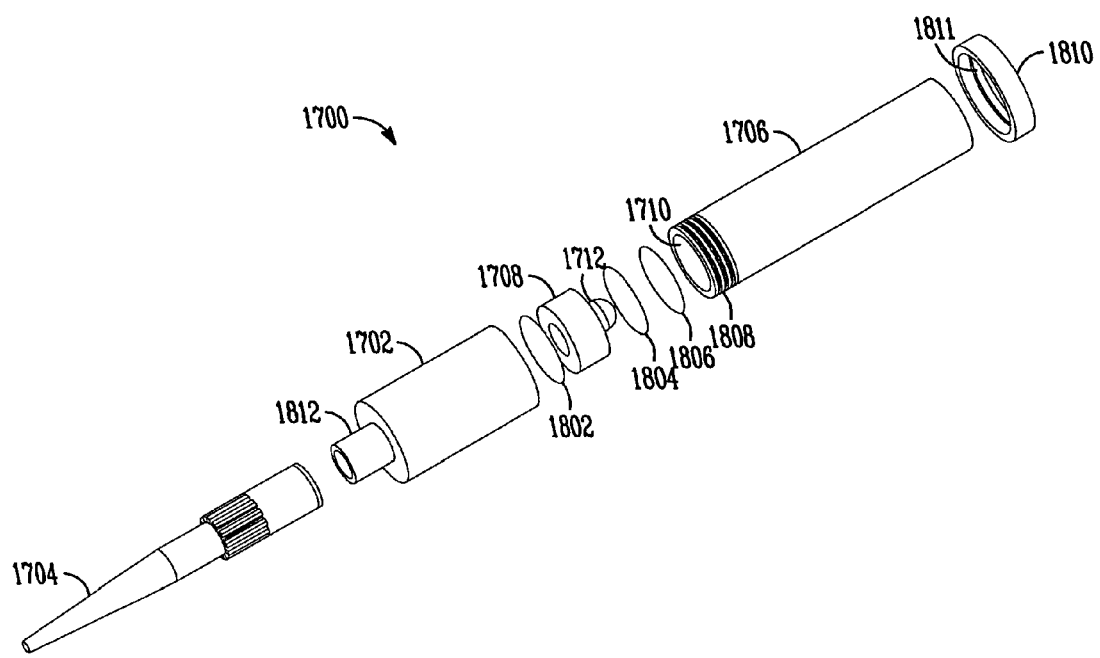

A device 1700 for the preparation and dispensing of a reagent 1700 is shown in FIGS. 17A, 17B and 18. Device 1700 includes a body 1702 and a dispensing reservoir tip 1704 coupled to an end of the body 1702. Dispensing reservoir tip 1704 is sized and shaped to receive and hold a specified amount of a reagent solution. In one example, a dispensing reservoir tip 1704 is constructed with but not limited to a transparent or semi-transparent material. The material of the dispensing reservoir tip 1704 permits viewing of the reagent solution prior to dispensing out of the tip 1704. The device 1700 further includes an activator 1706 sized and shaped for movable coupling with the body 1702. In one example, the activator 1706 includes a plunger sized and shaped to engage with an interior wall 1703 of the body 1702. The activator 1706 is slidably received along the wall and is depressable relative to the body 1702, for instance, with the thumb of a user.

Referring now to FIGS. 17B and 18, the device 1700 includes a reagent reservoir 1708 and solution reservoir 1710. The reagent reservoir 1708 in one example includes a reagent 1712 including, but not limited to, a lyophilized reagent, a liquid reagent, a powdered reagent and the like. In another example, the reagent reservoir 1708 includes multiple reagents, for instance, a first, second, third and fourth lyophilized reagent. In still another example, the body 1702 is sized and shaped to receive one or more reagent reservoirs 1708. A solution reservoir 1710 includes a solution 1711. The solution, in another example, includes saline, pH buffered water, a distilled water solution and the like. Optionally, the solution reservoir 1710 includes a pre-determined amount of solution 1711. The pre-determined amount of solution mixes with the reagent 1712 as the device 1700 is used to produce a specified amount of reagent solution having a specified concentration (in other words, sufficient solution is provided to fully consume the reagent without any excess solution).

The device 1700 further includes within the body 1702 a piercing element 1714. The piercing element 1714 is sized and shaped to engage with the reagent reservoir 1708 and the solution reservoir 1710 to penetrate through the reservoirs and communicate the contents of the reservoir 1708, 1710 with each other. Referring now to FIG. 18, the reagent reservoir 1708 includes a first and second seal 1802, 1804. In one example the seals 1802, 1804 include but are not limited to a frangible material such as a foil, a brittle plastic, a brittle metal or the like. In yet another example, the seal 1602, 1804 includes a pliable material that is piercable by the piercing element 1714 such as a plastic, a metal and the like. The seals 1802, 1804 are applied to the reagent reservoir 1708, for instance, by adhesives, welding and the like. In another example, the seals 1802, 1804 are integrally formed with the reagent reservoir immediately after positioning of the reagent 1712 within the reservoir 1708. The solution reservoir 1710 includes a seal 1806. The seal 1806 may include a frangible or pliable material sized and shaped for penetration by the piercing element 1714. As shown in FIGS. 17B and 18, reagent reservoir 1708 and the solution reservoir 1710 are constructed separately. The reagent reservoir 1708, for instance, is slid within the body 1702 into a first unused position as shown in FIG. 17B. The solution reservoir 1710 in yet another example is formed separately from the reagent reservoir and is included within the activator 1706 as shown in FIG. 17B and FIG. 18. Optionally, the solution reservoir 1710 is included as an entirely separate unit apart from the activator 1706 and is similarly slid into position within the housing 1702.

Referring again to FIG. 17B, the piercing element 1714 further includes opening 1715 (e.g., slits, preparations, passages and the like) through the wall of the piercing element 1714. The opening 1715 allows communication between the dispensing reservoir tip 1704 and the opened reagent reservoir 1708 and solution reservoir 1710. The reagent solution is thereby able to move from the body 1702 through the opening 1715 and into the dispensing reservoir tip 1704 prior to dispensing as described below.

The device 1700 further includes a gasket 1808 extending between the activator 1706 and the body interior 1703. In one example, the gasket 1808 is a soft gasket coupled with either the activator or body interior 1703 and sized and shaped to slidably engage against one or the other of the body 1702 or the activator 1706 to substantially prevent movement of solution or reagent solution between the activator 1706 and the body 1702 (i.e., leaking out of the device 1702 as opposed to moving through the dispensing reservoir tip 1704). In yet another example, the gasket 1808 includes a hard flange. For instance, a hard flange 1808 made out of the same material as the activator 1706. As shown in FIG. 18, the device 1700 further includes a collar 1810 sized and shaped to slide around activator 1706 and engage with the body 1702. Optionally, the collar 1810 is fixedly coupled with the body 1702 and presents an interior flange 1811 sized and shaped to engage with the gasket 1808. The interior flange 1811 as shown in FIG. 18 engages with the gasket 1808 to substantially prevent reverse movement of the activator 1706 and subsequent removal of the activator 1706 relative to the body 1702 after assembly of the device 1700. Additionally, engagement between the gasket 1808 and the interior flange 1811 substantially prevents accidental opening of the device 1700 and removal of the reagent reservoir 1708 after assembly of the device.

Figure 19:
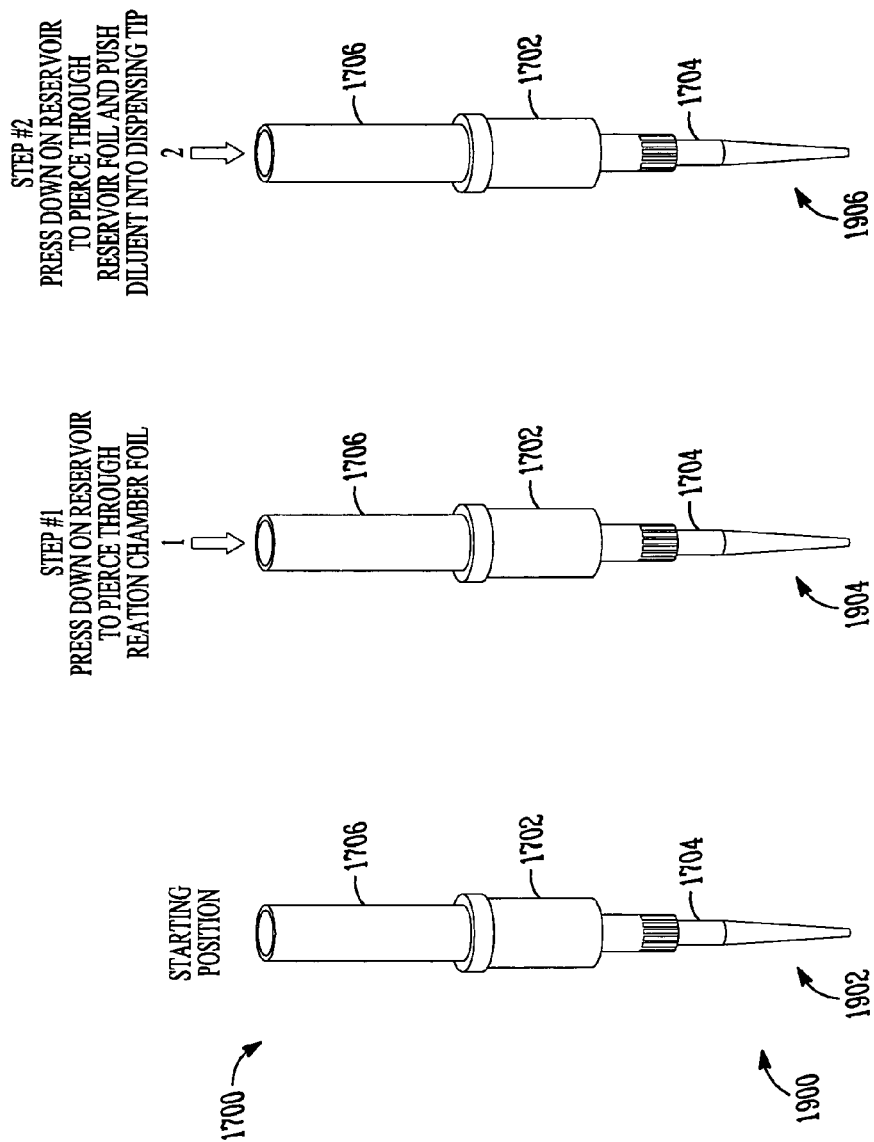

Referring now to FIG. 19, one example of a method 1900 for using the device 1700 (see FIGS. 17A, B and 18) is shown. Reference is made to elements shown in FIGS. 17A, B and 18 and included in the description of the method 1900 below.

At 1902, the device 1700 is shown in a starting position with the activator 1706 in an unused position relative to the housing 1702. The dispensing reservoir tip 1704 is coupled with the housing 1702 as previously described.

At 1904, the activator 1706 is depressed relative to the housing 1702. Referring now to FIGS. 17B and 18, movement of the activator 1705 presses the solution reservoir 1710 and the reagent reservoir 1708 toward the piercing element 1714. The piercing element 1714 engages with the seal 1702 and penetrates through the seal to open the reagent reservoir 1708 thereby communicating the contents of the reagent reservoir 1712 with an intermediate chamber 1716 (a reaction chamber) between the reagent reservoir 1708 and dispensing reservoir tip 1704.

At 1906, the activator 1706 is further depressed into the body 1702. Referring again to FIG. 17B, the piercing element 1714 engages against the seals 1804 on one end of the reagent reservoir 1708 and the solution reservoir seal 1806. The piercing element pierces the seals 1804 and 1806 thereby releasing the solution 1711 contained within the solution reservoir 1710. In one example, the solution 1711 flows by gravity over the reagent 1712 mixing with the reagent and forms a reagent solution within at least one of the reagent reservoir 1708 and the intermediate chamber 1716 within the body 1702. In another example, depression of the first activator 1706 pressurizes the solution 1711 as the piercing element 1714 is forced into the solution reservoir 1710 thereby forcing the solution 1711 over the reagent 1712 and into the intermediate chamber 1716. The specified amounts of the reagent solution generated by the mixing of the reagent 1712 and solution 1711 flows from the intermediate chamber 1716 through the opening 1715 in the piercing element 1714 and into the dispensing reservoir tip 1704. In one example, movement of the activator 1706 pressurizes the reagent solution through the dispensing reservoir tip 1704 and out of the device 1700. In another example, gravity acts on the solution in the intermediate chamber 1716 moving it into dispensing reservoir tip 1704 where the reagent solution subsequently flows out of the tip 1704.

Figure 20A:
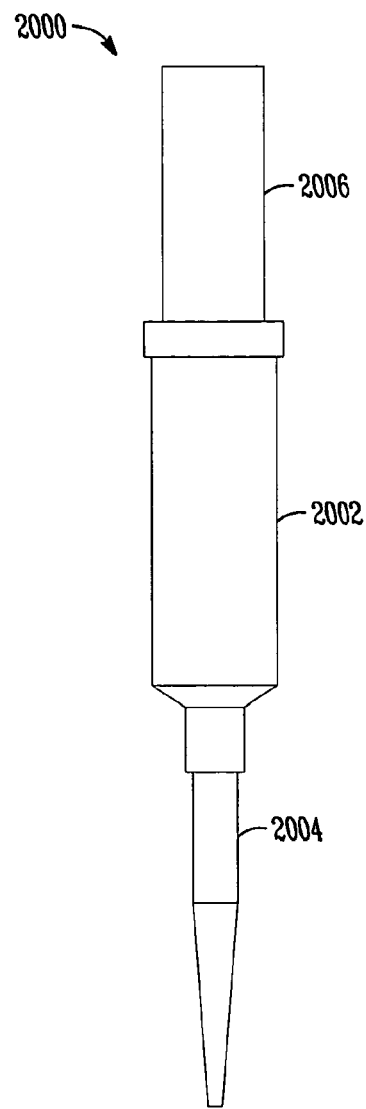
FIG. 20a is a side view of one example of a reagent preparation and dispensing device including a plunger activator with solution and reagent reservoirs separately loaded within the device housing.
Figure 20B:
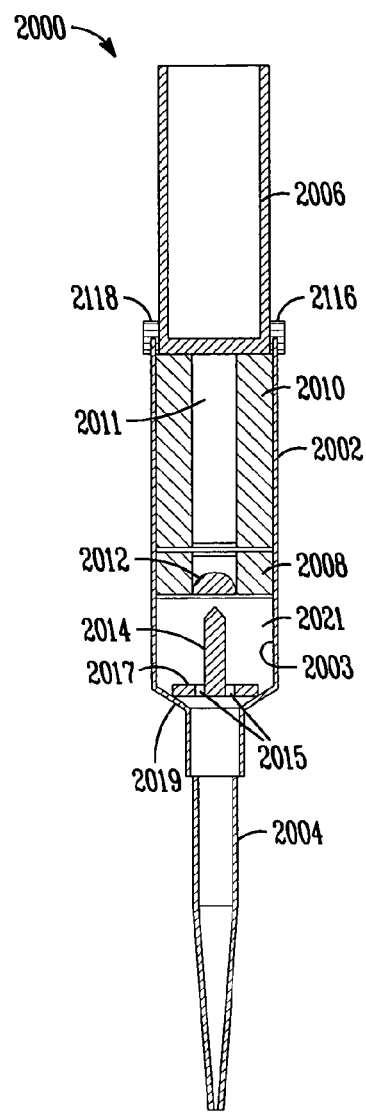
Figure 21:
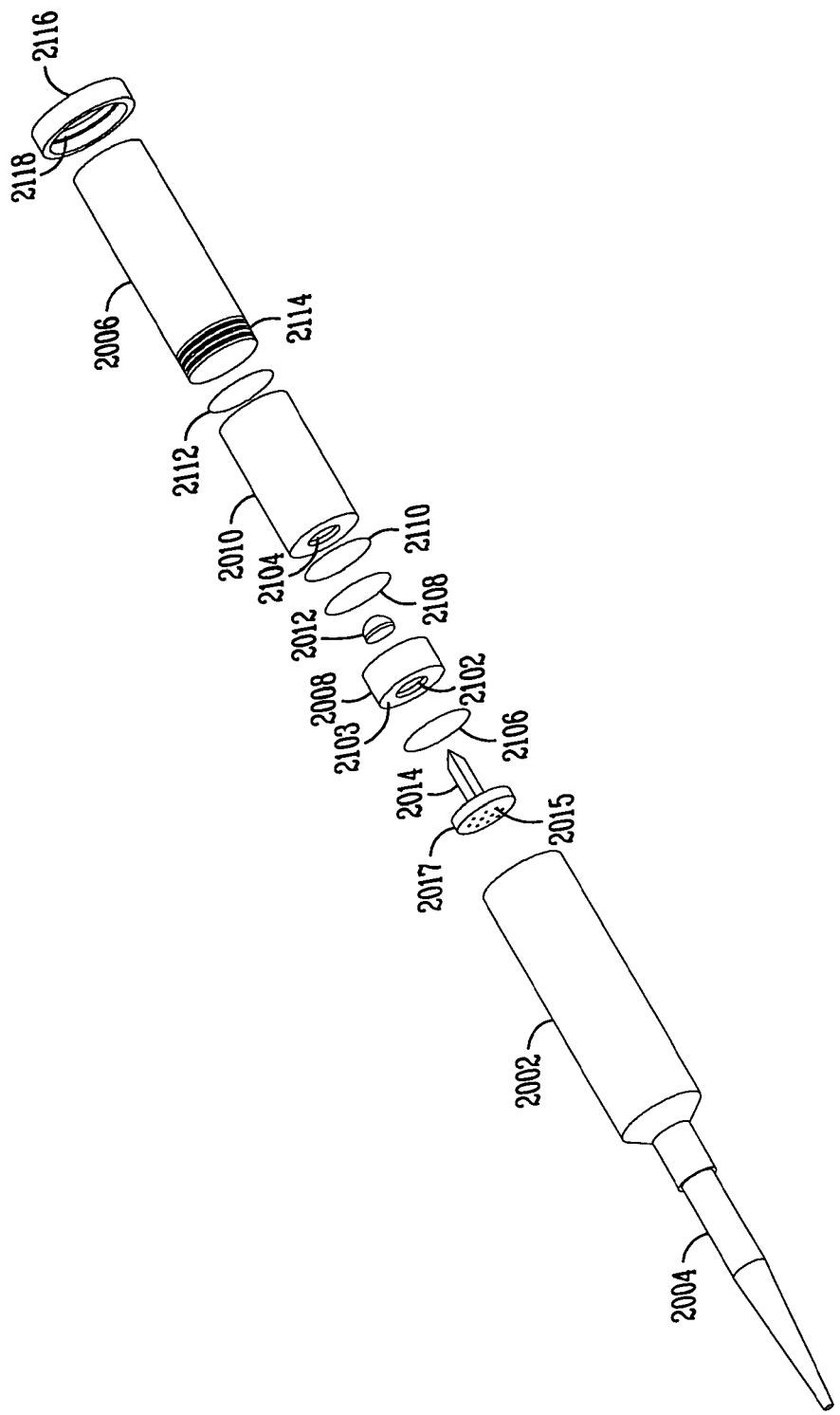

Another example of a reagent preparation and dispensing device 2000 is shown in FIGS. 20A, 20B, 21 and 22. The device 2000 is similar in at least some features to the device 1700 shown in FIG. 17A through 19. As shown in FIGS. 20A, 20B and 21 the device 2000 includes the body 2002, a dispensing reservoir 2004 and an activator 2006. The activator 2006 is movably coupled with the body 2002 and as previously described with device 1700 the activator 2006 is movable, for example, as a thumb activated plunger. A reagent reservoir 2008 containing a reagent 2012 is disposed within the body 2002 and a solution reservoir 2010 including a solution 2011 is disposed in the body 2002 as well. As previously described, the reservoir 2008 may include the reagent 2012 including but not limited to a lyophilized reagent (e.g., freeze-dried reagent), solution reagent, powder reagent and the like. A solution 2011 contained in the solution reservoir 2010 in another example includes a solution containing but not limited to saline, pH buffered water, distilled water and the like. Optionally, a specified amount of solution 2011 is contained within the solution reservoir mixed with the reagent 2012 to form a specified amount of reagent solution having a specified concentration.

Referring to FIGS. 20B and 21, the reagent reservoir 2008 and solution reservoir 2010 are shown as separate reservoirs that are loaded within the body 2002. For instance, reagent reservoir 2008 and solution reservoir 2010 are slidably loaded within the body 2002. In one example, a reagent reservoir 2008 containing a predetermined reagent and a solution reservoir 2010 including a predetermined solution prepared specifically for combination with the reagent 2012 are both selected and loaded individually within the body 2002. In other examples, various reservoirs having a variety of reagents and solution reservoirs including varied amounts of solution and various types of solution are chosen to achieve particular solution and reagent combinations for each device 2000 (e.g., for a particular diagnostic or testing scheme).

As shown in FIG. 21, the reagent reservoir 2008 includes a reservoir sidewall 2103 and an orifice 2102 extending through the reagent reservoir 2008. Similarly the solution reservoir 2010 includes a solution reservoir sidewall 2105 and an orifice 2104 extending through the solution reservoir 2010. The reagent reservoir 2008 includes seals 2106 and 2108 coupled at the ends of the reagent reservoir 2008 over the orifices 2102. The seals 2106 and 2108 seal off the reagent 2012 housed within the reservoir 2008. As previously described with the device 1700, the seals 2106 and 2108 include but are not limited to brittle seals, pliable seals and the like. Similarly with solution reservoir 2010, seals 2110 and 2112 are provided at either end of the solution reservoir and close the orifices 2104. The seals 2110 and 2112 in one example, include but are not limited to, pliable seals, brittle seals and the like. The seals 2106, 2108, 2110 and 2112 are configured to open with engagement of a piercing element as described further below.

A piercing element 2014 disposed within the body 2002 as shown in FIGS. 20B and 21. The piercing element 2014 is separately disposed within the body 2002. Optionally, the piercing element 2014 is integrally formed with the body 2002, for example, by molding. As shown in FIG. 21, the piercing element includes openings 2015 at a base flange 2017. As shown in FIG. 20B, the base flange 2017 is engaged with a bottom surface 2019 of the body 2002. Optionally, the base flange 2017 and the piercing element 2014 are fixably engaged with the body 2002, for example, by welding, adhesives and the like. As previously described with element 1714 of the device 1700, the piercing element 2014 of the device 2000 is similarly sized and shaped to engage with at least the seals 2106, 2108 and 2110. When engaged against the seals the piercing element 2014 penetrates through the seals thereby opening the reagent reservoir 2008 and solution reservoir 2011. Opening both of the reservoirs 2008, 2010 allows the reagent 2012 and solution 2011 to communicate and mix to form a reagent solution.

As shown in FIGS. 20B and 21, the reagent reservoir 2008, solution reservoir 2010 and activator 2006 are loaded in order in the body 2002. The activator 2006 includes a flange 2114. The flange 2114, in one example, includes a gasket sized and shaped to engage with the interior 2003 of the body 2002. The flange 2114 substantially prevents movement of solution 2011 between the activator 2006 and the body inner wall 2003. As previously described in other examples, the flange 2114 extends between the activator 2006 and the inner surface 2003. A collar 2116 is engaged against the body 2002 and includes a lip 2118 sized and shaped to engage the flange 2114. When the collar 2116 is positioned on the body 2002, as shown in FIG. 20B, the lip 2118 engages against the flange 2114 (FIG. 21) to prevent movement of the activator 2006 out of the body 2002 thereby ensuring the solution reservoir 2110 and reagent reservoir 2008 are securely held with the body 2002 during transport and prior to use. Advantageously, the separable nature of the reagent reservoir 2008, the solution reservoir 2010 and the activator 2006 allows for the assembly of the device 2000 having any of a variety of reagents 2012 and solutions 2011 into a single package 2000 for use in a variety of diagnostic and testing situations.

Figure 22:
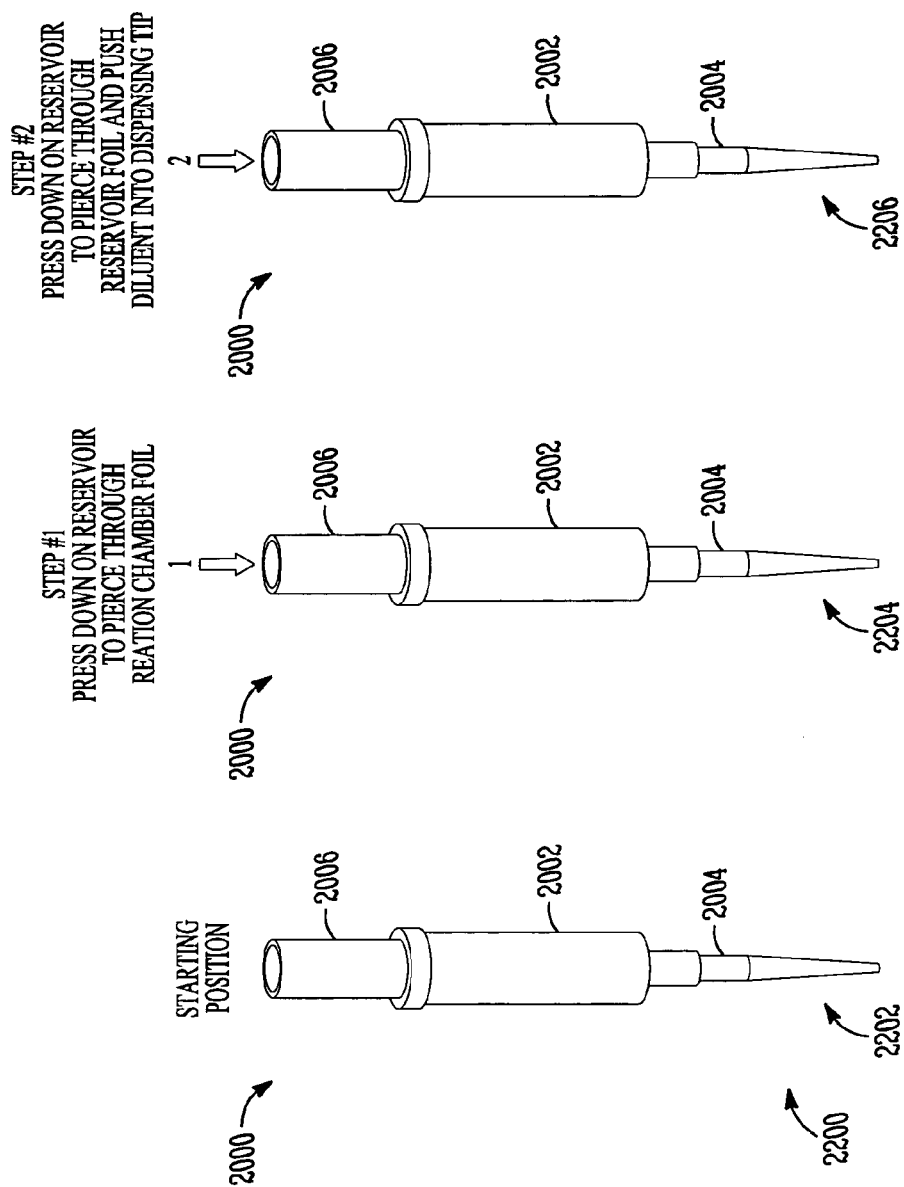

A method 2200 for using a agent preparation and dispensing device such as the device 2000 (as shown in FIGS. 20A-21) is shown in FIG. 22. At 2202 the device 2000 is shown in a starting position with the activator 2006 in a first position with the solution reservoir 2010 and reagent reservoir 2008 in unopened conditions as shown in FIG. 20B. The dispensing reservoir tip 2004 is positioned at one end of the body 2002.

At 2204, the activator 2006 is moved toward the dispensing reservoir tip 2004. As shown in FIG. 20b the reagent reservoir 2008 is moved toward the piercing element 2014 where the piercing element engages with the seal 2106 shown in FIG. 21. The piercing element 2014 engaged against the seal 2106, pierces the seal and opens the reagent reservoir 2008.

At 2206, the activator 2006 is further moved toward the dispensing reservoir tip 2004. The piercing element 2014 is thereby engaged with the seals 2108 and 2110 to penetrate the solution reservoir 2010 and release the solution 2011 therein. The solution 2011 flows by gravity, for example, over the reagent 2012 and into an intermediate chamber 2021. The solution 2011 and reagent 2012 mix together to form a reagent solution. In another example, the activator 2006 is moved down into the body 2002 and a pressure generated by the movement of activator 2006 forces the solution 2011 over the reagent 2012 into the intermediate chamber 2021 where it mixes. The solution then moves under pressure into the dispensing reservoir tip 2004. Optionally, the reagent solution flows from the dispensing reservoir tip 2004 by gravity. In another example, the activator 2006 is further moved into the body 2002 to move the reagent solution under pressure out of the dispensing reservoir tip 2004.

Figure 23A:
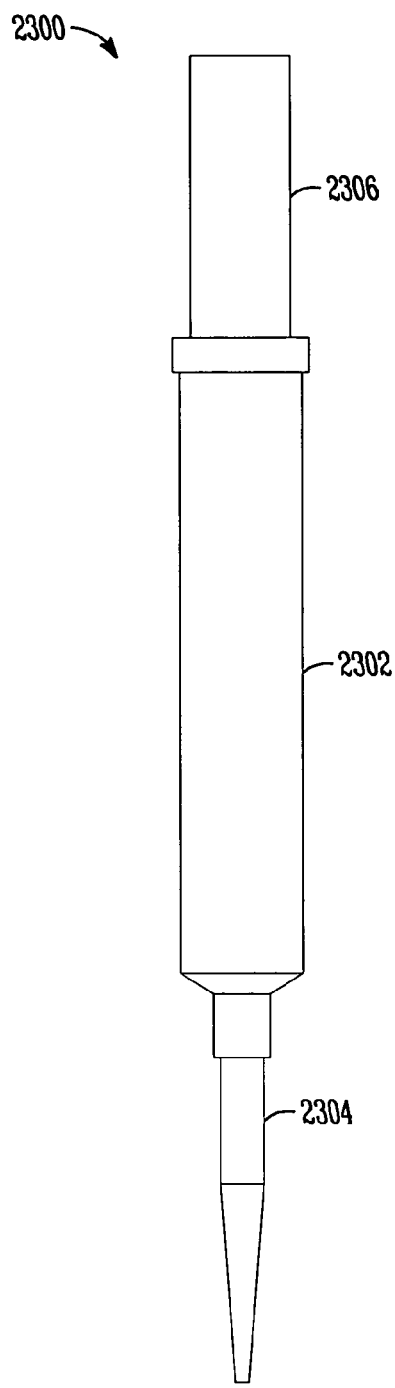
FIG. 23a is a side view of one example of a reagent preparation and dispensing device including a plunger activator having a piercing element coupled with the activator.
Figure 23B:
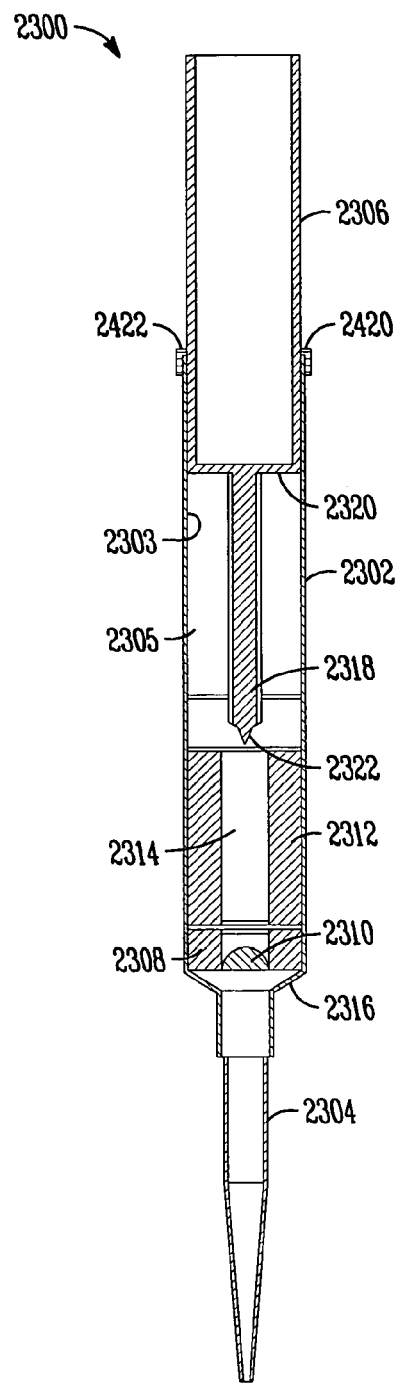

FIGS. 23A and 23B show another example of a reagent preparation and dispensing device 2300. The device 2300 includes a body 2302, a dispensing reservoir tip 2304 and an activator 2306. In one example, the dispensing reservoir tip 2304 is formed integrally with the body 2302, for instance, by molding. In another example, the dispensing reservoir tip 2304 is formed separately from the body 2302 and later coupled with the body, for instance, by welding, adhesives, mechanical inter-fitting and the like.

As shown in FIG. 23B, the activator 2306, in yet another example, includes a plunger slidably received within the body 2302. The plunger 2306 is shown engaged with an interior wall 2303. As described further below the activator 2306 is operated to open solution and reagent reservoirs to mix the reagent contained within a reagent reservoir with the solution contained in a solution reservoir to form a reagent solution for dispensing out of the device 2300 through the dispensing reservoir tip 2304.

Figure 24:
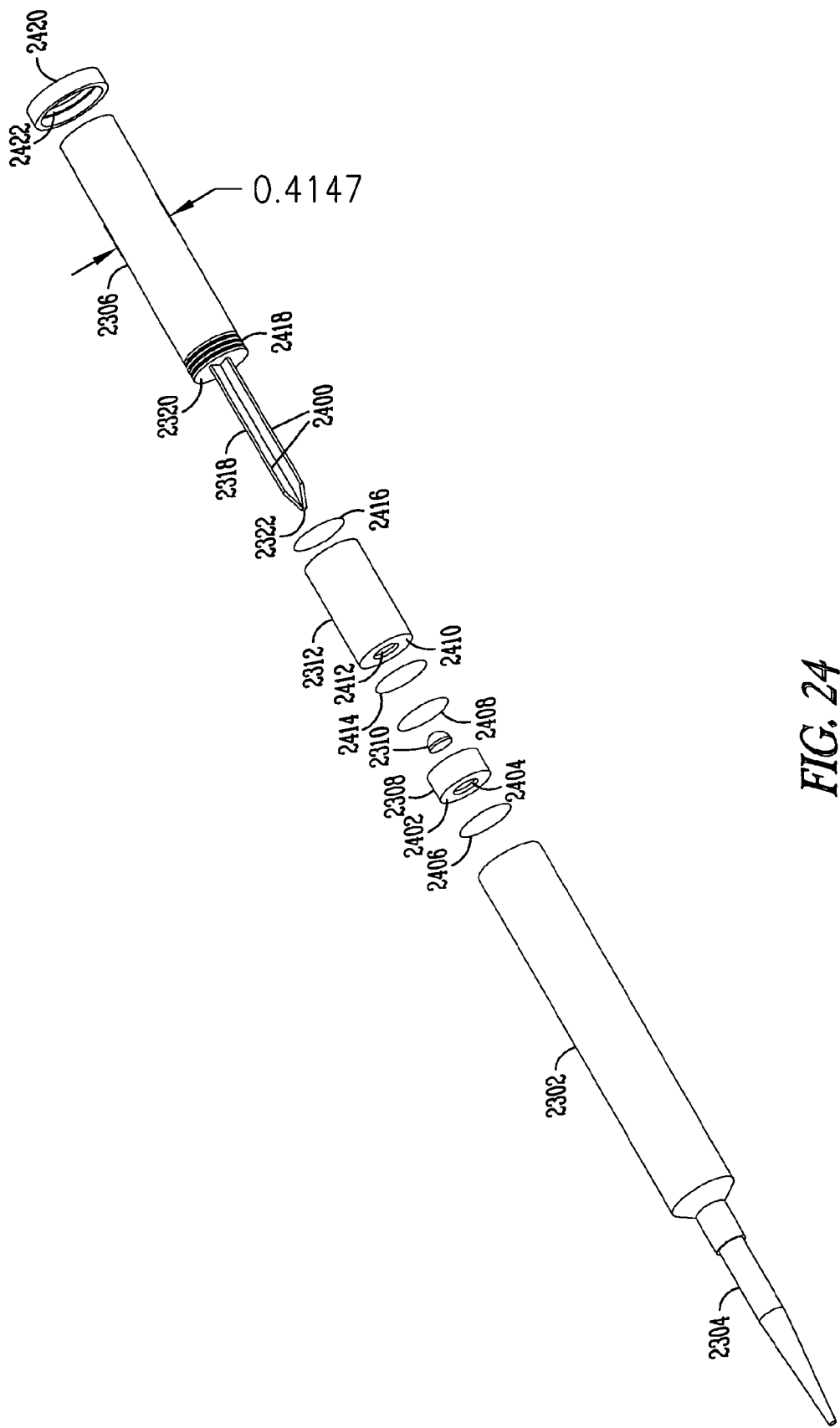

Referring now to FIGS. 23B and 24, the device 2300 further includes reagent reservoir 2308 and solution reservoir 2312. The reagent reservoir 2308 includes a reagent 2310. In one example, the reagent 2310 includes, but is not limited to, a lyophilized reagent, a solution reagent, a powder reagent and the like. A solution reservoir 2312 includes a solution 2314. Solution 2314, in one example, includes but is not limited to saline, pH buffered water, distilled water, and any other solution suitable for mixing with reagent 2310. Optionally, the solution reservoir 2312 includes a sufficient amount of solution 2314 to mix with reagent 2310 and form a specified amount of reagent solution having a specified concentration.

As shown in FIG. 24, the reagent reservoir 2308 and solution reservoir 2312 are separate components from the body 2302 positionable within the body along the body interior wall 2303. The reagent reservoir 2308 and solution reservoir 2312 are thereby selected from, for example, a variety of reagents and solutions for particular diagnostic or testing purposes. The device 2300 (as well as other devices described above and described below) may be rapidly assembled with one or more reagent reservoirs and solution reservoirs chosen from a catalog of available reagents and solutions to form the device for a particular diagnostic or testing scheme.

As shown in FIG. 24, the reagent reservoir 2380 includes a sidewall 2402 and at least one orifice 2404. Reagent 2310 is retained within the orifice 2404 and surrounded by the sidewall 2402. Seals 2406 and 2408, in one example, are coupled at either end of the sidewall 2402. Seals 2406 and 2408 include, but are not limited to, film members placed over the orifice 2404, such as pliable film members and the like. As described further below, the seals 2406, 2408 are opened by penetration of a piercing element coupled with the activator 2306. Solution reservoir 2312 similarly includes an orifice 2412 for retaining solution 2314 and a sidewall 2410 surrounding the solution 2314. Solution reservoir 2312 further includes seals 2414, 2416 coupled at either end of the solution reservoir 2312, in another example. As previously described, with regard to seal 2406 and 2408, seals 2414 and 2416 similarly include, but are not limited to, pliable seals, brittle seals and the like sized and shaped for piercing by a piercing element coupled with the activator 2306.

As shown in FIGS. 23B and 24, the solution reservoir 2312 and reagent reservoir 2308 are loaded in the body 2302. In one example, the reagent reservoir 2308 is loaded closer to the dispensing reservoir tip 2304 than the solution reservoir 2312. As shown in FIG. 23B, the reagent reservoir 2308 rests against a bottom flange 2316 of the body 2302. Once the reagent reservoir 2308 and solution reservoir 2312 (e.g., chosen for a particular diagnostic or testing purpose) are loaded within the body 2302 the activator 2306 is loaded within the body 2302, as previously described.

Referring now to FIG. 24, the activator 2306 includes a flange 2418 (e.g., a rigid flange, a pliable gasket or the like). Flange 2414 extends from the activator 2306 into engagement with the interior 2303 of the body 2302. In one example, the flange 2418 provides a sealing engagement between the activator 2306 and the body 2302 thereby preventing exit of solution 2314 between the interior 2303 of the body 2302 and the activator 2306 (as opposed to the dispensing reservoir tip 2304). Once the activator 2306 is positioned within the body 2302, optionally a collar 2420 is slid over the activator 2306 into engagement with the body 2302. As shown in FIGS. 24 and 23B the collar includes a lip 2422 sized and shaped to engage against the body 2302. In another example, the lip 2422 is sized and shaped to engage against the flange 2418 and substantially prevent movement of the activator 2306 out of engagement with body 2302. That is to say, the lip 2422 acts as a locking surface against reverse movement of the activator 2306 out of the body 2302. The collar 2420 in another example is coupled with the body 2302 with adhesives, welds, mechanical fitting and the like.

The activator 2306 includes a piercing element 2318 coupled with the activator along an activator flange 2320. In one example, the piercing element 2318 extends along the body 2302 in a substantially parallel fashion toward the solution reservoir 2312 and reagent reservoir 2308. The piercing element 2318 includes piercing tip 2322. In one example, piercing tip 2322 is sized and shaped to engage against the seals 2416, 2414, 2408 and 2406 to pierce the seals and thereby allow communication between the solution 2314, reagent 2310 and mixing of the same. Additionally, penetration of the seal 2406 allows the reagent solution formed in the reagent reservoir 2308 and solution reservoir 2312 to move by gravity or pressure into the dispensing reservoir tip 2304 prior to dispensing.

As shown in FIG. 24, the piercing element 2318 further includes grooves 2400. The grooves 2400 ensure annular engagement between the piercing element 2318 and the solution reservoir 2312 does not occur. The piercing element 2318 thereby penetrates the seals 2416, 2412, 2408, and 2404 by physical engagement with a piercing tip 2322. The seals 2406, 2408, 2414 and 2416 are thereby not ruptured by pressure created between engagement of a circular piercing element and a corresponding circular solution reservoir 2312 and circular reagent reservoir 2308. Undesirable flushing action through the seals is thereby prevented with corresponding violent dispensing of the solution (in a possibly unmixed state) through the dispensing reservoir tip 2304 also prevented.

Figure 25:
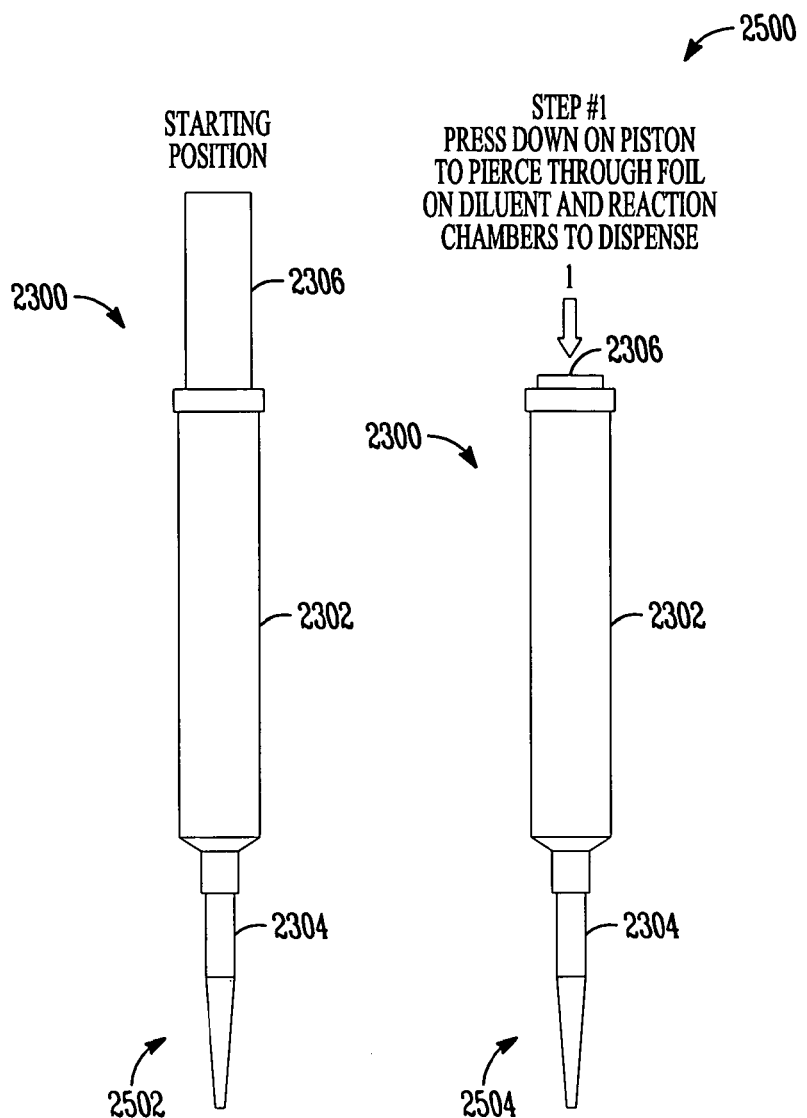

A method 2500 for using the reagent preparation dispensing device 2300 (see FIGS. 23A-24) is shown in FIG. 25. Reference is made to the elements and functions described in FIGS. 23A through 24 and included in the method herein.

At 2502, the device 2300 is shown in a starting position with the body 2302 having the dispensing reservoir tip 2304 coupled thereto. The activator 2306 is shown in a first position where the piercing element 2318 coupled with the activator 2306 has not been engaged with the seals on the reagent reservoir 2308 and the solution reservoir 2312.

At 2504, the activator 2306 has been moved toward the dispensing reservoir 2304. The piercing element is driven with the activator 2306 toward the seal 2416 of the solution reservoir 2312. The piercing tip 2322 pierces the seal 2416 and continued movement of the activator drives the piercing tip 2322 through the seals 2414, 2408 of the solution reservoir 2312 and solution reservoir 2308, respectively. The solution 2314 flows into the reagent reservoir 2308 (e.g., by gravity, pressure from the activator 2306 and the like) and mixes with the reagent 2310 to form the specified amount of the reagent solution.

Further depression of the activator 2306 toward the dispensing reservoir tip 2304 pierces the seal 2406 with the piercing tip 2322. The reagent solution is thereby able to flow (e.g., by gravity, pressure from the activator 2306 and the like) into the dispensing reservoir tip 2304. The reagent solution is then dispensed out of the dispensing reservoir tip 2304 by gravity, in one example. In another example, movement the activator 2306 applies pressure behind the reagent solution and expels the solution out of the dispensing reservoir tip 2304. Optionally, the dispensing reservoir tip 2304 is constructed with a transparent or semi-transparent material to allow inspection of the solution (e.g., for completion of mixing, verification of correct reagents such as by color, consistency and the like) prior to dispensing the reagent solution.

Figure 26A:
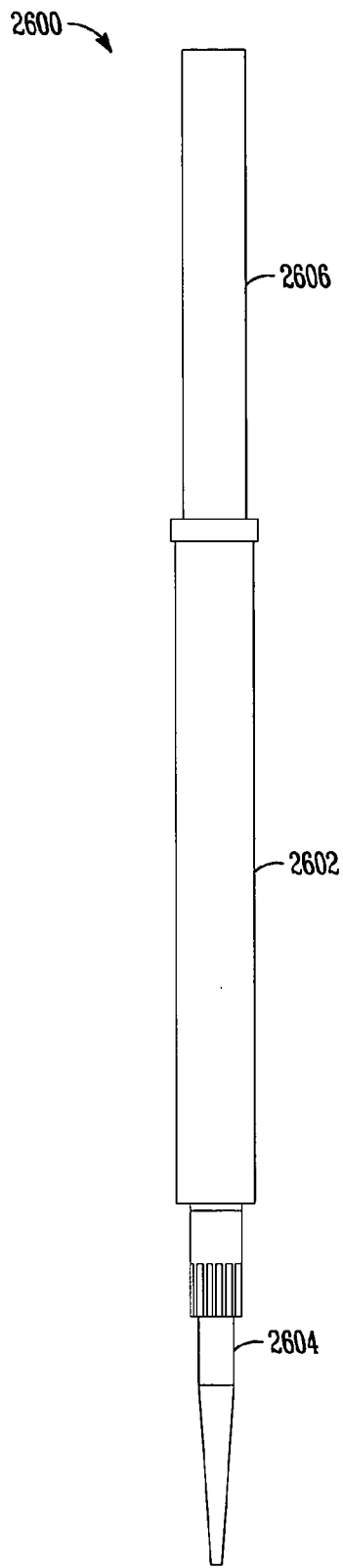
FIG. 26a is a side view of one example of a reagent preparation and dispensing device including reservoirs having piercing nozzles.
Figure 26B:
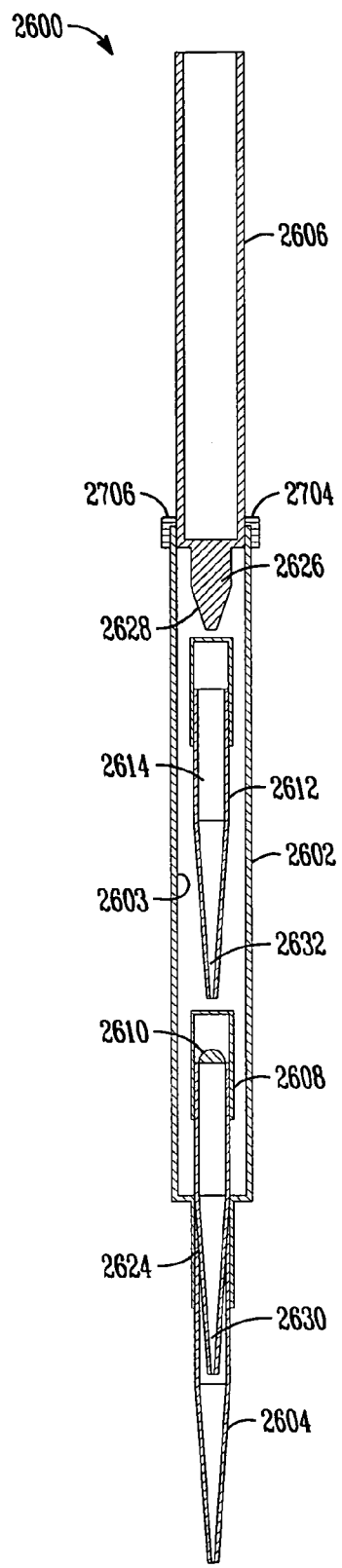
Figure 27:
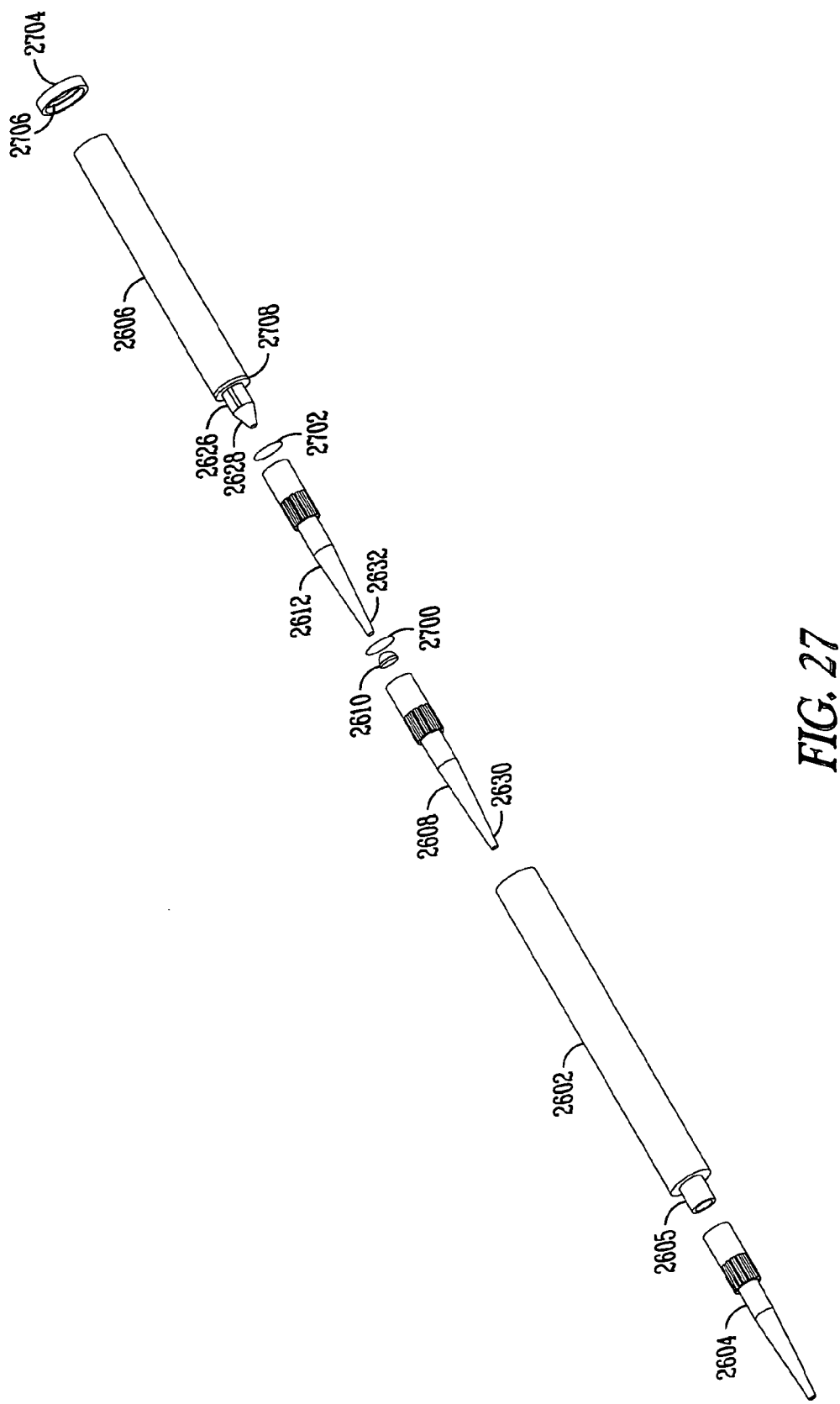

Another example of a reagent preparation and dispensing device 2600 is shown in FIGS. 26A-28. The device 2600 includes a body 2602, a dispensing reservoir tip 2604 coupled to the body and an activator 2606 movably coupled with the body 2602. In one example, the dispensing reservoir tip 2604 is integrally formed with the body 2602. In another example, as shown in FIG. 27, a dispensing reservoir tip 2604 is a separate piece from the body 2602 and is coupled with the body 2602 at a nozzle fitting 2605. For instance, the dispensing reservoir tip 2604 is coupled with the nozzle fitting 2605 by welding, adhesives, mechanical inter-fitting and the like.

Referring now to FIGS. 26B and 27, the device 2600 further includes a reagent reservoir 2608 and a solution reservoir 2612. The reagent reservoir 2608 includes at least one reagent 2610. In one example, the reagent 2610 includes but is not limited to a lyophilized reagent, a powdered reagent, a solution reagent and the like. The solution reservoir 2612 includes a solution 2614 configured to mix with the reagent 2610 and form a reagent solution. Optionally a predetermined amount of solution 2614 is provided to mix with the reagent 2610 and form a specified amount of a reagent solution having a concentration (i.e., the solution amount 2614 fully consumes the reagent 2610 without leaving any excess un-reacted solution).

As shown in FIG. 27, the reservoirs 2608, 2612 include seals 2700, 2702. The seals 2700, 2702 in one example include, but are not limited to, pliable seals, brittle seals and the like. As described below, seals 2700, 2702 are configured for piercing by elements on the activator 2606 and the solution reservoir 2612. Opening of the seals 2700, 2702 allows communication between the solution reservoir 2612 and reagent reservoir 2608. The reservoirs 2608 and 2612 further include graduated nozzle elements 2630, 2632. The graduated nozzle element 2630 of the reagent reservoir 2608 is sized and shaped to engage against a corresponding surface 2624 in the body 2602 and dispensing reservoir tip 2604. The corresponding surface 2624 receives the reagent reservoir 2608 and holds it in place relative to the device 2700. The graduated nozzle element 2632 of the solution reservoir 2612 provides a piercing surface sized and shaped to engage against the seal 2700 on the reagent reservoir 2608. As described below, the graduated nozzle element 2632 engages against the seal 2700 and pierces the seal allowing communication between the solution reservoir 2612 and reagent reservoir 2608. In yet another example, the graduated nozzle element 2632 of the solution reservoir 2612 provides a small orifice for the solution reservoir. When sealed, the solution reservoir 2612 provides a vacuum to hold the solution 2614 within the solution reservoir 2612. Once the seal 2702 is opened (described below) the vacuum within the solution reservoir 2612 is released thereby allowing the solution 2614 to flow out of the solution reservoir and into the reservoir 2608 (where the seal 2700 has been previously broken).

Referring now to FIGS. 26B and 27, the activator 2606 is shown with a piercing element 2626 having a piercing tip 2628. The piercing tip 2628 is sized to engage with the seal 2702 on the solution reservoir 2612 and pierce the seal 2702 thereby releasing the vacuum holding the solution 2614 within the solution reservoir. In one example, the piercing tip 2628 has a blunt geometry relative to the geometry of the graduated nozzle element 2632 of the solution reservoir 2612. The blunt configuration of the piercing tip 2628 ensures that when the piercing tip is engaged with the seal 2702 the solution reservoir 2612 is driven toward the reagent 2608 without initially piercing the seal 2702. Instead, the graduated nozzle element 2632 of the solution reservoir 2612 is driven into the seal 2700 of the reagent reservoir 2608. The graduated nozzle element 2632 pierces the reagent reservoir seal 2700 thereby allowing communication between the reservoirs 2608, 2612. Continued movement of the activator 2606 seats the solution reservoir 2612 with the reagent reservoir 2608 and the piercing tip 2628 pierces through the solution reservoir seal 2702 thereby releasing the vacuum on the solution reservoir 2612. The solution 2614 is then free to flow into the reagent reservoir 2608 from the solution reservoir 2612. In still another example, the seals 2700 and 2702 are selected so the seal 2702 is made of a stronger material relative to the seal 2700 (e.g., the seal 2702 is more resistant to piercing). Engagement of the activator 2606 against the seal 2702 thereby pushes the solution reservoir 2612 including the graduated nozzle element 2632 into engagement with the seal 2700 and pierces the seal. The piercing tip 2628 then subsequently pierces the robust seal 2702 and releases the vacuum within the solution reservoir 2612 to allow the solution 2614 to flow into the now opened reagent reservoir 2608.

Referring now to FIG. 27, a collar 2704 is shown having lip 2706. The collar 2704 is slid over the activator 2606 into engagement with the body 2602, in one example (see FIG. 26B, 26A). The collar 2704 is coupled with the body 2602 for instance by mechanical interfitting, welding, adhesives and the like. The activator 2606, in yet another example, includes a flange 2708. The flange 2708 optionally includes a soft gasket sized and shaped to extend between the activator 2606 and a body interior 2603. The soft gasket 2708 substantially prevents movement of fluids, such as solution 2614, out of the body 2602 while the activator 2606 is being depressed relative to the body 2602. Additionally, the gasket 2708 substantially prevents the intrusion of particulate matter, fluids and other unwanted materials into the body 2602 during transport and prior to use. In still another example, the flange 2708 includes a hard flange sized and shaped to extend between the activator 2606 and the body interior 2603. The hard flange prevents movement of liquids such as the solution 2614 between the activator 2606 and the body 2602 (i.e., movement of the solution out of the device 2600 near the activator 2606 as opposed to out of the dispensing reservoir tip 2604). The flange 2708 engages against the lip 2706 and substantially prevents removal of the activator 2606 relative to the body 2602 when the activator 2606 is moved away from the reservoir tip 2604.

As previously described with other examples, the device 2600 allows the user to select the reagent reservoir 2608 with a particular reagent and a solution reservoir 2612 with a particular solution according to the diagnostic or testing needs of the particular application. In one example, the user chooses a reagent or reagents from a catalog along with the appropriate solutions and assembles the device 2600 by loading the body 2602 with the appropriate reagent reservoirs and solution reservoirs. The activator 2606 is coupled with the body 2602 to close the device and the optional collar 2704 is slid over the activator and engaged with the body 2602 to substantially prevent disassembly of the device 2600.

Figure 28:
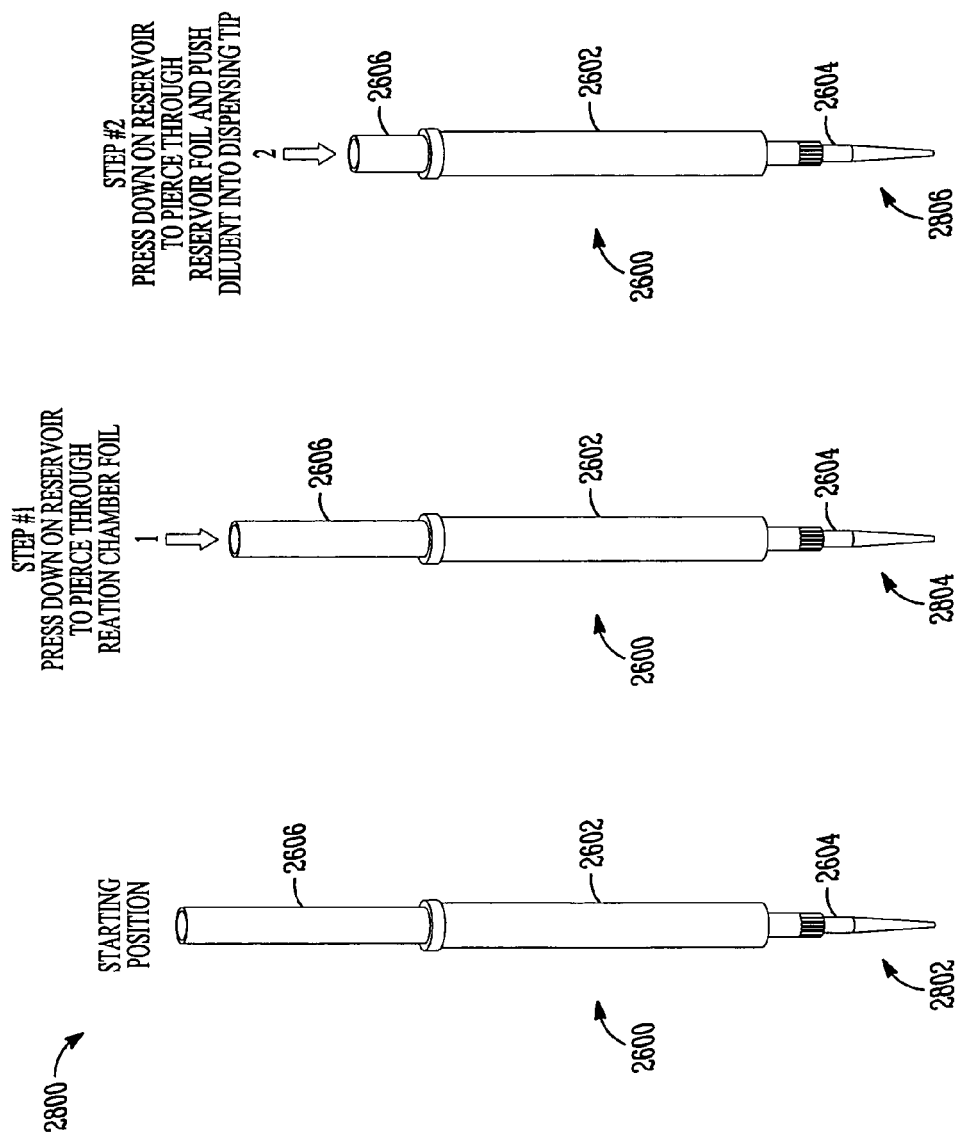

A method 2800 for using the reagent preparation and dispensing device 2600 (see FIGS. 26A through 27) is shown in FIG. 28. Reference is made to the elements and functions described in FIGS. 26A through 27 and included as examples in the method herein.

At 2802, the device 2600 is shown in a starting position. The dispensing reservoir tip 2604 is coupled with the body 2602 and the activator 2606 is in a first position away from the dispensing reservoir tip 2604. The reagent reservoir 2608 and solution reservoir 2612 are loaded within the body 2602 and have their seals 2700, 2702 in a non-pierced state.

At 2804, the activator 2606 (e.g., a plunger) is moved toward the dispensing reservoir tip 2604. As previously described, the piercing tip 2628 of the activator 2606 engages against the seal 2602 of the solution reservoir 2612. The graduated nozzle element 2632 of the solution reservoir 2612 is moved into engagement with the seal 2700 of the solution reservoir 2608 and thereby pierces the seal 2700 allowing communication between the solution reservoir 2612 and reagent reservoir 2608.

At 2806, the activator 2606 is further moved toward the dispensing reservoir tip 2604. The continued movement of the activator 2606 moves the solution reservoir 2612, in one example, into engagement with the reagent reservoir 2608. The piercing tip 2628 of the piercing element 2626 thereafter penetrates the seal 2702 releasing the vacuum within the solution reservoir 2612. The solution 2614 flows through the solution reservoir 2612, for instance through the graduated nozzle element 2632 and into the reagent reservoir 2608. The solution 2614 mixes with the reagent 2610 to form a specified amount of a reagent solution. In one example, the reagent solution flows by gravity into the dispensing reservoir tip 2604 through the graduated nozzle element 2630 of the reagent reservoir 2608. The reagent solution flows out of the dispensing reservoir tip 2604 and out of the device 2600. In another example, continued movement of the activator 2606 applies pressure behind the reagent solution forcing the solution out of the reagent reservoir 2608 and into the dispensing reservoir tip 2604. Continued movement of the activator 2606 forces the solution out of the dispensing reservoir tip 2604 and out of the device 2700. Optionally the dispensing reservoir tip 2604 is substantially transparent or semi-transparent and allows the user to visually identify the reagent solution within the dispensing reservoir tip and confirm the completion of mixing between the solution and reagent prior to dispensing the solution out of the device 2600.

Figures 29A, 29B:
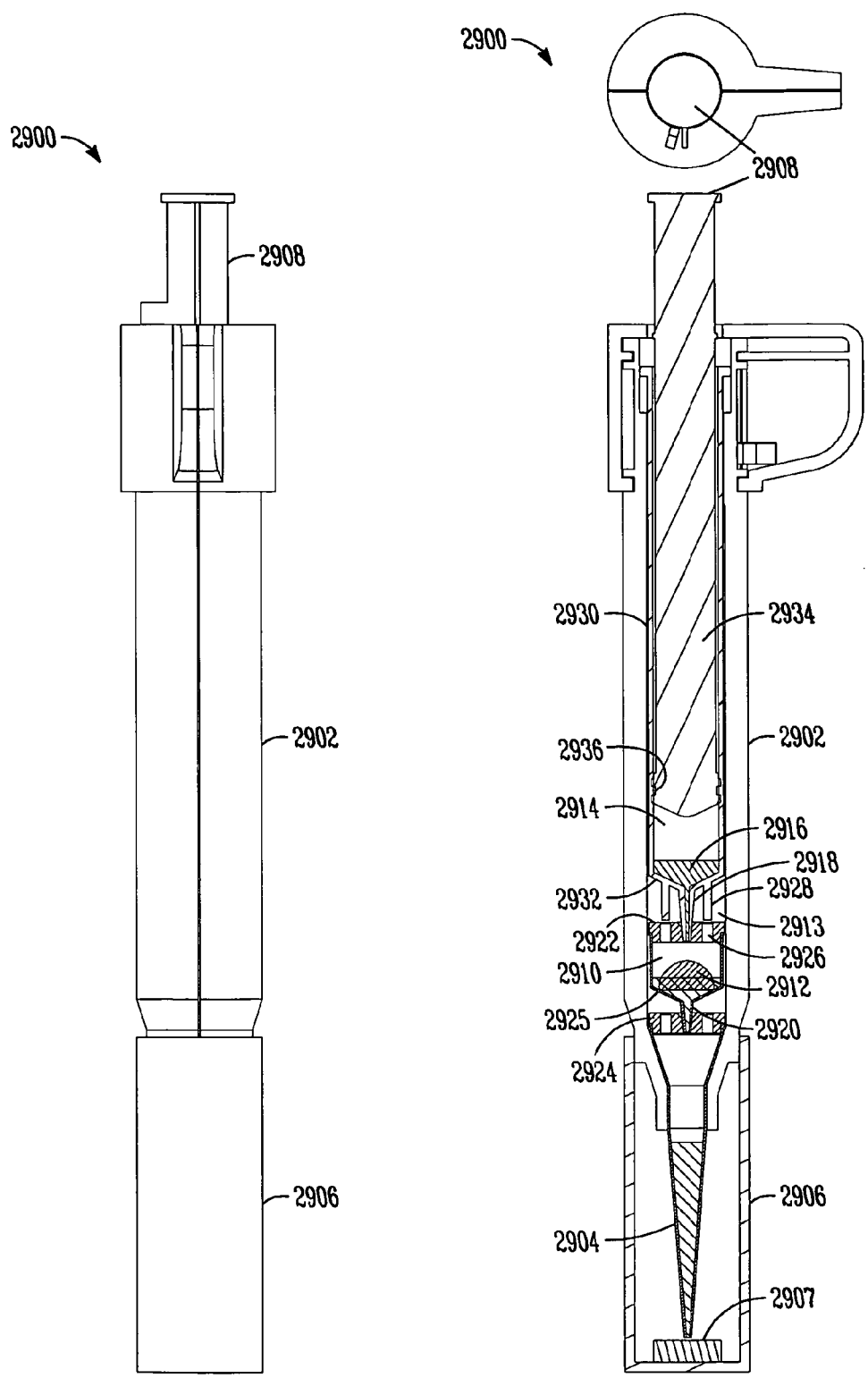

Yet another example of a reagent preparation and dispensing device 2900 is shown in FIGS. 29A, B, 30 and 31. Device 2900 includes a body 2902 and a dispensing reservoir tip 2904 coupled with the body 2902. A cover 2906 is coupled with the body 2902 and extends over the dispensing reservoir tip 2904 during storage and transportation. The cover 2906 substantially prevents damage to the dispensing reservoir tip during transportation and prior to use. In one example, the cap 2906 includes a desiccant 2907 positioned adjacent to the dispensing reservoir tip nozzle. Desicant 2907 is provided to absorb moisture within the cap and dispensing reservoir tip prior to use of the device. Positioning the desiccant near the dispensing reservoir tip nozzle ensures the desiccant will draw moisture out of the dispensing reservoir tip and maintain a dry environment around reagents. As described further below, the reagent used with the device 2900 in one example includes a lyophilized reagent. The desiccant 2907 substantially prevents introduction of moisture to the lyophilized reagent prior to its reconstitution through a solution provided in the device 2900. The device 2900 further includes an activator 2908 sized and shaped to move relative to the body 2902. In one example, the activator 2908 includes a plunger sized and shaped to slide relative to the body 2902. As described below, the activator 2908 is operable to open solution reservoirs, reagent reservoirs and mix a solution with reagents to form a specified amount of a reagent solution for dispensing out of the dispensing reservoir tip 2904.

Figure 30:
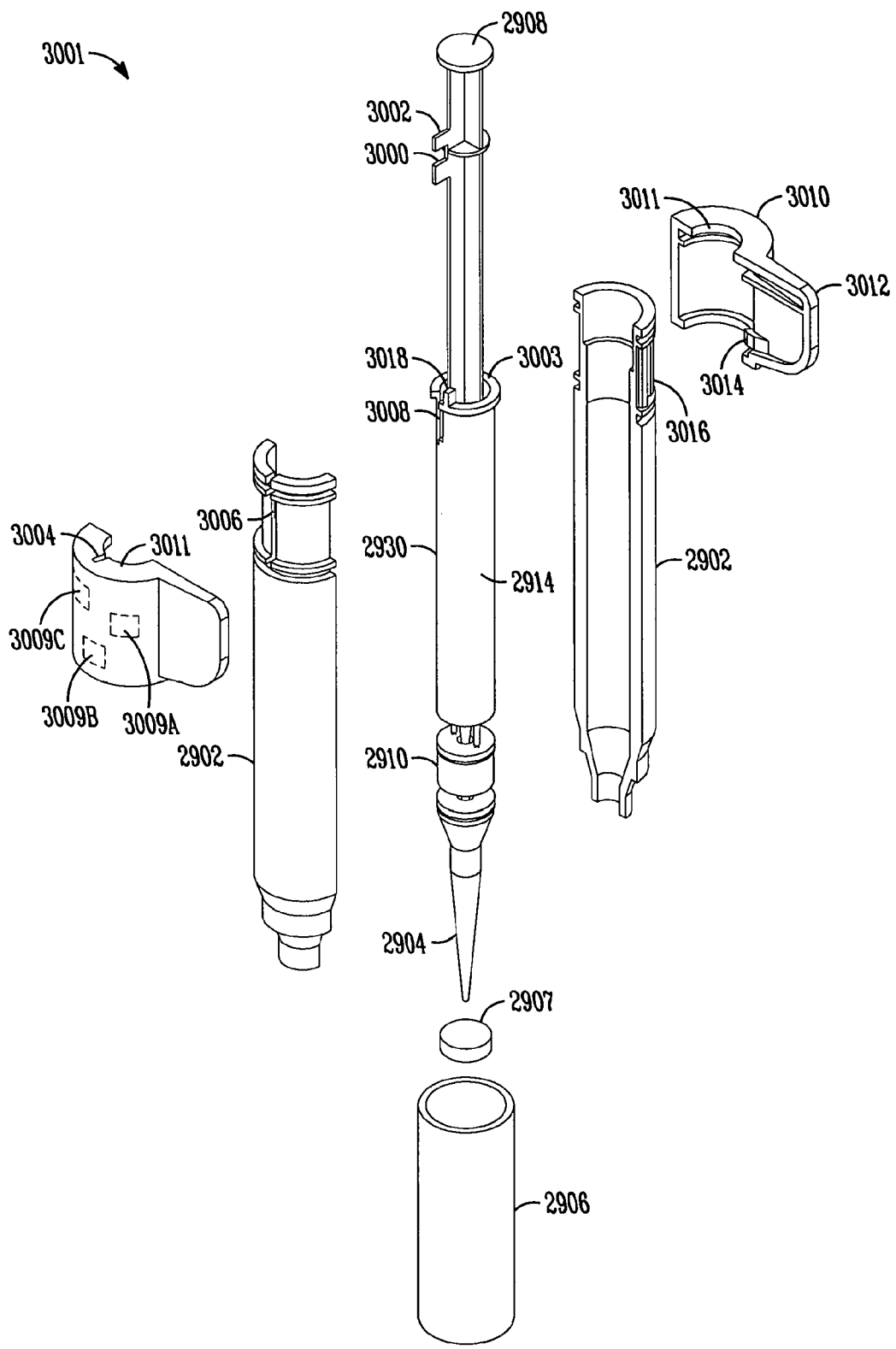

Referring now to FIGS. 29B and 30, a reagent reservoir 2910 is shown enclosed within the body 2902. A solution reservoir 2914 is disposed adjacent to the reagent reservoir within the body 2902. In one example, the reagent reservoir 2910 contains a reagent 2912 including but not limited to a lyophilized reagent (e.g., a freeze-dried reagent), a solution reagent, a powdered reagent and the like. The solution reservoir 2914 includes a solution 2916. The solution 2916 is mixed with the reagent 2912 to form a specified amount of the reagent solution. The solution 2916 includes but is not limited to saline, distilled water, pH buffered water and the like. As shown in FIG. 29B, the reservoirs 2910, 2914 include seals. For example, the reagent reservoir 2910 includes a dispensing reservoir tip seal 2924 interposed between the dispensing reservoir tip 2904 and the reagent reservoir 2910. The device 2900 further includes a reagent reservoir seal 2922 interposed between the solution reservoir 2914 and the reagent reservoir 2910. As shown in FIG. 29B, in one example, the reagent reservoir seal 2922 includes a plug disposed within the reagent reservoir 2910. Seals 2924 and 2922 in another example, include a frangible seal capable of fracturing when pressure is applied. In yet another example, the seals 2924 and 2922 are pliable seals capable of being pierced by a piercing element as described below.

As shown in FIG. 30 the reagent reservoir 2910 and solution reservoir 2914 are separate bodies loaded within the body 2902. In one example, the reagent reservoir 2910 and solution reservoir 2914 are prepackaged devices including the reagent 2912 and solution 2916. In another example, a user may select a reagent reservoir 2910 and a solution reservoir 2914 appropriate to a specific diagnostic or testing purpose. Optionally, the user may select the reagent reservoir and solution reservoir from a catalog of agents and solutions to assemble a device 2900 configured for a specific diagnostic or testing purpose. The device 2900 thereby provides a flexible system for containing and preparing reagents and solutions for a variety of diagnostic and testing schemes.

Referring again to FIG. 29B, the reagent reservoir 2910 is shown with a piercing nozzle 2920. Similarly, the solution reservoir 2914 is shown with a piercing nozzle 2918. Piercing nozzles 2918 and 2920 are sized and shaped to penetrate through the seals 2922 and 2924. By penetrating the seal 2922 with the piercing nozzle 2918 (described below) the solution reservoir 2914 is put into communication with the reagent reservoir 2912. Similarly, piercing the seal 2924 with the piercing nozzle 2920 allows communication between the reagent reservoir 2912 and the dispensing reservoir tip 2904 thereby allowing dispensing of the reagent solution.

In one example, seal 2922 includes vents 2926 disposed adjacent to the location where the piercing nozzle 2918 extends through the seal 2922. The solution reservoir 2914, in another example, includes prongs 2928 sized and shaped to penetrate through the seal 2922 at vents 2926. Piercing of the seal 2922 through the vents 2926 allows pressure built up between the solution reservoir 2914 as it moves toward the reagent reservoir 2910 to escape out of the reagent reservoir 2910 and into the space 2913 between the reagent reservoir 2910 and solution reservoir 2914. This substantially prevents a violent expulsion of the solution 2916 into the reagent reservoir 2910 and aids in preventing premature opening of the seal 2924 from increased pressure.

As shown in FIG. 29B and FIG. 30 the solution reservoir 2914 in one option includes a composite body constructed with the activator 2908 and intermediate housing 2930. As shown, the activator 2908 is slid into engagement with the intermediate housing 2930 to form a sealed environment for the solution 2916. As previously described, the reagent reservoir 2910 and solution reservoir 2914 are separate devices that are loaded within the body 2902. The composite solution reservoir 2914 constructed the intermediate housing 2930 and the activator 2908 is similarly a separate device from the body 2902. In one example, the activator 2908 is positioned within the intermediate housing 2930, the activator 2908 is then drawn away from the piercing nozzle 2918 to draw the solution 2916 into the solution reservoir 2914. The solution 2916 is retained within the solution reservoir 2914 through a vacuum, in one example. After the solution 2916 is disposed within the solution reservoir 2914 the assembled solution reservoir 2914 is loaded within the body 2902.

Referring now to FIG. 30, the device 2900 is shown with a key and lock system 3001. The activator 2908, for example, includes a key 3002. As described below, the key 3002 is moved through the body 2902 and intermediate body 2930 to allow discrete movements of the activator 2908 to open the seal 2922 (FIG. 29B), seal 2924, move the solution 2916 into the reagent reservoir 2910, move the reagent solution into the dispensing reservoir tip 2904, dispense the solution out of the device 2900. Referring again to FIG. 30, the key and lock system 3001 includes a locking collar 3010 having a lever 3012 extending from the collar 3010. The locking column 3010 is disposed around the body 2902 and sized and shaped rotate relative to the body 2902. As shown, the locking collar 3010 includes at least one groove 3004. The groove 3004 is sized and shaped to receive the key 3002 on the activator 2908. The locking collar 3010, in another example, includes a feature, such as a pawl or detent 3014 sized and shaped to engage with ridges 3016 extending around at least a portion of the body 2902. The detent 3014 and ridges 3016 cooperate to ensure one way movement of the locking collar relative to the body 2902. One way movement of the locking collar 3010 correspondingly allows a single movement direction of the activator 2908. For instance, the activator 2908 is only allowed to move toward the dispensing reservoir tip 2904. Withdrawing of solution and/or reagent solution into the intermediate body 2930 of the solution reservoir 2914 is thereby prevented. That is to say one way movement through the device 2900 is allowed with respect to the solution 2916 and reagent solution formed by mixing the solution 2916 with the reagent 2912.

The key and lock system 3001 includes the first groove 3004, a second groove 3006 and a third groove 3008. The locking collar 3010 includes, in one example, projections 3009a, b, c on the interior of the tower 3010. The key 3002 is sized and shaped to pass through the grooves 3004, 3006, 3008 and engage with the projections 3009a, b, c (described below). Movement through the grooves 3004, 3006, 3008 and engagement with the projections 3009a, b, c allows discrete selective movement of the activator 2908 and thereby permits selective opening of the reservoirs 2910, 2914, mixing of the solution 2916 and reagent 2912, and dispensing of the reagent solution through a dispensing reservoir tip 2904 (FIG. 29B).

Figure 31:
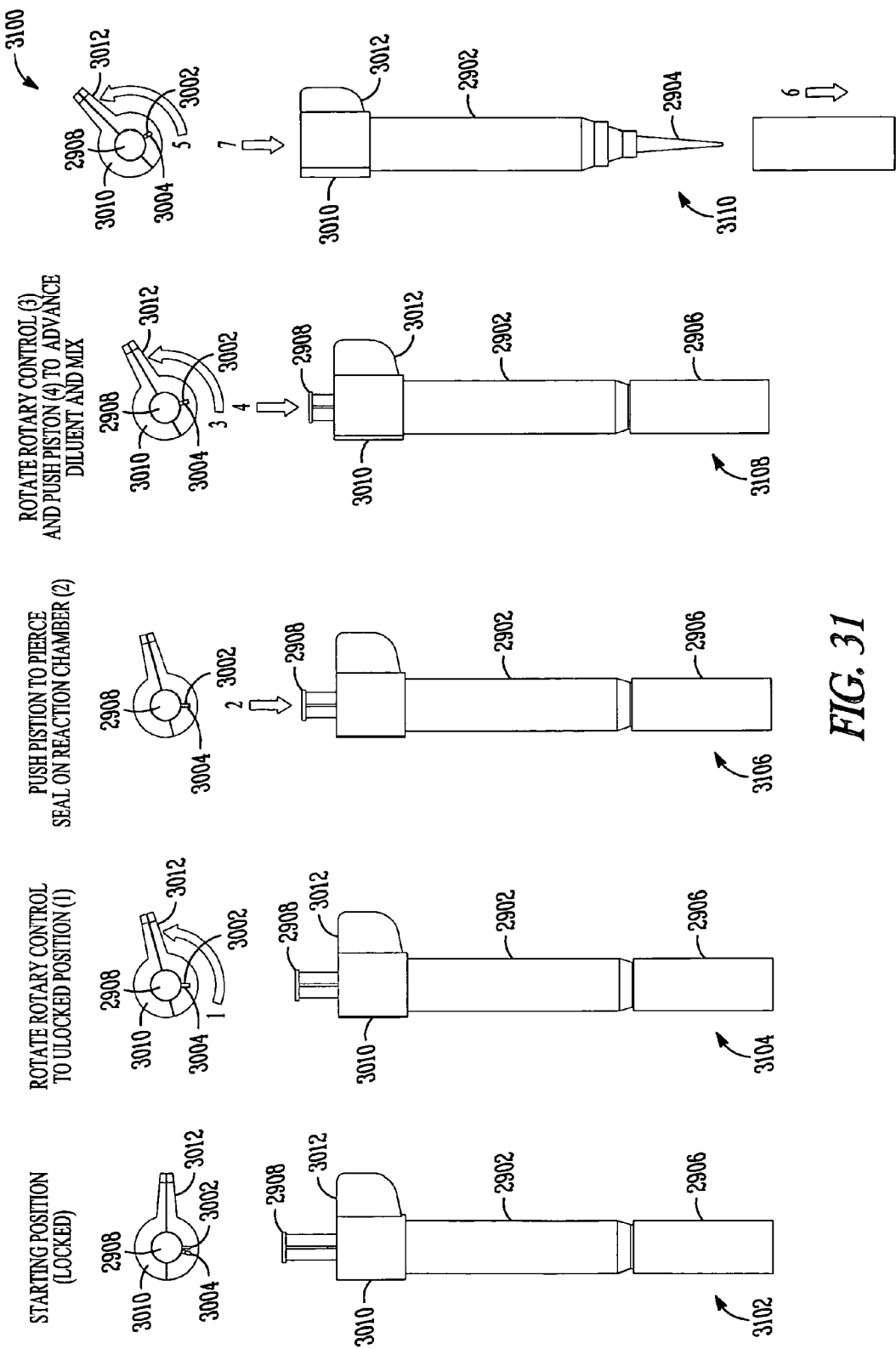

A method 3100 for using the reagent and dispensing device 2900 shown in FIGS. 29A through 30 is shown in FIG. 31. As examples, reference is made with the method 3100 to elements and functions described above and shown in FIGS. 29A-30.

At 3102 the device 2900 is shown in the starting position with the cap 2906 positioned over the dispensing reservoir tip 2904 and the activator 2908 in a first position. The locking collar 3010 having the groove 3004 is out of phase with the key 3002 of the activator 2908 thereby locking the activator 2908 in the position shown. Referring again to FIG. 30, the key 3002 includes a groove 3000. In the starting position a flange 3011 in the locking collar 3010 is received within the groove 3000 thereby preventing movement of the activator 2908 forward or backward relative to the dispensing reservoir tip 2904.

At 3104 the locking collar 3010 is rotated relative to the body 2902. Rotation of the locking collar 3010 brings the groove 3004 into alignment with the key 3002 thereby allowing the activator 2908 to move relative to the body 2902. In another example, the key 3002 is disposed within the groove 3006 on the body 2902 thereby allowing the key 3002 to pass through at least a portion of the body 2902 while the activator 2908 is moved to pierce the seals 2922 and 2924, and move the solution 2916 into the reagent reservoir 2910 as described below.

At 3106 the activator 2908 is depressed towards the dispensing reservoir tip 2904 (FIG. 29B and FIG. 30). The key 3002, in one example, engages against flange 3003 of the intermediate body 2930. Movement of the activator 2908 is thereby transmitted through the key 3002 to the intermediate body 2930. Movement of the body 2930 correspondingly moves the piercing nozzle 2918 into engagement with the seal 2922 interposed between the solution reservoir 2914 and reagent reservoir 2910. The piercing nozzle 2918 is driven through the seal 2922 to allow communication between the solution reservoir 2914 and the reagent reservoir 2910. In one example, after movement of the activator 2908 into a position where the piercing nozzle element 2918 is driven through the seal 2922, the key 3002 is engaged against a projection 3009A on the locking collar 3010. The projection 3009A arrests movement of the activator 2908 and prevents the driving of the intermediate body 2930 toward the dispensing reservoir tip.

At 3108 the locking collar 3010 is rotated again relative to the body 2902. Rotation of the locking collar 3010 moves the projection 3009A out of engagement with the key 3002 thereby allowing movement of the activator 2908 toward the dispensing reservoir tip 2904. The key 3002 is engaged by the projection 3009c on the interior of the locking column 3010. Engagement between the projection 3009c and the key 3002 rotates the activator 2908 relative to the groove 3008 of the intermediate body 2930 thereby allowing movement of the key 3002 along the groove 3008. The activator 2908 is then moved toward the dispensing reservoir tip 2904. The activator 2908 moves relative to the intermediate body 2930 thereby moving the solution 2916 out of the solution reservoir 2914 and into the reagent reservoir 2910 where it mixes with the reagent 2912 to form the specified amount of a reagent solution. In one example, the activator 2908 including the key 3002 is engaged with the projection 3009B on the interior of the locking tower 3010. Engagement of the key 3002 with the projection 3009B arrests further movement of the activator 2908 toward the dispensing reservoir tip 2904.

At 3110 the locking tower 3010 is rotated again relative to the body 2902. Rotation of the locking column 3010 moves the key 3002 out of engagement with the projection 3009B on the interior of the column 3010. The activator 2908 is thereby able to move relative to the body 2902. In one example, movement of the activator 2908 engages an activator head 2934 of the activator against a bottom surface 2932 of the solution reservoir 2914. Continued movement of the activator 2908 is transmitted through intermediate body 2930 and drives the intermediate body 2930 into the reagent reservoir and the piercing nozzle 2920 of the reagent reservoir 2910 is driven into the seal 2924 and pierces the seal 2924. Further movement of the reagent reservoir 2910 toward the dispensing reservoir tip 2904 is arrested by engagement between the bottom surface 2925 of the reagent reservoir with the remains of the seal 2924. The activator 2908 however continues to move toward the dispensing reservoir tip and the further movement of the activator 2908 pressurizes the reagent solution formed in the reagent reservoir 2910 and forces it into the dispensing reservoir tip 2904 for inspection by the user where the dispensing reservoir tip is transparent or semi-transparent. Further movement of the activator 2908 pushes the reagent solution out of the device 2900 through the dispensing reservoir tip 2904.

In another example, the activator 2908 is grasped and held by activator detent 2936 extending between activator 2908 and intermediate body 2930 as shown in FIG. 29B. As the activator 2908 is grasped by intermediate body 2930 movement of the activator 2908 is transmitted by the intermediate body and subsequently transmitted through the bottom surface 2932 of the solution reservoir 2914 into the reagent reservoir 2912 thereby driving the piercing nozzle 2920 into the seal 2924 and piercing the seal 2904. Continued movement of the activator 2908 overcomes the resistance provided by the activator detent 2936 thereby allowing the activator 2907 to move relative to the intermediate housing 2930 again. Continued movement of the activator 2908 applies a pressure behind the reagent solution formed within the reagent reservoir 2910 and forces the solution into the dispensing reservoir tip 2904. Continued movement of the activator 2908 forces the reagent solution out of the dispensing reservoir tip 2904.

Continued movement of the activator 2908 forces the reagent solution through the dispensing reservoir tip 2904 and out of the device 2900.

Figure 32A:
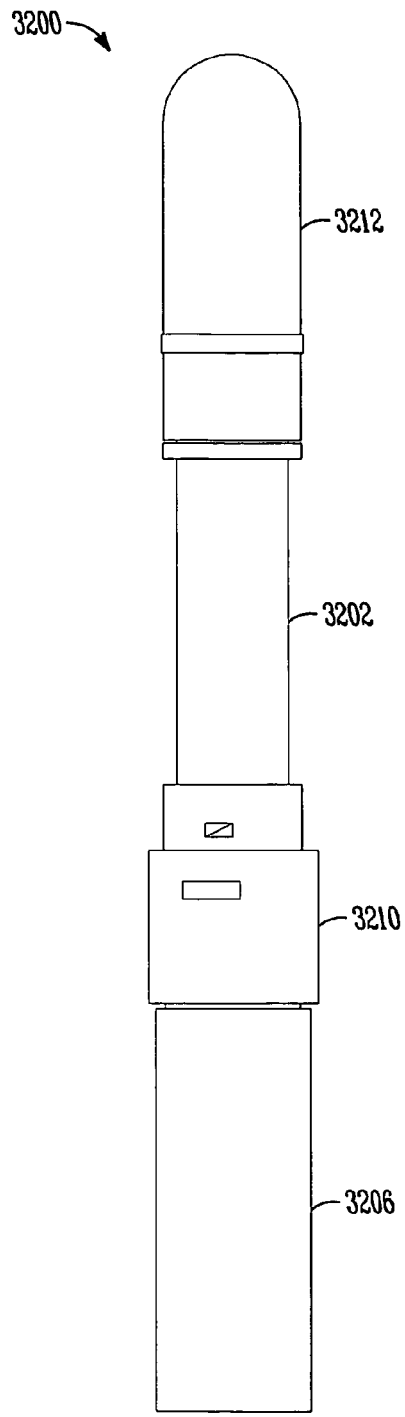
FIG. 32a is a side view of one example of a reagent preparation and dispensing device including a multi-stage key and lock system.

Another example of a reagent preparation and dispensing device 3200 is shown in FIGS. 32A, B, 33 and 34. Referring to FIGS. 32A and B the device 3200 includes a body 3202, dispensing reservoir tip 3204 coupled with the body 3202 and first and second activators 3210 and 3212. Device 3200 further includes a reagent reservoir 3214 containing a reagent 3216. The reagent 3216 includes, but is not limited to, a lyophilized reagent, solution reagent, powder reagent and the like. In yet another example, the solution reservoir 3214 includes multiple reagents. A solution reservoir 3218 is coupled with the body 3202. The solution reservoir contains a solution 3220. Solution 3220 is configured to mix with reagent 3216 and form a specified amount of the reagent solution.

Figure 32B:
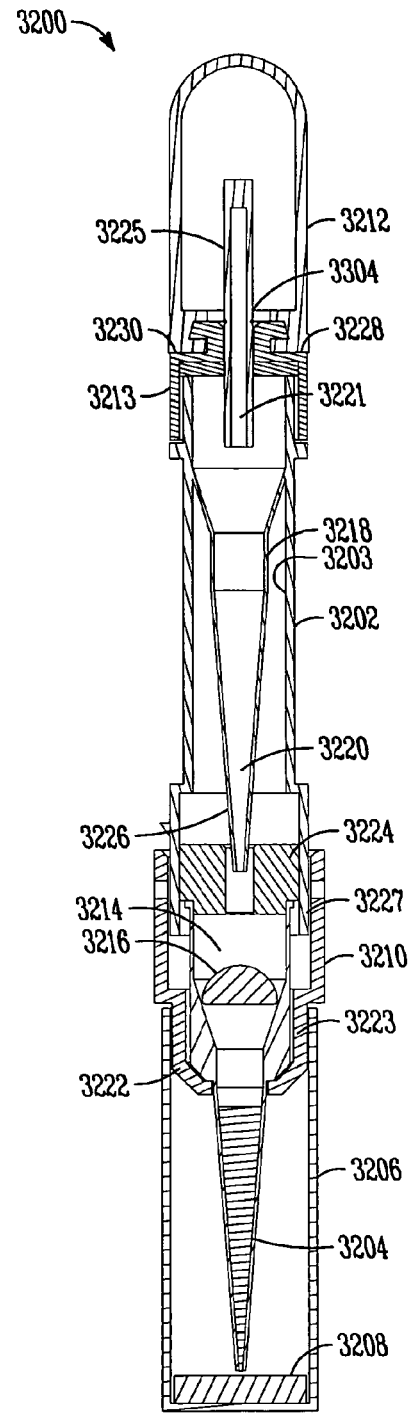
Figure 33:
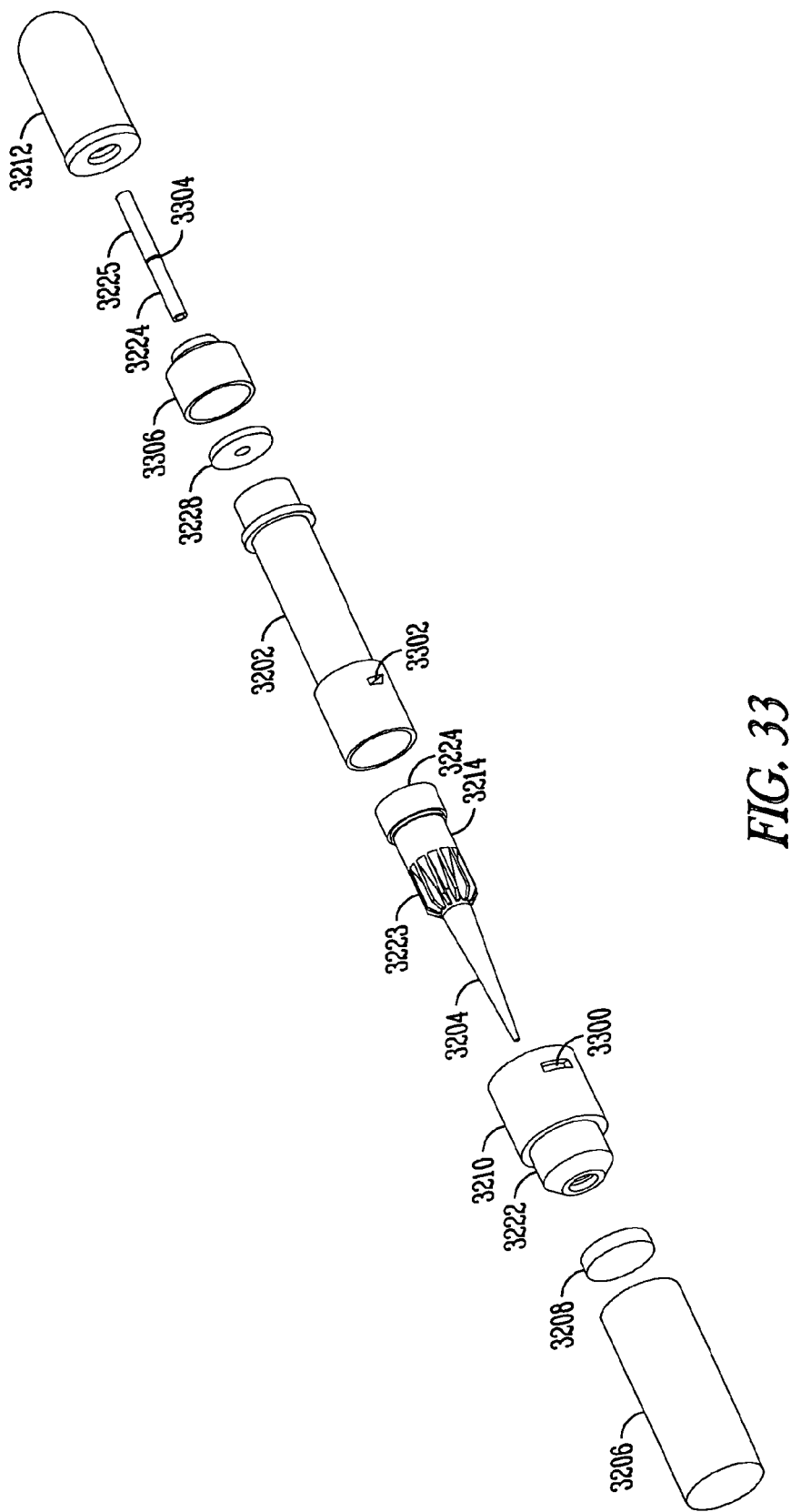

Turning now to FIGS. 32B and 33, in one example, the reagent reservoir 3214 is a composite device coupled with the body 3202. The reagent reservoir 3214, as previously described, includes the reagent 3216 and also includes the dispensing reservoir tip 3204. The reagent reservoir 3214 couples with the body 3202 and the first activator 3210. In another example, the first activator 3210 couples over the reagent reservoir 3214 and engages with the body 3202. The first activator 3210 includes a tip flange 3222 sized and shaped to engage against a corresponding surface 3223 of the dispensing reservoir tip 3204. The first activator 3210 thereby engages with the corresponding surface 3223, and the activator 3210 when coupled with the body 3202 retains the dispensing reservoir tip 3204 and reagent reservoir 3214 against the body 3202. In one example, the first activator 3210 is slidable relative to the body 3202. Movement of the activator 3210 relative to the body 3202 thereby advances the reagent reservoir 3214 toward the solution reservoir 3218 within the body 3202. In yet another example, the first activator 3210 includes a feature such as threaded engaged with corresponding threading on the body 3202. Rotation of the activator 3210 thereby moves the first activator toward or away from the solution reservoir 3218 as further described below. As shown in FIG. 33, the first activator 3210 includes orifices 3300 sized and shaped to slide over projections 3202 on the body 3202. As described below, as the first activator 3210 is advanced along the body 3202 the orifices 3300 slide over the projections 3302 thereby locking the first activator in place along the body 3202 thereby substantially preventing removal of the first activator and holding the reagent reservoir 3214 in place against the solution reservoir piercing nozzle element 3226 (described below).

Referring now to FIG. 32B the solution reservoir 3218 is shown positioned within the body 3202. As shown the solution reservoir 3218 includes a piercing element 3226 (e.g., a graduated nozzle element). The reagent reservoir 3214 includes a seal 3224 interposed between the piercing nozzle element 3226 and the reservoir space. In one example, the seal 3224 includes but is not limited to a pliable seal, a frangible seal and the like. Seal 3224 is sized and shaped for penetration by the piercing nozzle element 3226 by movement of the first activator 3210 as described below.

Solution reservoir 3218 retains the solution 3220 by a vacuum, in yet another example. As shown in FIG. 32B and FIG. 33 the solution reservoir includes a capillary tube 3221 extending at least partially into the solution reservoir 3218. The capillary tube 3221 includes a weakened portion 3204 such as a score line, weakened material and the like. While the capillary tube is in an unbroken condition the capillary tube maintains the vacuum within the solution reservoir 3218 thereby holding the solution 3220 within the solution reservoir 3218. The graduated nozzle element 3226 provides a narrow opening space that substantially prevents movement of the solution out of the solution reservoir prior to opening of the capillary tube 3221. In one example, a gasket 3228 is positioned around the capillary tube 3221 and is placed over an end of the solution reservoir 3218 on the body 3202. The second activator mount 3215 is position over the gasket 3228 and tightly engages the gasket 3228 with the body 3202 to maintain the vacuum within the solution reservoir 3218. In one example the second activator mount 3230 is fixably coupled at the body 3202, for instance, by threading, mechanical interfitting, adhesives, welding and the like. The second activator 3212 is then coupled with the second activator mount 3213.

The second activator 3212, in one example, includes a bulb configured for deflection relative to the body 3202. As shown in FIG. 32B, a portion of the capillary tube 3225 extends into the second activator 3212. A portion of the second activator 3212 is moved to engage with the portion 3225 (e.g., grasps the portion 3225). Engagement with the portion 3225 allows the user to fracture the capillary tube at the weakened portion 3304 thereby releasing the vacuum within the solution reservoir 3218. In one example, the second activator 3212 is then operated, for instance, by deflecting the bulb to apply a pressure to the solution 3220 and force the solution out of the solution reservoir 3218 and into the reagent reservoir 3214. In yet another example, vents 3230 are provided between the second activator mount 3213 and second activator 3212 thereby allowing the introduction of atmospheric gas into the second activator 3212. The solution 3220 is thereby able to flow out of the solution reservoir 3218 as gas will pass through the vents 3213 into the second activator 3212 and flow through the capillary tube 3221.

The device 3200 further includes a cap 3206 positioned over the dispensing reservoir tip 3204 during transport and just prior to use to protect the dispensing reservoir tip from contaminants and the like. In one example, the cap 3206 includes a desiccant 3208. The desiccant 3208 is configured to remove moisture from the dispensing reservoir tip 3204 and reagent reservoir 3214 prior to use. Use of the desiccant 3208 maintains a dry environment around the reagent 3216 thereby ensuring the proper mixing of the reagent 3216 with the solution 3220.

In one example, the solution reservoir 3218 is a separate piece from the body 3202. The solution reservoir 3218 is positioned within the body 3202 and held in position by the interior wall 3203 of the body 3202. As previously described in other embodiments, where at least one of the solution reservoir 3218 and reagent reservoir 3214 are separable from the body 3202 a variety of reservoirs with varying reagents 3216 and solutions 3220 are available for selection and assembly with the device 3200. The user is thereby able to assemble a device 3200 having a variety of diagnostic and testing purposes based on the selection of reagents and solutions.

Figure 34:
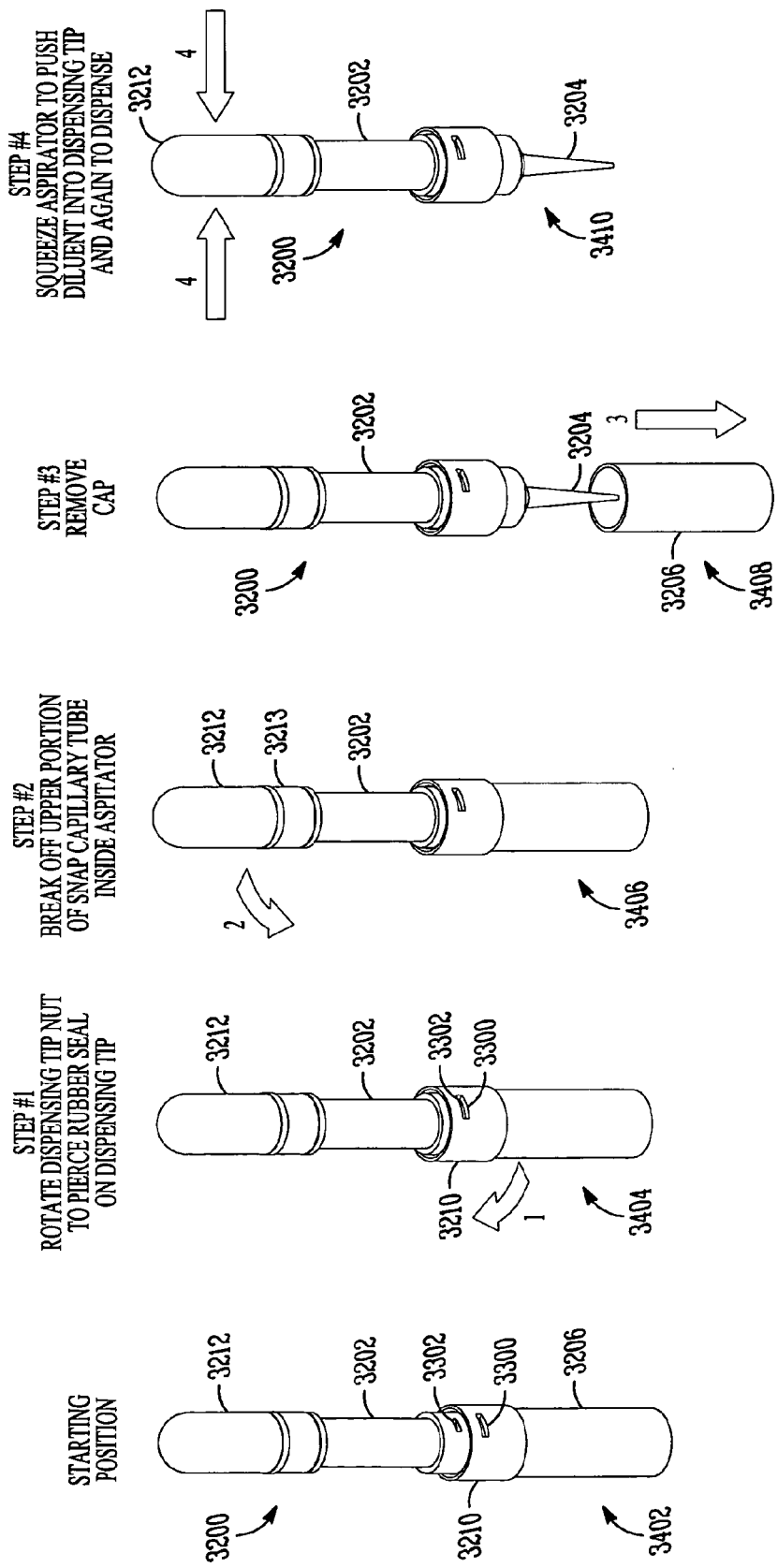

A method 3400 for using the device 3200 is shown in FIG. 34. Reference is made to FIGS. 32A, 32B and 33, and for convenience elements and functions described in those figures and in the preceding passages is included in the description of the method 3200.

At 3402 the device 3200 is shown in a starting position. At the starting position the cap 3206 is positioned over a dispensing reservoir tip 3204. The first activator 3210 is in a starting position relative to the body 3202. As shown in FIGS. 34 and 33, an orifice 3300 on the first activator 3210 is shown positioned away from a projection 3302 on the body 3202 as described further below engagement of this orifice with the protrusion 3302 acts to prevent movement of the first activator 3210 away from the body 3202.

At 3404, the first activator 3210 is rotated relative to the body 3202. As previously described, the first activator 3210 and the body 3202 are threaded so that rotation of the first activator moves the first activator axially along the body 3202. As shown in 3404 the orifices 3300 are slid over the projections 3302 substantially preventing movement of the first activator 3210 away from the body 3202. In yet another example, the first activator 3210 is slidable (e.g., axially) along the body 3202 and into the position shown at 3404. Movement of the activator 3210 correspondingly moves the dispensing reservoir tip 3204 towards the piercing nozzle element 3226 of the solution reservoir 3218. The piercing element 3226 as shown in FIG. 32 engages the seal 3224, pierces the seal and allows communication between the solution reservoir 3218 and the reagent reservoir 3214.

At 3406, the second activator 3212 is moved relative to the body 3202. In one example, the second activator 3212 includes the deflectable bulb and deflection of the bulb correspondingly engages with the capillary tube 3224 shown in FIGS. 32B and 33. The capillary tube 3224 is fractured along a weakened portion 3304 thereby allowing communication between the second activator 3212 and the solution reservoir 3218. Optionally, vents 3230 extend between the second activator 3212 and the second activator mount 3213 after the capillary tube 3224 is fractured. In this example, air is allowed to pass through the vents 3230 into the second activator 3212 and through the capillary tube 3224 thereby allowing the solution 3220 to move into the reagent reservoir 3214.

At 3408, the cap 3206 is removed from the device 3200. The dispensing reservoir tip 3204 is thereby exposed prior to use of the device 3200.

At 3410, the second activator 3212 is moved relative to the body 3202 (e.g., by deflection of a deflectable bulb). Movement of the activator 3212 moves the solution 3220 out of the solution reservoir 3218 and into the reagent reservoir 3214 where it mixes with the reagent 3216 to form a reagent solution. A reagent solution settles to the bottom of the dispensing reservoir tip 3204. In one example, where the dispensing reservoir tip 3204 is constructed with transparent or semi-transparent material the user is then able to inspect the reagent solution prior to dispensing. The second activator 3212 is then moved again (e.g., by deflection of the bulb) to apply pressure to the reagent solution in the dispensing reservoir tip 3204 and dispense the solution out of the tip and out of the device 3200.

Figure 35:
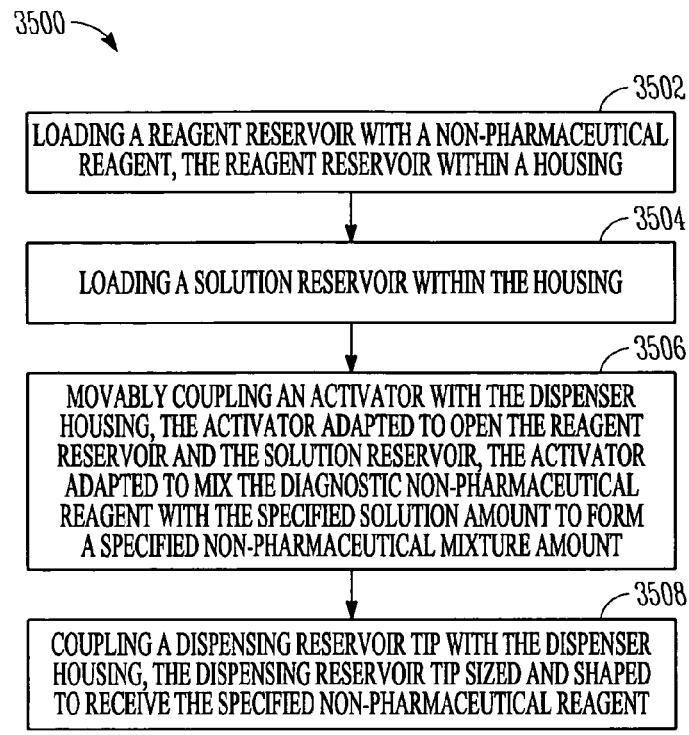
FIG. 35 is a block diagram showing one example of a method of making the devices shown in FIGS. 17a-34.

A method 3500 for making a reagent preparation and dispensing device (e.g., the devices 1700, 2000, 2300, 2600, 2900 and 3200 shown in FIGS. 17A through 34) is shown in FIG. 35. Reference is made to the devices shown in FIGS. 17A through 34 and previously described above. Additionally, the method 3500 is not limited to the devices shown in FIGS. 17A through 34, and where applicable reference is made to elements shown in the previous figures and description (e.g., such as FIG. 1A through FIG. 16).

At 3502 a reagent reservoir is loaded with a reagent. The reagent reservoir is placed within a housing. In one example, the reagent reservoir is slidably coupled with the housing and retained by the interior surface of the housing prior to use. In another example, the reagent includes one or more reagents configure to mix with a solution as described below to form a specified amount of a reagent solution. The reagent includes but is not limited to a lyophilized reagent (e.g., a freeze-dried reagent), a solution reagent, a powdered reagent and the like.

At 3504 a solution reservoir is loaded within the housing. In one example, the solution reservoir includes a separate reservoir from the reagent reservoir. In another example, the solution reservoir is an integral portion of an activator loaded in the housing as described in example devices above. The solution reservoir in yet another example includes a sufficient amount of solution configured to mix with the reagent and form a specified amount of a reagent solution. For instance, the solution reservoir includes a predetermined amount of solution and mixes with the reagent to form a specified amount of solution having a specified concentration (in other words the solution amount is predetermined to fully consume the reagent without having excess solution).

At 3506, an activator is moveably coupled with the dispenser housing. The activator is adapted to open the reagent reservoir and the solution reservoir. The activator is further adapted to mix the diagnostic reagent with the specified solution amount to form a specified amount of reagent solution. As previously described above, the activator includes but is not limited to a plunger, a deflectable bulb, a rotatable or slidable collar and the like. In yet another example, the activator operates to open the reservoirs by piercing seals on the reservoirs and allowing intermixing of the contents of the reservoirs (e.g., the reagents and the solutions). In still another example, the activator includes a tube that provides a vacuum within the reservoir. A portion of the tube is engaged with another portion of the activator that allows release of the vacuum and subsequent movement of the solution out of the solution reservoir and into the reagent reservoir containing the reagent.

At 3508, a dispensing reservoir tip is coupled with the dispenser housing. The dispensing reservoir tip is sized and shaped to receive the specified amount of reagent solution. In one example, the dispensing reservoir tip is constructed with, but not limited to, a transparent or semi-transparent material that allows viewing of the reagent solution prior to dispensing. The user may thereby verify that the reagent solution is the proper solution for the diagnostic or testing purpose. As previously described, the dispensing reservoir tip may be integrally formed with the housing. Optionally, the dispensing reservoir tip may be a separate piece from the housing that is coupled with the housing by welding, adhesives, mechanical interfitting and the like.

Figure 36:
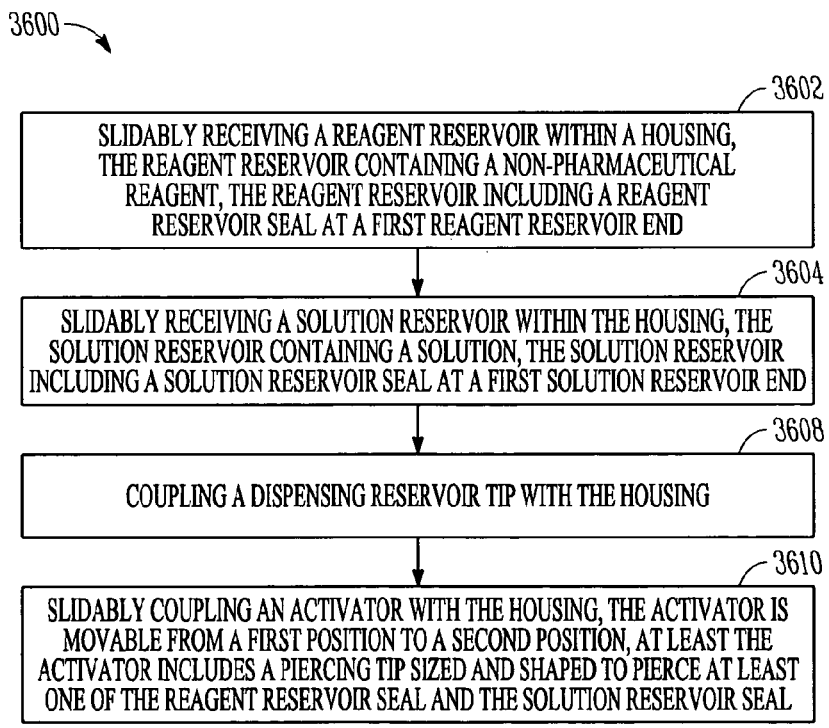
FIG. 36 is a block diagram showing another example of a method of making the devices shown in FIGS. 23a-31.

Another method 3600 for making a reagent preparation and dispensing device (e.g., devices 2300, 2600, and 2900 as shown FIGS. 23A through 31) is shown in FIG. 36. References are made with regard to the method 3600 to devices shown in FIGS. 23A through 31 including each of the elements shown in those drawings and previously described above. Additionally, the method 3600 is not limited to the devices shown in FIGS. 23A-31, and where applicable reference is made to elements shown in the previous figures and description (e.g., such as FIGS. 1A-22).

At 3602, a reagent reservoir is slidably received within the housing. The reagent reservoir contains a reagent including, but not limited to, a lyophilized reagent, a solution reagent, a powdered reagent and the like. In one example, the reagent reservoir includes at least one seal at a an end of the first reagent reservoir. In another example, the reagent reservoir includes seals at ends of the reagent reservoir. As previously described above, the seals include, in one example, a piercable seal sized and shaped to receive a piercing element. The seals include, but are not limited to, pliable seals, brittle seals and the like. In still another example, the reagent reservoir is separate from the housing and is slidably received inside an interior of the housing. The housing thereby receives the reagent reservoir and protects the reservoir during transport and prior to use. Additionally, the user has the capability to select from a variety of reagents held within individual reagent reservoirs and load one or more reagent reservoirs within the housing prior to use. As described above this allows the user to have flexibility when assembling the devices by selecting the reagents and solutions (described previously, and further described below) according to the desired diagnostic or testing purpose of the device.

At 3604, a solution reservoir is slidably received within the housing. The solution reservoir contains a solution configured to mix with the reagent to form a specified amount of the reagent solution. Similarly to the reagent reservoir, the solution reservoir includes at least one seal at an end of the solution reservoir. In another example, the solution reservoir includes seals on at least two ends of the solution reservoir. As previously described, the seals are sized and shaped to receive piercing elements that open the solution reservoir and allow movement of the solution over the reagent to form the reagent solution. In another example, the seal includes a frangible tube, for example, a capillary tube to maintain a vacuum within the solution reservoir. Fracturing the capillary tube allows release of the vacuum and movement of the solution out of the solution reservoir and into engagement with the reagent.

At 3608, a dispensing reservoir tip is coupled with the housing. As previously described, the dispensing reservoir tip may be integrally formed with the housing. In another example, the dispensing reservoir tip is a separate piece that is coupled with the housing, for instance by welding, adhesives and the like. As presented with regard to all of these example devices, the term coupling of the dispensing reservoir tip with the housing is intended to include an integral forming of the dispensing reservoir tip with the housing as well as coupling of a separate dispensing reservoir with the housing as described above. In one example, the dispensing reservoir tip is transparent or semi-transparent thereby allowing the user to inspect the reagent solution for completion of mixing and verification of the proper reagent within the solution for the particular diagnostic or testing purpose of the device.

At 3610, an activator is slidably coupled with the housing. The activator is movable from a first position to at least a second position. In one example, the activator includes a piercing tip, for example a piercing nozzle, that is sized and shaped to pierce at least one of the reagent reservoir seal and the solution reservoir seal. In another example, the piercing tip of the activator is sized and shaped to pierce multiple seals on the solution reservoir and the reagent reservoir. Piercing of the seals allows the contents of the solution reservoir (a solution) to mix with the reagent in the reagent reservoir and form the specified amount of the reagent solution. In yet another example, movement of the activator relative to the housing applies pressure behind the reagent solution and moves the pharmaceutical reagent solution into the dispensing tip reservoir for inspection. Further movement of the activator moves the reagent solution out of the dispensing reservoir tip and out of the device.

Several options for the method 3600 follow. In one example, the method 3600 further includes coupling a second piercing tip with a solution reservoir. The second piercing tip is sized and shaped to pierce the reagent reservoir seal and movement of the activator engages the activator with the solution reservoir and moves the activator and correspondingly moves the second piercing tip towards the reagent reservoir seal. Engagement of the piercing tip with the reagent reservoir seal opens the reagent reservoir and allows communication between the solution reservoir and the reagent reservoir. In another example, the method includes a gasket coupled around the solution reservoir (e.g., between the housing and the solution reservoir). The gasket is coupled between the solution reservoir and the housing to substantially prevent any solution released from the solution reservoir from flowing between the solution reservoir and the housing thereby escaping the device and not exiting through the dispensing reservoir tip. Additionally, the gasket provides a seal that maintains a pressurized environment within the device and allows pressure developed by the activator to force the reagent solution through the dispensing reservoir tip.

Figure 37:
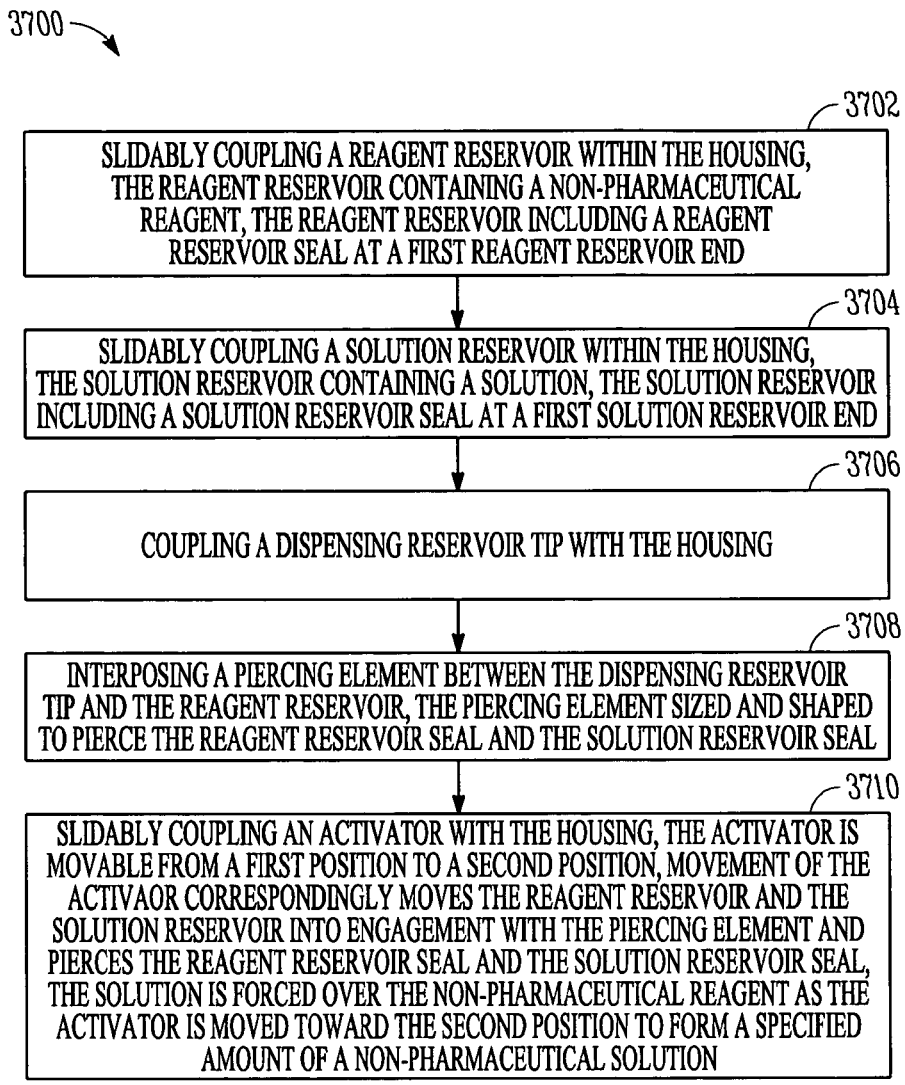
FIG. 37 is a block diagram showing another example of a method of making the devices shown in FIGS. 17a-22.

Another example of a method 3700 for making a preparation and dispensing device (such as the devices 1700 and 2000 as shown in FIGS. 17A through 22) is shown in FIG. 37. Reference is made to the devices shown in FIGS. 17A through 22 and described above. For convenience, elements from devices 1700 and 2000 will be discussed with specific element numbers for the method 3700.

At 3702, a reagent reservoir 1708, 2008 is slidably coupled within the housing. The reagent reservoir 1708, 2008 contains a reagent 1712, 2012 including but not limited to a lyophilized reagent, a solution reagent, a powdered reagent and the like. In one example, the reagent reservoir 1708, 2008 includes at least one seal 1802, 2106 at an end of the reagent reservoir. In another example, the reagent reservoir 1708, 2008 includes seal 1802, 2106 on one end and a seal 1804, 2108 at another end of the reagent reservoir. The seals are sized and shaped for piercing or rupturing by an element (previously described above) to open the reagent reservoir and allow contents of the reagent reservoir, the reagents, to mix with solutions in the dispensing reservoir tip as further described below.

At 3704, a solution reservoir 1710, 2020 is slidably coupled with the housing 1702, 2002. The solution reservoir 1710, 2020 contains the solution for mixing with the reagent to form a reagent solution. In one example, the solution reservoir 1710, 2010 include seals 1806, 2110 sized and shaped to seal at least one end of the solution reservoir. In another example, as shown in FIG. 21, the solution reservoir 2010 includes seals 2110 and 2112 sized and shaped to seal at least two ends. The solution reservoir seals 2110, 2112, in a similar manner to the reagent reservoir, are sized and shaped for penetration by a piercing element and/or rupturing by a feature of the devices. Upon opening of the seals the contents of the solution reservoir (the solutions) are communicated with the reagents to form a reagent solution.

At 3706, a dispensing reservoir tip 1704, 2004 is coupled with the housing 1702, 2002. As shown in FIG. 21 the dispensing reservoir 2004 in another example is an integral device formed with the housing 2002. Referring to FIG. 18, the dispensing reservoir tip 1704 is shown as a separate piece and is coupled to a nozzle feature 1812 of the body 1702. The dispensing reservoir tip 1704 slides over the nozzle feature 1812 and is retained against the nozzle by, for example, mechanical fitting, welding, adhesives and the like.

At 3708, a piercing element 1714, 2014 is interposed between the dispensing reservoir tip 1704, 2004 and the reagent reservoir 1708, 2008. The piercing element 1714, 2014 is sized and shaped to pierce the reagent reservoir seal and the solution reservoir seal. Engagement of the piercing element 1714, 2014 with the seals thereby allows communication between the reservoirs and intermixing of the solution with the reagent. In one example, the piercing element 1714 (shown in FIG. 17B) is integrally formed with the housing 1702. In yet another example, shown in FIG. 20B, the piercing element 2014 is a separate element that is positioned along a bottom receiving surface 2019 of the body 2002. The piercing elements 1714, 2014 include features such as channels 1715 (FIG. 17B) and orifices 2015 (FIG. 20B) that allow movement of a reagent solution past the piercing element 1714, 2014 and into the dispensing reservoir tip 1704, 2004.

At 3710, an activator 1706, 2006 is slidably coupled with the housing 1702, 2002. The activator 1706, 2006 is movable from a first position to a second position (e.g., a starting position to a dispensing position). Movement of the activator 1706, 2006 correspondingly moves the reagent reservoir 1708, 2008 and the solution reservoir 1710, 2010 into engagement with the piercing element 1714, 2014 and pierces the reagent reservoir seal and solution reservoir seal. The solution is then forced over the reagent as the activator is moved toward the second position to form a specified amount of reagent solution. In one example, slidably coupling the activator with the housing includes slidably coupling a composite structure including the activator 1706 and the solution reservoir 1710, as shown in FIGS. 17B and 18. The solution reservoir 1710 and activator 1706 come as a preassembled unit and are load as a single unit with the housing 1702.

Figure 38:
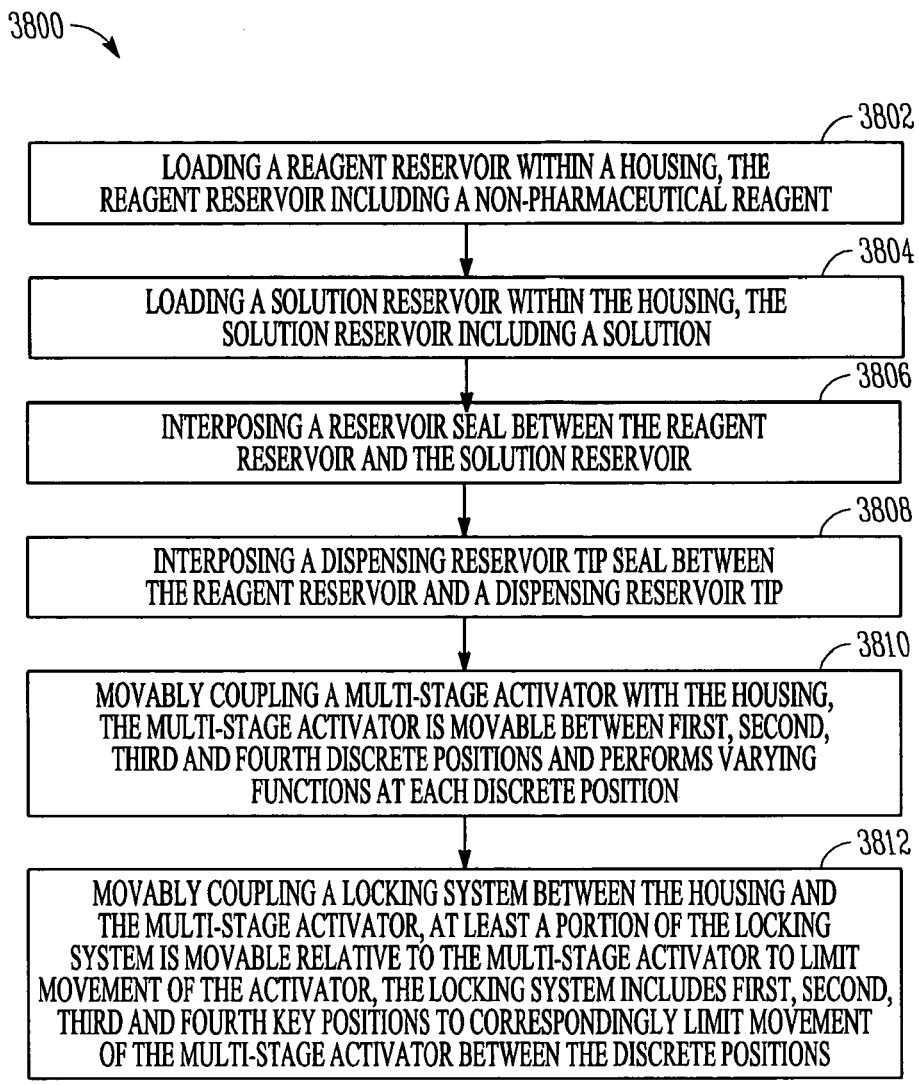
FIG. 38 is a block diagram showing another example of a method of making the devices shown in FIGS. 29a-31.

Another method 3800 for making a reagent preparation and dispensing device (for instance, the device 2900 shown in FIGS. 29A, B, 30 and 31) is shown in FIG. 38. Reference is made to the device 2900 shown in FIGS. 29A, B, 30 and 31 as described above. For convenience elements from the device 2900 will be discussed with specific elements herein.

At 3802, a reagent reservoir 2910 is loaded within a housing 2902. The reagent reservoir 2910 includes a reagent 2912 such as a reagent. In one example, the reagent includes, but is not limited to, a lyophilized reagent, a solution reagent, a powder reagent and the like. Optionally, the reagent reservoir 2910 includes multiple reagents. In still another example, multiple reagent reservoirs 2910 are included in the body 2902.

At 3804, a solution reservoir 2914 is loaded within the housing 2902. The solution reservoir 2914 includes a solution 2916. For instance, a solution configured to mix with the reagent 2912 and form a reagent solution. As previously described in another example, a predetermined amount of solution 2916 is included and when mixed with the reagent 2912 substantially consumes the entire reagent 2912 and forms a specified amount of reagent solution having a specified concentration.

At 3806, a reservoir seal 2922 is interposed between the reagent reservoir 2910 and solution reservoir 2914. For instance, the reservoir seal 2922 includes a plug fitted within one end of the reagent reservoir 2912.

At 3808, a dispensing reservoir tip seal 2924 is interposed between the reagent reservoir 2910 and a dispensing reservoir tip 2904 (see FIG. 29B). The seals 2922, 2924 are sized and shaped for piercing by elements of the solution reservoir 2914 and reagent reservoir 2910. Piercing of these seals allows communication between the reservoirs and movement of the reagent solution into the dispensing reservoir tip 2904.

At 3810, a multistage activator 2908 is coupled with the housing 2902. The multistage activator 2908 is movable between two or more discrete positions. In one example, the multistage activator 2908 is movable between first, second, third and fourth discrete positions. Each of the positions the activator 2908 is moved to provides a different function for the solution reservoir 2914, reagent reservoir 2910, dispensing reservoir tip 2904 and the seals 2922, 2924 interposed therebetween. For instance, when the multistage activator 2908 is moved from the first position to a second discrete position the reservoir seal 2922 is pierced. In another example, where the multistage activator 2908 is moved from the second discrete position to the third discrete position the solution 2916 is forced from the solution reservoir 2914 over the reagent 2912 within the reagent reservoir 2910. The solution 2916 mixes with the reagent 2912 to form the reagent solution. In still another example, where the multistage activator is moved from the third discrete position to the fourth discrete position the dispensing reservoir tip seal 2924 is pierced and the reagent solution flows into the dispensing reservoir tip and then flows out of the dispensing reservoir tip, as previously described.

At 3812, a locking system 3001 is movably coupled between the housing 2902 and the multistage activator 2908. At least a portion of the locking system 3001 is movable relative to the multistage activator 2908 to limit movement of the activator. Locking system includes a plurality of key retaining positions. In one example, the locking system 3001 includes at least first, second, third and fourth key locking positions. The multistage activator 2908 is movable through a particular range of motion for each one of the key locking positions, for example, where the portion of the locking system 3001 is in a first key locking position the multistage activator 2908 is not movable from the first discrete position. In another example, the multistage activator 2908 is only movable from the first discrete position to the second discrete position where the portion of the locking system is in the second key locking position. In another example, the multistage activator 2908 is only movable from the second discrete position to the third discrete position when the portion of the locking system is in the third key locking position. In yet another example, the multistage activator 2908 is only movable from the third discrete position to the fourth discrete position when the portion of the locking system is in the fourth key locking position. As shown in FIGS. 29A, B, 29, 30 and 31, in one example, the locking system 3001 (e.g., a key and lock system) includes a locking collar 3010 coupled between the housing 2902 and a multistage activator 2908. The locking collar 3010 optionally extends around the body 2902 and provides a lever 3012 sized and shaped to permit movement of the locking collar around the body 2902 by a user. The locking system 3001 further includes a key 3002 formed on the activator 2908. The key is sized and shaped to engage with the locking collar 3010 and selectively prevent movement of the activator 2908 according to a position of the activator and locking collar.

Figure 39:
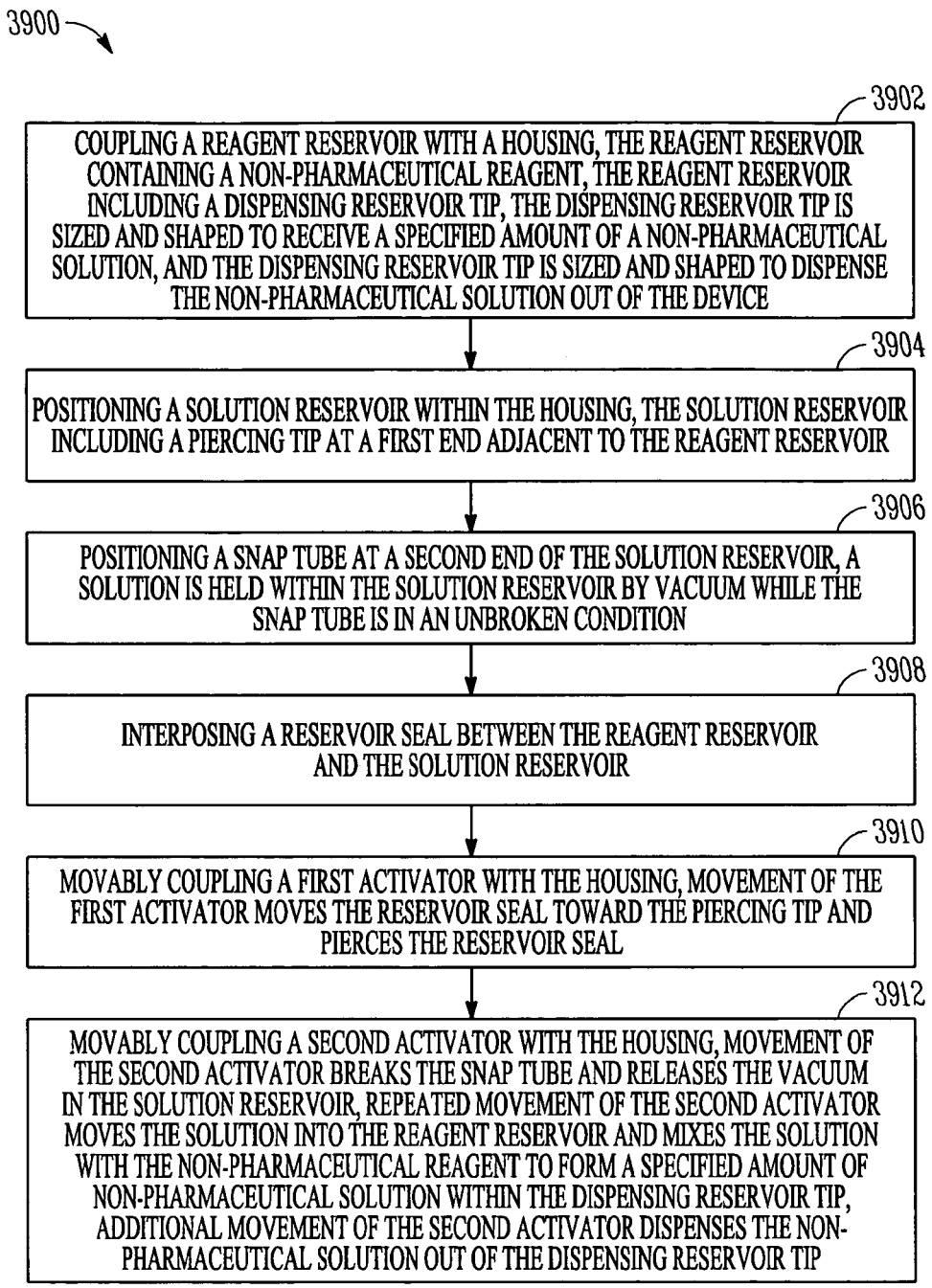
FIG. 39 is a block diagram showing another example of a method of making the devices shown in FIGS. 32a-34.

Still another example of a method 3900 for making a preparation dispensing device (such as the device 3200 shown in FIGS. 32A, B, 33 and 34) is shown in FIG. 39. Reference is made to the device 3200 as well as the elements included in the device. For convenience those elements shown in FIGS. 32A, B, 33 and 34 will be discussed with specific elements herein.

At 3902, a reagent reservoir 3214 is coupled with the housing 3202. The reagent reservoir 3214 includes a reagent 3216. The reagent includes, but is not limited to, a lyophilized reagent, solution reagent, powder reagent and the like. Reagent reservoir 3214 further includes a dispensing reservoir tip 3204. The dispensing reservoir tip 3204 is sized and shaped to receive a specified amount of a reagent solution. Additionally, the dispensing reservoir tip is sized and shaped to include a nozzle for dispensing the reagent solution out of the device 3200.

At 3904, a solution reservoir 3218 is positioned within the housing 3202. The solution reservoir 3218 includes a piercing nozzle element 3226 (e.g., a piercing tip). The piercing nozzle element 3226 is at a first end of the solution reservoir 3218 adjacent to the reagent reservoir 3214.

At 3906, a capillary snap tube 3225 is positioned near a second end of the solution reservoir 3218. A solution 3220 is held within the solution reservoir 3218 by a vacuum maintained by the unbroken capillary tube 3225. As described above and shown in FIG. 33, the capillary tube 3225 in one example includes a weakened portion 3204 sized and shaped to allow fracture of the capillary tube 3225 at the weakened portion and release of the vacuum.

At 3908, a reservoir seal 3224 is interposed between the reagent reservoir 3214 and solution reservoir 3218. As shown in FIG. 33, in one example, the reservoir seal 3224 is sized and shaped for positioning within the reagent reservoir 3214 as a plug. In another example, the seal 3224 includes a film placed over the reagent reservoir and adhered thereto, for example, with welding, adhesives and the like.

At 3910, a first activator 3210 is coupled with housing 3202. Movement of the first activator 3210 moves the reservoir seal 3224 toward the piercing nozzle element 3226 and pierces the reservoir seal 3224. Piercing of the reservoir seal 3224 allows communication between the solution reservoir 3218 and reagent reservoir 3214 thereby allowing mixing of the solution 3220 and reagent 3216.

At 3912, a second activator 3212 (e.g., second activator 3212 and second activator mount 3306) is movably coupled with the housing 3202. Movement of the second activator 3212 breaks the capillary tube 3225 and releases the vacuum in the solution reservoir 3218. The solution 3220 is thereby free to flow out of the solution reservoir into the reagent reservoir 3214 where the seal 3224 has already been pierced. Repeated movement of the second activator 3212, for instance, compression of a deflectable bulb, moves the solution 3220 out of the solution reservoir 3218 and into the reagent reservoir 3214 allowing the solution 3220 to mix with the reagent 3216 and form a specified amount of reagent solution. A reagent solution then settles within the dispensing reservoir tip 3204 prior to dispensing. Additional movement of the second activator 3212 dispenses the solution out of the dispensing reservoir tip 3204.

Figure 40:
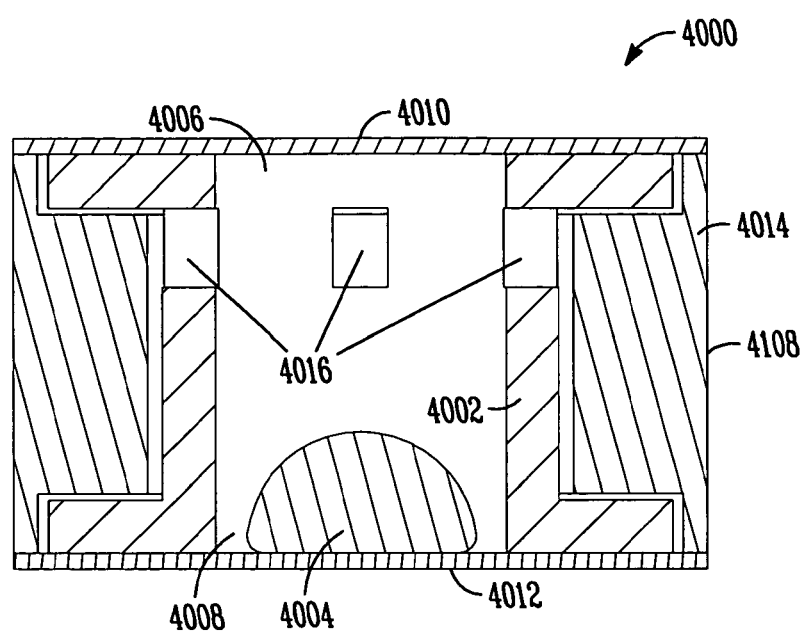
FIG. 40 is a side cross-sectional view of one example of a reagent reservoir assembly having a desiccant shell usable with the devices shown in FIGS. 1a-39.
Figure 41:
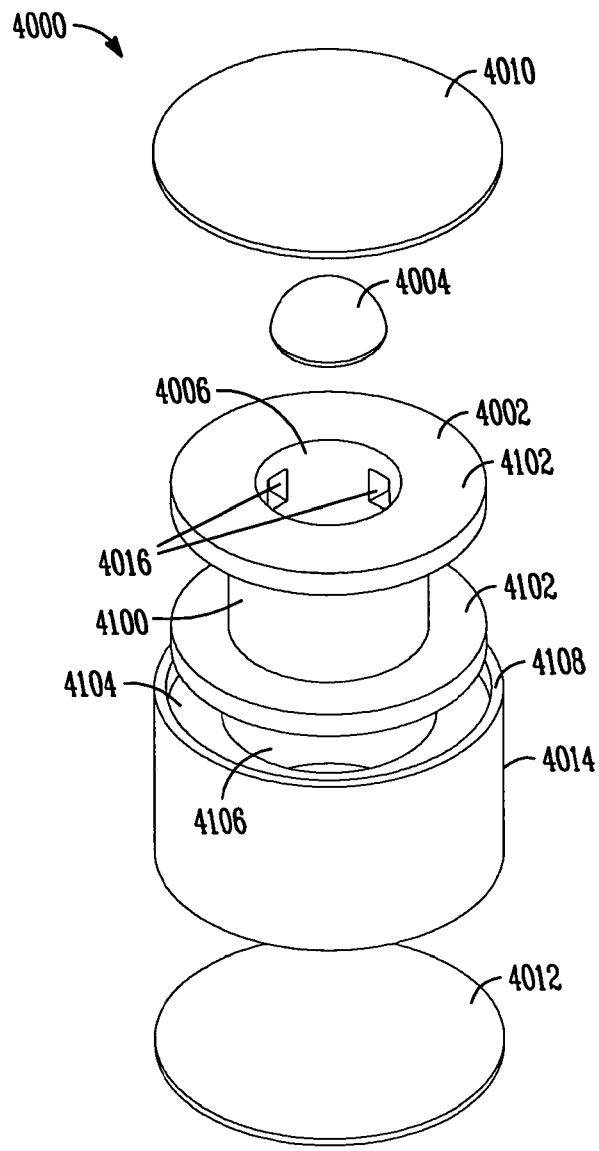
FIG. 41 is an exploded view of the reagent reservoir assembly shown in FIG. 40.

One example of a reagent reservoir assembly 4000 is shown in FIGS. 40 and 41. In one example, the reagent reservoir assembly 4000 is used within at least one of the devices previously described. The reservoir 4000 includes a reservoir shell 4002 extending around a reagent 4004. In one example, the reagent 4004 includes but is not limited to a lyophilized reagent, powder reagent, solution reagent and the like. The reagent 4004 is held within an orifice 4008 within the reservoir shell 4002. Reservoir shell 4002, in one example, includes orifices 4006 and 4008. The orifices 4006, 4008 allow for positioning of the reagent 4004 within the reservoir shell 4002.

As shown in FIGS. 40 and 41, seals 4010 and 4012 are coupled with the reservoir shell 4002 at either end. Optionally, the reservoir shell 4002 is formed with a single orifice, for instance, the reservoir shell has a closed end and an open end where the seal is positioned over the open end. The seals 4010, 4012 include, but are not limited to pliable seals, brittle seals and the like. The seals are configured for opening by piercing elements included in the devices previously described. Optionally, the seals 4010, 4012 are configured for opening by a rupturing means, for instance, a piston engaged against the reservoir shell 4002 in an annular manner with the orifices 4006 or 4008. In one example, the seals 4010, 4012 include foil seals disposed over the orifice 4006, 4008. The seals 4010, 4012 are coupled with the reservoir shell 4002 with adhesives, welds, mechanical interfittings such as crimping and the like.

The reagent reservoir assembly 4000 further includes a desiccant shell 4014 extending around at least a portion of the reservoir shell 4002. As shown in FIGS. 40 and 41, the reservoir shell 4002 includes vents 4016 allowing communication between the exterior of the reservoir shell 4002 and the interior where the reagent 4004 is held. The desiccant shell 4014 is thereby able to absorb any moisture within the reservoir assembly 4000 and around the reagent 4004. This ensures the reagent 4004 is within a dry environment substantially preventing reconstitution of the reagent 4004 (e.g., a powder or lyophilized reagent) prior to intentional introduction of a solution.

As shown in FIG. 41, the desiccant shell 4014 includes at least one countersunk flange 4104. As shown in FIG. 40, the countersunk flange is mirrored at either end of the desiccant shell 4014. A desiccant shell orifice 4106 is sized and shaped to receive the reservoir shell 4002. The desiccant shell 4014 tightly engages with the reservoir shell 4002 to substantially prevent the intrusion of particulate matter, contaminants and the like through the vents 4016. Vents 4016 allow operation of the desiccant shell 4014 to remove moisture from around the reagent 4004. The reservoir shell 4002 includes a barrel 4100 having a corresponding geometry to the desiccant shell orifice 4106. Similarly, the reservoir shell 4002 includes reservoir flanges 4102 at either end of the reservoir shell 4002 for positioning within the desiccant shell countersunk flanges 4104. Lips 4106 extend from the desiccant shell 4014 to extend around the reservoir flanges 4102. This stepped configuration between the engagement of the desiccant shell 4014 with the reservoir shell 4002 substantially prevents the intrusion of particulate matter, contaminants and moisture beyond the desiccant shell 4014 thereby ensuring the reagent 4004 is within a clean environment having substantially no moisture, contaminants and the like.

The reagent reservoir assembly 4000 is assembled in one example by positioning the desiccant shell 4014 around the reservoir shell 4002, for example, the desiccant shell 4014 is sectioned into halves and then positioned around the reservoir shell 4002. In another option, the desiccant shell is slid over the reservoir shell 4002 where the reservoir shell has a single reservoir flange 4102. At least one of the seals 4010, 4012 is coupled over the reservoir shell orifice 4008, 4006 and retained over the orifice 4006, 4008 as shown in FIG. 40. In another example, at least one of the seals 4010, 4012 is similarly coupled with the lip 4108 of the desiccant shell 4014. Coupling of the seals 4010, 4012 across the reservoir shell 4002 and desiccant shell 4014 assists in prevent the intrusion of contaminants, moisture and the like into the reagent reservoir orifice 4008. Coupling of one of the seals 4010, 4012 closes one of the orifices 4006, 4008 within the reagent reservoir assembly 4000. The reagent 4004 is then positioned within the reservoir assembly 4000. The remaining seal 4010, 4012 is coupled over the remaining orifice 4006, 4008 to seal the reagent reservoir assembly 4000. The reagent reservoir assembly 4000 is then ready for packaging within the reagent preparation and dispensing devices described previously above.

Figure 42:
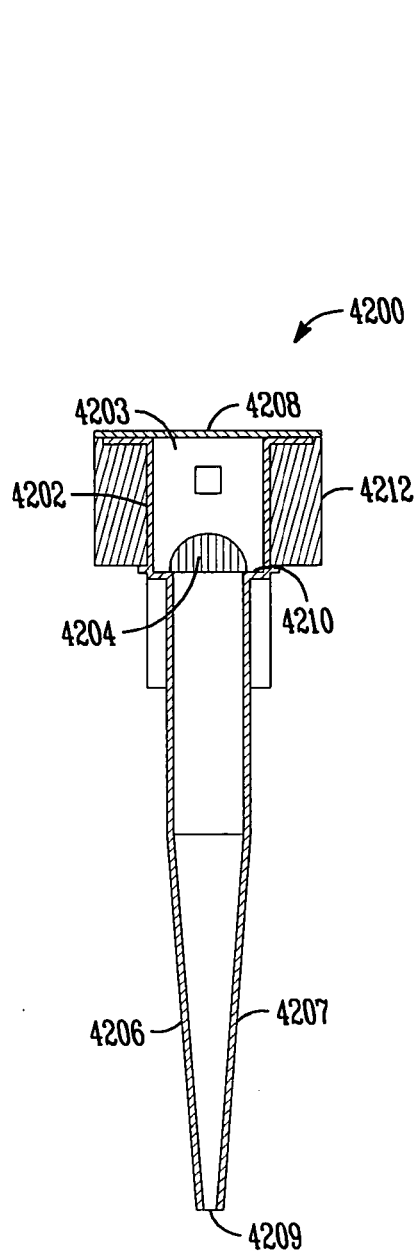
FIG. 42 is a side cross-sectional view of one example of a reagent reservoir tip assembly usable with the devices shown in FIGS. 1a-39.
Figure 43:
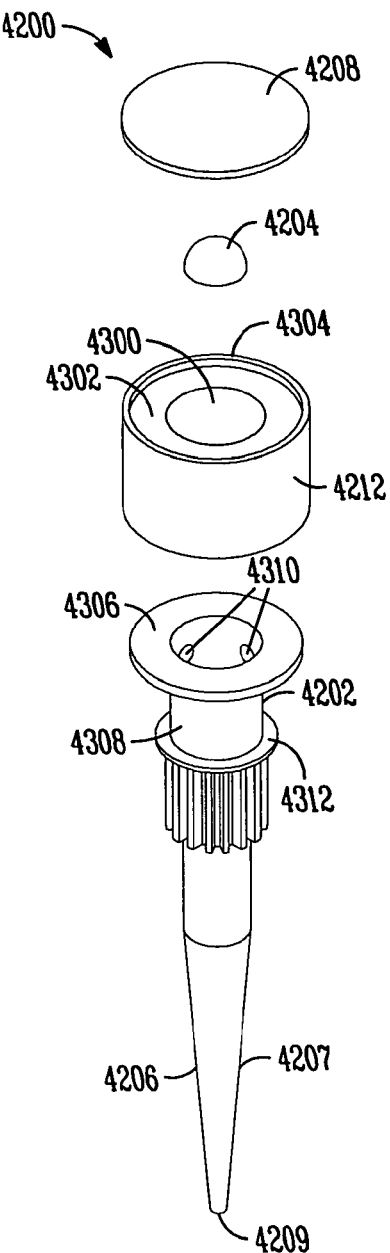
FIG. 43 is an exploded view of the reagent reservoir tip assembly shown in FIG. 42.

Referring now to FIGS. 42 and 43, one example of a reagent reservoir tip assembly 4200 is shown. The tip assembly 4200 includes a reagent reservoir 4202 containing a reagent 4204. The reagent, in one example, includes but is not limited to, a lyophilized reagent, solution reagent, powdered reagent and the like. The assembly 4200 further includes a dispensing reservoir tip 4206. The dispensing reservoir tip 4206 is sized and shaped to have sufficient volume to receive a reagent solution formed by mixing the reagent 4204 with a solution to form a specified amount of solution. As shown in FIGS. 42 and 43 the dispensing reservoir tip 4206 includes a graduated nozzle 4207 and a blunt nozzle tip 4209. In one example, the graduated nozzle 4207 and blunt nozzle tip 4209 provide a wedge shaped geometry that easily contains the reagent solution prior to dispensing, for instance, the solution is held within the dispensing reservoir tip 4206 by a vacuum contained within the reagent preparation and dispensing device. With the application of pressure or movement of the solution by gravity the solution exits the dispensing reservoir tip through the blunt nozzle 4209. The graduated nozzle 4207 and blunt nozzle tip 4209 ensure that the solution when it exits the dispensing reservoir tip 4206 has a consistent clean solution strain.

A seal 4208 is disposed over a reagent reservoir orifice 4203. The seal 4208 includes but is not limited to a brittle seal, pliable seal and the like. The seal 4208 is sized and shaped for piercing by elements of the reagent preparation and dispensing devices as previously shown above. Piercing of the seals 4208 allows the introduction of solution into the reagent reservoir 4202 and mixing of the solution with the reagent 4204 to form a reagent solution. In another example, at the opposed end of the reagent reservoir 4202 and the seal 4208 the reagent 4204 is rested upon the reservoir tip flange 4210. Optionally, the reagent 4204 is retained along the flange 4210 to substantially prevent movement of solution past the reagent 4204 prior to mixing with the reagent. As the reagent 4204 is broken down the mixed solution is able to pass by the remnants of the reagent 4204 and move into the reservoir tip 4206.

Desiccant shell 4212 is shown in FIGS. 42 and 43. Desiccant shell 4212 at least partially surrounds the reagent reservoir 4202. As shown in FIG. 43, the reagent reservoir 4204 includes vents 4310 allowing communication between the reagent reservoir 4202 and the desiccant shell 4212. As previously described, the desiccant within the desiccant shell 4212 removes moisture within the reagent reservoir 4202 thereby maintaining a dry environment around the reagent 4204 and substantially preventing unwanted reconstitution of the reagent 4204 prior to introduction of the solution from the reagent preparation and dispensing device. Referring to FIG. 43, the desiccant shell 4212 includes an orifice 4300 surrounded by the desiccant shell 4212. The desiccant shell 4212 further includes a countersink 4302 sized and shaped to receive a reservoir flange 4306. A reservoir lip 4304 is sized and shaped to extend around a reservoir flange 4306 and thereby provide a stepped configuration as shown in FIG. 42 to substantially prevent the intrusion of moisture, contaminants and the like around the desiccant shell 4212 and through the vents 4310. Additionally, the reservoir flange 4306 cooperates with a reservoir ridge 4312 to engage the desiccant shell 4212 and retain it around the reagent reservoir 4202 thereby substantially preventing movement of the desiccant shell 4212 relative to the reagent reservoir 4202. The seal 4208 is positioned over the reservoir flange 4306 and optionally engaged with the desiccant shell lip 4304. Coupling of the seal 4208 with the desiccant shell 4212 and the reservoir flange 4306 substantially prevents intrusion of moisture, contaminants and the like either directly through the orifice 4203 of the reagent reservoir 4202 or between the desiccant shell 4212 and reagent reservoir 4202 and into the vents 4310.

The reagent reservoir assembly 4200 is assembled in one example by coupling the desiccant shell 4212 around the reagent reservoir 4202. In one example, the desiccant shell 4212 is slid over the dispensing reservoir tip 4206 and into engagement with the reservoir flange 4306. For example the desiccant shell 4212 is deflected as it moves over the reservoir ridge 4312 and then locked into place on the reagent reservoir 4202 by engagement between the reservoir flange 4306 and reservoir ridge 4312. The reagent 4204 is placed within the reagent reservoir 4202, for instance, along the reagent lip 4210. As previously described, in one option the reagent 4204 is retained along the reagent lip 4210, for instance, by mechanical interfitting with the reagent lip 4210 (e.g., interference fitting). The seal 4208 is then coupled with the reagent reservoir 4202 at the reservoir flange 4206 and optionally coupled with the desiccant shell at the desiccant shell lip 4304. The reagent reservoir assembly 4200 is then ready for positioning within a reagent preparation and dispensing device as shown in at least some of the examples previously described.

Figure 44:
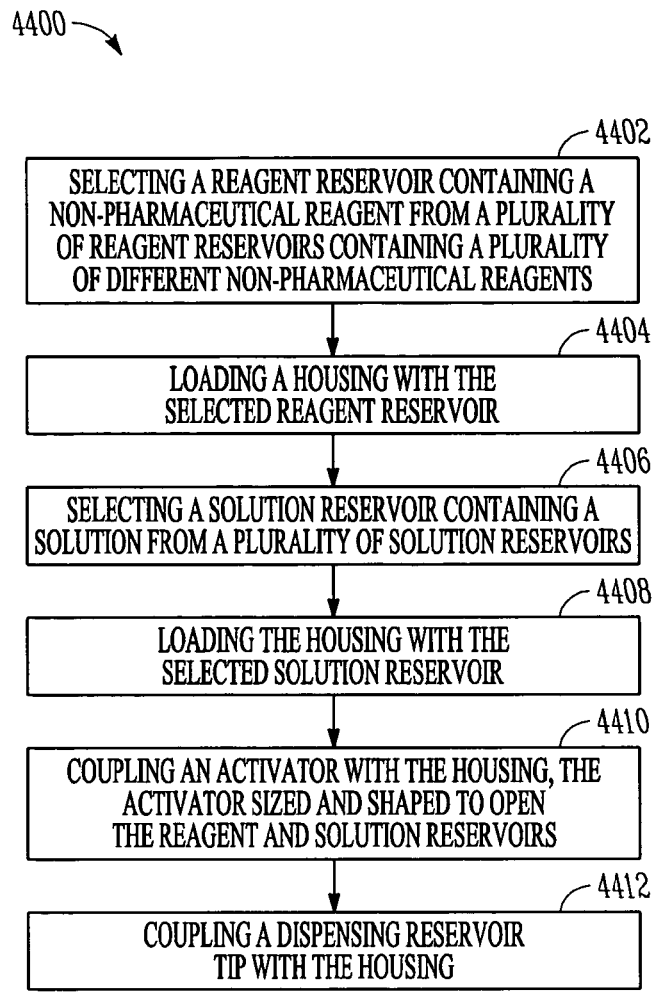
FIG. 44 is a block diagram showing still another example of a method of making the devices shown in FIGS. 1a-43.

Another method 4400 for making a preparation and dispensing device, such as the devices shown in FIGS. 1*a*-43 is shown in FIG. 44. References are made with regard to the method 4400 to devices shown in FIGS. 1*a*-43 including each of the elements shown in those drawings and previously described above.

At 4402, a reagent reservoir containing a reagent is selected from a plurality of reagent reservoirs containing a plurality of different reagents. For instance, the reagent reservoir is chosen from a catalog of reagents, where each of the reagent reservoirs is interchangeable with a device housing. In one example, the reservoirs include reagents for biological testing, environmental testing, diagnostic testing and the like. In another example, the reservoirs include one or more reagents. In yet another example, the reagents include, but are not limited to, lyophilized reagents, liquid reagents, powdered reagents and the like.

At 4404, the selected reagent reservoir is loaded within a housing. As previously described, the reagent reservoir is slidably coupled and held within a device housing, in one example. In another example, the reagent reservoir is positioned within the device housing. In yet another example, the reagent reservoir is included within the device housing. The reagent reservoir is sized and shaped for interchangeable loading within the housing as previously shown and described above.

At 4406, a solution reservoir containing a solution is selected from a plurality of solution reservoirs. For instance, the solution reservoir is chosen from a catalog of solutions, where each of the solution reservoirs is interchangeable with the device housing. In one example, the reservoirs include solutions for the preparation of reagents used in biological testing, environmental testing, diagnostic testing and the like. In another example, the reservoirs contain samples, including but not limited to liquid samples (e.g., blood, urine, perspiration, saliva, mucous, water, plant and animal bodily fluids, salt water, chemicals and the like), samples suspended in solution (e.g., fecal matter, explosives, explosive residues, chemical residues, soil, plant and animal tissue and the like). Sample solutions are mixed with the reagents in the devices described above so the reagent may react with the sample solution and provide a testing or diagnostic result. The combined sample solution is examined through the device housing (e.g., through the transparent or semi-transparent dispensing reservoir tip or housing) or dispensed into a container.

At 4408, the housing is loaded with the selected solution reservoir. Similarly to the reagent reservoir, in one example, the solution reservoir is slidably coupled and held within the device housing. In another example, the solution reservoir is positioned within the device housing. In yet another example, the solution reservoir is included within the device housing. The solution reservoir is sized and shaped for interchangeable loading within the housing as previously shown and described above.

At 4410 an activator is coupled with the housing. The activator is sized and shaped to open the reagent and solution reservoirs. In one example, the activator facilitates communication between the reagent and solution reservoirs. In another example, the activator allows communication of the reagent solution with a dispensing reservoir tip, for instance, for dispensing of the reagent solution. In still another example, the activator forces the solution over the reagent, and forces the resulting reagent solution out of the device through the dispensing reservoir tip. As previously described, the activator includes, but is not limited to, a plunger, a deflectable bulb, a rotatable and translatable feature, a slidable feature and the like.

At 4412 a dispensing reservoir tip is coupled with the housing. In one example, the dispensing reservoir tip is sized and shaped to receive the specified amount of reagent solution prior to dispensing through a nozzle in the dispensing reservoir tip. The dispensing reservoir tip is transparent or semi-transparent to allow inspection of the reagent solution, in another example. In still another example, coupling the dispensing reservoir tip with the housing includes molding the dispensing reservoir tip with the housing.

Several options for the method 4400 follow. In one example, the method 4400 includes forming the reagent in an environment isolated from at least the housing. For instance, the reagent includes a lyophilized reagent that is formed through freeze-drying. Freeze-drying the reagent requires harsh environmental conditions that may damage the device (e.g., the structural integrity, precise interfitting between parts and the like) were the reagent frozen while within the device. The reagent is then packaged within the reagent reservoir (e.g., with a seal, such as a foil seal, pliable seal, frangible seal and the like) and is ready for loading within the housing as described above.

Figure 45A:
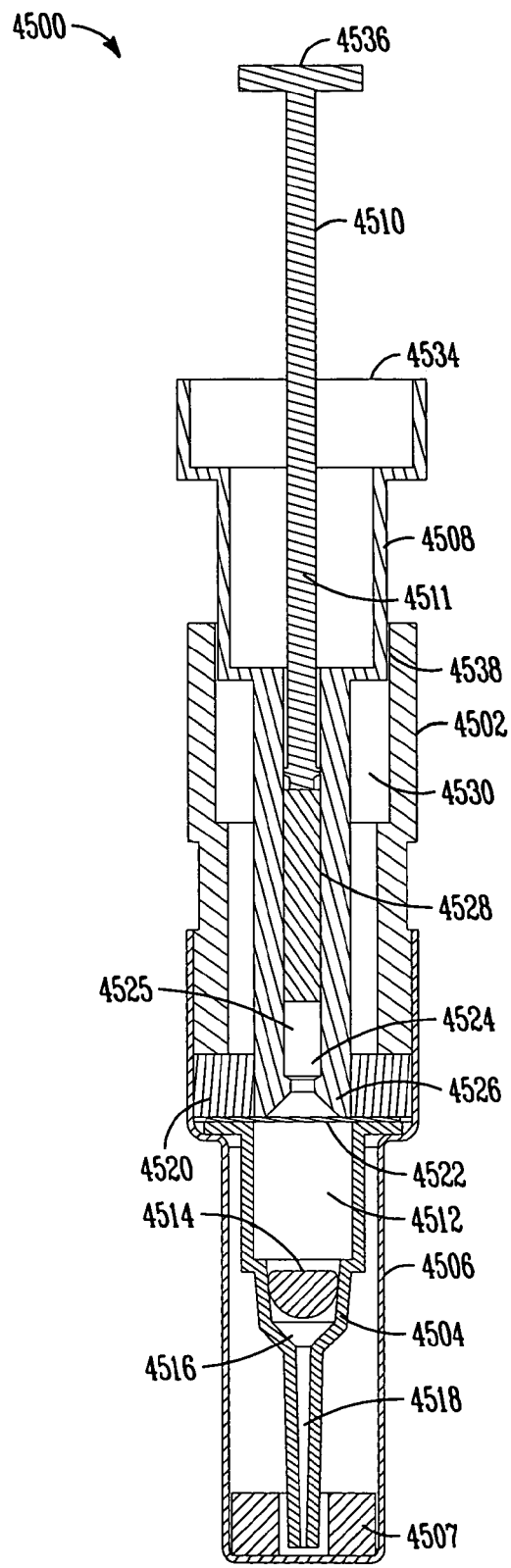
FIG. 45a is a cross-sectional view of one example of a reagent preparation and dispensing device including a seal piercing barrel in a first orientation.
Figure 45B:
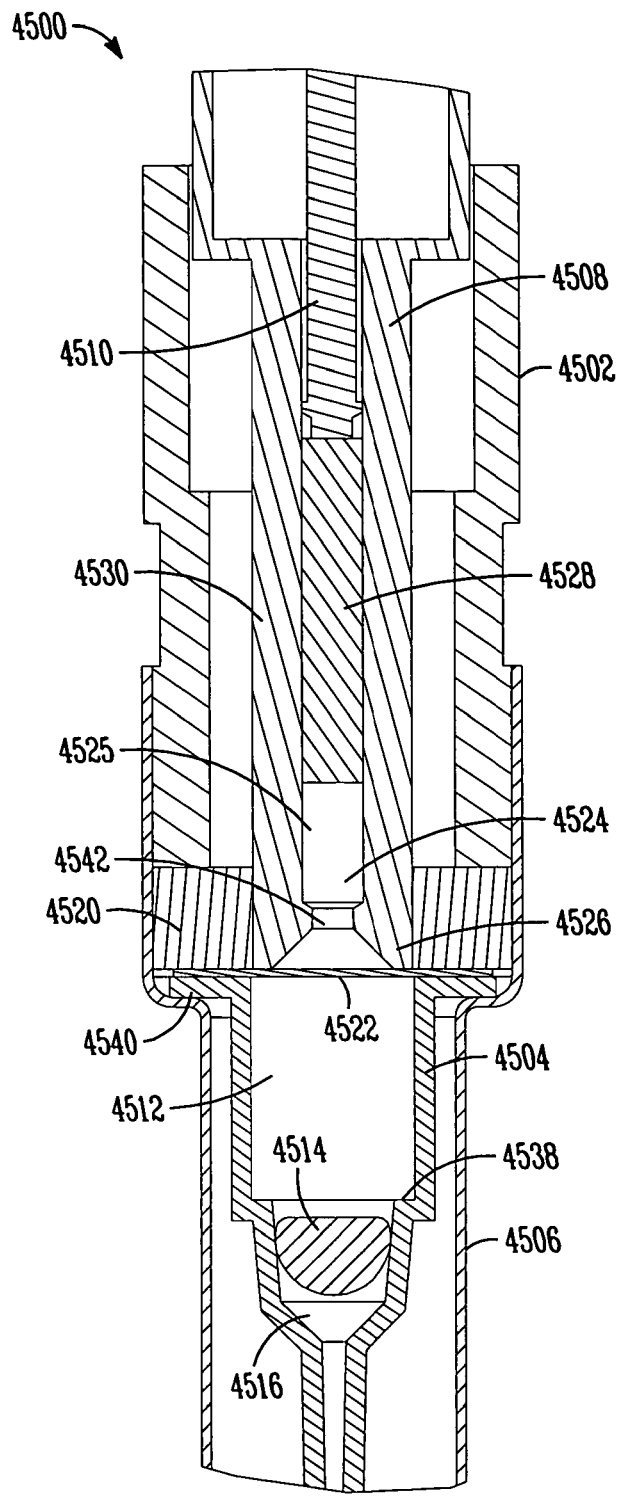

Another example of a reagent preparation and dispensing device 4500 is shown in FIGS. 45a, b. The device 4500 includes a body 4502 coupled with a dispensing reservoir tip 4504. As shown in FIG. 45a, b, a cap 4506 is coupled around the dispensing reservoir tip 4504 and a portion of the body 4502. Similarly to other examples, the dispensing reservoir tip 4504 includes a reagent reservoir 4512 containing a reagent 4514 (e.g., a lyophilized reagent, solution reagent, powder reagent, and the like). A barrel 4508 is movably coupled with the body 4502. For instance, the barrel 4508 is able to rotate relative to the body 4502. In another example, the barrel 4508 is able to move axially toward the dispensing reservoir tip 4504 through the barrel 4508. The barrel 4508 as shown in FIGS. 45a and 45b includes a solution reservoir 4524 containing a solution 4528. As discussed in other examples, the solution reservoir 4524 includes a specified amount of a solution 4528. The specified amount of the solution 4528 is configured to mix with the reagent 4514 to form a specified amount of a reagent mixture. For instance, enough solution 4528 is provided for mixing with the reagent 4514 without any of the solution 4528 being unreacted.

An activator 4510 extends through the barrel 4508 and into the solution reservoir 4524. As shown in FIG. 45a, the activator shaft 4511 forms one of the ends of the solution reservoir 4524. The other end of the solution reservoir 4524 is covered by a reagent reservoir seal 4522. As shown in FIG. 45a, the reagent reservoir seal 4522 extends across the reagent reservoir 4512 thereby separating the solution reservoir 4524 from the reagent reservoir 4512. In one example, the reagent reservoir seal 4522 is coupled with the dispensing reservoir tip 4504. In another example, the reagent reservoir seal 4522 is grasped between the dispensing reservoir tip 4504 and an interconnecting gasket 4520 positioned between the body 4502 and the dispensing reservoir tip 4504.

As described above, the dispensing reservoir tip 4504 includes the reagent 4514 within the reagent reservoir 4512. As shown in FIG. 45a, the reagent 4514, in one example, is contained within a reagent recess 4516 formed near a center portion of the dispensing reservoir tip 4504 (i.e., between a dispensing reservoir nozzle 4518 and the remainder of the reagent reservoir 4512). The reagent recess 4516 is adjacent to the dispensing reservoir nozzle 4518 which extends away from the body 4502. Optionally, the reagent 4514 is grasped and held within the reagent recess 4516, for instance, by mechanical interfitting. The cap 4506 is shown coupled over the dispensing reservoir tip 4504. As shown, a desiccant 4507 is contained within an end of the cap 4506. When the cap 4506 is coupled with the device 4500 the reagent 4514 is effectively sealed against interaction with an outside environment. The reagent reservoir 4512 is sealed at one end with the reagent reservoir seal 4522 and the cap 4506 engages with the dispensing reservoir tip 4504 on an exterior of the dispensing reservoir tip to effectively seal the reagent reservoir 4512. Optionally, a cap gasket is provided on the interior of the cap 4506 for sealing engagement against at least one of the dispensing reservoir tip 4504, interconnecting gasket 4520 and body 4502. Referring to FIG. 45b, the cap 4506 is shown engaged against a dispensing reservoir tip flange 4540. In one example, the cap 4506 is tightly engaged against the dispensing reservoir tip flange 4540 thereby providing a tight seal between the dispensing reservoir tip 4504 and the cap 4506. As shown in FIG. 45b, the reagent reservoir seal 4522 extends across the reagent reservoir 4512 and is engaged against the dispensing reservoir tip flange 4540. The reagent reservoir seal 4522 includes, but is not limited to, a foil seal, a resin seal, a laminate seal including plastics and foil, and the like.

As shown in greater detail in FIGS. 45b, c, the barrel shaft 4530 extends toward the dispensing reservoir tip 4504. The barrel shaft 4530 defines the solution reservoir 4524. The solution reservoir 4524 includes a solution reservoir nozzle 4542. As shown in FIGS. 45b, c, the solution reservoir 4542, in one example, has an annular conical geometry. The annular conical geometry of the solution reservoir nozzle 4542 is defined by a piercing edge 4526 extending around the barrel shaft 4530. The piercing edge 4526 is configured to pierce through the reagent reservoir seal 4522 thereby allowing communication between the solution reservoir 4524 and the reagent reservoir 4512. As described below, relative movement between the body 4502 and barrel 4508 moves the barrel shaft 4530 and correspondingly moves the piercing edge 4526 into the reagent reservoir seal 4522, and once the seal 4522 is pierced the barrel shaft 4530 moves into the reagent reservoir 4512. The interconnecting gasket 4520 engages around the barrel shaft 4530 and provides sealing engagement around the barrel shaft 4530 thereby preventing the movement of fluids such as the solution 4528 past the barrel shaft 4530 and into the space between the body 4502 and barrel 4508. During use the solution 4528 is therefore kept within the reagent reservoir 4512 to allow full mixing of the solution 4528 and the reagent 4514.

The dispensing reservoir tip 4512, in another example, includes a piercing edge seat 4538 sized and shaped to receive the piercing edge 4526 of the barrel shaft 4530. The piercing edge seat 4538 receives the piercing edge 4526 when the barrel shaft 4530 is moved into the reagent reservoir 4512. Engagement of the piercing edge 4526 with the piercing edge seat 4538 thereby minimizes the volume of the reagent reservoir 4512 allowing a full reaction between the specified amount of solution 4528 and the reagent 4514. The mixture of the reagents and the solution is thereby contained in a smaller space allowing for a more compact activator. Additionally, the smaller reagent reservoir 4512 is free of grooves, recesses and the like to substantially prevent entrapment of the solution 4528 or the reagent 4514. Because of the small space of the reagent reservoir the compact activator 4510 is able to easily push the mixture of the reagent through the dispensing reservoir nozzle 4518 of the dispensing reservoir tip 4504 shown in FIG. 45a. In one example, the piercing edge seat 4538 defines the reagent recess 4516. When the piercing edge 4526 is engaged with the piercing edge seat 4538, the reagent recess 4516 of the reagent reservoir 4512 serves as the reaction chamber for reconstitution of the reagent.

Referring again to 45a, the barrel 4508 is shown disposed within the body 4502. As previously discussed, the barrel 4508 is movably coupled with the body 4502 allowing for relative movement of the barrel relative to the body. In one example, the barrel 4508 is movably engaged with the body 4502 with threading 4538 extending between the barrel and the body. Rotation of the barrel 4508 relative to the body 4502 moves the barrel 4508 and the barrel shaft 4530 longitudinally toward the dispensing reservoir tip 4504. Because the activator 4510 is coupled within the barrel 4508, for instance the activator shaft 4511 is disposed within the barrel recess 4534, the activator 4510 moves with the barrel 4508 during rotation and axial movement of the barrel relative to the body 4502.

Figure 46A:
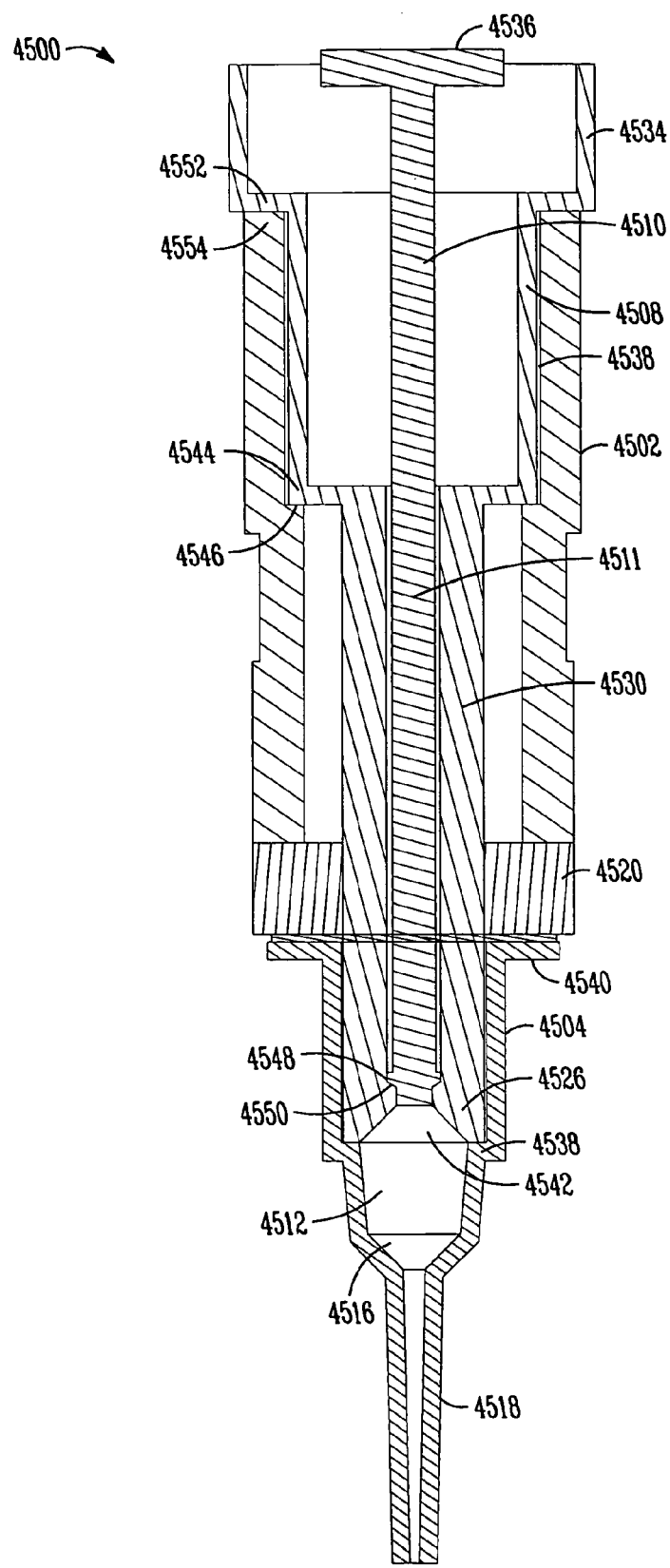
FIG. 46a is a cross-sectional view of the device shown in FIG. 45a in a second orientation for mixing and dispensing of a reagent mixture.

The reagent preparation and dispensing device 4500 is shown in an activated orientation in FIGS. 46a, b. The barrel 4508 is moved axially toward the dispensing reservoir tip 4504. As shown in FIG. 46a, the barrel shaft 4530 extends into the dispensing reservoir tip 4504 and into the reagent reservoir 4512. As described above, the piercing edge 4526 is received along the piercing edge seat 4538. In another example, as shown in FIG. 46a, a first barrel flange 4544 of the barrel 4508 is engaged against a first body flange 4546. In yet another example, the barrel includes a second barrel flange 4552 engaged against a second body flange 4554. Longitudinal movement of the barrel 4508 is constrained by engagement between at least one set of these flanges, the piercing edge and seats within the body and dispensing reservoir tip to ensure the barrel shaft 4530 is consistently received at the proper location within the dispensing reservoir tip 4504. Because of this consistent positioning of the barrel shaft 4530 within the reagent reservoir 4512, the reagent reservoir 4512 has a consistently smaller volume when mixing the solution 4528 and the reagent 4514 relative to the volume of the reagent reservoir 4512 shown in FIG. 45a in a non-activated orientation.

Figure 46B:
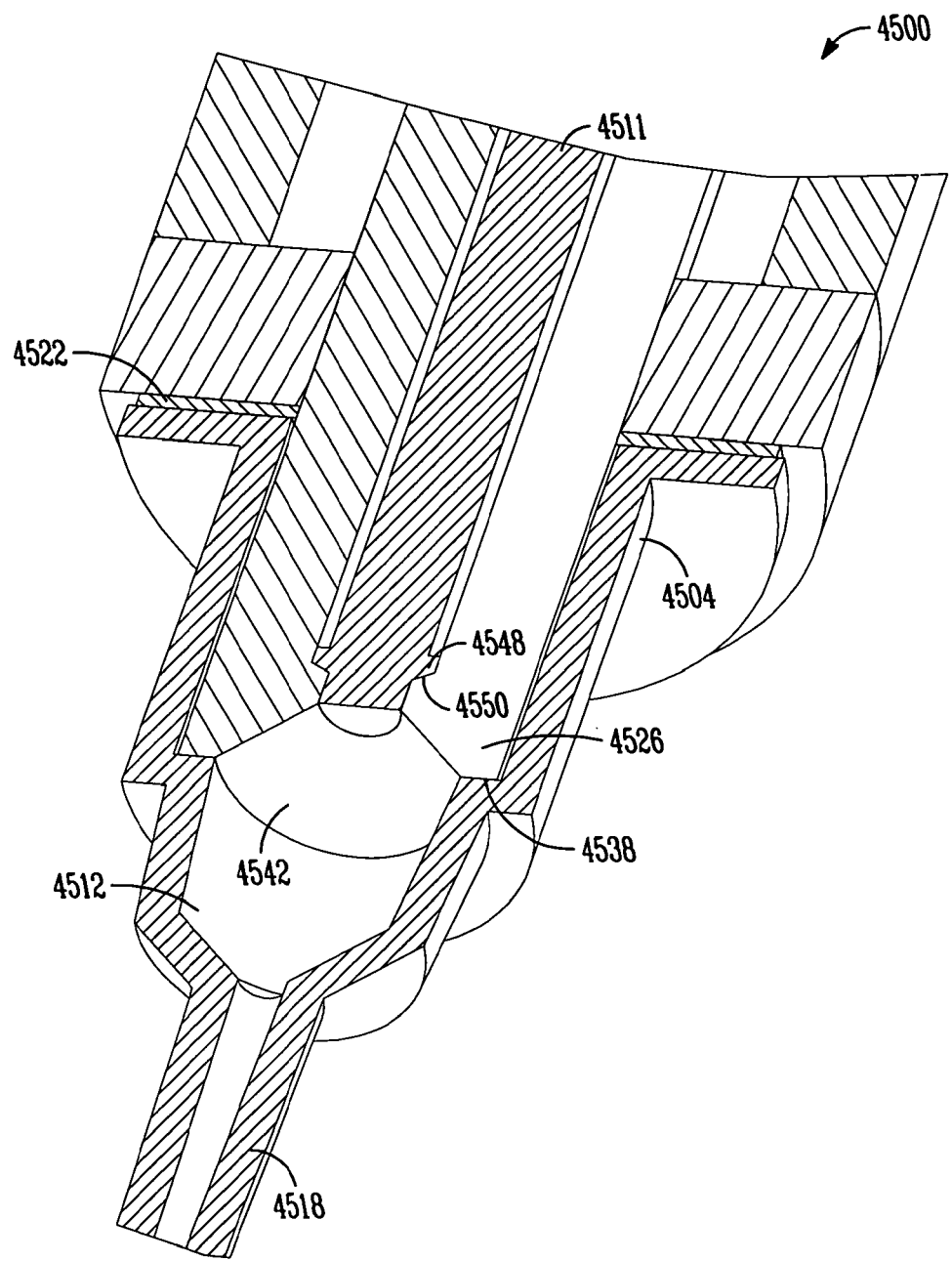
FIG. 46b is a detailed cross-sectional perspective view of dispensing reservoir tip in the second orientation.

As shown in FIGS. 46a, b, the barrel shaft 4530 has been driven through the reagent reservoir seal 4522. The reagent reservoir seal 4522 is shown in a transparent configuration to assist in reference of the Figures. As previously described, the piercing edge 4526 is driven through the reagent reservoir seal 4522 and is positioned against the piercing edge seat 4538. Because the reagent reservoir seal 4522 is pierced by the piercing edge 4526 the activator 4510 (e.g., a plunger) is free to move forward through the barrel shaft 4530 thereby moving the solution 4528 (shown in FIG. 45a) into the reagent reservoir 4512 where it mixes with the reagent 4514 (FIG. 45a). As shown in FIGS. 46a, b, the solution reservoir nozzle 4542 having the conical geometry is positioned immediately adjacent the reagent reservoir 4512, for instance, the reagent recess 4516. The solution 4528 is thereby correspondingly pushed into the reagent reservoir 4512 immediately adjacent the reagent 4514 ensuring a consistent and full reconstitution of the reagent 4514. As shown in FIG. 46b, the activator shaft 4511 includes an activator stopper 4548. The activator stopper 4548 includes, but is not limited to a stopper integral to the activator shaft 4511, a stopper separate from and coupled to the shaft 4511 and the like. The activator stopper 4548 is engaged against an activator stopper seat 4550 when the activator 4510 has been activated (e.g. fully moved toward the reagent reservoir for mixing of the solution and dispensing of the mixture). Engagement between the activator stopper 4548 and the seat 4550 substantially prevents movement of the activator into the reagent reservoir 4512 thereby ensuring the reagent reservoir 4512 has a consistent volume for full reaction of the reagent 4514 and solution 4528.

Referring again to FIGS. 45a-c, in one example, the solution reservoir 4524 includes a predetermined amount of flushing gas 4525. As shown in FIG. 45a the flushing gas 4525 is positioned relatively below the solution 4528 (e.g., the solution 4528 is drawn up into the barrel shaft 4530 by vacuum and held above the flushing gas 4525). In yet another example, the flushing gas 4525 is disposed above the solution 4528. For instance, the solution 4528 is drawn into the barrel shaft after the activator 4510 has already been partially drawn back. Upon activation of the activator 4510 the solution 4528, as previously described, is moved into the reagent reservoir 4512 for mixing with the reagent 4514 to form the specified amount of the reagent mixture. The introduction of the flushing gas 4525 forces the reagent mixture out of the dispensing reservoir tip 4504 through the dispensing reservoir nozzle 4518 and out of the device 4500.

The mechanical interfitting between the flanges 4552, 4544 and seats 4554 and 4546 as well as the piercing edge 4526 seated against the piercing edge seat 4538 provides a consistent positioning of the barrel shaft 4530 and the activator 4510 coupled thereto within the dispensing reservoir tip 4504. Further, the engagement between the activator stopper 4548 and the activator seat 4550 substantially ensures that the proper amount of solution 4528 and flushing gas 4525 are introduced to the reagent reservoir 4512. These mechanical interfittings and dimensioning ensure that a consistent amount of solution is applied to the reagent 4514 to create a consistent amount of a reagent mixture. Similarly, the mechanical interfittings ensure a large amount of flushing gas 4525 relative to the smaller volume of the reagent reservoir 4512 is applied to the reagent mixture to dispense a consistent amount of the mixture through the dispensing reservoir nozzle 4518. A user is thereby able to confidently and accurately dispense the specified amount of the reagent mixture having a desired concentration without the need for time consuming technician expertise. Additionally, as described in other examples, the device 4500 stores and separates the reagent from the solution reservoir containing the solution during transport and prior to use. The device 4500 further provides a quick and easy single step mechanical device that allows one single activation action. For instance, depression of the thumb against the thumb flange 4536 of the activator to move the solution into the reagent reservoir allowing mixing of the solution and the reagent, and subsequent dispensing of the reagent mixture out of the dispensing reservoir tip 4504. Further, the provision of the barrel 4508 threadably coupled with the body 4502 substantially prevents accidental opening of the reagent reservoir seal 4522. Instead, the user consciously rotates the barrel 4508 relative to the body 4502 to pierce the seal 4522 and allow communication between the solution reservoir 4524 and the reagent reservoir 4512.

Figure 47:
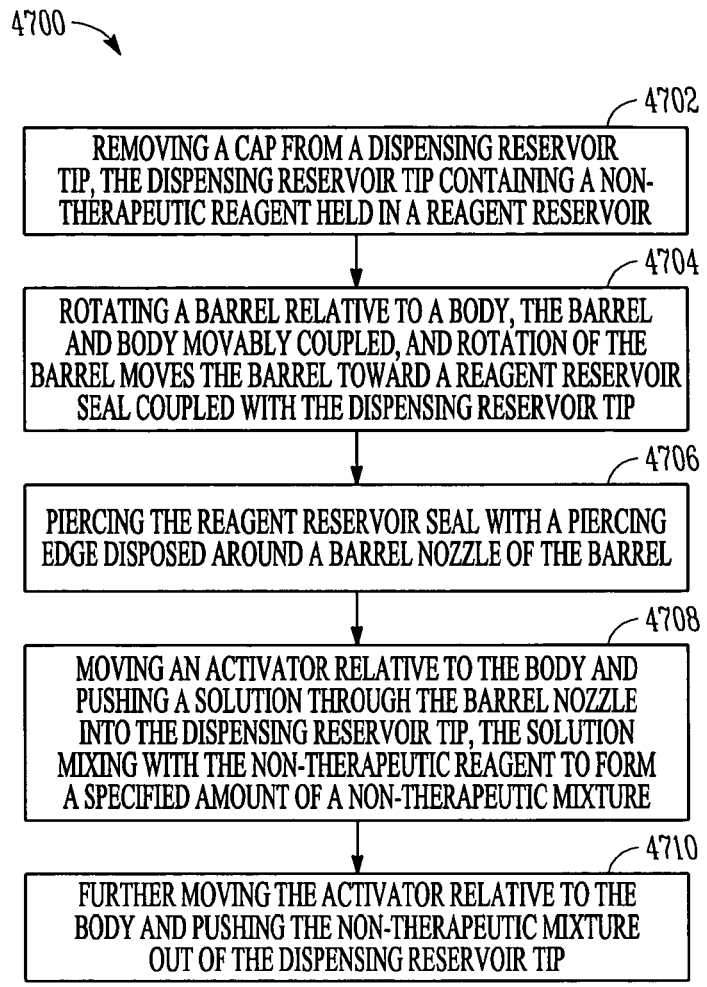
FIG. 47 is a block diagram showing one example of a method of using the device shown in FIGS. 45a-46b.

FIG. 47 shows one example for a method 4700 of using a reagent preparation and dispensing device, such as the device 4500 shown in FIGS. 45a-c and 46a, b. Reference is made in regard to the method 4700 to the device 4500 shown in FIGS. 45a-c and FIGS. 46a, b, including the elements shown in those drawings and previously described above.

At 4702, a cap 4506 is removed from a dispensing reservoir tip 4504. The dispensing reservoir tip 4504 contains a reagent 4514 held in a reagent reservoir 4512. In one example, the reagent 4514 is held in a reagent recess 4516, as described above. As shown in FIG. 45a, the cap includes a desiccant 4507 to minimize the presence of moisture within the dispensing reservoir tip 4504, in another example.

At 4704, a barrel 4508 is rotated relative to a body 4502. The barrel 4508 and the body 4502 are movably coupled, for instance, by threading 4538. Rotation of the barrel 4508 moves the barrel longitudinally toward a reagent reservoir seal 4522. The reagent reservoir seal 4522 is coupled with the dispensing reservoir tip 4504, as previously described above. In one example, the barrel 4508 includes the solution reservoir 4524 containing the solution 4528, and the activator 4510 extends through the barrel 4508. Rotation of the barrel 4508 relative to the body 4502 thereby moves the barrel 4508, the solution reservoir 4524, and the activator 4510 toward the dispensing reservoir tip 4504 and the reagent reservoir 4512.

At 4706, the reagent reservoir seal 4522 is pierced with the piercing edge 4526 of the barrel shaft 4530. As shown in FIGS. 45b, c the piercing edge 4526 is disposed around a piercing nozzle 4542. As described in method step 4704, rotation of the barrel 4508 relative to the body 4502 moves the barrel shaft 4530 relative to the body 4502 and the dispensing reservoir tip 4504 thereby moving the piercing edge 4526 and the barrel shaft 4530 through the reagent reservoir seal 4522 and positioning at least a portion of the barrel shaft 4530 and the piercing edge 4526 within the reagent reservoir 4512.

At 4708, an activator 4510 is moved relative to the body 4502. Movement of the activator 4510 pushes the solution 4528 through the barrel nozzle (e.g., barrel shaft 4530) and into the dispensing reservoir tip 4504. In the reagent reservoir 4512 of the dispensing reservoir tip 4504 the solution 4528 mixes with the reagent 4514 to form a specified amount of a mixture. As shown in FIGS. 46a, b, the movement of the barrel shaft 4530 into the dispensing reservoir tip 4504 and positioning of the piercing edge 4526 along the piercing edge seat 4538 minimizes the volume of the reagent reservoir 4512 thereby allowing the solution 4528 to immediately come in contact with the reagent 4514 and reconstitute the reagent 4514 within the smaller volume of the reagent reservoir 4512.

At 4710, the activator 4510 is further moved relative to the body 4502. Further movement of the activator 4510 pushes the reagent mixture out of the dispensing reservoir tip 4504 through the dispensing reservoir nozzle 4518. As described previously and shown in FIG. 45a, in one example, the solution reservoir 4524 includes a flushing gas 4525. Further movement of the activator 4510 pushes the flushing gas 4525 into the reagent reservoir 4512 shown in FIG. 46a, b. Introduction of the flushing gas 4525 into the smaller reagent reservoir 4512 moves the reagent mixture out of the dispensing reservoir tip 4504 through the dispensing reservoir nozzle 4518.

Figure 45C:
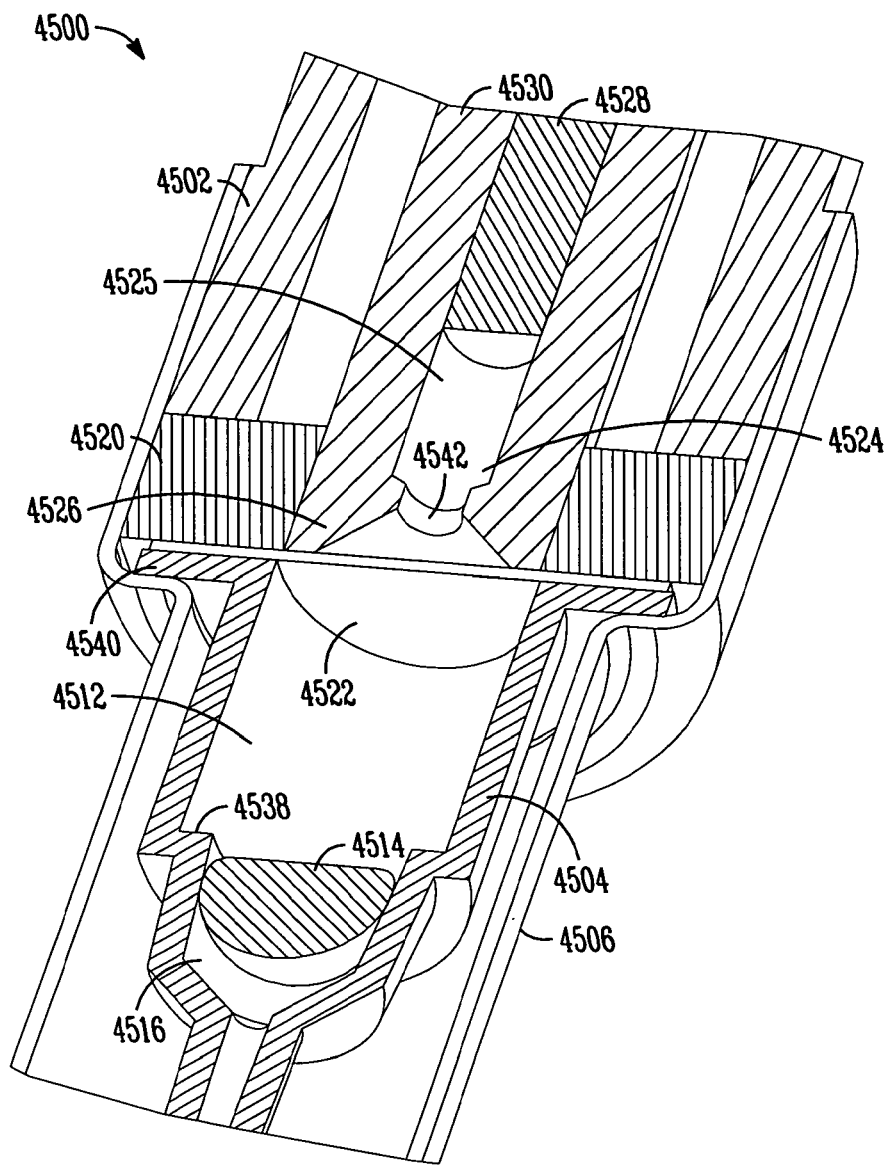
FIG. 45c is a detailed cross-sectional perspective view of the reagent and solution reservoirs of the device shown in FIG. 45a, b.

Several options for the method 4700 are described below. In one example, moving the activator 4510 in step 4708 and further moving the activator in step 4710 include moving the activator 4510 in a single motion, for instance, a single thumb press of the activator flange 4536 shown in FIG. 45a. In another example, moving the barrel shaft 4530 into the reagent reservoir 4512 shrinks the reagent reservoir 4512, as shown in FIGS. 45a-c showing the larger reservoir and FIGS. 46a, b showing the smaller reservoir. In yet another example, at least one of moving the activator 4510 as described in method 4708 and further moving the activator described in method step 4710 includes positioning a portion of the activator 4510 including an activator flange 4536 substantially within a barrel recess 4534.

Figure 48:
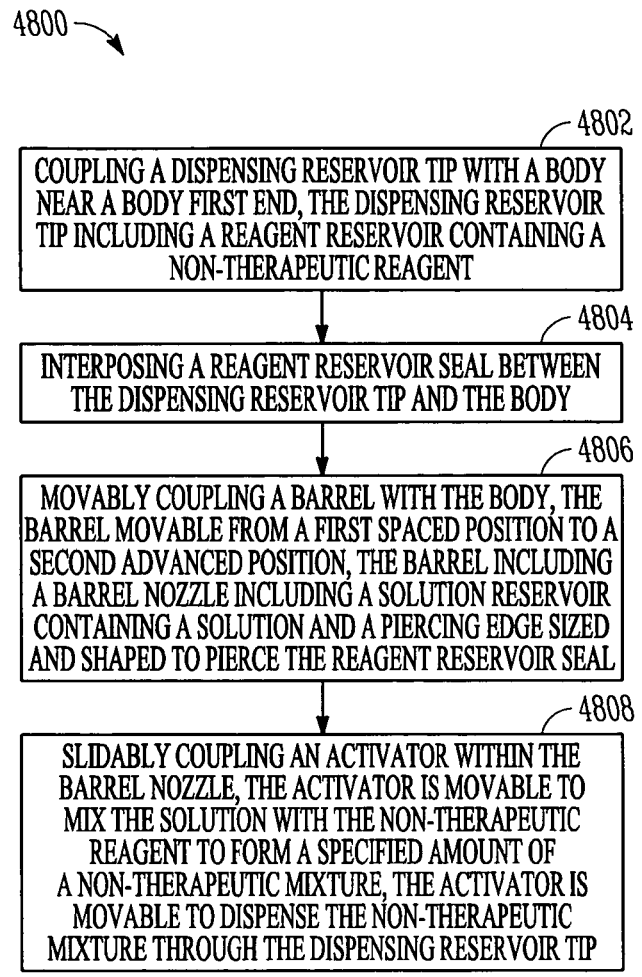
FIG. 48 is a block diagram showing one example of a method of making the device shown in FIGS. 45a-46b.

A method for making a reagent preparation and dispensing device such as the device 4500 shown in FIGS. 45a-c and FIG. 46 a, b, is shown in FIG. 48. Reference is made regarding the method 4800 to the device 4500 including the elements described in FIGS. 45a-c and FIG. 46a, b as well as the associated description provided above.

At 4802, a dispensing reservoir tip 4504 is coupled with a body 4502 near a body first end, for instance, the end of the body 4502 adjacent to the interconnecting gasket 4520. The dispensing reservoir tip 4504 includes a reagent reservoir 4512 containing a reagent 4514, as shown in FIG. 45a. In one example shown in FIG. 45a, the reagent 4514 is positioned within a reagent recess 4516. The reagent recess 4516 is sized and shaped to grasp the reagent 4514 during transport and prior to use. The reagent recess 4516 thereby maintains the structural integrity of the reagent and sustains its presence within the dispensing reservoir tip 4504 without the risk of any portion of the reagent breaking apart within the reagent reservoir 4512 and falling out of the dispensing reservoir nozzle 4518.

At 4804, a reagent reservoir seal 4522 is interposed between the dispensing reservoir tip 4504 and the body 4502. As shown in FIGS. 45a-c, the reagent reservoir seal 4522 is positioned along a dispensing reservoir tip flange 4540. In one example, the reagent reservoir seal 4522 is coupled with the dispensing reservoir tip flange 4540 with an adhesive, a weld and the like. In another example, the reagent reservoir seal 4522 is engaged along the dispensing reservoir tip flange 4540 and held there by deformable engagement of the interconnecting gasket 4520 against the dispensing reservoir tip 4504.

At 4806, a barrel 4508 is movably coupled with the body 4502. The barrel 4508 is movable from a first spaced position, for instance, the position shown in FIGS. 45a-c to a second advanced position such as the position shown in FIGS. 46a, b. The barrel 4508 includes a barrel nozzle, such as the barrel shaft 4530 including a solution reservoir 4524 containing a solution 4528. As shown in FIG. 45a, the barrel 4508 further includes a piercing edge 4526 positioned around a conical solution reservoir nozzle 4542 (see also FIGS. 45b, c). As previously described, the piercing edge 4526 is sized and shaped to pierce the reagent reservoir seal 4522 and allow communication between the reagent reservoir 4512 and the reagent 4514 housed therein and the solution reservoir 4524 containing the solution 4528.

At 4808 an activator 4510 (e.g., a plunger) is slidably coupled within the barrel nozzle, such as the barrel shaft 4530. The activator 4510 is movable to mix the solution 4528 with the reagent 4514 by moving the solution 4528 into the reagent reservoir 4512. Mixing of the solution with the reagent forms a specified amount of a mixture. The activator is further removable to dispense the mixture through the dispensing reservoir tip 4504 (e.g., the dispensing reservoir nozzle 4518).

Figure 49A:
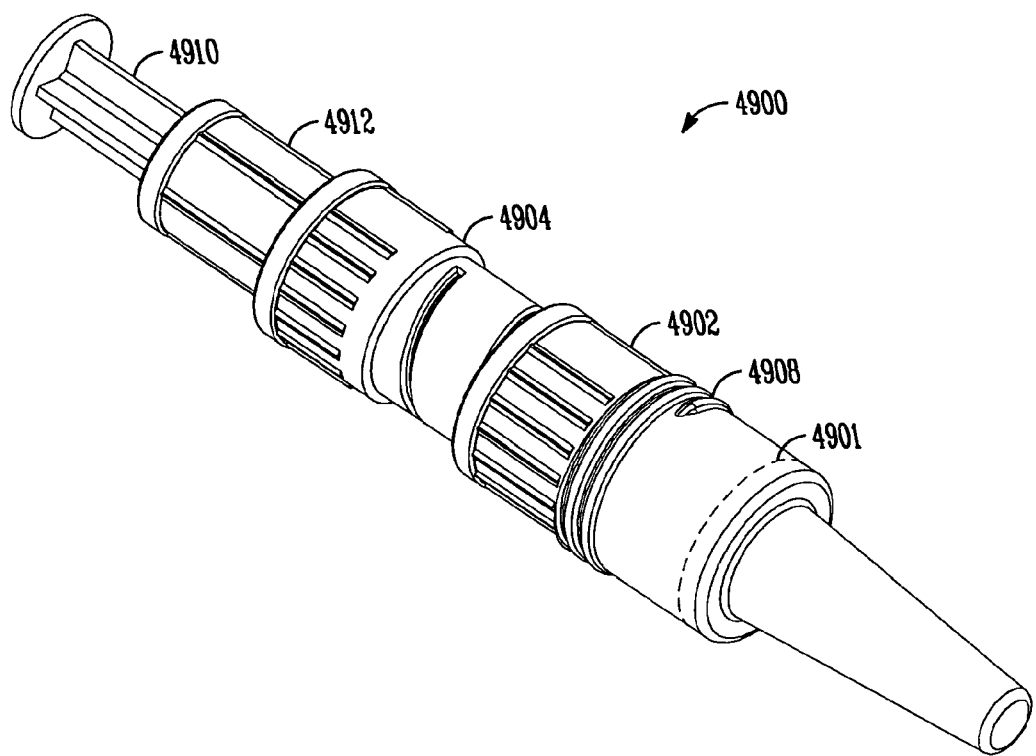
FIG. 49a is a perspective view of one example of a reagent preparation and dispensing device including a plural activator mechanism.
Figure 49B:
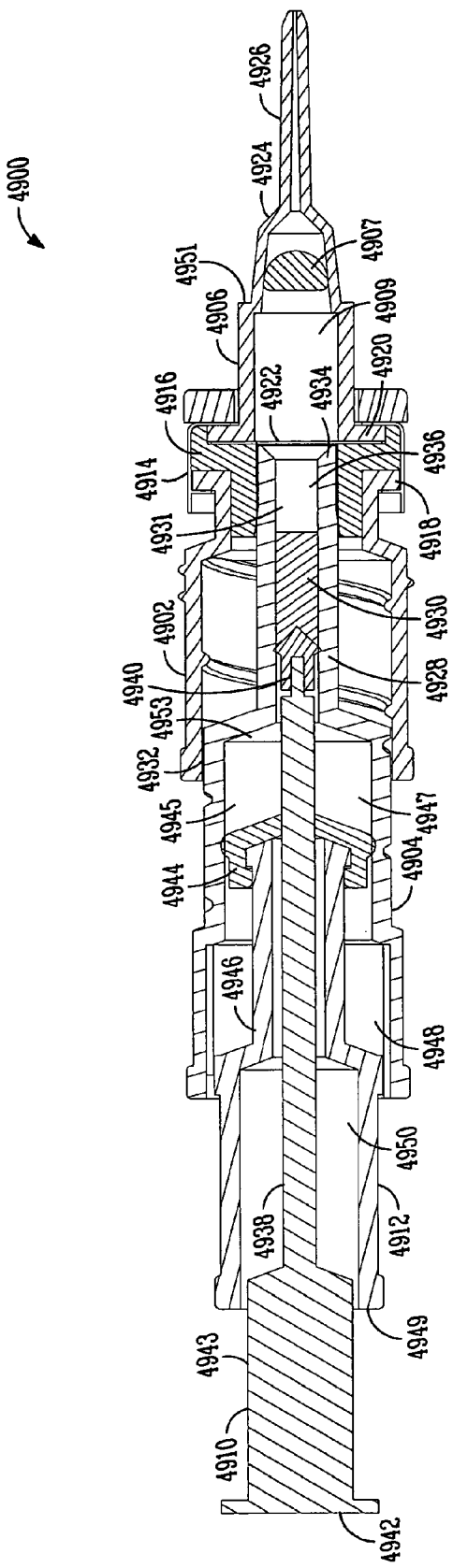

Another example of a reagent preparation and dispensing device 4900 is shown in FIG. 49a. The device 4900 includes a body 4902 and a barrel 4904 moveably coupled with the body 4902. In one example, the barrel 4904 is rotatably coupled with the body 4902. Referring to FIG. 49b a dispensing reservoir tip 4906 is coupled with the body 4902. The dispensing reservoir tip 4906 includes a reagent 4907 such as a lyophilized reagent disposed therein. As shown in FIG. 49b, in one example, the reagent 4907 is disposed within a reagent recess 4924. The reagent recess 4924, in one option, is sized and shaped to receive the reagent 4907 and grasp the reagent 4907 during storage and transport thereby protecting the reagent 4907 from physical impacts, vibration and the like.

Referring now to FIGS. 49a, b the device 4900 further includes a primary activator 4910 movably coupled with a secondary activator 4912. The primary and secondary activators 4910, 4912 are moveably coupled with at least one of the body 4902 and barrel 4904. In one example, the primary and secondary activators 4910, 4912 include a plunger slidably received within the barrel 4904 and body 4902. In yet another example, a cap 4908 is fitted over a portion of the body 4902 thereby covering the dispensing reservoir tip 4906. As described in previous examples, the cap 4908 includes a desiccant positioned around the dispensing reservoir tip nozzle 4926. The desiccant is configured to remove moisture from within the cap and any incidental moisture that makes it way into the dispensing reservoir tip 4906 thereby creating a dry environment for the reagent 4907. The dry environment preserves the structural integrity of the reagent 4907 during transport and prior to use.

Referring again to FIG. 49b, the dispensing reservoir tip 4906 is coupled with the body 4902 for instance with a crimp ring 4914 extending between the dispensing reservoir tip 4906 and the body 4902. An interconnecting gasket 4916 is coupled between the body 4902 and the dispensing reservoir tip 4906. The crimp ring 4914 is sized and shaped to extend around a body flange 4918 and dispensing reservoir tip flange 4920. The crimp ring 4914 compresses the interconnecting gasket 4916 therebetween forming a tight seal between the body 4902 and dispensing reservoir tip 4906. The tight seal between the body 4902 and tip 4906 substantially prevents leaking of reagent mixtures formed in a reagent reservoir (i.e., a reaction chamber) 4909 defined within the dispensing reservoir tip 4906. In another example, the interconnecting gasket 4916 is constructed with but not limited to a deformable material such as butyl rubber configured to substantially prevent the ingress or egress of fluids including the reagent mixture through the interconnecting gasket 4916.

A reagent reservoir seal 4922 is interposed between the interconnecting gasket 4916 and the dispensing reservoir tip flange 4920. The reagent reservoir seal 4922, in one example, is a laminate seal including a foil laminated with a resin. Optionally, the reagent reservoir seal 4922 is coupled with the dispensing reservoir tip flange 4920 thereby closing the reagent reservoir 4909 when the cap 4908 is coupled with the body 4902.

As previously described, the barrel 4904 is moveably coupled with the body 4902. In one example, the barrel 4904 and body 4902 are movably coupled together with threading interposed therebetween. Rotation of the barrel 4904 relative to the body 4902 thereby moves the barrel longitudinally 4904 relative to the body 4902. As shown in FIG. 49b, the barrel 4904 includes a barrel shaft (e.g., a barrel nozzle) 4928 forming a solution reservoir 4931 to contain a solution 4930. The barrel shaft 4928 further includes a solution reservoir dispensing nozzle 4936. As described below, the solution 4930 is moved through the solution reservoir dispensing nozzle 4936 after piercing of the seal 4922 to allow intermixing between the reagent 4907 and the solution 4930. The barrel shaft 4928 further includes a piercing edge 4934 extending at least part way around the solution reservoir nozzle 4936. The piercing edge 4934 is sized and shaped for engagement with the reagent reservoir seal 4922 to puncture the seal 4922 and allow communication between the solution reservoir 4931 and the reagent reservoir 4909. As described below, rotation of the barrel 4904 relative to the body 4902 moves the barrel shaft 4928 and the piercing edge 4934 into engagement with the reagent reservoir seal 4922 thereby piercing the seal and allowing communication.

As shown in FIG. 49b, and described above the device 4900 includes a primary activator 4910 and a secondary activator 4912. The primary and secondary activators 4910, 4912 are disposed within the barrel 4904. As shown in FIG. 49b, the primary and secondary activators 4910, 4912 are slidably received within the barrel 4904. The primary activator includes a thumb rest 4942 and a primary activator body 4943. A primary activator shaft 4948 extends from the primary activator body 4943. The primary activator shaft 4938 extends through a secondary activator shaft 4946 and a secondary stopper gasket 4944. As shown in FIG. 49b, the primary activator shaft 4938 enters the solution reservoir 4931 and a primary stopper gasket 4940 coupled with the shaft 4938 (e.g., attached or integrally formed) closes the solution reservoir 4931 thereby sealing the solution 4930 within the solution reservoir.

In one example, the primary stopper gasket 4940 is constructed with but not limited to a deformable material such as butyl rubber configured to prevent the ingress or egress of moisture across the primary stopper gasket 4940 thereby preventing exit or entrance of moisture into the solution reservoir 4931. In another example, the primary stopper gasket 4940 is integrally coupled to the primary activator shaft 4938 (e.g., molded, machined and the like from the same material). The secondary activator 4912 is movably coupled with the barrel 4904. As shown in FIG. 49b, the secondary activator 4912 is slidably coupled with the barrel 4904 by the secondary stopper gasket 4944. The secondary stopper gasket 4944 is coupled around the secondary activator shaft 4946. In still another example, the secondary stopper gasket 4944 is integrally coupled with the secondary activator shaft 4946 (e.g., molded, machined and the like from the same material). As shown in FIG. 49b, the secondary stopper gasket 4944 provides a tight seal between the secondary activator 4912 and barrel 4904 thereby preventing the escape of flushing gas 4945 contained within a flush chamber 4947 of the barrel 4904. Additionally, the secondary stopper gasket 4944 tightly engages with the primary activator shaft 4938 thereby preventing movement of the flushing gas 4945 between the secondary stopper gasket 4944 and primary activator shaft 4938. The secondary stopper gasket 4944 thereby allows relative movement of the primary activator 4910 including the primary activator shaft 4938 through the secondary stopper gasket 4944 without allowing the flushing gas 4945 to escape through the hollow secondary activator shaft 4946.

As previously described, the primary activator 4910, the secondary activator 4912 and the barrel 4904 are all movable relative to each other. Further, these three features are movable relative to the body 4902. Each of these components of the reagent preparation and dispensing device 4900 are movable to perform specific functions relative to the formation of a reagent mixture and dispensing of the same. For example, the barrel 4904 is movable relative to the body 4902. As previously described, the barrel shaft 4928 is movable into the reagent reservoir 4909 of the dispensing reservoir tip 4906. As shown in FIG. 49b, the dispensing reservoir tip 4906 includes a receiving seat 4951 sized and shaped to receive the piercing edge 4934. Upon engagement of the piercing edge 4934 with the receiving seat 4951 movement of the barrel 4904 relative to the body 4902 is arrested. Similarly, as the primary activator 4910 is moved into a secondary activator recess 4950 and barrel 4904 the thumb rest flange 4942 engages against a secondary activator flange 4949 thereby preventing further movement of the primary activator 4910 relative to the secondary activator 4912. In another example, the secondary activator shaft 4946 is sized and shaped so that movement of the secondary activator 4912 and primary activator 4910 when both activators are coupled together is arrested when the secondary stopper gasket 4944 engages with a bottom seat 4953 of the flushing chamber. The primary activator 4910, the secondary activator 4912, the barrel 4904, the body 4902 and the dispensing reservoir tip 4906 are all configured so each component performs a desired function without undesirably dispensing a partially mixed solution of the reagent 4907 and solution 4930 prior to full reconstitution of the reagent with the solution. The device 4900 is thereby able to consistently mix the reagent 4907 and solution 4930 through the use of full ranges of motion of, for example, the primary activator 4910, the secondary activator 4912 and the barrel 4904 without any risk of undesirably dispensing the mixture prior to the desired moment for dispensing. The need for precise measuring and operation of devices with a wide range of motion, such as pipettes, syringes and the like is thereby avoided.

Figure 50A:
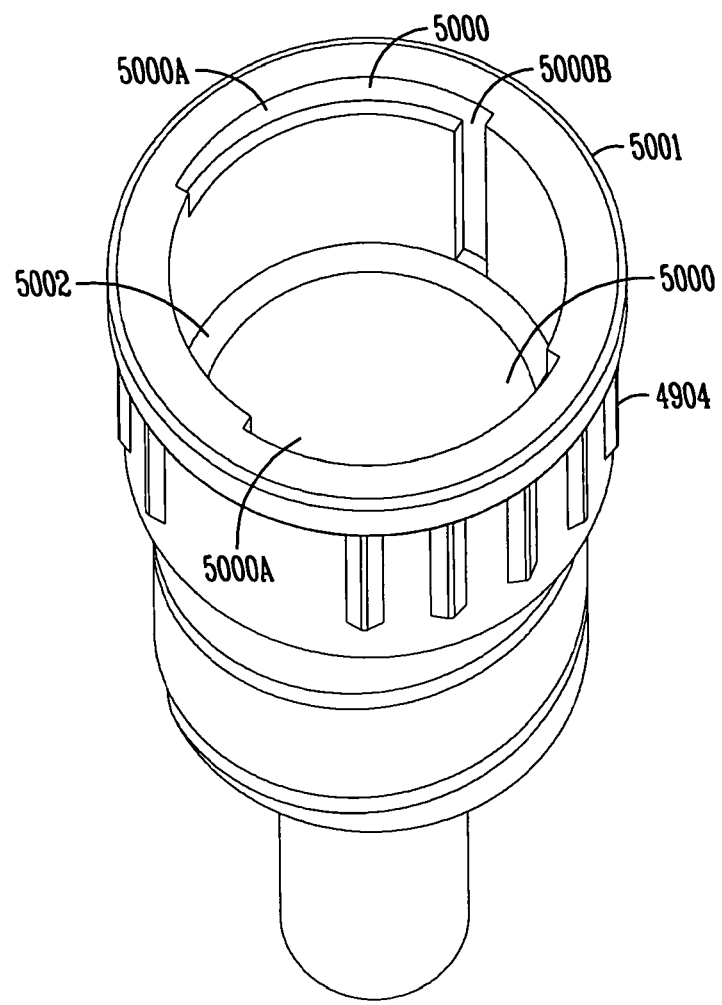
FIG. 50a is a perspective view of one example of the barrel including a safety groove.

As shown in FIG. 50a, the barrel 4904 includes a safety groove 5000 extending around at least a portion of the barrel head 5001. As shown in FIG. 50a, a plurality of grooves 5000 is included around the barrel 4904. Optionally, one groove or a plurality of grooves includes a horizontal portion 5000A extending arcuately around the barrel 4904 approximately 90 degrees. The safety groove 5000 further includes a vertical portion 5000B extending axially through a portion of the barrel head 5001. As described further below, the safety groove 5000 substantially prevents unwanted movement of the second activator 4912 during movement of the primary activator 4910 toward the dispensing reservoir tip 4906.

Figure 50B:
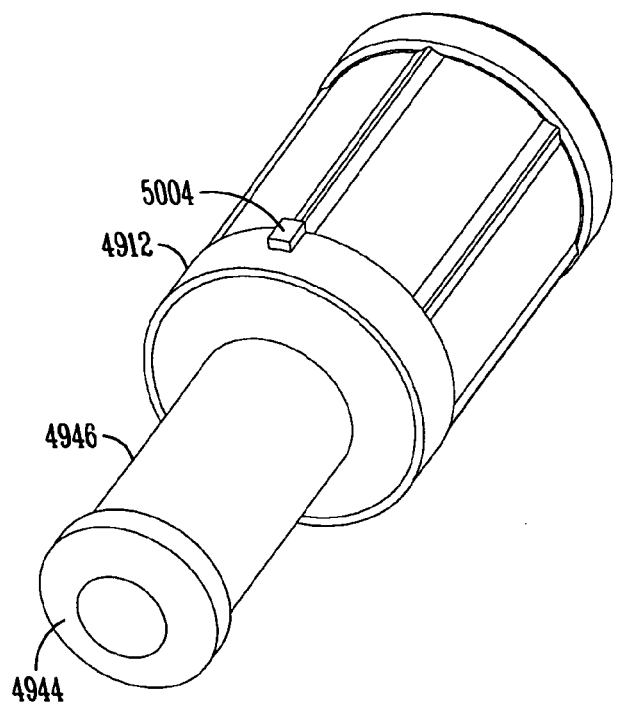
FIG. 50b is a perspective view of one example of the secondary activator including a safety tab.
Figure 50C:
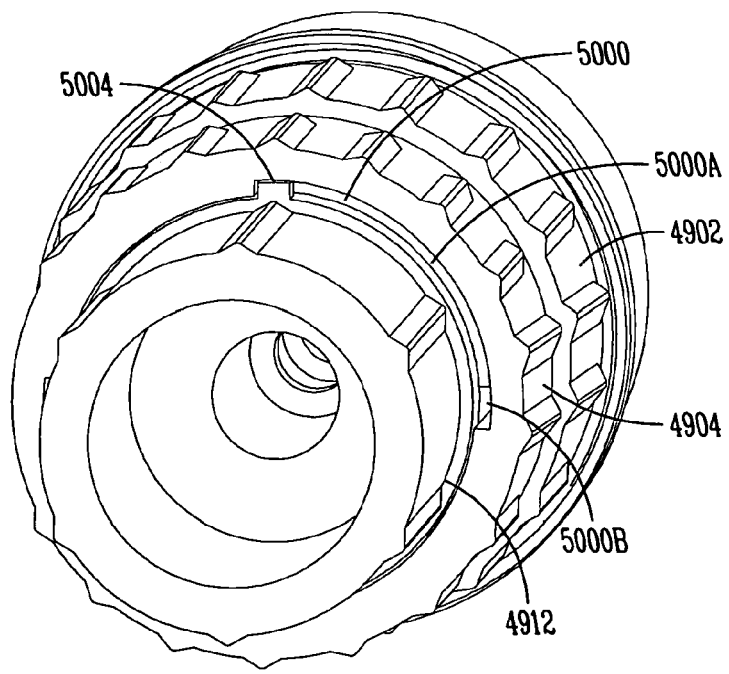
FIG. 50c is a perspective view of the secondary activator movably coupled with the barrel with the safety tab positioned within the safety groove.

Referring now to FIG. 50b, the secondary activator 4912 includes a safety tab 5004. The safety tab 5004, for instance a projection, extends from the secondary activator 4912 at a position spaced from the secondary activator shaft 4946 and secondary stopper gasket 4944. The safety tab 5004 is sized and shaped for movement along the safety groove 5000 of the barrel 4904. Engagement of the safety tab 5004 of the secondary activator 4912 is shown in FIG. 50c. The safety tab 5004 is moveably disposed within the horizontal portion 5000A of the safety groove 5000. As shown, the secondary activator 4912 is thereby prevented from moving axially toward the dispensing reservoir tip 4906 (FIGS. 49a, b) because the safety tab 5004 is positioned within the horizontal portion 5000A of the safety groove 5000. Upon rotation of the safety tab 5004 to the vertical portion 5000B of the safety groove 5000 the second activator 4912 is able to move longitudinally relative to the barrel 4904 and body 4902 thereby allowing movement of the flushing gas 4945 out of the flushing chamber 4947 and into the reagent reservoir 4909 at the proper time after mixing of the reagent 4907 and solution 4930 as described below.

The safety groove 5000 and safety tab 5004 thereby interfit to substantially prevent undesirable dispensing of a partially mixed or separated reagent in the solution prior to completion of the reconstitution of the reagent. For example, after complete reconstitution of the reagent with the solution to form a reagent mixture the secondary activator 4912 and the safety tab 5004 are rotated relative to the barrel 4904 to position the safety tab 5004 in the vertical portion 5000A of the safety groove 5000 thereby allowing movement of the secondary activator 4912 as well as the primary activator 4910 toward the dispensing reservoir tip to dispense the reagent mixture out of the dispensing reservoir tip 4906. Precise technique (e.g., for measurement, observation of the complete reconstitution of the reagent and the like) for the reconstitution of a reagent with the solution and subsequent dispensing are thereby avoided by relying on the interaction of, for instance, the barrel 4904 and secondary activator 4912 through the safety tab 5000 and safety groove 5000. The interaction of the safety tab 5000 and the safety groove provides a staged reconstitution of the reagent prior to dispensing.

Figure 51A:
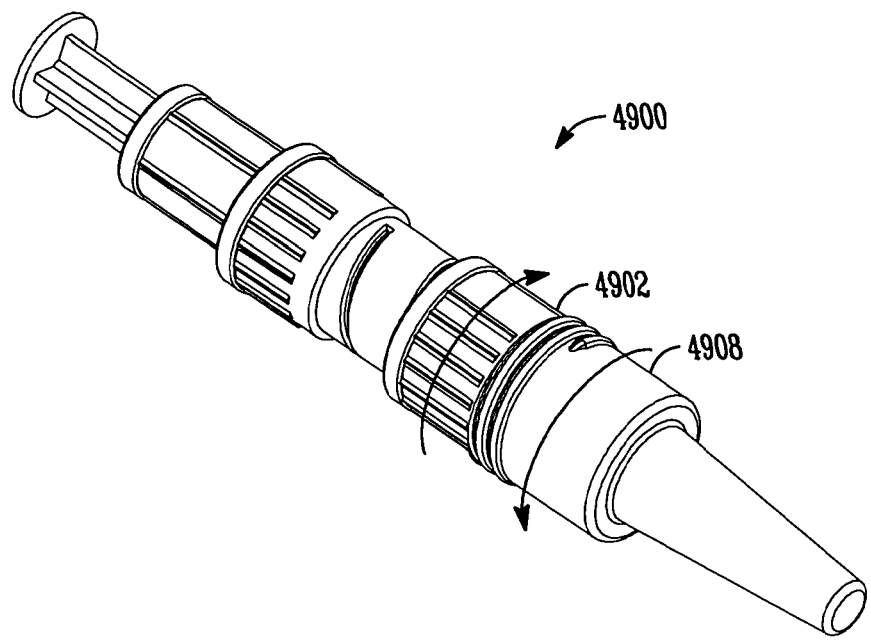
FIG. 51a is a perspective view of the device shown in FIGS. 49a, b in a first orientation.
Figure 51B:
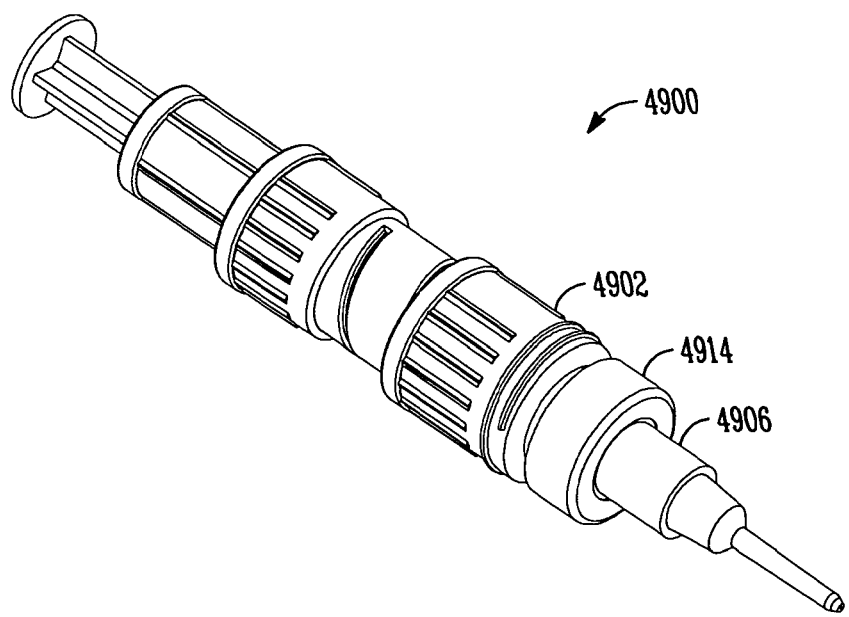
FIG. 51b is a perspective view of the device shown in FIG. 49a, b with a cap removed.
Figure 51C:
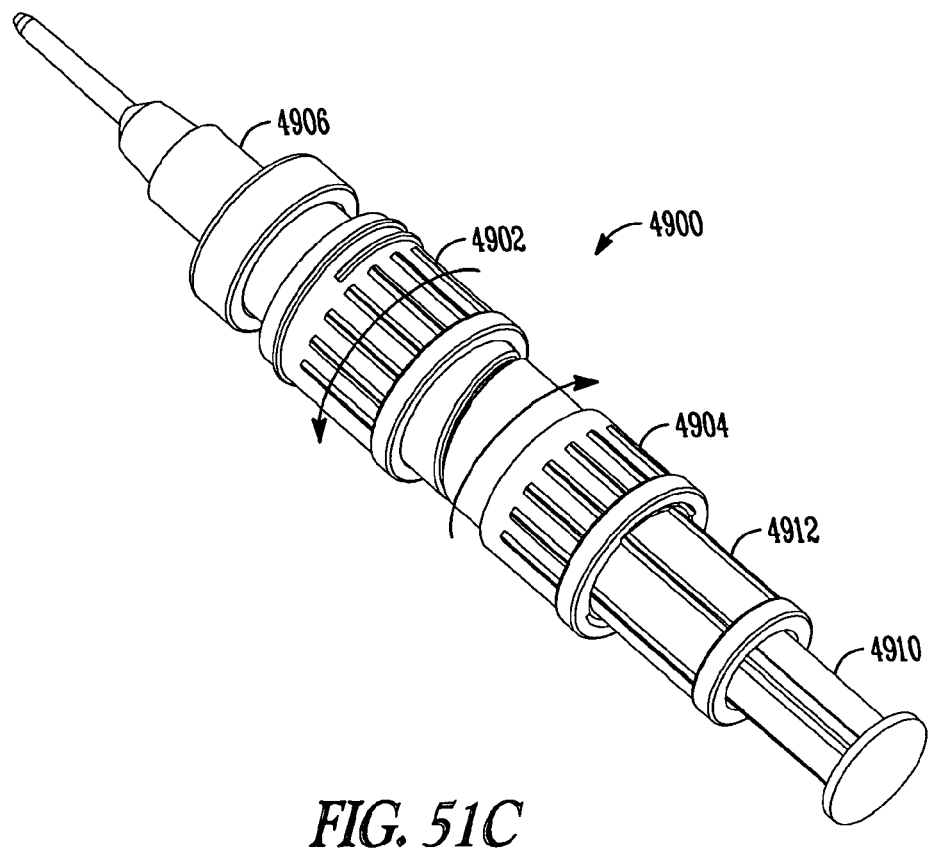
FIG. 51c is a perspective view of the device shown in FIGS. 49a, b with the barrel rotated relative to the body.

Referring now to FIGS. 51a through 51i, a method of using the device 4900 is described. In FIG. 51a, the device 4900 is shown with the cap 4908 coupled with the body 4902. In one example, the cap 4908 is coupled with the body 4902 with a mechanical fitting such as a friction interfit. In another example, the cap 4908 is coupled to body 4902 with threading therebetween. As shown in FIG. 51a, relative rotation of the cap 4908 relative to the body 4902 allows for removal of the cap 4908. Referring back to FIGS. 49a, b, the cap 4908 is shown coupled with the body 4902. As shown in FIG. 49a, a cap seal 4901 is included in the interior of the cap 4908. Cap seal 4901 is sized and shaped to engage against the crimp ring 4914 when the cap 4908 is coupled with the body 4902. The cap seal 4901 cooperates with the interconnecting seal 4916 within the crimp ring 4914 and the reagent reservoir seal 4922 to substantially seal the reagent reservoir 4909 shown in FIG. 49B. Referring now to FIG. 51b, after rotation of the cap 4908 relative to the body 4902 the cap is removed from the body 4902 thereby exposing the crimp ring 4914 and the dispensing reservoir tip 4906.

Figure 51D:
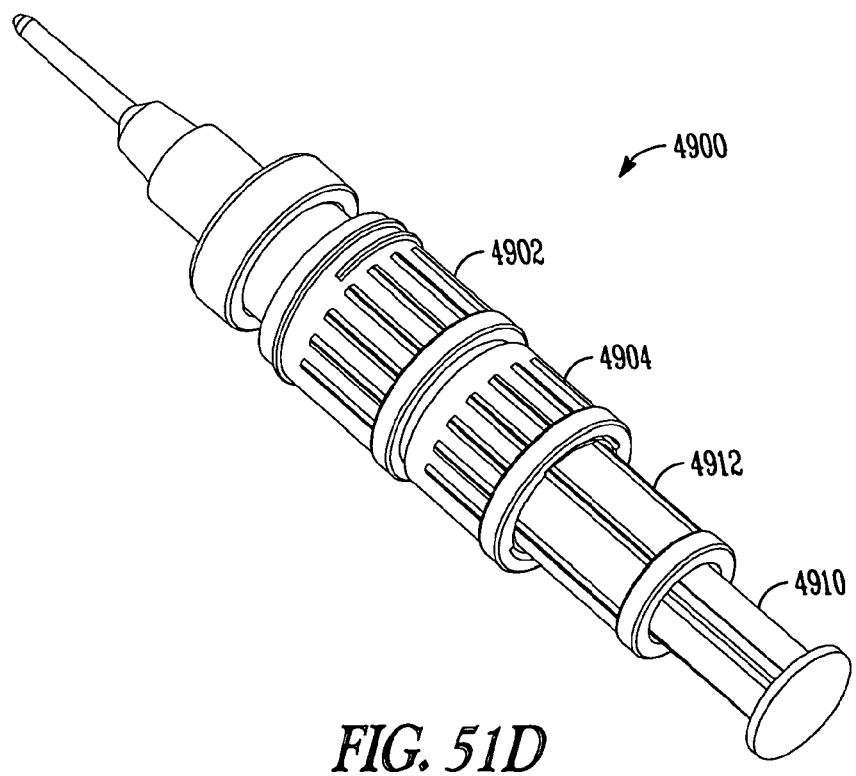
FIG. 51d is a perspective view of the device shown in FIGS. 49a, b with the barrel moved longitudinally toward the body to pierce the reagent reservoir seal.

As previously described, in one example, the body 4902 and barrel 4904 are movably coupled together. In one example, the barrel 4904 and body 4902 are coupled together with threading 4932 (FIG. 49b) extending therebetween. Rotation of the barrel 4904 relative to the body 4902 longitudinally moves the barrel 4904 relative to the body 4902 (e.g., moving the barrel 4904 towards the dispensing reservoir tip 4906) shown by arrows in FIG. 51c. As shown in FIG. 51d, with movement of the barrel 4904 towards the body 4902 the secondary activator 4912 and primary activator 4910 are moved with the barrel 4904 as a single unit. Referring back to FIG. 49b, movement of the barrel 4904 relative to the body 4902 moves a barrel shaft 4928 relative to the body 4902. Movement of the barrel shaft 4928 engages the piercing edge 4934 against the reagent reservoir seal 4922 thereby puncturing the seal 4922 and allowing communication between the reagent reservoir 4909 and solution reservoir 4931. Optionally, the device 4900 is held at an elevated orientation, for instance, with the dispensing reservoir tip 4906 angled upwardly relative to the horizontal axis thereby retaining the solution 4930 within the solution reservoir 4931 and avoiding undesirable dispensing through the dispensing reservoir tip 4906. Referring again to FIG. 49b, movement of the barrel shaft 4928 relative to the body 4902 is performed over the interconnecting gasket 4916. The interconnecting gasket 4916 provides a tight seal around the barrel shaft 4928 thereby preventing any unwanted movement of the solution 4930 around the barrel shaft 4928 and into the other cavities of the body 4902 or out of the reagent reservoir 4909. For instance, past the reagent reservoir flange 4920. In yet another example, the barrel 4904 is coupled to the body 4902 with a different feature, for instance, a slidable feature allowing the barrel 4904 to slide longitudinally relative to the body 4902 (e.g., as a piston within a cylinder).

Referring now to FIGS. 51e and 51f, the reagent preparation and dispensing device 4900 is shown in FIG. 51e in an inverted orientation with the solution reservoir 4931 shown in FIG. 49b disposed below the reagent reservoir 4909 containing the reagent 4907. The primary activator 4910 is in an orientation with the thumb rest flange 4942 positioned away from the secondary activator 4912. In one example, pressure is applied to the thumb rest flange 4942 moving the primary activator 4910 relative to the secondary activator 4912. As shown in FIG. 51f, the thumb rest flange 4942 comes to rest and is arrested from further movement by the secondary activator 4912. Referring again to FIG. 49*b*, movement of the primary activator 4910 relative to the secondary activator 4912 and barrel 4904 forces the primary activator shaft 4938 and primary stopper gasket 4940 into the solution reservoir 4931 moving the solution 4930 into the reagent reservoir 4909 through the solution reservoir nozzle 4936. As previously described, the piercing edge 4934 has pierced through the reagent reservoir seal 4922 and the barrel shaft 4928 has entered the reagent reservoir 4909. The piercing edge 4934 comes to rest against the piercing edge seat 4951 positioning the solution reservoir 4931 immediately adjacent to the reagent 4907. Movement of the primary activator 4910 thereby pushes the solution 4930 into close proximity with the reagent 4907 allowing immediate reaction and reconstitution of the reagent 4907 into a reagent mixture. Because the solution reservoir 4931 is brought into such close proximity to the reagent 4907 additional mixing steps such as turning the reagent device 4900 upside down shaking the device 4900 and other similar steps are thereby avoided. Instead the pressurized stream of the solution 4930 due to the movement of the primary activator 4910 forces the solution 4930 over the reagent 4907 allowing for rapid reconstitution of the reagent 4907. As previously described in other examples, the solution 4930 in one example is a specified amount of solution configured to mix with the reagent 4907 and form a corresponding specified amount of reagent mixture. For instance, the solution 4930 mixes with the reagent 4907 to fully reconstitute the reagent without having any excess solution 4930 that is otherwise not mixed with the reagent.

Referring now to FIGS. 51*g*, *h* and *i*, as well as FIGS. 50*a, b, c* the reagent preparation dispensing device 4900 is in the proper orientation for dispensing of the reagent mixture out of the device 4900. As shown in FIG. 51G, in one example, the device 4900 is returned to a relatively vertical orientation with the dispensing reservoir tip 4906 pointing relatively downward and the primary activator and secondary activator 4910, 4912 are orientated in an upward fashion relative to the barrel 4904 and body 4902. The secondary activator 4912 is then rotated relative to the barrel 4904. As shown in FIGS. 50*a-c* the safety tab 5004 of the secondary activator 4912 is moved along the horizontal portion 5000*a* of the safety groove 5000 and positioned directly above the vertical portion 5000*b* of the safety groove. The primary and secondary activators 4910, 4912 are thereafter allowed to move in a longitudinal direction toward the dispensing reservoir tip 4906. As shown in FIGS. 51*h* and 51*i*, the primary activator 4910 seated against the secondary activator 4912 are moved together as a single unit into the barrel 4904. As will be described further below, movement of the secondary activator 4912 and primary activator 4910 together forces the secondary stopper gasket 4944 to move toward the barrel seat 4953 thereby forcing the gas 4945 within the flushing chamber 4947 around the primary activator shaft 4938 and into the reagent reservoir 4909. Movement of the gas 4945 into the reagent reservoir 4909 forces the reagent mixture out of the dispensing reservoir tip 4906, and as shown, moves the mixture through the dispensing reservoir nozzle 4926. As shown in the figures and described above, the interconnections between the primary and secondary activators 4910, 4912, the barrel 4904, the body 4902 and the dispensing reservoir tip 4906 allow discreet movements of individual components of the reagent preparation and dispensing device 4900. The user is thereby able to confidently open the seal between the reagent reservoir 4909 and solution reservoir 4930 in a single step, and in a second discrete step is able to reconstitute the reagent 4907 with the specified amount of solution 4930. In a third discrete step, the user is thereby able to unlock longitudinal movement of the assembly of the primary activator 4910 and secondary activator 4912 by rotation of the secondary activator relative to the barrel through the use of the safety tab 5004 and the safety groove 5000. This distinct movement then allows axial movement of the primary activator 4910 and secondary activator 4912 to dispense the reconstituted reagent mixture out of the dispensing reservoir tip 4906. Having these discrete steps that are performed in relation to the various components of the device 4900 minimizes the need for technician expertise and allows quick and easy use of the device 4900 to accurately reconstitute and then dispense a specified amount of the reagent mixture.

Figure 52A:
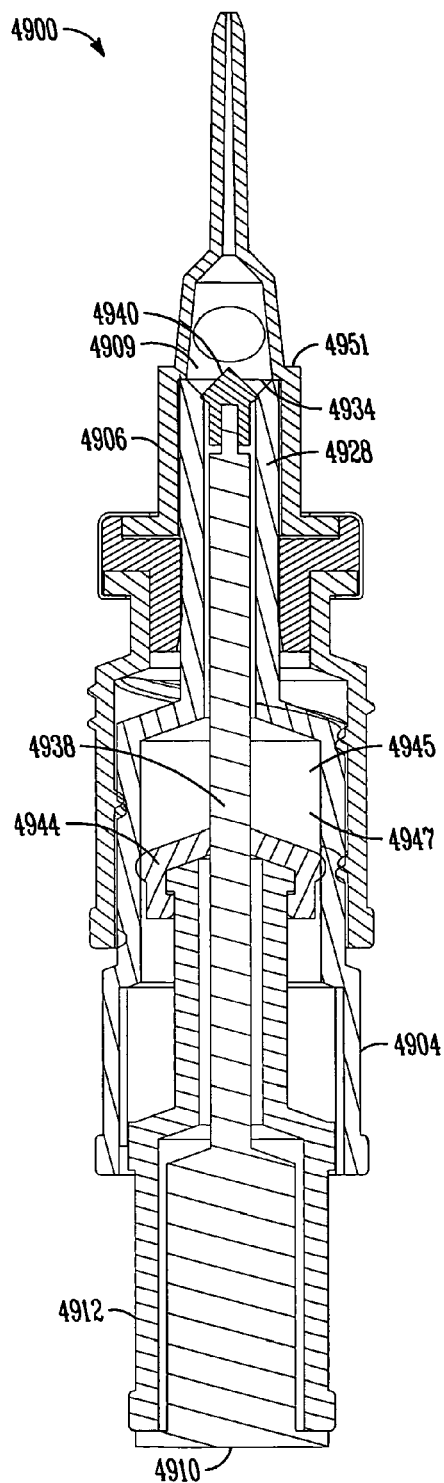
FIG. 52*a* is a cross-sectional view of the device shown in FIGS. 49*a, b* and 51*f, g, h* with the solution within the reagent reservoir after movement of the primary activator.

Referring now to FIGS. 52*a, b*, the reagent preparation and dispensing device 4900 is shown in two separate intermediate orientations prior to dispensing for the reagent mixture. As shown in FIG. 52*a*, the device 4900 is in a substantially inverted orientation with the barrel shaft 4928 fully positioned within the reagent reservoir 4909. As shown, the piercing edge 4934 is seated against the piercing edge seat 4951 thereby arresting further movement of the barrel shaft 4928 into the reagent reservoir 4909. Movement of the barrel shaft 4928 into the reagent reservoir 4909 shrinks the reagent reservoir 4909 thereby providing a smaller space configured to hold the full amount of the solution 4930 and the reagent 4907 (shown in FIG. 49*b*) while the reagent and solution are reconstituted. The relatively small space of the reagent reservoir 4909 is shown FIG. 52*a* relative to the larger space of the reagent reservoir 4909 shown in FIG. 49*b*. The small space of the reagent reservoir 4909 allows for easier dispensing of the reagent mixture with a more compact feature such as the compact flushing chamber 4947 including the flushing gas 4945. The size of the reagent preparation and dispensing device 4900 is thereby minimized for ease of storage, transport and the like.

Figure 52B:
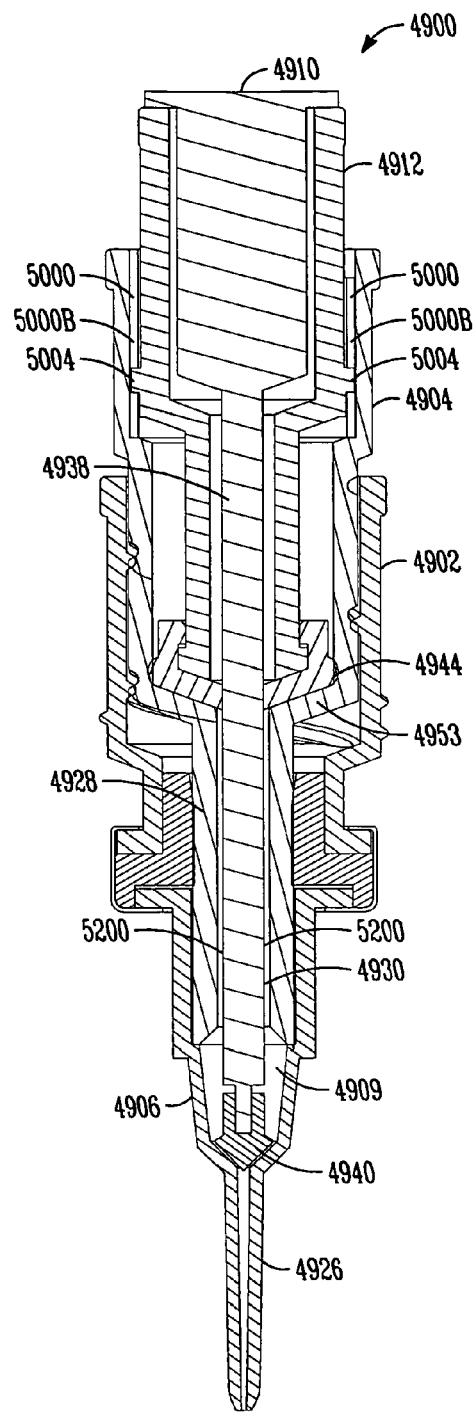
FIG. 52*b* is a cross-sectional view of the device shown in FIGS. 49*a, b* and 51*i* with the mixture dispensed through the dispensing reservoir tip after movement of the primary and secondary activators toward the barrel and the body.

Referring now to FIG. 52*b* the reagent preparation and dispensing device 4900 is shown in another orientation where the reagent mixture is dispensed through the dispensing reservoir nozzle 4926. As shown the primary activator 4910 and secondary activator 4912 are fully depressed into the body 4902 and barrel 4904. Movement of the primary activator 4910 and secondary activator 4912 as a unit has moved the primary activator shaft 4938 through the barrel shaft 4928. Movement of the primary activator shaft 4938 relative to the barrel shaft 4928 moves the primary stopper gasket 4940 out of engagement with the barrel shaft 4928. As shown in FIG. 52*b*, disengagement of the primary stopper gasket 4940 with the barrel shaft 4928 opens passages 5200 between the flushing chamber 4947 and the reagent reservoir 4909 (the flushing chamber 4947 is shown in FIG. 52*a*). Movement of the secondary activator 4912 at the same time with the primary activator 4910 moves the secondary stopper gasket 4944 forcing the flushing gas 4945 out of the flushing chamber 4947 and along passages 5200 around the primary activator shaft 4938. The flushing gas 4945 enters the reagent reservoir 4909 forcing the reagent mixture out of the dispensing reservoir tip 4906 and through the dispensing reservoir nozzle 4926 thereby moving the reagent mixture out of the device 4900.

As shown in FIG. 52*b*, the relative size of the reagent reservoir 4909 with the barrel shaft 4928 positioned within the reagent reservoir is small compared with the flushing chamber 4947. The flushing gas 4945 present in the flushing chamber 4947 thereby easily moves the reagent mixture out of the dispensing reservoir tip 4906 and through the dispensing nozzle 4926. A large amount of flushing gas 4945 relative to the size of the reagent reservoir 4909 is able to easily and completely move the entire specified amount of the reagent mixture out of the dispensing reservoir tip 4906. Moving the relatively large amount of gas 4945 through the relatively small reagent reservoir 4909 consistently dispenses the entire amount of the specified reagent out of the device 4900. The user thereby has a measure of confidence that the entire specified amount of the mixture has been dispensed ensuring accuracy for testing and diagnostic purposes.

Figure 53:
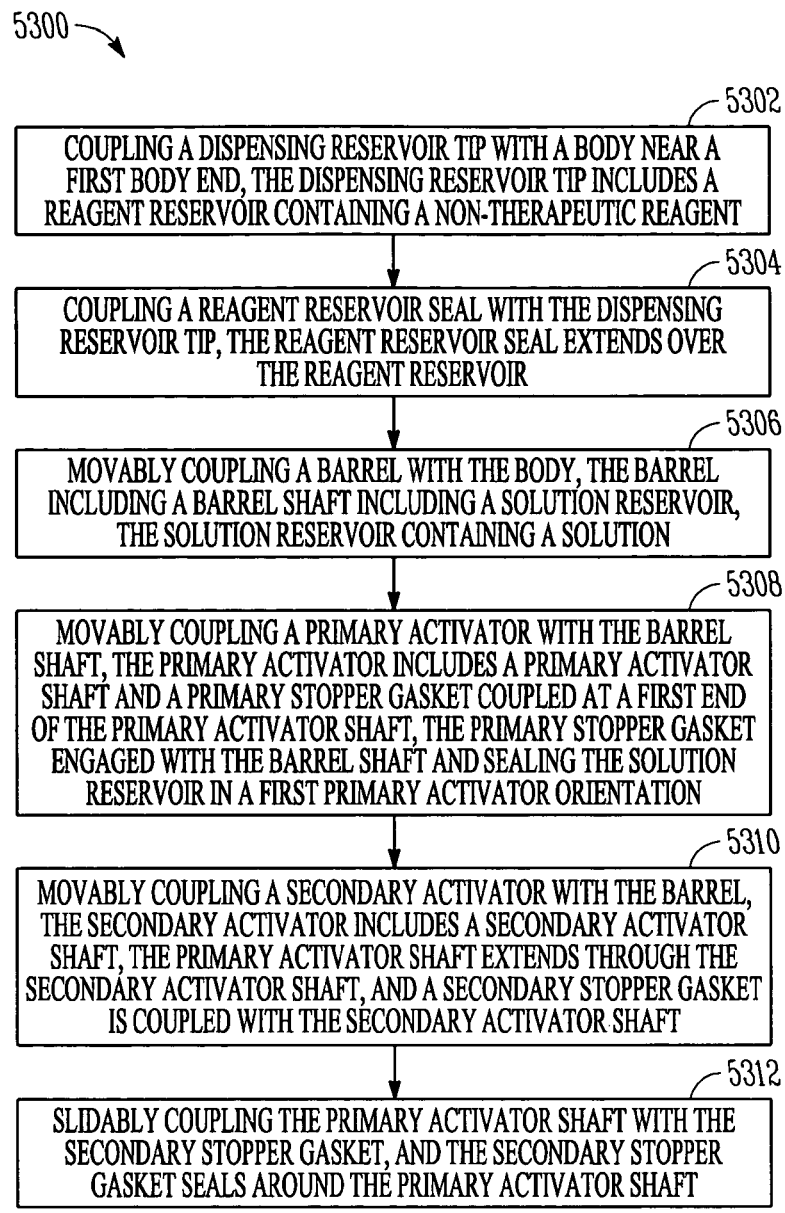
FIG. 53 is a block diagram showing one example of a method for making the device shown in FIGS. 49*a, b*.

FIG. 53 shows one example of a method 5300 for making a reagent preparation and dispensing device such as the device 4900 shown in FIGS. 49a, b. Reference is made with regard to the method 5300 to the device shown in FIGS. 49b, b, 50a-c, and 51a-i as well as FIGS. 52a, b.

At 5302, a dispensing reservoir tip 4906 is coupled with a body 4902 near a first body end (e.g., the body end shown closest to the dispensing reservoir tip in FIGS. 49a, b). The dispensing reservoir tip 4906 includes a reagent reservoir 4909 containing a reagent 4907. As previously described, the dispensing reservoir tip 4906 has sufficient volume to hold the reagent 4907 when mixed with the solution 4930 to form a specified amount of a reagent mixture. The mixture is held within the dispensing reservoir tip 4906 in the reagent reservoir 4909 prior to dispensing out of the tip.

At 5304, a reagent reservoir seal 4922 is coupled with the dispensing reservoir tip 4906. For instance, the reagent reservoir seal 4922 is coupled with a dispensing reservoir tip flange 4920. In another example, the reagent reservoir seal 4922 is adhered to the dispensing reservoir tip flange 4920. In yet another example, the dispensing reservoir seal 4922 is tightly held in place on the dispensing reservoir tip flange 4920 by tight engagement of the metal crimp ring 4914 with the interconnecting gasket 4916, as previously described above. The reagent reservoir seal 4922 extends over the reagent reservoir 4909 thereby separating the reagent reservoir from the solution reservoir 4931.

At 5306, a barrel 4904 is movably coupled with the body 4902. The barrel 4904 includes a barrel shaft 4928 including the solution reservoir 4931. The solution reservoir 4931 contains a solution 4930. In one example, the solution reservoir 4931 contains sufficient solution 4930 for mixing with the reagent 4907 to form a specified amount of reagent mixture. Optionally, the solution 4930 fully mixes with the reagent 4907 so none of the solution 4930 is left unreacted after the reagent 4907 and solution 4930 mix.

At 5308, a primary activator 4910 is movably coupled with the barrel shaft 4928. The primary activator 4910 includes a primary activator shaft 4938 and a primary stopper gasket 4940. The primary stopper gasket 4940, in one example, is coupled at a first end of the primary activator shaft 4938 positioned away from the thumb rest flange 4942 of the primary activator 4910. In at least a first orientation the primary stopper gasket 4940 is engaged with the barrel shaft 4928 and seals the solution reservoir 4931 in a first primary activator orientation as shown in FIG. 49b. As previously discussed above, movement of the primary activator 4910 and secondary activator 4912 (discussed below) moves the primary stopper gasket 4940 out of engagement with the barrel shaft 4928 thereby allowing movement of flushing gas 4945 out of the flushing chamber 4947 and into the reagent reservoir 4909 for dispensing of the non-pharmaceutical reagent mixture out of the device 4900.

At 5310, a secondary activator, such as the secondary activator 4912 is movably coupled with the barrel 4904. The secondary activator 4912 includes a secondary activator shaft 4946 the primary activator shaft 4938 extends through the secondary activator shaft 4946. A secondary stopper gasket 4944 is coupled with the secondary activator shaft 4946. The secondary stopper gasket 4944 provides a tight sealing engagement with the barrel 4904 within the barrel recess 4948 to thereby form the sealed flushing chamber 4947 containing the flushing gas 4945.

At 5312, the primary activator shaft 4938 is slidably coupled with the secondary stopper gasket 4944. As previously discussed above, the secondary stopper gasket 4944 slidably engages along the primary activator shaft 4938 thereby providing a tight seal between the primary activator and the secondary activator 4910, 4912 during movement of the primary activator 4910 relative to the secondary activator 4912.

Several options for the method 5300 are provided below. In one example, the method 5300 includes forming fluid flushing passages, such as passages 5200 shown in FIG. 52b, between the primary activator shaft 4938 and the barrel shaft 4928. The fluid flushing passages 5200 extend between the flushing chamber 4947 and the reagent reservoir 4909 where the primary stopper gasket 4940 is disengaged from the barrel shaft 4928. As described above, disengagement of the primary stopper gasket 4940 allows for movement of the flushing gas 4945 into the reagent reservoir 4909 thereby forcing the specified amount of the reagent mixture out of the dispensing reservoir tip 4906. In another example, the method 5300 includes crimping a crimp ring, such as crimp ring 4914, between a dispensing reservoir tip flange 4920 and a body flange 4918. In one option, an interconnecting gasket 4916 is interposed between the body flange 4918 and the dispensing reservoir tip flange 4920. Application of the crimp ring 4914 deforms the interconnecting gasket 4916 thereby providing a tight seal between the body flange 4918 and the dispensing reservoir tip flange 4920.

Yet another example of a reagent preparation and dispensing device 5400 is shown in FIGS. 54A, B. In some regards the device 5400 is similar to the device 4900 shown in FIGS. 49A through 53 as well as the other preceding examples. The reagent preparation and dispensing device 5400 includes a dispensing reservoir tip 5406 coupled with a housing or body 5402. The body 5402 is movably coupled with a barrel 5404. As shown in FIG. 54A the barrel 5404 is movable rotationally and longitudinally relative to the body 5402. In another example, the barrel 5404 is movable longitudinally relative to the body 5402, for instance, by sliding. The body and barrel 5402, 5404, respectively, include in one example, a mechanical interfitting 5422 extending therebetween as shown in FIG. 54A. The mechanical fitting 5422 includes threading that allows rotation of the barrel 5404 relative to the body 5402 to longitudinally move the barrel 5404 relative to the body. As will be described in further detail below, movement of the barrel 5404 relative to the body 5402 penetrates a reagent reservoir seal 5432 separating the reagent reservoir 5409 and the solution reservoir 5420.

The dispensing reservoir tip 5406 includes a reagent reservoir 5409 including a reagent 5407. In one example, the reagent 5407 includes a freeze dried (e.g., lyophilized) reagent. Reagent 5407 is hydrophilic and capable of immediate reconstitution when contacted by a liquid such as the solution 5421 contained within the solution reservoir 5420 shown in FIGS. 54A and 54B. A reagent reservoir seal 5432 separates the reagent reservoir 5409 from the solution reservoir 5420. The solution reservoir 5420 is formed in part by the barrel 5404 and a first plunger gasket 5416 received in the barrel 5404 to close a portion of the barrel 5404 and allow for retention of the solution 5421 therein.

The reagent preparation and dispensing device 5400 further includes an activator 5410. The activator 5410 is movable relative to the barrel 5404, body 5402 and dispensing reservoir tip 5406. As shown in FIG. 54A, the activator 5410 is coupled with a first plunger 5412 extending into the barrel 5404. The first plunger gasket 5416 is coupled with the first plunger 5412 to seal a portion of the barrel 5404 for reception and retention of the solution 5421 of the solution reservoir 5420. As further shown in FIG. 54A, the activator 5410 is also coupled with a second plunger 5412 having a second plunger gasket 5418. As will be described in further detail below, the second plunger 5414 and associated gasket 5418 are configured to move a mixture of the solution 5421 and reagent 5407 out of the dispensing reservoir tip 5406. The second plunger 5414 is shown in FIG. 54A as integral to the activator 5410. In another example, the second plunger 5414 is a second component separate from the first activator 5410 and coupled thereto.

FIG. 54B shows a detailed cross-sectional view of the reagent preparation and dispensing device 5400 shown in FIG. 54A. The body 5402 is coupled with a dispensing reservoir tip 5406 as previously described. As shown in FIG. 54B, an interconnecting gasket 5426 is coupled between the body 5402 and the dispensing reservoir tip 5406. A crimp sleeve 5427 extends between the body 5402 and dispensing reservoir tip 5406 and is crimped around the two elements to squeeze the interconnecting gasket 5426 and create a tight seal between the body 5402 and dispensing reservoir tip 5406 substantially preventing leaking of a reconstituted mixture of the reagent 5407 and solution 5421. The first plunger 5412 extends into the solution reservoir 5420 where a first plunger gasket 5416 closes one end of the solution reservoir 5420 and retains a solution 5421 therein. One end of the barrel 5404 includes a piercing edge 5424 sized and shaped to engage against the reagent reservoir seal 5432 and rupture the seal to allow communication between the solution reservoir 5420 and reagent reservoir 5409. In one example, the reagent reservoir seal 5432 includes, but is not limited to, a foil seal, a laminated seal, a composite seal, a multilayered seal and the like.

Again referring to 54B, the reagent 5407 is disposed within a reagent recess 5425 of the dispensing reservoir tip 5406. The reagent 5407 is retained within the recess 5425, for instance, by mechanical interfitting that substantially prevents the reagent 5407 from disengaging from the dispensing reservoir tip 5406. Additionally, the positioning of the reagent 5407 at the base of the dispensing reservoir tip ensures that the solution 5421 when forced into the reagent reservoir 5409 contacts the reagent 5407 (and thereby mixes with the reagent) prior to dispensing through the dispensing reservoir tip nozzle 5411.

As further shown in FIG. 54B, the reagent preparation and dispensing device 5400 includes a cap 5408 coupled with the body 5402. The cap closes off the dispensing reservoir tip 5406 substantially preventing interaction of the reagent 5407 with an exterior environment including an environment having moisture sufficient to cause undesired reconstitution of the reagent 5407. For instance, the cap 5408 includes a threaded interfitting 5428 with the body 5402. The cap 5408 is tightly coupled with the body 5402, for instance by rotation, and a gasket 5430 interposed between the body 5402 and a portion of the cap 5408 is squeezed by the rotation of the cap to create a tight seal between the dispensing reservoir tip 5406 and the cap 5408. The seal substantially prevents the ingress of moisture into the dispensing reservoir tip 5406. In another example, and as previously described in other embodiments, a desiccant (e.g., desiccant 5413) is disposed within the cap to substantially remove any moisture from atmosphere that somehow enters the cap 5408.

One example of the reagent preparation and dispensing device 5400 in an intermediate configuration is shown in FIGS. 55A and B. The barrel 5404 is advanced relative to the body 5402 and the piercing element 5424 of the barrel pierces through the reagent reservoir seal 5432 shown originally in FIGS. 54A, B. The solution reservoir 5420 is thereafter in communication with the reagent reservoir 5409. The reagent 5407 and solution 5421 are still separated from each other as the first plunger 5412 has not been advanced relative to the barrel 5404 to force the solution into the reagent reservoir 5409. As previously described in FIG. 54A, a mechanical interfitting 5422 between the body 5402 and barrel 5404 allows for advancement of the barrel 5404 relative to the body. For instance, in one example, the barrel 5404 is rotated relative to the body 5402 to correspondingly advance the piercing edge 5424 through the reagent reservoir seal 5432.

Referring now to FIG. 55B, a detailed view of the reagent reservoir 5409 and solution reservoir 5420 shown in FIG. 55A is provided. As previously discussed, the barrel 5404 is advanced relative to the body 5402 to rupture the reagent reservoir seal 5432 with the piercing element 5424. The barrel 5404 is advanced into the reagent reservoir 5409 substantially shrinking the reagent reservoir 5409 and creating a small compact environment for the reconstitution of the reagent 5407 by mixing with the solution 5421. That is to say, by providing a smaller reagent reservoir 5409 in this intermediate stage the solution 5421, when moved into the reservoir 5409, is forced into more intimate contact with the reagent 5407 than in the otherwise larger reservoir. The solution 5421 is thereby able to fully and rapidly reconstitute the reagent 5407 and ensure that a specified amount of a reagent mixture is formed when the solution and reagent mix. As described in other examples previously, the solution reservoir 5420 includes a specified amount of solution 5421 configured to fully reconstitute the reagent 5407 without diluting the reagent 5407 when forming the mixture or leaving any of the reagent 5407 unreconstituted.

FIGS. 56A, B and C show the reagent preparation and dispensing device 5400 in a second intermediate configuration where the first plunger 5412 is advanced into the reagent reservoir 5409 forcing the solution 5421 into intimate contact with the reagent 5407 and allowing mixing of the reagent and solution to form a specified amount of a reagent mixture. FIGS. 56A and 56B show the device 5400 in the same intermediate orientation. The device 5400 in FIG. 56B is rotated 90 degrees around the longitudinal axis of the device relative to the view shown in FIG. 56A. Movement of the activator 5410 relative to the barrel 5404 and body 5402 moves the first plunger 5412 including the first plunger gasket 5416 forcing the solution 5421 (FIGS. 55A and 55B) into the reagent reservoir 5409. Movement of the activator 5410 is transmitted to the first plunger 5412 by engagement between one or more drive lugs 5606 shown in FIG. 56B with the surfaces defining a drive lug recess 5604 of the second plunger 5414. The recess 5604 is shown in FIG. 56A and the drive lug 5606 is shown in FIG. 56B.

Because the drive lugs 5606 are engaged with the second plunger 5414 (coupled with the activator 5410) movement of the activator 5410 correspondingly moves the first plunger 5412 through the solution reservoir 5420 pushing the solution 5421 into the reagent reservoir 5409. Referring to FIG. 56A the drive lug recess 5604 is in communication with one or more drive lug slots 5608. As will be described in further detail below, when the activator 5410 is rotated relative to the first plunger 5412 the drive lugs 5606 are aligned with the drive lug slots 5608 allowing for relative movement between the activator 5410 and the first plunger 5412. This allows the activator 5410 and the second plunger 5414 to move downward into the body 5402 and force flushing fluid into the reagent reservoir 5409 to dispense the reagent mixture from the dispensing reservoir tip 5406. That is to say, the activator and first plunger 5412 are selectively locked together in the orientation shown in FIGS. 56A and 56B so that movement of the activator 5410 is transmitted to the first plunger 5412 to move the first plunger when the activator is moved. Positioning of the drive lugs 5606 out of the drive lug recess 5604 unlocks the activator 5410 (and the second plunger 5414) from the first plunger 5412 allowing relative movement therebetween.

In the example shown in FIGS. 56A, B and C, the first plunger includes a first plunger stop 5601 shown in FIGS. 56B and 56C. The first plunger stop 5601 is sized and shaped to engage within a first stop seat 5600 shown in FIGS. 56A and 56C. As the first plunger 5412 is advanced into the body 5402 the first plunger gasket 5416 is advanced out of the barrel 5405 and beyond the piercing edge 5424 (described further below). Disengagement of the first plunger gasket 5416 from the piercing edge 5424 allows for flushing fluid (gas, liquid and the like) to move past the first plunger 5412 and into the reagent reservoir 5409 to force the reagent mixture out of the dispensing reservoir tip 5406. Engagement of the first plunger stop 5601 within the first stop seat 5600 arrests the movement of the first plunger 5412 substantially preventing movement of the first plunger gasket 5416 further into the reagent reservoir 5409 and substantially preventing unwanted dispensing of the reagent mixture prior to full reconstitution of the reagent 5407. Referring again to FIGS. 56A and 56B, the first plunger stop 5601 is shown as engaging the first stop seat 5600 in FIG. 56B. In FIG. 56A, the first plunger stop 5600 is absent. In other words, the first plunger stop 5601 extends around a portion of the first plunger 5412 allowing for flushing fluid (air, liquid and the like) moved by the second plunger 5414 to move around the first plunger 5412 through one or more flushing passages 5602 and into the reagent reservoir 5409.

In another example shown in FIG. 56B, the reagent preparation and dispensing device 5400 further includes an activator stop 5614. The barrel 5404 includes a corresponding activator stop seat 5616 sized and shaped to receive the activator stop 5614 of the activator 5410. The activator stop 5614 on the activator 5410 is configured to cooperate with the first plunger stop 5601 (described above). The activator stop 5614 engages with the surfaces defining the activator stop seat 5616 after the activator 5410 is depressed into the body 5402. The first plunger stop 5601 and activator stop 5614 cooperate to substantially arrest the movement of the first plunger 5412 after the solution 5421 has been moved into the reagent reservoir 5409 and the first plunger gasket 5416 is disengaged from the piercing edge 5424 of the barrel 5404. Referring to FIG. 56A, the reagent preparation and dispensing device 5400 further includes activator stop slots 5618 sized and shaped to receive the activator stop 5614 with rotation of the activator 5410 relative to the barrel 5404. Rotation of the activator 5410 relative to the barrel 5404 and first plunger 5412 allows for continued longitudinal movement of the activator 5410 and the second plunger 5414 into the body 5402 to dispense the specified amount of reagent mixture from the dispensing reservoir tip 5406.

Referring now to FIGS. 56B and 56C, a flushing vent and flushing passages are described in further detail. In the ready configuration shown in FIGS. 54A, 54B, the intermediate configuration shown in FIGS. 55A and 55B, and the second intermediate configuration shown in FIGS. 56A through 56C a flushing fluid vent is maintained from a flushing chamber 5610 between the first plunger 5412 and the barrel 5404. The flushing fluid vent allows venting of the fluid within the flushing chamber 5610 to ambient atmosphere. Providing this flushing fluid vent allows gas within the flushing chamber 5610 to vent to atmosphere in any of these configurations shown in FIGS. 54A-56C. This assures there is no uncontrolled pressure difference between the flushing chamber 5610 and the reagent reservoir 5409 where mixing of the reagent 5407 and solution 5421 takes place. Control of the pressure within the flushing chamber 5610 substantially prevents uncontrolled pressures that could otherwise expel the specified amount of reagent mixture too quickly or allow for retrograde flow of the reagent mixture into the flushing chamber 5610 as opposed to through the dispensing reservoir tip 5406. In the detailed view shown in FIG. 56C, one example of the flushing chamber 5610 is shown with flushing fluid vents 5612 extending around the second plunger gasket 5418 and along the second plunger 5414. The flushing fluid vent continues along the activator stop slots 5618 allowing the flushing chamber 5610 to vent to atmosphere until the second plunger gasket 5418 engages with the barrel 5404 after the activator 5410 and second plunger 5414 are depressed relative to the barrel 5404 and first plunger 5412 as described below and shown in FIGS. 57A, B. Once the second plunger gasket 5418 engages with the barrel 5404 the flushing chamber 5610 is sealed preventing the escape of flushing fluid out of the flushing chamber except through and along the flushing passage 5602 shown in FIGS. 56A and 56C. That is to say the venting function of the flushing fluid vents 5612 and the activator stop slots 5618 is arrested while the second plunger 5418 moves the flushing fluid into the dispensing reservoir tip 5406 for dispensing of the specified amount of reagent mixture from the dispensing reservoir tip 5406.

Figure 57A:
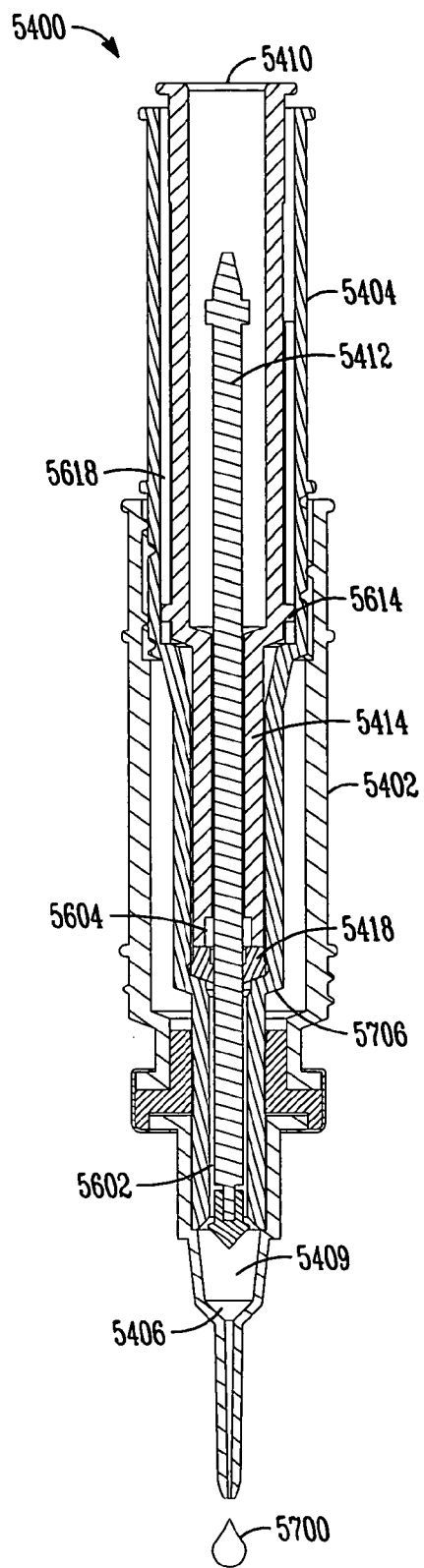
FIG. 57*a* is a cross-sectional view of the reagent preparation and dispensing device of FIG. 54*a* showing the second plunger advanced to move the reagent mixture out of the device.
Figure 57B:
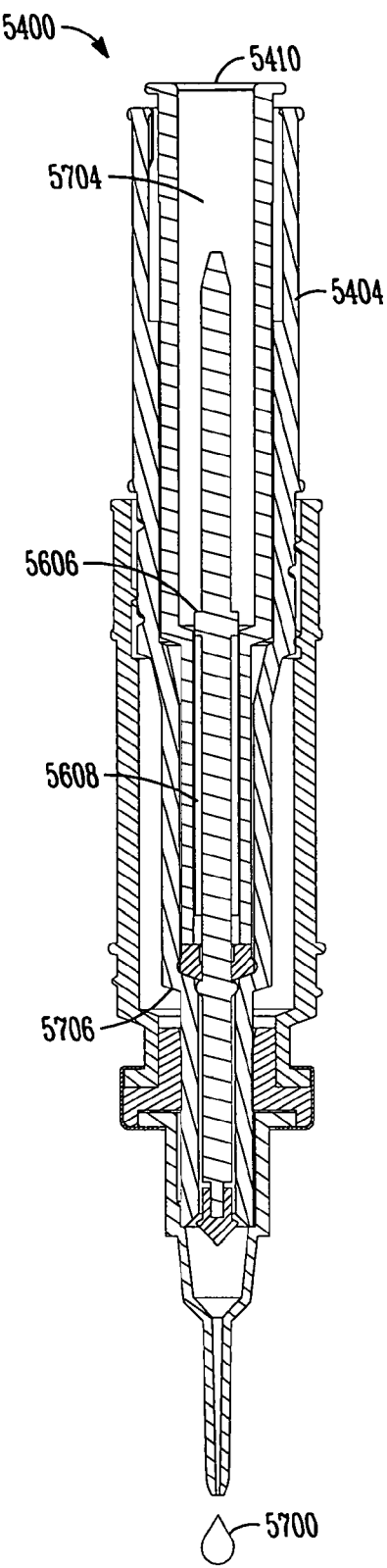
FIG. 57*b* is a cross-sectional view of the reagent preparation and dispensing device in the orientation shown in FIG. 57*a* with the device rotated 90 degrees around the device longitudinal axis to show the disengagement of the drive lugs and travel through the plunger slots.

A dispensing configuration for the reagent preparation and dispensing device 5400 is shown in FIGS. 57A and 57B. As shown in both of the Figures the activator 5410 is depressed again relative to the barrel 5404 and body 5402. Further, the second plunger 5414 including the second plunger gasket 5418 is advanced relative to the barrel 5404 and the first plunger 5412. Movement of the second plunger through depression of the activator 5410 moves flushing fluid from the flushing chamber 5610, shown in FIGS. 56A through 56C, into the reagent reservoir 5409 to dispense the specified amount of reagent mixture 5700 from the dispensing reservoir tip 5406.

As previously shown in FIGS. 56A, C and described above, the flushing passages 5602 extend along the first plunger 5412 and the barrel 5404 and into the reagent reservoir 5409. Because the first plunger stop 5601 extends around a portion of the first plunger 5412 the flushing fluid from the flushing chamber 5610 is able to move around the first plunger stop 5601 and through the flushing passage 5602 into the reagent reservoir 5409 to force the specified amount of reagent mixture 5700 from the dispensing reservoir 5406. Because the first plunger gasket 5416 is disengaged from the piercing edge 5424 of the band 5404 the flushing fluid moves from the flushing passage 5602 into the reagent reservoir 5409. That is to say, the combination of the passage through the first stop seat 5600 around the first plunger stop 5601 into the flushing passage 5602 and around the first plunger gasket 5614 allows the flushing fluid from the flushing chamber 5610 to move into the reagent reservoir 5409 and dispense the specified amount of reagent mixture 5700 from the dispensing reservoir tip 5406.

As previously described, the drive lug 5606 engaged with the surfaces defining the drive lug recess 5604 substantially prevents movement of the second plunger 5414 relative to the first plunger 5412 and barrel 5404. In the dispensing configuration shown in FIGS. 57A, 57B the activator 5410 and second plunger 5414 are rotated relative to the first plunger 5412 thereby moving the drive lug 5606 out of alignment with the surfaces defining the drive lug recess 5604 and allowing the drive lug 5606 to move within the drive lug slot 5608 shown in FIGS. 56A and 57B. Referring to FIG. 57B, the drive lug 5606 is shown positioned within an activator cavity 5704. The second plunger 5414 and the activator 5410 with the drive lug slot 5608 slide over the drive lug 5606 of the first plunger 5412 as the activator 5410 is moved relative to the first plunger.

In another example, where the reagent preparation and dispensing device 5400 includes the activator stop 5614 and activator stop seat 5616, the activator 5410 is further prevented from moving relative to the barrel 5404 and first plunger 5412 by engagement between the activator stop 5614 and the activator stop seat 5616. When it is desired to move the activator 5410 and the second plunger 5414 relative to the first plunger 5412 and the barrel 5404 rotation of the activator 5410 that moves the drive lug 5606 into alignment with the drive slug slot 5608 also moves the activator stop 5614 into alignment with the activator stop slots 5618. Movement of the activator 5410 and second plunger 5414 into the barrel 5404 and body 5402 is thereafter allowed. The activator stop 5614 and activator stop seat 5616 thereby provide a redundant safety system to substantially prevent unwanted movement of the activator 5410 and second plunger 5414 into the flushing chamber 5610 shown in FIG. 56C.

The positioning of the drive lug 5606 within one of the drive lug recess 5604 and the drive lug slot 5608 depending on the orientation of the activator 5410 relative to the drive lug allows the activator 5410 to selectively move one of the first plunger 5412 and second plunger 5414. In the first configuration where the drive lug 5606 is positioned within the drive lug recess 5604 movement of the activator 5410 moves the first plunger 5412 relative to the barrel 5404 and forces the solution 5421 out of the solution reservoir 5420 and into intimate contact with the reagent 5407 in the reagent reservoir 5409. In the second dispensing configuration the activator 5410 is rotated relative to the drive lug 5606. The drive lug 5606 is aligned with the drive lug slot 5608 allowing movement of the activator 5410 and second plunger 5414 relative to the first plunger 5412. Movement of the activator 5410 in this configuration seals the flushing chamber 5610 once the second plunger gasket 5418 engages against the inner wall of the barrel 5404 and forces the flushing fluid contained within the sealed flushing chamber 5610 along the flushing passage 5602 and around the first plunger gasket 5416 into the reagent reservoir 5409 to dispense the specified amount of reagent mixture 5700 from the dispensing reservoir tip 5406 (FIGS. 57A, 57B). The activator 5410 thereby provides a single element that operates the first plunger 5412 and the second plunger 5414 in separate isolated steps. In other words, the activator 5410 is able to move the first plunger 5412 and second plunger 5414 in a staged manner to first mix the solution 5421 with the reagent 5407 and then, in the second dispensing configuration, force the specified amount of reagent mixture 5700 out of the dispensing reservoir tip 5406.

Referring again to FIGS. 57A and 57B, the second plunger 5414 including the second plunger gasket 5418 is shown as moving along a stroke length 5702. Stroke length 5702 corresponds to the movement of the second plunger between a position where the second plunger gasket 5418 engages with the barrel 5404 to seal the flushing chamber 5610 and a second position where the second plunger gasket 5418 is seated at a second plunger gasket seat 5706. The stroke length 5702 of the second plunger 5414 is configured so the second plunger gasket 5418 can smoothly and slowly move along the barrel 5404 to make sure all the reagent mixture is expelled from the reagent reservoir 5409. A long stroke length, such as the length 5702 shown in FIGS. 57A, B, allows the user to gradually depress the activator 5410 and correspondingly gradually move the flushing fluid in the flushing chamber 5610 into the reagent reservoir 5409. This gradual forcing of the flushing fluid into the reagent reservoir 5409 substantially prevents splitting of the reagent mixture thereby avoiding retention of a residual amount of the reagent mixture within the reagent reservoir 5409 after the activator 5410 is fully depressed. That is to say, the long stroke length 5702 substantially ensures that a specified amount of the reagent mixture such as the specified amount 5700 shown in FIGS. 57A, 57B is consistently dispensed from the reagent preparation and dispensing device 5400 thereby removing any operator errors and inconsistencies that could otherwise appear with the operation of other devices having a shorter stroke length.

Referring now to FIGS. 58A through 58D, a method for using the reagent preparation and dispensing device 5400 (shown in FIGS. 54A through 57B) is provided. In FIG. 58A, the reagent preparation and dispensing device 5400 is in a ready position where the cap 5408 is coupled with the body 5402 and the barrel 5404 is moveably coupled with the body 5402. The reagent reservoir seal 5432 is interposed between the reagent reservoir 5409 and the solution reservoir 5420. In other words, the piercing edge 5424 of the barrel 5404 is not penetrating the seal. Further, the activator 5410 is in an non-depressed state where neither the first plunger 5412 or second plunger 5414 (FIGS. 54A through 57B) are moved toward the reagent reservoir tip 5406 to reconstitute the reagent 5407 housed within the reagent reservoir 5409.

Referring now to FIG. 58B, the reagent preparation and dispensing device 5400 is shown in a first intermediate configuration where the barrel 5404 is advanced relative to the body 5402. As previously shown in FIG. 54A, the barrel 5404 and body 5402, in one example, include a mechanical interfitting 5422 such as threading. Rotation of the barrel 5404 relative to the body 5402 with such a mechanical interfitting 5422 moves the piercing edge 5424 (shown in FIG. 54B) into engagement with the reagent reservoir seal 5432 and pierces the seal to allow for communication between the solution reservoir 5420 and reagent reservoir 5409 (FIGS. 55A and 55B).

As shown in FIG. 58C, the reagent preparation and dispensing device 5400 is in a second intermediate configuration where the activator 5410 is partially depressed relative to the barrel 5404. As shown in FIGS. 56A-C, depression of the activator 5410 moves the first plunger 5412 and the first plunger gasket 5416 through the solution reservoir 5420 (FIGS. 55A and 55B) and into the reagent reservoir 5409. Movement of the first plunger 5412 forces the solution 5421 into the reagent reservoir 5409. The reagent 5407 begins reconstitution with the solution 5421. As previously described, in one example the first plunger 5412 includes a first plunger stop 5601 that engages with a first stop seat 5600 to substantially prevent further movement of the first plunger 5412 into the reagent reservoir 5409. Unwanted dispensing of the reagent mixture prior to full reconstitution of the reagent is thereby prevented. That is to say, the first plunger 5412 is arrested from further movement allowing the reagent 5407 and solution 5421 to fully mix and reconstitute the reagent into the specified amount of reagent mixture.

FIG. 58D shows the reagent preparation and dispensing device 5400 in a dispensing configuration where the activator 5410 is depressed again relative to the barrel 5404 and body 5402. As described above, in the intermediate configuration shown in FIG. 58C the drive lug 5606 of the first plunger 5412 is disposed within the drive lug recess 5604 thereby substantially preventing movement of the activator and second plunger 5414 relative to the first plunger 5412. Positioning of the drive lug 5606 within the drive lug recess 5604 correspondingly prevents movement of flushing fluid from the flushing gas chamber 5610 into the reagent reservoir 5407 for dispensing of the specified amount of reagent mixture 5700. As shown in FIG. 58C, the activator 5410 is rotated relative to the first plunger 5412 to align the drive lug 5606 with the drive lug slot 5608 extending through the second plunger 5414. The activator 5410 is thereby able to be depressed relative to the first plunger 5412. Depression of the activator 5410 engages the second plunger gasket 5418 with the inner wall of the barrel 5404 and seals the flushing chamber 5610. Continued movement of the activator 5410 and second plunger 5414 after alignment of the drive lug 5606 with the drive lug slot 5608 forces the flushing fluid within the sealed flushing chamber 5610 through the flushing passage 5602 (shown in FIG. 56C) along the first plunger 5412 and the adjacent barrel 5404. The flushing fluid flows around the first plunger gasket 5416, which is disengaged from the piercing edge 5424, and moves into the reagent reservoir 5409 where the flushing gas forces the specified amount of reagent mixture 5700 out of the dispensing reservoir tip 5406 as shown in FIG. 57A, 57B.

Figure 59:
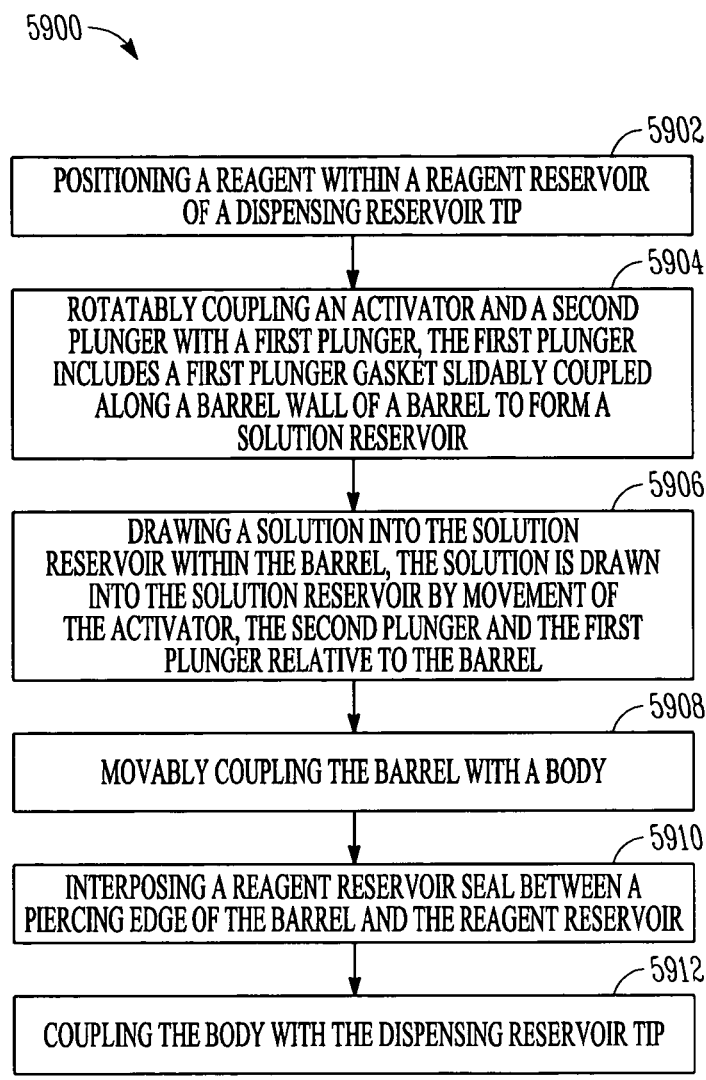
FIG. 59 is a block diagram showing one example of a method for making the device shown in FIGS. 54*a, b*.

FIG. 59 shows one example of a method 5900 for making a reagent preparation and dispensing device such as the device 5400 shown in FIGS. 54a, b. Reference is made with regard to the method 5900 to the device shown in FIGS. 54a-58d.

At 5902, a reagent 5407 is positioned within a dispensing reservoir tip 5406. The dispensing reservoir tip 5406 includes a reagent reservoir 5409 containing the reagent 4907. As previously described, the dispensing reservoir tip 5406 has sufficient volume to hold the reagent 5407 when mixed with the solution 5421 to form a specified amount of a reagent mixture. The mixture is held within the dispensing reservoir tip 5406 in the reagent reservoir 5409 prior to dispensing out of the tip.

At 5904, an activator 5410 and a second plunger 5414 are rotatably coupled with a first plunger 5412. The first plunger 5412 includes a first plunger gasket 5416 slidably coupled along a barrel wall 5417 of a barrel 5404 to form a solution reservoir 5420.

At 5906, a solution 5421 is placed within the solution reservoir 5420. In one example, the solution 5421 is drawn into the solution reservoir 5420 by movement of the activator 5410, the second plunger 5414 and the first plunger 5412 relative to the barrel 5404.

At 5908, the barrel 5404 is movably coupled with the body 5402. For example, the barrel 5404 is rotatably coupled with the body 5402 with a mechanical interfitting 5422 (e.g., threading). The mechanical interfitting translates rotation of the barrel 5404 relative to the body 5402 into longitudinal movement of the barrel 5404.

At 5908, a reagent reservoir seal 5432 is interposed between the a piercing edge 5424 of the barrel 5404 and the reagent reservoir 5409. The reagent reservoir seal 5432 extends over the reagent reservoir 5409 thereby separating the reagent reservoir from the solution reservoir 5420.

At 5910, the body 5402 is coupled with the dispensing reservoir tip 5406.

Several options for the method 5900 are provided below. In one example, rotatably coupling the activator 5410 and the second plunger 5414 with the first plunger 5412 includes positioning drive lugs 5606 of the first plunger 5412 within drive lug recesses 5604 of one of the activator 5410 and the second plunger 5414. The method 5900 further includes forming at least one drive lug slot 5608 in one or more of the activator 5410 and the second plunger 5414, the drive lug slot 5608 in communication with the drive lug recess 5604, and the drive lugs 5606 are configured to slide within the drive lug slot. In another example, the method 5900 further includes recessing a second plunger gasket 5418 coupled with the second plunger 5414 from the barrel wall 5417 to form a flushing vent 5612 between a flushing chamber 5610 and ambient atmosphere. The flushing chamber 5610 is formed between with the barrel wall 5417 and the second plunger gasket 5418.

CONCLUSION

The reagent preparation and dispensing devices described above and shown in the Figures provide compact and easy to use assemblies for the reconstitution of reagents for a variety of diagnostic, life science research and testing purposes. Each device includes a specified amount of solution to mix with the loaded reagents. The solution and reagent are held in separate reservoirs and reconstituted as needed by the technician. The loaded devices are storable for long periods of time and immediately usable. Additionally, because the devices include measured amounts of solution that reconstitute the reagent (or reagents) without leaving excess solution, a reagent solution having a specified concentration is consistently formed. The all-in-one device places the solution, the reagent, the mixing device and the dispensing feature in a single housing and thereby substantially eliminates user based variables that may negatively impact the quality and function of a reagent. The device eliminates many measuring and handling steps so that high level manufacturing quality standards for the reagent are carried forward and maintained during preparation of the reagent. Proper preparation of the reagent with the devices described herein is thereby not dependent on the skill, experience, competency or technique of the user. Having the specified amount and concentration of reagent solution ensures a testing or diagnostic scheme is accurately performed and provides the technician with a confident diagnostic or test result.

User errors including inaccuracies in drawing solution amounts, for instance through a pipette, are avoided. Further, repeated drawing of solution is avoided because each device includes the needed solution. Technician labor (and possible attendant error) is thereby decreased as multiple movements from the test solution reservoir to draw up solution with a pipette to separate racks of reagent and test samples are avoided. Instead, the technician mixes the reagent solution and dispenses the reagent solution from a single device into a rack with a test sample. Additionally, providing the solution and reagents in a protected environment (e.g., within the device housings and within separate sealed reservoirs) protects the reagents from contaminants and moisture, thereby avoiding breakdown of the reagent and environmental errors in the concentration and content of the reagent solution.

Many of the example devices described above include the solutions and reagents within sealed reservoirs separate from the devices that are then loaded within the device housings. A user may select reagent and solution reservoirs for use in a particular device from a catalog of reagents and solutions. The reservoirs are then loaded within the device to form the pre-packaged preparation and dispensing device. Each device thereby has the flexibility to contain a variety of reagent and solution reservoirs for the desired diagnostic or testing purpose. Manufacturing and assembly of separate devices each directed toward a particular diagnostic or testing scheme is avoided by using a device that is designed to accept reagent and solution reservoirs interchangeably depending on the diagnostic or testing need.

The reagent and preparation devices prepare and dispense reagent solutions, and also allow examination of the solutions prior to dispensing. The devices include dispensing reservoir tips having transparent or semi-transparent materials that allow visual inspection of the reconstituted reagent prior to dispensing. The dispensing reservoir tips are sized and shaped to receive the reagent solution and confirm the correct reagent is mixed with the solution (e.g., by color, clarity and the like), the proper amount of reagent solution has been produced and mixing of the solution and reagent is complete.

The methods for making the preparation and dispensing devices describe loading separate reagent and solution reservoirs into the device housings. The reagents, such as lyophilized reagents, that are freeze-dried under exacting conditions are prepared in separate steps from the construction of the devices, in one example. The lyophilized reagents are then loaded within the reservoirs to seal the reagents away from the exterior environment and place the reagent in a package interchangeable with the devices. Because the lyophilized reagents are prepared separately from the devices, the devices are not subject to the harsh environments needed to form the lyophilized reagents. Structural integrity of the devices, precision fitting of parts and the like are maintained as the devices are isolated from these steps for preparing the reagent.

Many of the example devices described above include diagnostic and testing solutions and reagents. Each of the devices previously described and claimed herein is similarly applicable for use in therapeutic and pharmaceutical applications, such as drug reconstitution, administration and the like. To the extent reagents, mixtures and preparation or dispensing devices are described and claimed herein, therapeutic and pharmaceutical reagents, mixtures and devices are similarly considered within the scope of the description, figures and the claims.

Although the present invention has been described in reference to preferred embodiments, persons skilled in the art will recognize that changes may be made in form and detail without departing from the spirit and scope of the invention. For example, in alternative embodiments the devices and methods presented in the detailed description are applicable to at least some pharmaceutical applications that do not require administration to a subject by injection of with a syringe needle, for instance topical applications. In another embodiment, the devices and methods presented are similarly applicable to environmental applications (e.g., biological, ecological, anti-terrorism and the like). For example, the devices and methods are applicable for storing and reconstituting solutions and reagents needed to reconstitute reagent solutions used to detect explosives, explosive residues, toxins and the like.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. A method of making a reagent preparation and dispensing device comprising:

positioning a solution reservoir within a body, the solution reservoir including a solution therein;

lyophilizing a reagent, wherein lyophilizing of the reagent is isolated from the body and the solution reservoir, and the body and the solution reservoir are not subject to lyophilizing conditions;

coupling a reagent reservoir with the body, the reagent reservoir including the lyophilized reagent therein, the reagent reservoir separate from the body;

coupling an activator with the body, the activator operable to:

open the solution reservoir and the reagent reservoir, mix the solution with the lyophilized reagent and form a reagent mixture, and dispense the reagent mixture from the body.

2. The method of claim 1, wherein coupling the activator includes coupling a first and a second plunger with the body.

3. The method of claim 1, further comprising forming a flushing chamber within the body, the flushing chamber including a flushing gas, and dispensing of the reagent mixture includes forcing the flushing gas into the reagent reservoir, the flushing gas correspondingly flushes the reagent mixture from the body while the flushing gas does not mix with the reagent mixture.

4. The method of claim 3, wherein forming the flushing chamber includes forming a flushing gas vent from the flushing chamber to ambient atmosphere, and mixing of the solution with the lyophilized reagent closes the flushing gas vent and seals the flushing chamber.

5. A reagent preparation and dispensing device comprising:

a body;

a reagent reservoir containing a reagent, the reagent reservoir disposed within the body;

a solution reservoir containing a solution, the solution reservoir disposed within the body;

an activator movably coupled with the body to open the reagent reservoir and the solution reservoir, the activator movable to mix the solution with the reagent to reconstitute the reagent and form a reagent mixture;

a flushing chamber within the body, the flushing chamber includes flushing gas therein;

a dispensing tip coupled with the body; and a plunger movably coupled with the body and coupled with the activator, the plunger is configured to force flushing gas into the reagent reservoir from the flushing chamber, and the flushing gas correspondingly forces the reagent mixture through the dispensing tip while the flushing gas does not mix with the reagent mixture.

6. The reagent preparation and dispensing device of claim 5, wherein the plunger is movable relative to the body between an unsealed condition and a sealed condition, and:

in the unsealed condition a flushing gas vent extends from the flushing chamber and out of the body allowing the flushing gas in the flushing chamber to vent to atmosphere, and in the sealed condition the flushing gas vent is closed and movement of the activator and the plunger forces the flushing gas into the reagent reservoir.

7. The reagent preparation and dispensing device of claim 6, wherein the plunger seals and unseals the flushing chamber.

8. The reagent preparation and dispensing device of claim 6, wherein a flushing passage extends directly from the flushing chamber to the reagent reservoir.

9. The reagent preparation and dispensing device of claim 8, wherein the flushing passage is opened in the sealed condition, and the plunger is configured to force flushing gas from the flushing chamber to the reagent reservoir through the flushing passage.

10. The reagent preparation and dispensing device of claim 8, wherein the flushing passage includes at least a portion of the flushing gas vent.

11. The reagent preparation and dispensing device of claim 5, wherein the plunger includes:
 a first plunger movably coupled with the body and the first plunger is coupled with the activator, the first plunger is configured to move the solution into the reagent reservoir; and
 a second plunger movably coupled with the body and the second plunger is coupled with the activator, the second plunger is configured to force the flushing gas into the reagent reservoir and correspondingly force the reagent mixture through the dispensing tip.

12. The reagent preparation and dispensing device of claim 11 comprising a barrel movably coupled with the body, the barrel includes:
 a barrel nozzle including the solution reservoir, and
 a piercing edge sized and shaped for piercing of a reagent reservoir seal, the piercing edge near a first barrel end.

13. The reagent preparation and dispensing device of claim 12, wherein the second plunger is configured for selective sealing with the barrel, and the barrel and the second plunger form the flushing chamber.

14. The reagent preparation and dispensing device of claim 12, wherein the barrel nozzle is positioned within the reagent reservoir and decreases a reagent reservoir volume while the activator mixes the solution with the reagent.

15. The reagent preparation and dispensing device of claim 11, wherein the first plunger is engaged with the activator in a first configuration and the first plunger and the activator move together in the first configuration, and the first plunger is slidably coupled with the activator and the second plunger in a second configuration, and the activator and the second plunger move relative to the first plunger in the second configuration.

16. The reagent preparation and dispensing device of claim 5, wherein the reagent is a dried reagent.

17. The reagent preparation and dispensing device of claim 5, wherein the flushing chamber includes air as the flushing gas.

18. The reagent preparation and dispensing device of claim 5, wherein the flushing chamber has a flushing gas volume larger than a reagent reservoir volume.

19. The reagent preparation and dispensing device of claim 5, wherein the reagent reservoir includes a conical bottom in communication with the dispensing tip, and the plunger is configured to force flushing gas into the reagent reservoir with the reagent mixture positioned in the conical bottom.

20. The reagent preparation and dispensing device of claim 5, wherein the activator is configured to eliminate a solution reservoir containing the solution.

21. A method of using a reagent preparation and dispensing device comprising:
 opening a reagent reservoir disposed within a body, the reagent reservoir contains a reagent;
 mixing a solution with the reagent to reconstitute the reagent and form a reagent mixture; and
 dispensing the reagent mixture through a dispensing tip, dispensing the reagent mixture includes:
  forcing flushing gas out of a flushing chamber and into the reagent reservoir with a plunger coupled with an activator, and
  forcing the reagent mixture out of the dispensing tip with the flushing gas, the flushing gas does not mix with the reagent mixture.

22. The method of claim 21 comprising venting flushing gas within the flushing chamber to atmosphere through a flushing gas vent; and
 dispensing the reagent mixture includes closing the flushing gas vent with the plunger.

23. The method of claim 21, wherein dispensing the reagent mixture includes delivering the forced flushing gas from the flushing chamber to the reagent reservoir through a flushing passage.

24. The method of claim 23, wherein dispensing the reagent mixture includes opening the flushing passage.

25. The method of claim 21, wherein dispensing the reagent mixture includes forcing flushing gas out of the flushing chamber and directly into the reagent reservoir through a flushing passage, and the flushing chamber includes a flushing gas volume greater than a reagent reservoir volume of the reagent reservoir.

26. The method of claim 21, wherein dispensing the reagent mixture includes forcing flushing gas into the reagent reservoir with the reagent mixture positioned between the flushing gas and the dispensing tip.

27. The method of claim 21 comprising shrinking the reagent reservoir before mixing the solution with the reagent.

28. The method of claim 27, wherein shrinking the reagent reservoir includes moving a barrel nozzle movably coupled with the body into the reagent reservoir to fill a portion of a reagent reservoir volume.

29. The method of claim 21, wherein the plunger includes a first plunger coupled with the activator and a second plunger coupled with the activator, the first and second plungers are movably coupled with the body;
 mixing the solution with the reagent includes moving the first plunger and the activator together; and
 dispensing the reagent mixture includes moving the second plunger with the activator relative to the first plunger.

30. The method of claim 29, wherein dispensing the reagent mixture includes opening a flushing passage between the flushing chamber and the reagent reservoir, and opening the flushing passage includes disengaging a portion of the first plunger from a barrel coupled with the body.

31. The method of claim 29, wherein dispensing the reagent mixture includes engaging the second plunger with a barrel coupled with the body, and engaging the second plunger with the barrel closes the flushing chamber.

32. The method of claim 21, wherein opening the reagent reservoir includes piercing a piercing edge of a barrel through a reagent reservoir seal, and the barrel is movably coupled with the body.

33. The method of claim 21, wherein mixing the solution with the reagent includes eliminating a solution reservoir containing the solution.

* * * * *